(12) United States Patent
Guzzo et al.

(10) Patent No.: US 8,273,770 B2
(45) Date of Patent: Sep. 25, 2012

(54) 5-PYRIDINONE SUBSTITUTED INDAZOLES

(75) Inventors: Peter Guzzo, Niskayuna, NY (US); Matthew David Surman, Albany, NY (US); Alan John Henderson, Albany, NY (US); Mark Hadden, Albany, NY (US)

(73) Assignee: Albany Molecular Research, Inc., Albany, NY (US)

( * ) Notice: Subject to any disclaimer, the term of this patent is extended or adjusted under 35 U.S.C. 154(b) by 582 days.

(21) Appl. No.: 12/176,144

(22) Filed: Jul. 18, 2008

(65) Prior Publication Data

US 2009/0082359 A1    Mar. 26, 2009

Related U.S. Application Data

(60) Provisional application No. 60/951,201, filed on Jul. 21, 2007.

(51) Int. Cl.
*A61K 31/4439* (2006.01)
*C07D 401/04* (2006.01)

(52) U.S. Cl. .................................... 514/338; 546/275.7

(58) Field of Classification Search ............... 546/275.7; 514/338
See application file for complete search history.

(56) References Cited

U.S. PATENT DOCUMENTS

| | | | |
|---|---|---|---|
| 5,182,403 | A | 1/1993 | Brickner |
| 5,225,565 | A | 7/1993 | Brickner |
| 5,232,931 | A | 8/1993 | Prucher et al. |
| 5,393,735 | A | 2/1995 | Lange et al. |
| 5,502,027 | A | 3/1996 | Lange et al. |
| 5,631,209 | A | 5/1997 | Lange et al. |
| 5,650,513 | A | 7/1997 | Langhals et al. |
| 5,763,469 | A | 6/1998 | Delucca |
| 6,107,300 | A | 8/2000 | Bakthavatchalam et al. |
| 6,974,869 | B2 | 12/2005 | DeLucca |
| 2003/0114448 | A1 | 6/2003 | Zhang et al. |
| 2003/0144277 | A1 | 7/2003 | DeLucca |
| 2003/0171380 | A1 | 9/2003 | Arvanitis et al. |
| 2003/0212054 | A1 | 11/2003 | Quan et al. |
| 2005/0049253 | A1 | 3/2005 | Tegley |
| 2005/0054670 | A1 | 3/2005 | Tegley et al. |
| 2005/0137243 | A1 | 6/2005 | Souers et al. |
| 2005/0187279 | A1 | 8/2005 | Souers et al. |
| 2005/0272735 | A1 | 12/2005 | Xie et al. |
| 2005/0277638 | A1 | 12/2005 | Souers et al. |
| 2009/0082359 | A1 | 3/2009 | Guzzo et al. |
| 2010/0105679 | A1 | 4/2010 | Guzzo et al. |

FOREIGN PATENT DOCUMENTS

| | | |
|---|---|---|
| DE | 4018830 | 12/1991 |
| DE | 4338784 | 5/1995 |
| DE | 19651712 | 6/1998 |
| DE | 101 04 279 A1 | 8/2002 |
| EP | 1 741 703 | 1/2007 |
| EP | 1 939 194 | 2/2008 |
| JP | 03-253852 | 11/1991 |
| WO | 97/08150 | 3/1997 |
| WO | 97/12884 | 4/1997 |
| WO | 03/024401 | 3/2003 |
| WO | 03/033476 A1 | 4/2003 |
| WO | 2004/032848 | 4/2004 |
| WO | 2004/092181 A1 | 10/2004 |
| WO | 2004/112719 | 12/2004 |
| WO | 2005/018557 | 3/2005 |
| WO | 2005/042541 A1 | 5/2005 |
| WO | 2005/085200 | 9/2005 |
| WO | 2006/017257 | 2/2006 |
| WO | 2007/029847 | 3/2007 |
| WO | 2008/086404 | 7/2008 |
| WO | 2009/015037 | 1/2009 |

OTHER PUBLICATIONS

International Search Report for PCT/US2008/050601 (Jun. 11, 2008).
Written Opinion of the International Search Authority for International Patent Application No. PCT/US2008/050601 (Jun. 11, 2008).
International Preliminary Report on Patentability of the International Preliminary Examining Authority for International Patent Application No. PCT/US2008/050601 (May 22, 2009).
Souers et al., "Synthesis and Evaluation of Urea-Based Indazoles as Melanin-Concentrating Hormone Receptor 1 Antagonists for the Treatment of Obesity," Bioorganic & Medicinal Chemistry Letters, 15:2752-2757 (2005).
International Search Report for PCT/US2008/070535 (Mar. 23, 2009).
Written Opinion of the International Search Authority for International Patent Application No. PCT/US2008/070535 (Mar. 23, 2009).
International Preliminary Report on Patentability of the International Preliminary Examining Authority for International Patent Application No. PCT/US2008/070535 (Feb. 4, 2010).
Communication for European Application No. 08 796 320.3 (Dec. 17, 2010).
Anxiety (online), http://www.medicinenet.com/anxiety/article.htm (retrieved Sep. 9, 2010).
Nonalcoholic Fatty Liver Disease (online), http://www.mayoclinic.com/health/nonalcoholic-fatty-liver-disease/DS00577 (retrieved Sep. 9, 2010).
Vippagunta et al., Advanced Drug Delivery Reviews, 48:3-26 (2001).
Office Action dated Sep. 13, 2010 for U.S. Appl. No. 12/522,657.
Office Action dated Apr. 22, 2011 for U.S. Appl. No. 12/522,657.

*Primary Examiner* — Patricia Morris
(74) *Attorney, Agent, or Firm* — LeClairRyan, a Professional Corporation

(57) ABSTRACT

5-pyridinone substituted indazoles of the formula

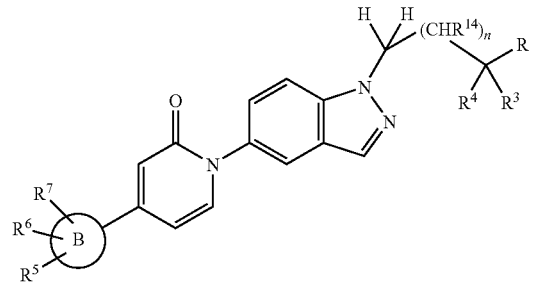

and methods of their use are presented.

22 Claims, No Drawings

5-PYRIDINONE SUBSTITUTED INDAZOLES

CROSS-REFERENCE TO RELATED APPLICATIONS

This application claims priority from U.S. Provisional Application Ser. No. 60/951,201, filed Jul. 21, 2007, the entire contents of which are incorporated herein by reference.

FIELD OF THE INVENTION

The invention relates to human melanin-concentrating hormone ($MCH_1$) receptor-selective antagonist 5-pyridinone substituted indazoles that are useful for treating obesity, to pharmaceutical compositions comprising these compounds, and to methods for the treatment of obesity, anxiety, depression, and psychiatric disorders in a mammal.

BACKGROUND OF THE INVENTION

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, A. Chronic infusion of MCH causes obesity in mice Am. J. Physiol. Endocrinol. Metab. 284, E583, 2002). Mice lacking MCH are hypophagic and lean with increased metabolic rate, whereas animals over-expressing MCH gain excess weight on both standard and high fat diets. MCH is thought to have effects on other nervous system functions as well (Rocksz, L. L. Biological Examination of Melanin Concentrating Hormone 1: Multi-tasking from the hypothalamus Drug News Perspect 19(5), 273, 2006). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, M. D. Recent advances in the discovery of melanin-concentrating hormone receptor antagonists Curr. Opin. Drug Disc. & Dev. 9(4), 496, 2006).

SUMMARY OF THE INVENTION

There is provided, in accordance with an embodiment of the invention, A compound of formula I:

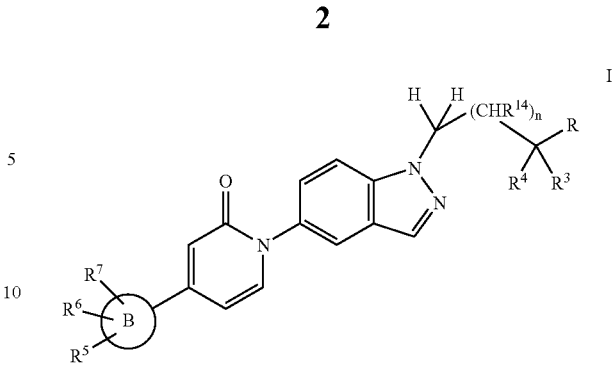

wherein
n is 0 or 1; R is $NR^1R^2$, wherein $R^1$ and $R^2$ are each independently H and optionally substituted alkyl, or $R^1$ and $R^2$, together with the N atom to which they are attached, form a 4-7 membered optionally substituted non-aromatic heterocyclic ring which optionally contains 1 or 2 heteroatoms in addition to the N atom shown; $R^3$ and $R^4$ are each independently H or alkyl; or R may combine with either $R^3$ or $R^4$ to form an optionally substituted pyrrolidin-2-yl; B is selected from ary, heteroaryl, and cycloalkyl; $R^5$, $R^6$, $R^7$ are each independently selected from H, —OH, —O-alkyl, alkyl, halo, —$CF_3$, and —CN, —O-aryl, heteroaryl, and heterocyclyl; and $R^{14}$ is H or —OH; and provided that when n is 0, $R^3$ and $R^4$ are H and R is pyrrolidin-1-yl, then (a) when B is a 5-7-membered monocyclic aromatic heterocycle, at least one heteroatom of said monocyclic aromatic heterocycle is adjacent to the position where B attaches to the pyridinone moiety, and (b) when B is phenyl which is substituted at the 2-position by methoxy or at the 3-position by methyl, there is at least one additional substituent on the phenyl ring. In some embodiments, when n is 0, $R^3$ and $R^4$ are H and R is pyrrolidin-1-yl, then when B is a bicyclic aromatic heterocycle, either (i) at least one heteroatom of said bicyclic aromatic heterocycle is adjacent to the position where B attaches to the pyridinone moiety, or (ii) the ring of said bicyclic aromatic heterocycle which attaches to the pyridinone moiety does not contain a heteroatom.

In accordance with some embodiments of the invention, R is selected from the group consisting of pyrrolidin-1-yl, 3-hydroxypyrrolidin-1-yl, morpholin-4-yl, 3-hydroxymethylpyrrolidin-1-yl, dimethylamino, piperazin-1-yl, amino, and 2-oxa-5-azabicyclo[2.2.1]heptane-5-yl. In some embodiments, R is selected from S-3-hydroxypyrrolidin-1-yl, R-3-hydroxypyrrolidin-1-yl, S-3-hydroxymethylpyrrolidin-1-yl, R-3-hydroxymethylpyrrolidin-1-yl, and (1S,4S)-2-oxa-5-azabicyclo[2.2.1]heptane-5-yl. In some embodiments, R combines with either $R^3$ or $R^4$ to form pyrrolidin-2-yl. In accordance with some embodiments of the invention, $R^3$ and $R^4$ are both H. In some embodiments, n is 0. In other embodiments, n is 1.

In some embodiments of the invention, B is phenyl. In some embodiments, B, taken together with $R^5$, $R^6$ and $R^7$, is selected from the group consisting of phenyl, 4-chlorophenyl, 4-fluorophenyl, 3-chlorophenyl, 3-phenoxyphenyl, 4-trifluoromethylphenyl, 3-trifluoromethylphenyl, 2,4-dichlorophenyl, 4-methylphenyl, 4-trifluoromethoxyphenyl, 4-cyanophenyl, 4-methoxyphenyl, 2-cyano-4-fluorophenyl, 2,4-dimethoxy-phenyl, 2,4-difluorophenyl, 4-isopropoxyphenyl, 2,4-di-trifluoromethylphenyl, 4-n-butoxy-2-methylphenyl, 2-methylphenyl, 4-benzyloxy-2-methylphenyl, 4-chloro-2-methoxyphenyl, benzodioxol-5-yl, 4-methoxy-2-methylphenyl, 2-chloro-4-trifluoromethylphenyl, and 4-chloro-2-fluorophenyl, 4-trifluoromethyl-2-fluorophenyl, 4-methoxy-2- fluorophenyl, 4-methoxy-2-chlorophenyl, 4-ethoxyphenyl, 4-trifluoromethoxy-2-fluorophenyl, and 4-trifluoromethoxy-2-methylphenyl, 4-(piperidine-2-yl)phenyl, and 4-(1H-pyrazol-1-yl)phenyl. In other embodiments of the invention, B, taken together with $R^5$, $R^6$ and $R^7$, is selected from napthalen-1-yl and naphthalen-2-yl. In some embodiments of the invention, B, taken together with $R^5$, $R^6$ and $R^7$, is benzothiophene or benzofuran. In some embodiments, B, taken together with $R^5$, $R^6$ and $R^7$, is selected from benzothio-phene-2-yl and benzofuran-2-yl. In some embodiments of the invention, B is indole. In some embodiments, B is N-alkyl substituted indole. In some embodiments, B, taken together with $R^5$, $R^6$ and $R^7$, is selected from 1-methylindol-2-yl, 1-methylindol-5-yl, 5-methoxyindol-2-yl, and 1-methyl-5-methoxyindol-2-yl. In some embodiments of the invention, B is pyridine. In some embodiments, B, taken together with $R^5$, $R^6$ and $R^7$, is selected from 5-methylpyridine-2-yl, 5-chloropyridin-2-yl and 5-trifluoromethylpyridin-2-yl. In some embodiments of the invention, B, taken together with $R^5$, $R^6$ and $R^7$, is selected from quinoline, quinazoline and optionally substituted pyridazine. In some embodiments, B, taken together with $R^5$, $R^6$ and $R^7$, is selected from quinolin-2-yl, quinazolin-2-yl, 6-trifluoromethylpyridazin-3-yl. In some embodiments, B, taken together with $R^5$, $R^6$ and $R^7$, is 1-methylindazol-5-yl. In some embodiments, B, taken together with $R^5$, $R^6$ and $R^7$, is 5-methylbenzisoxazol-2-yl. In some embodiments, B, taken together with $R^5$, $R^6$ and $R^7$, is 4-methylcyclohex-1-enyl. In some embodiments, B, taken together with $R^5$, $R^6$ and $R^7$, is 4-methylcyclohex-1-yl.

In some embodiments of the invention, the compound is selected from one of the following:

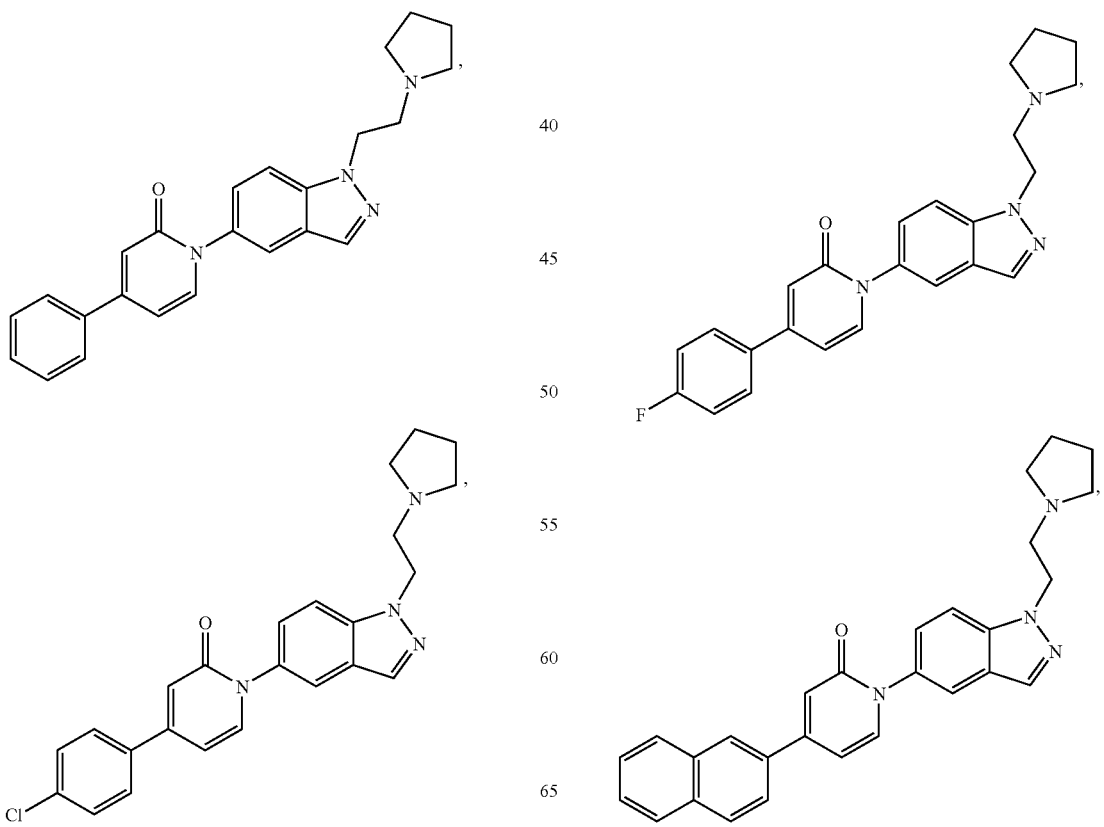

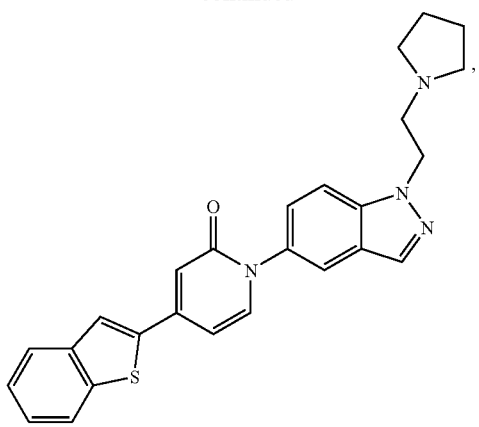

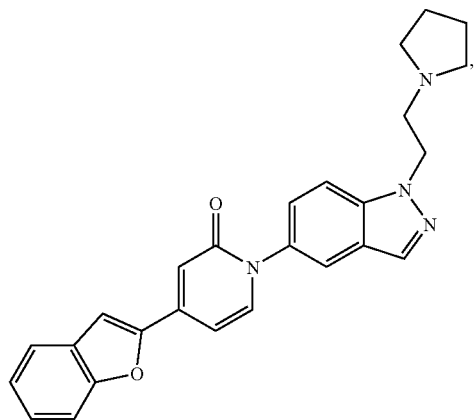

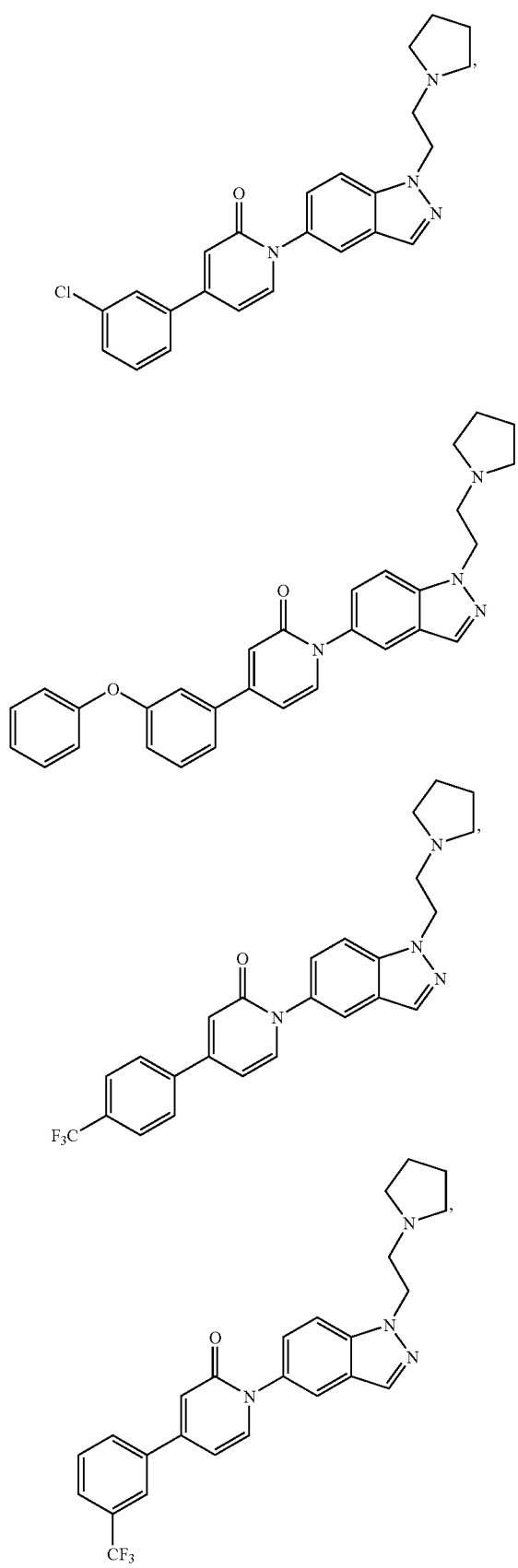
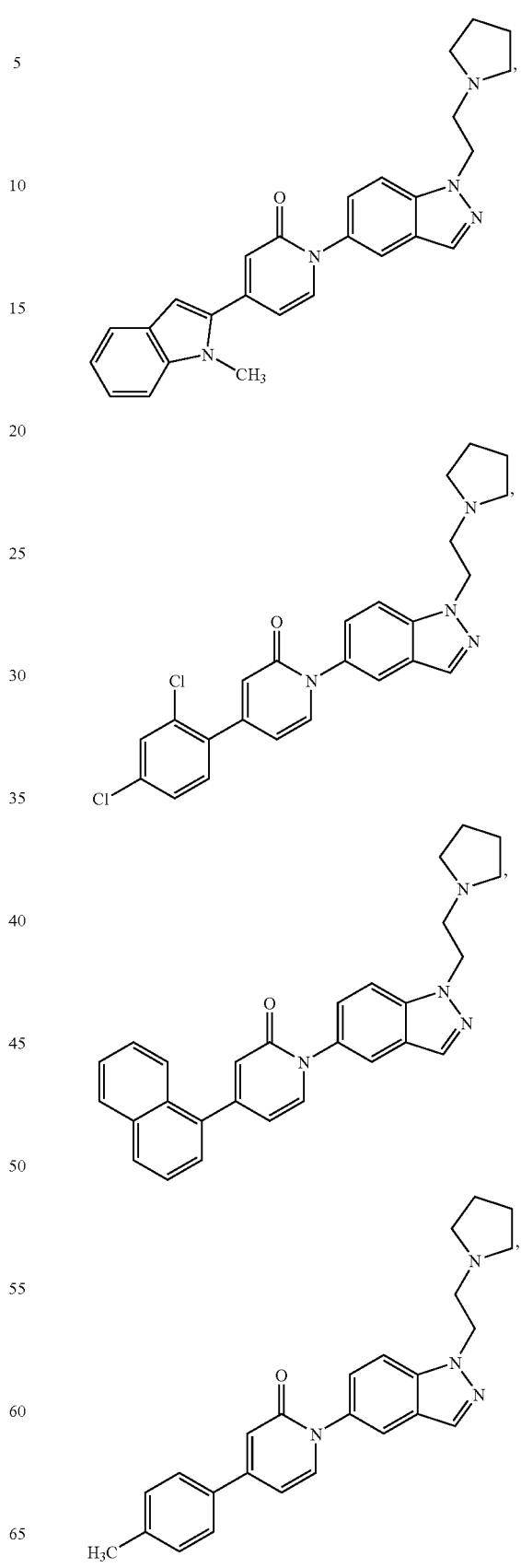

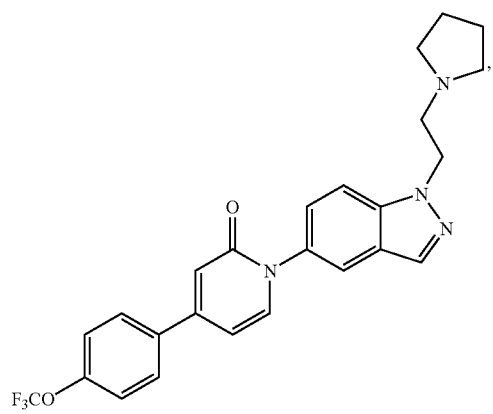
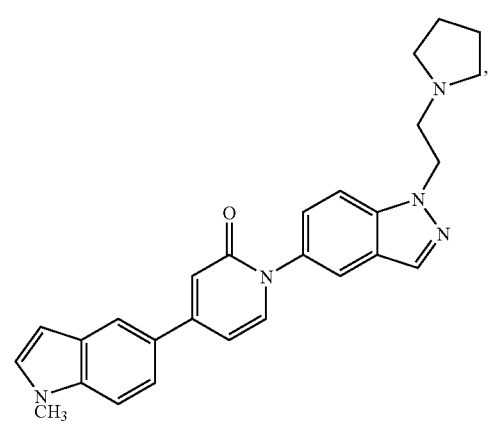
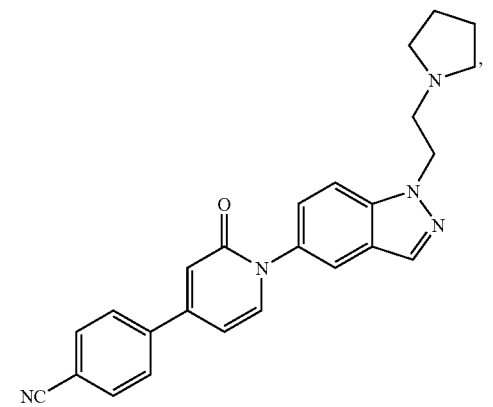
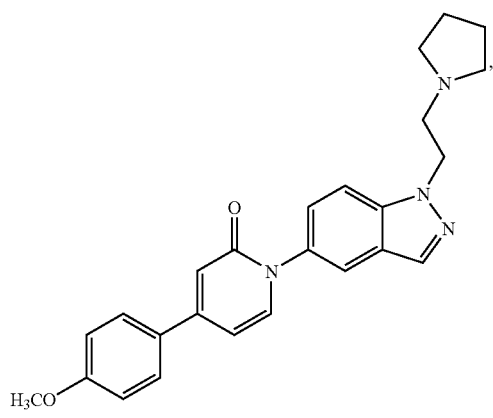
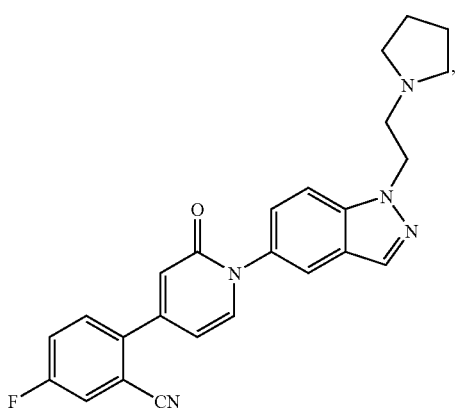
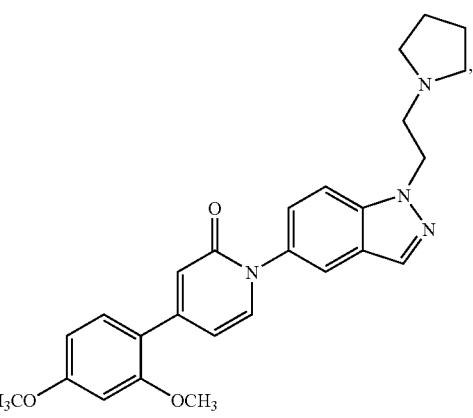
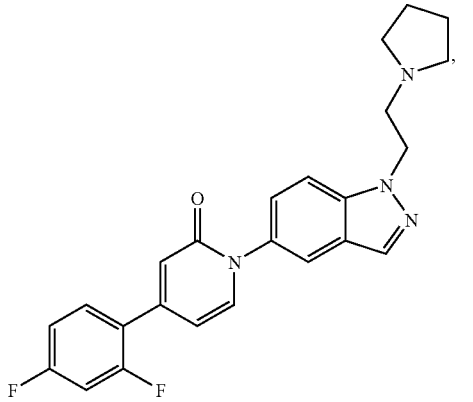
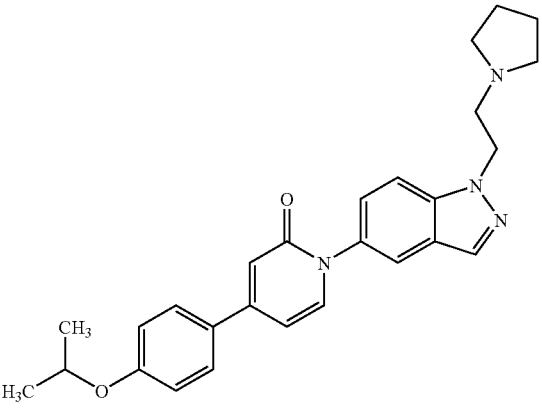

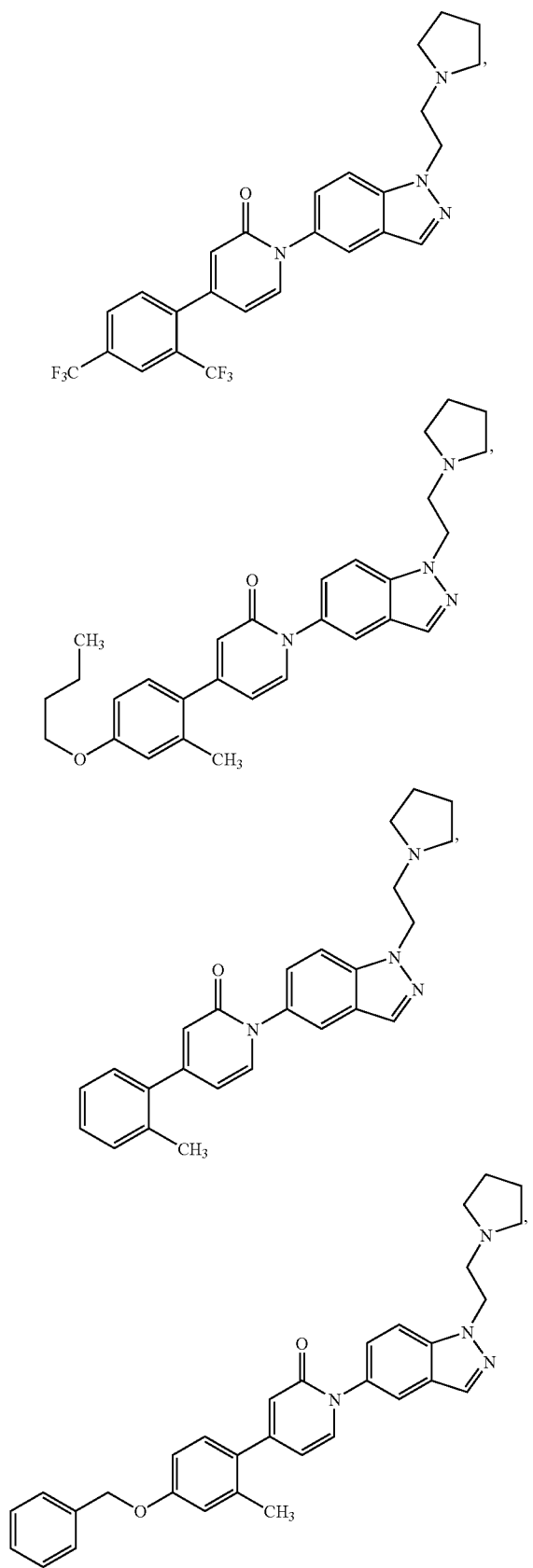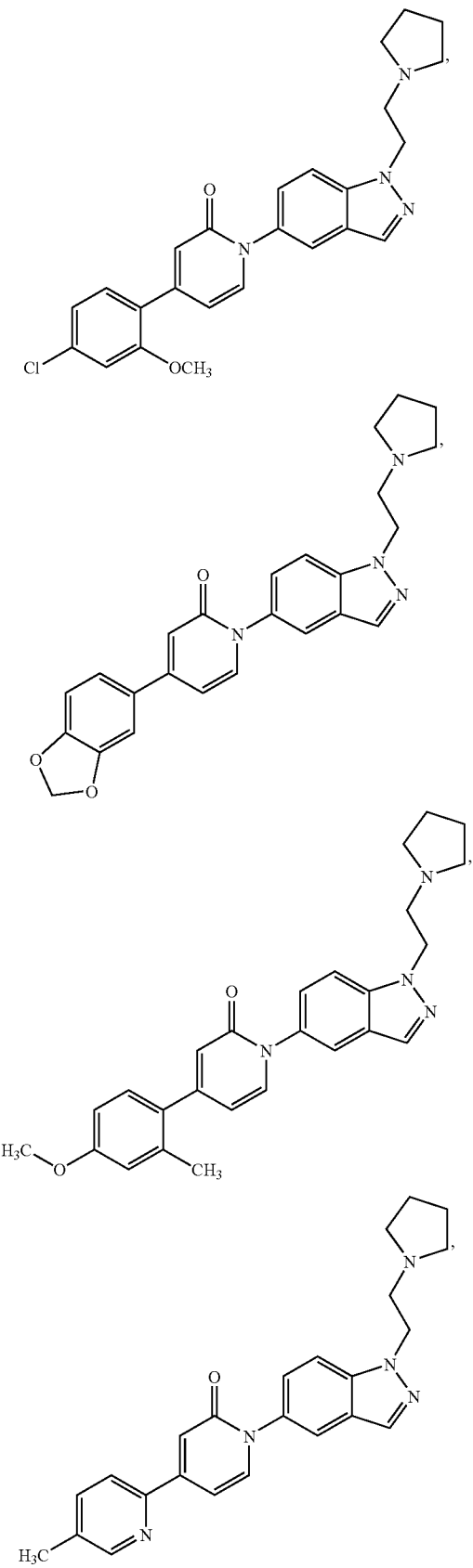

-continued
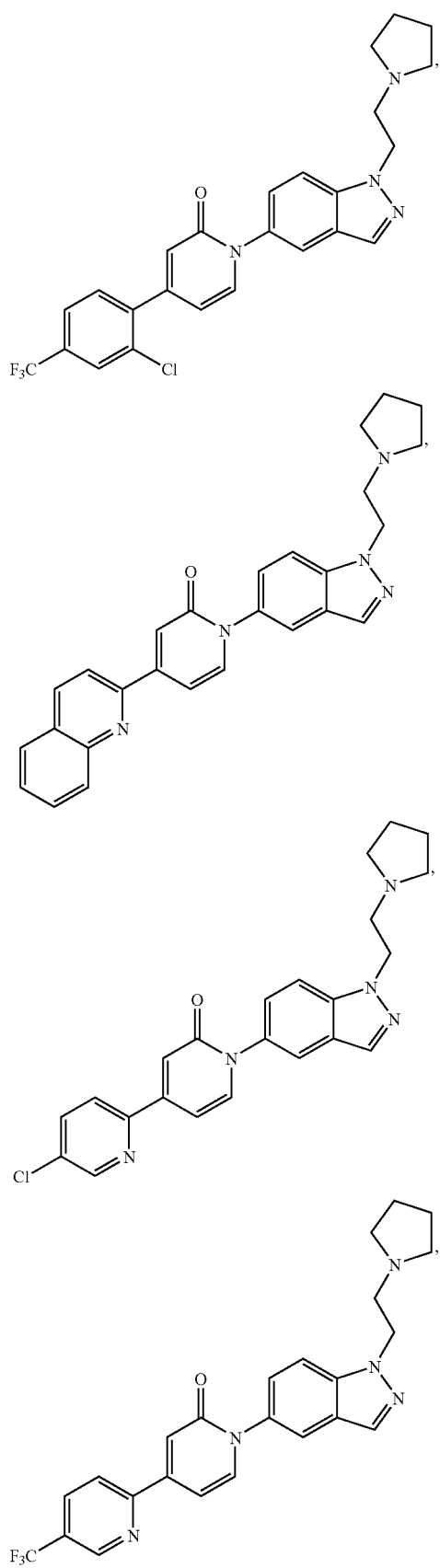
-continued
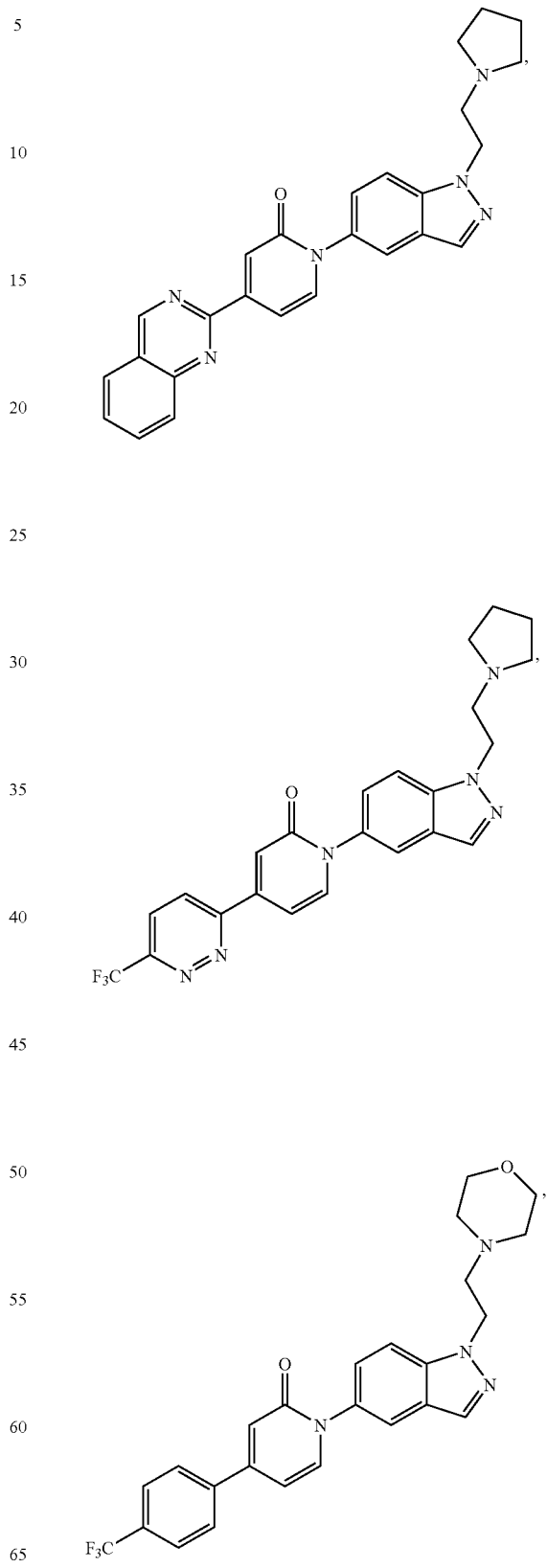

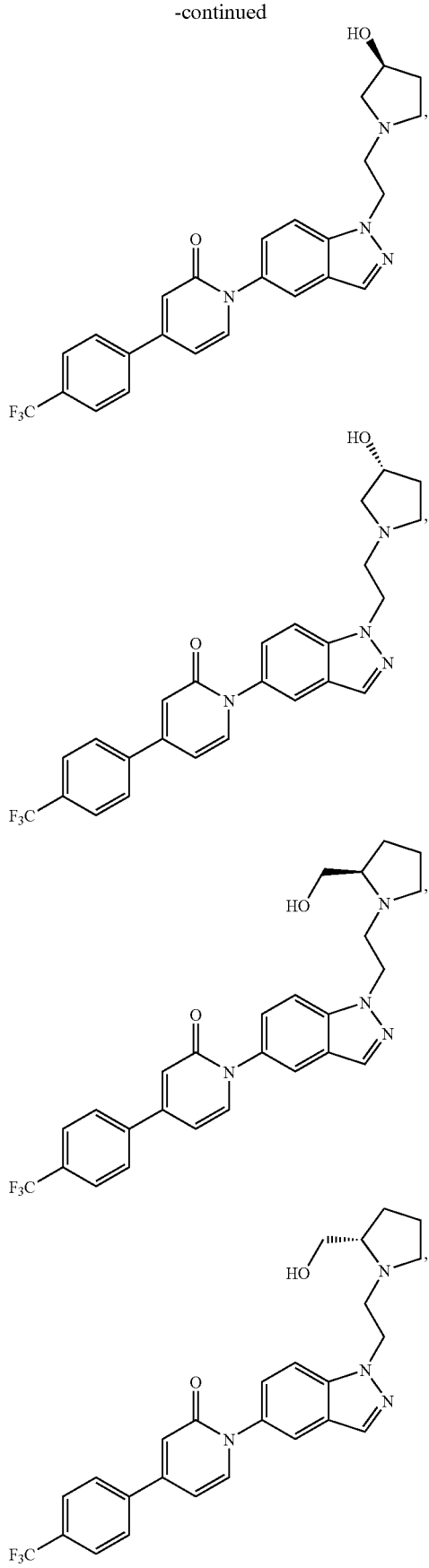
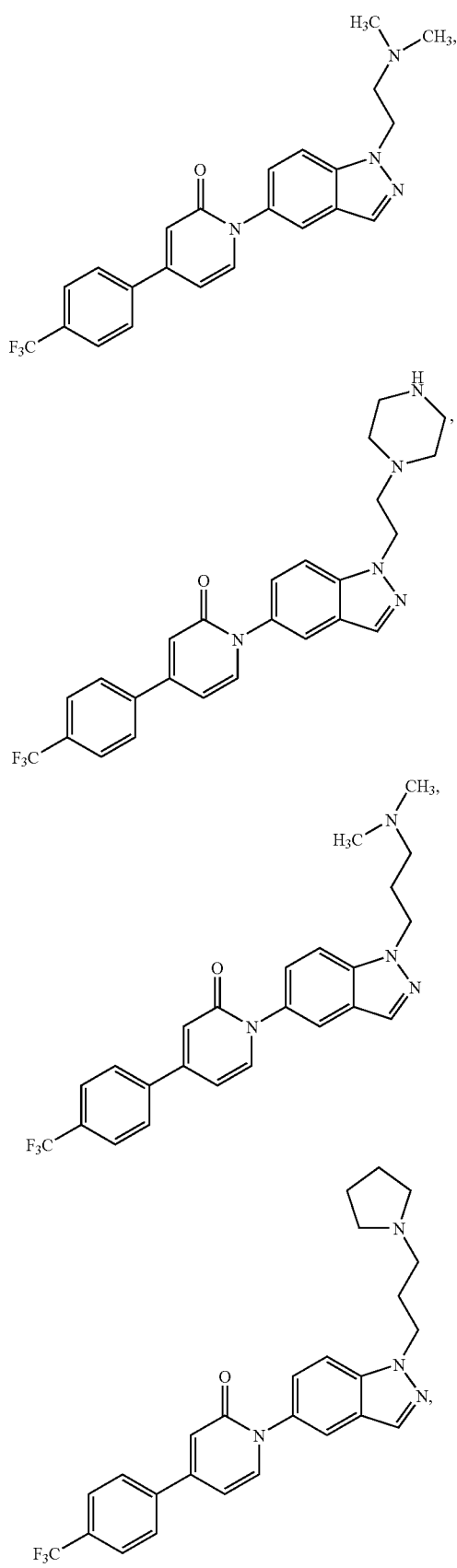

15
-continued
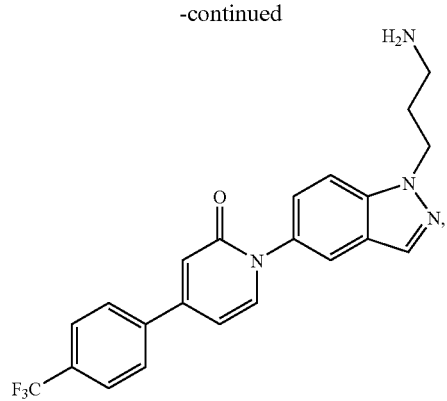
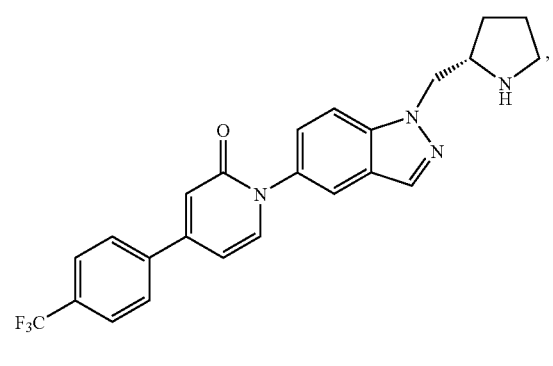
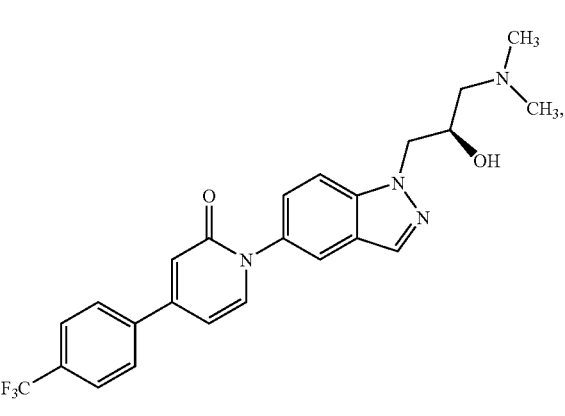
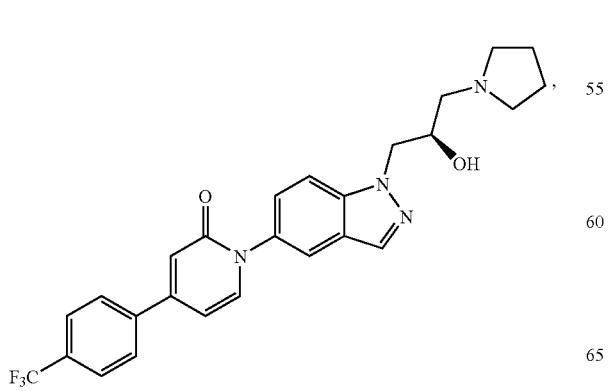
16
-continued
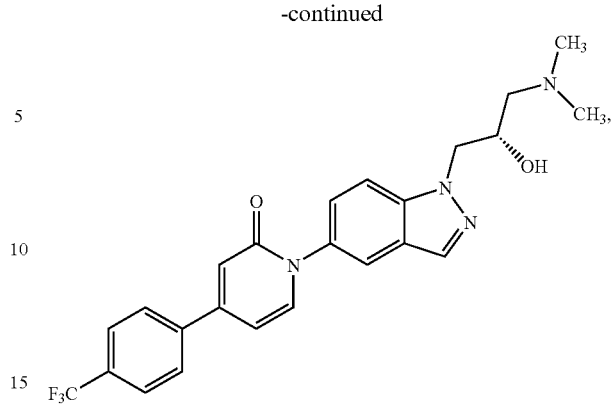
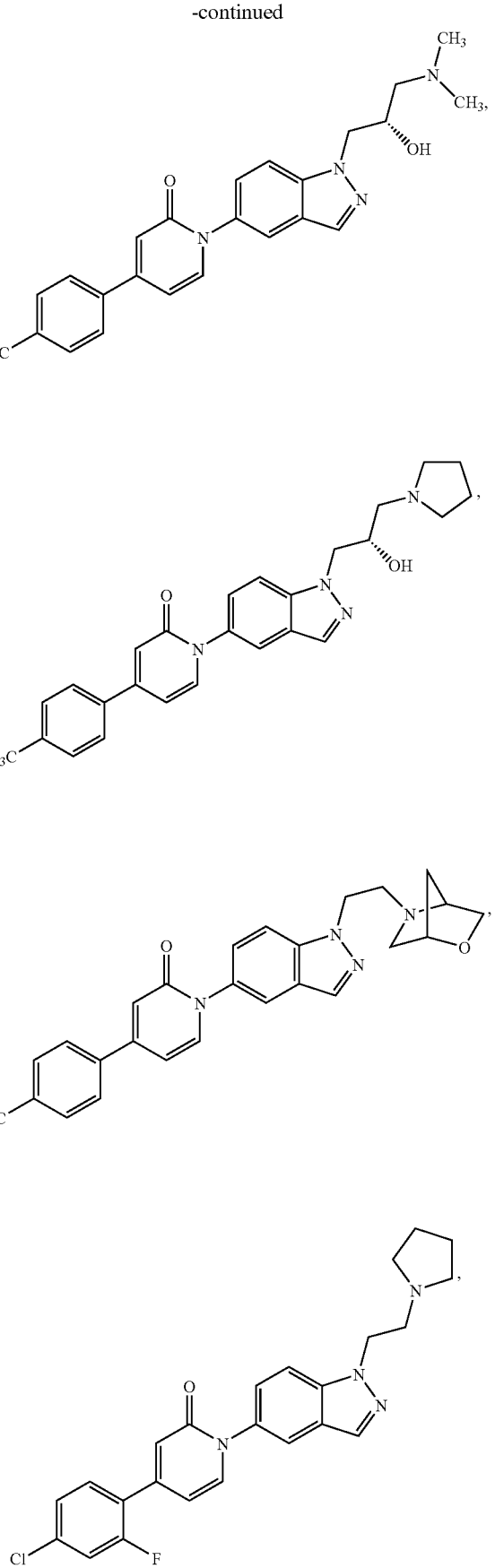

-continued
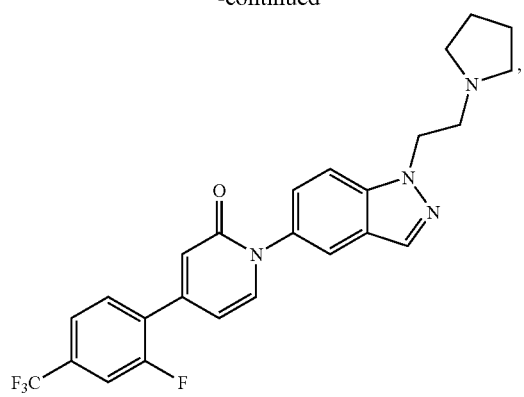
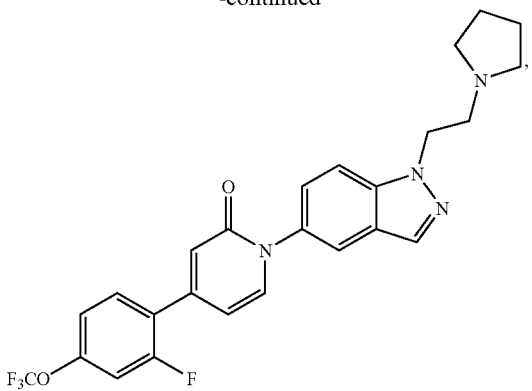

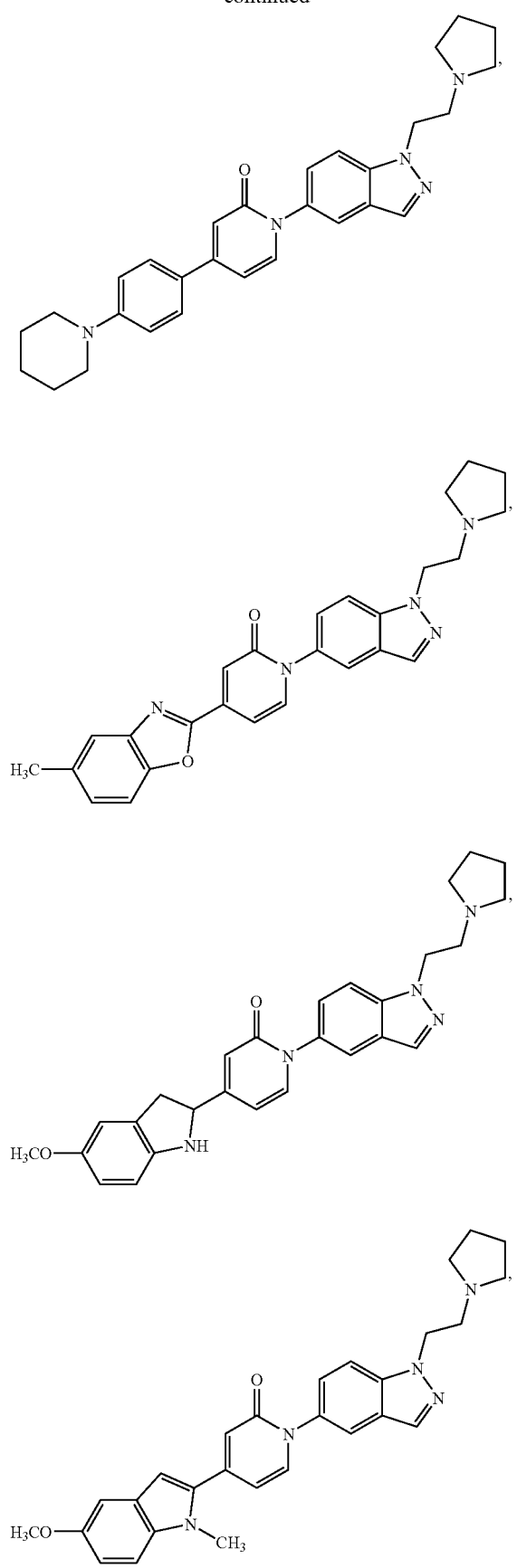
or a pharmaceutically acceptable salt form of the foregoing. In an embodiment of the invention, the pharmaceutically acceptable salt form comprises an HCl salt.
In some embodiments of the invention, the compound is selected from the group comprising:

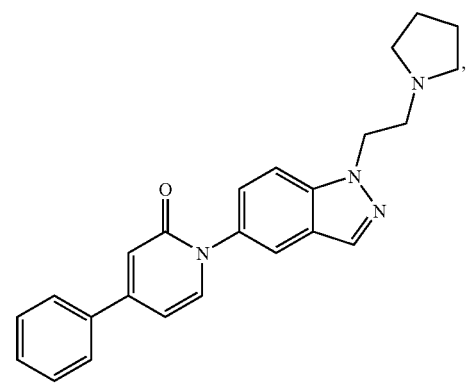
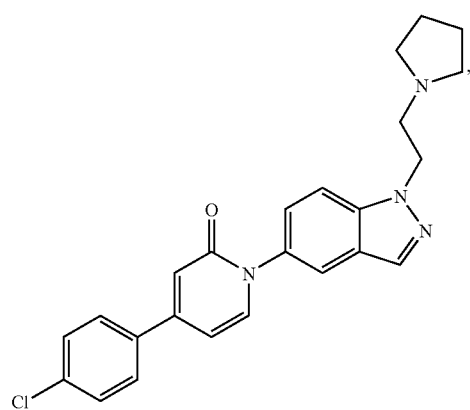
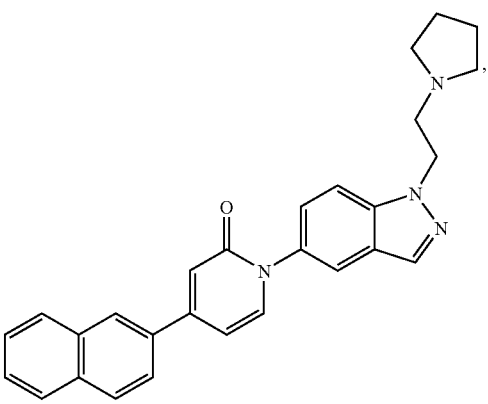
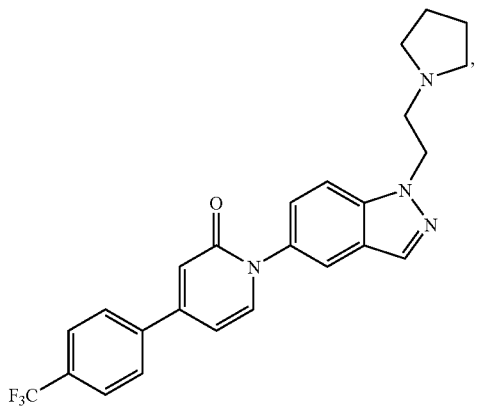
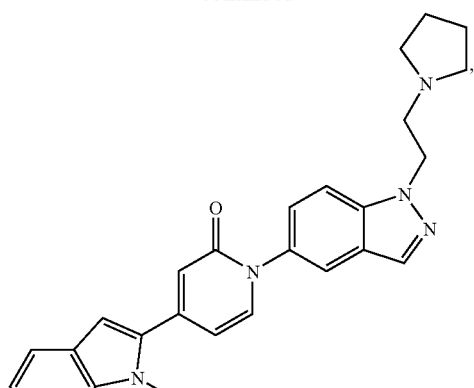
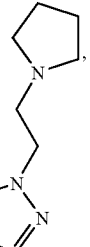
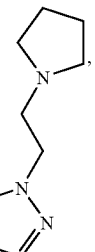

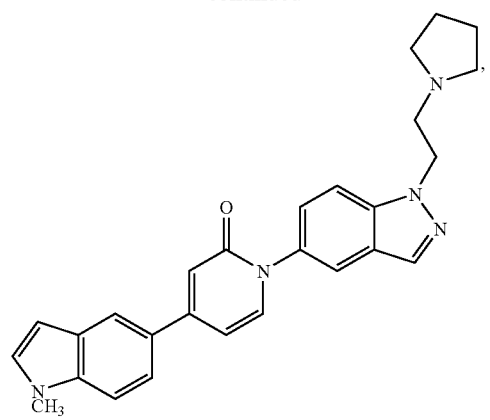
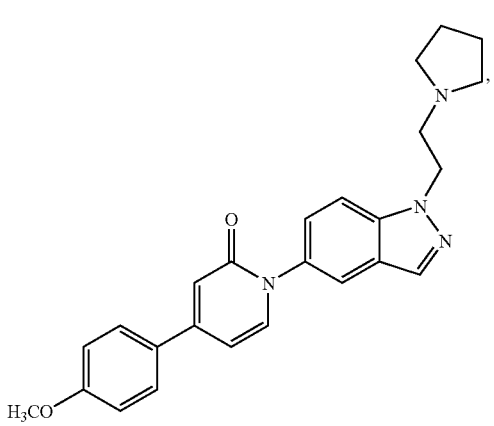
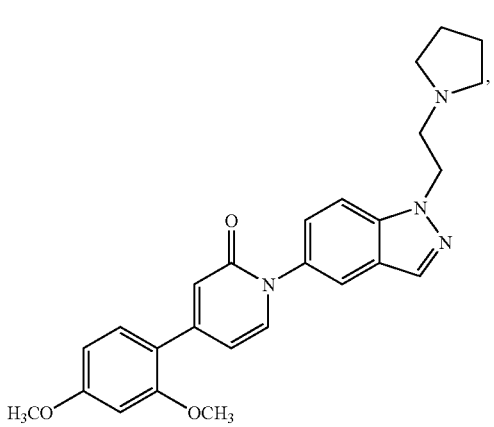
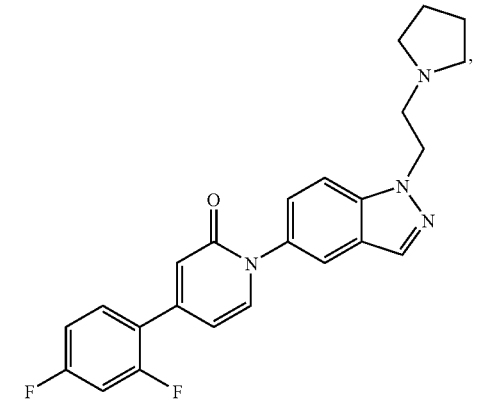
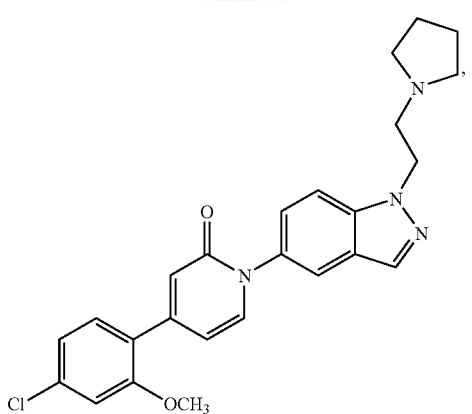
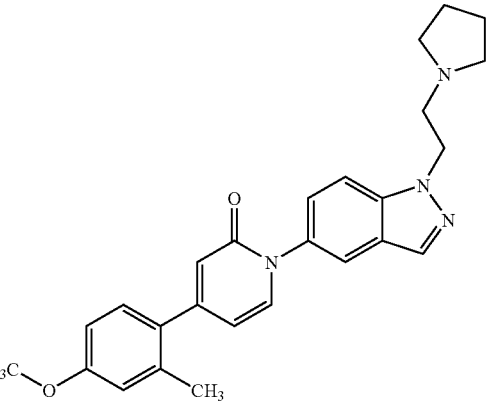
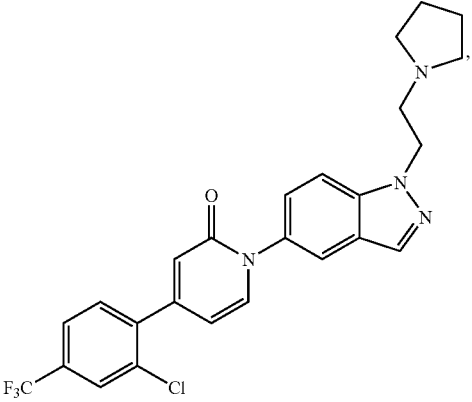
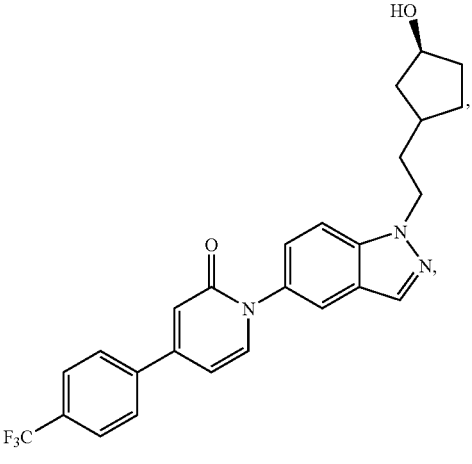

25
-continued
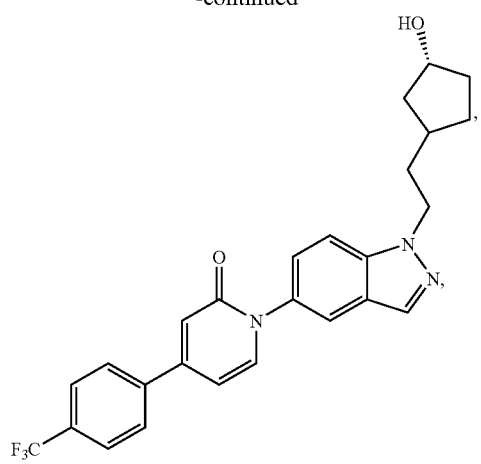
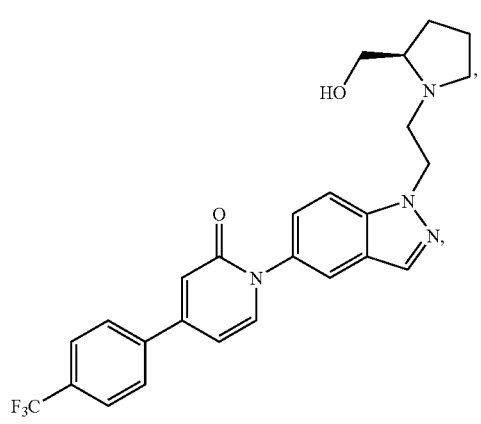
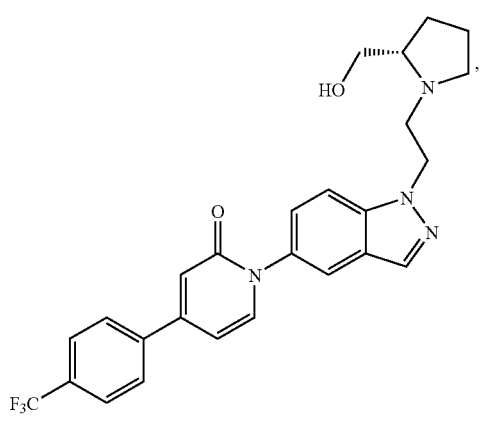
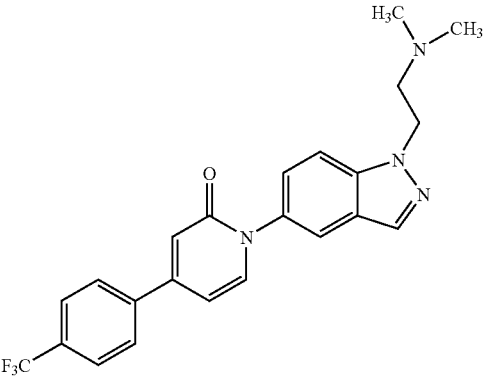
26
-continued
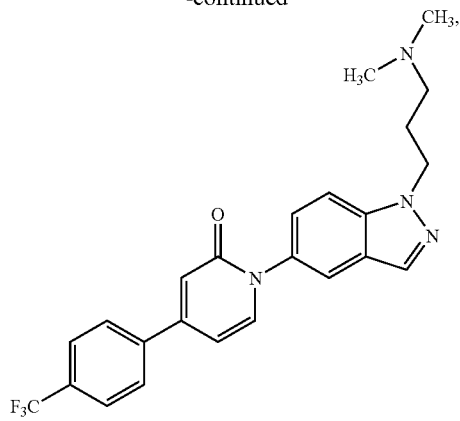
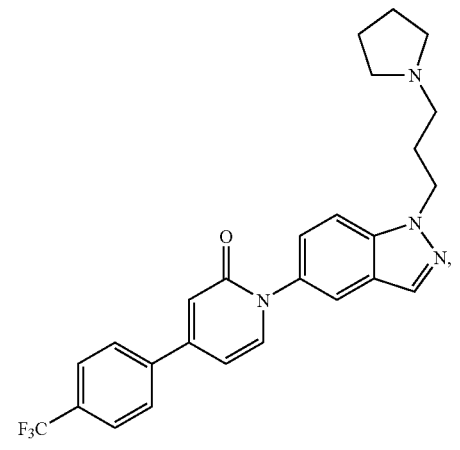
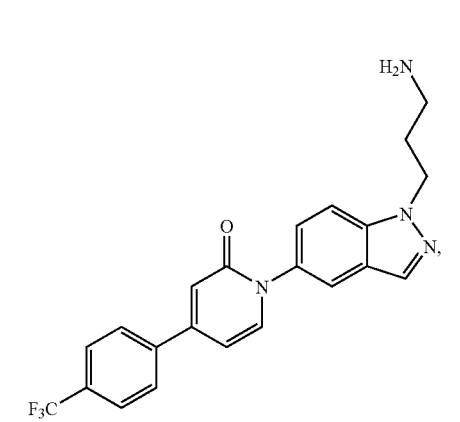
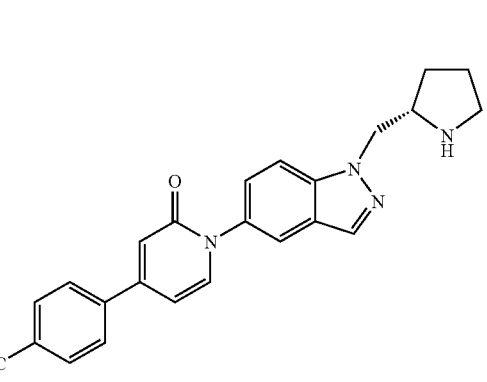

27
-continued
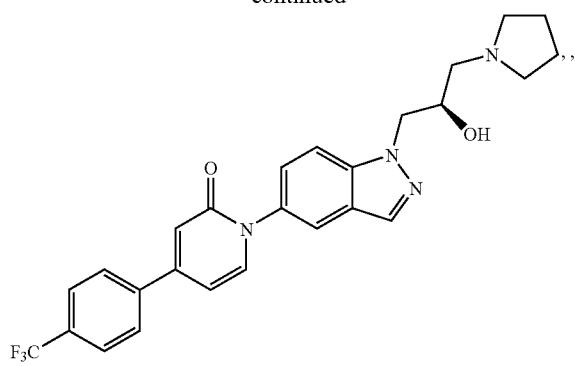
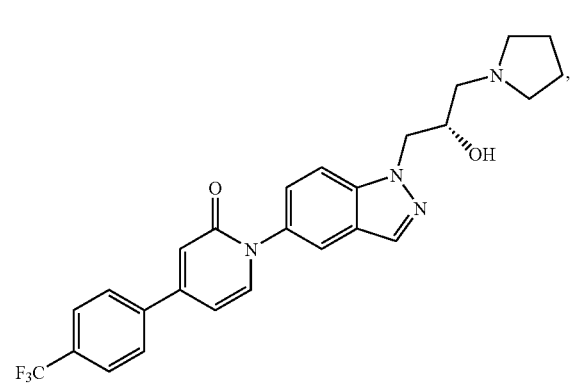
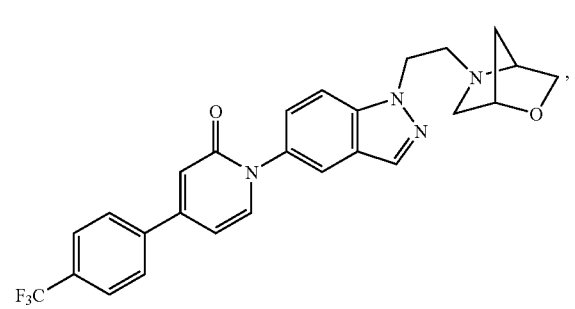
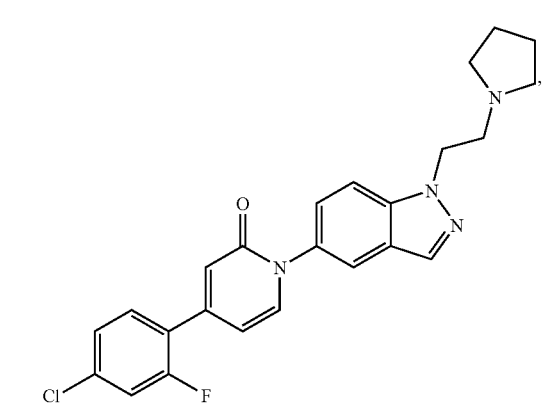
28
-continued
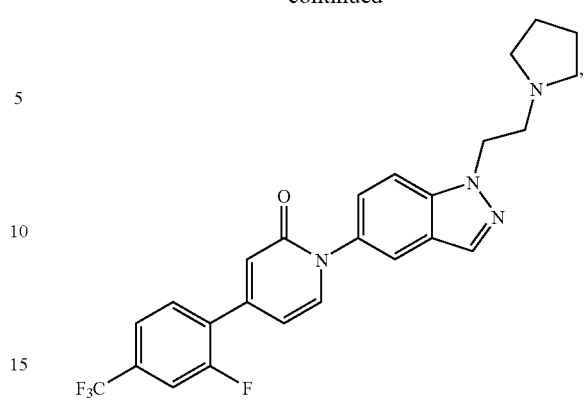
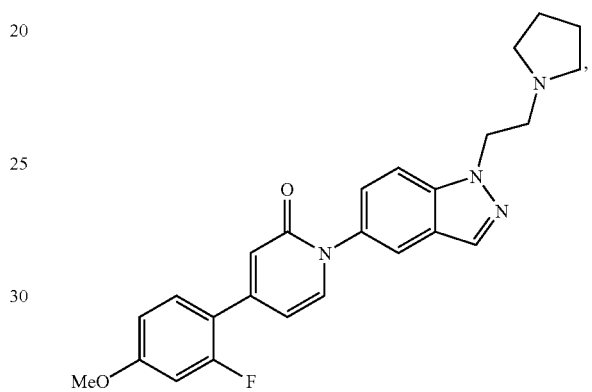
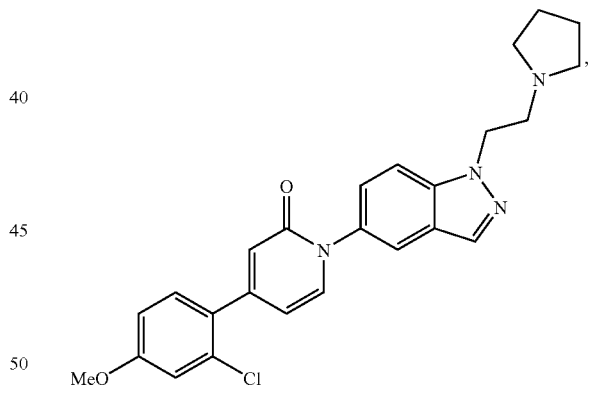
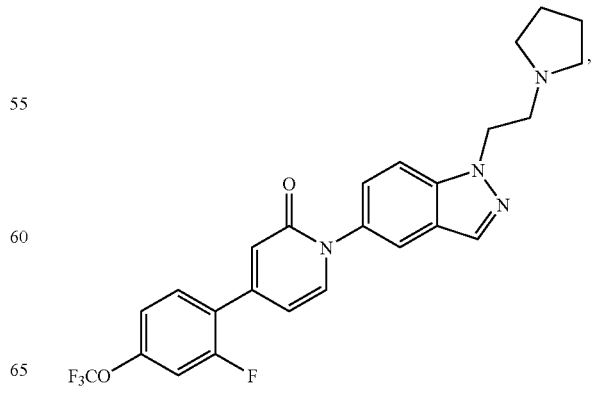

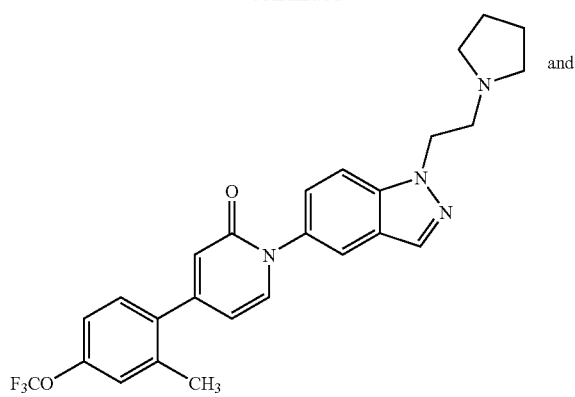
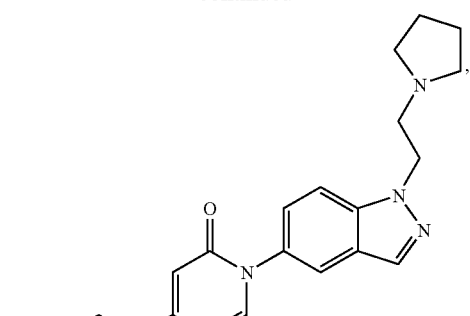
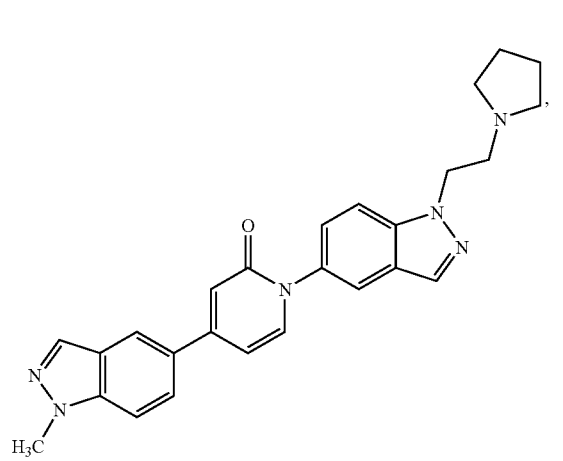
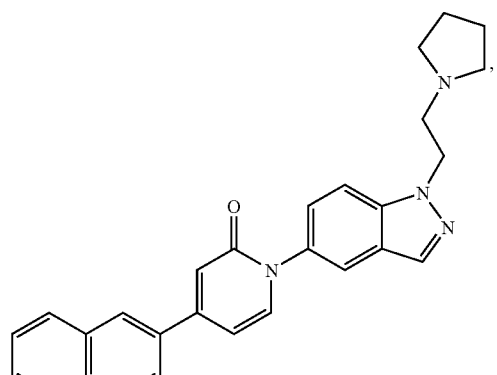
or a pharmaceutically acceptable salt form of the foregoing. In an embodiment of the invention, the pharmaceutically acceptable salt form comprises an HCl salt.
In some embodiments of the invention, the compound is selected from the group comprising:
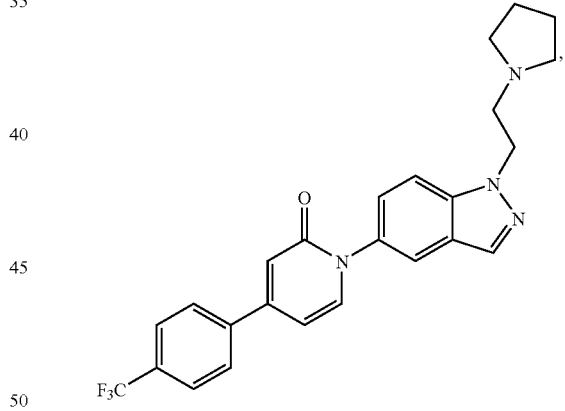
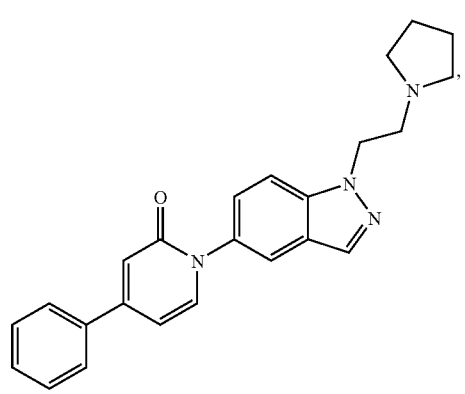
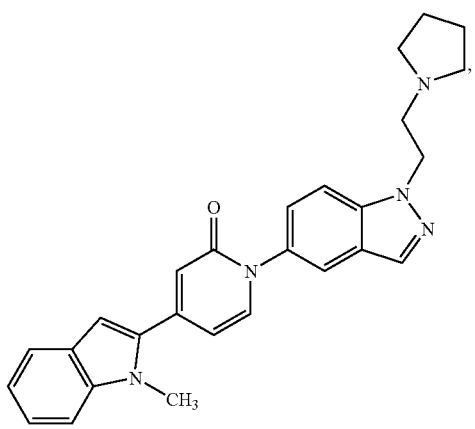

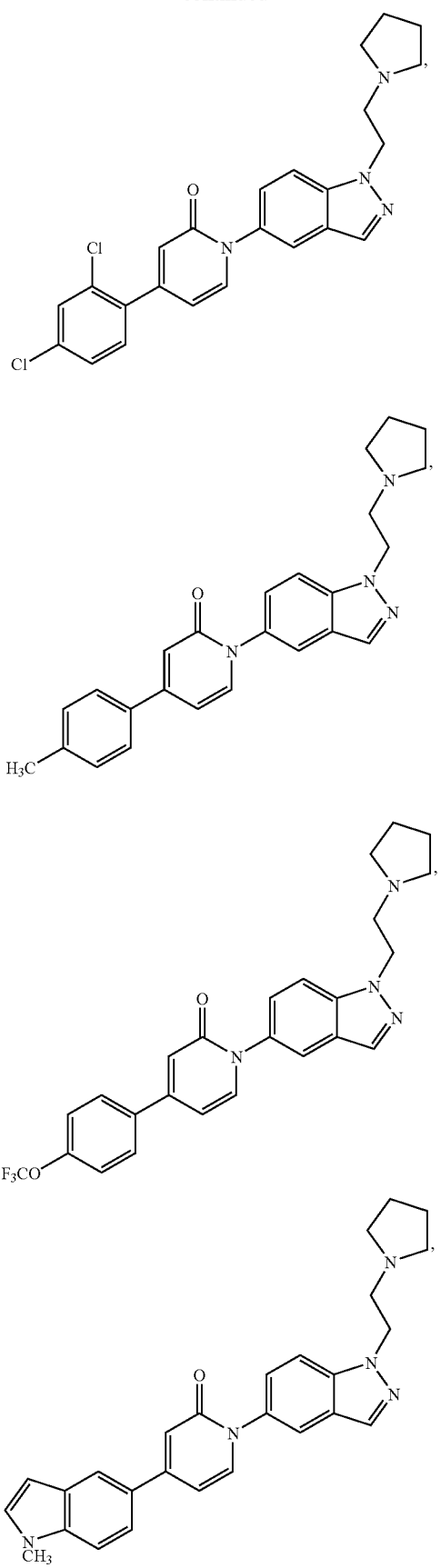
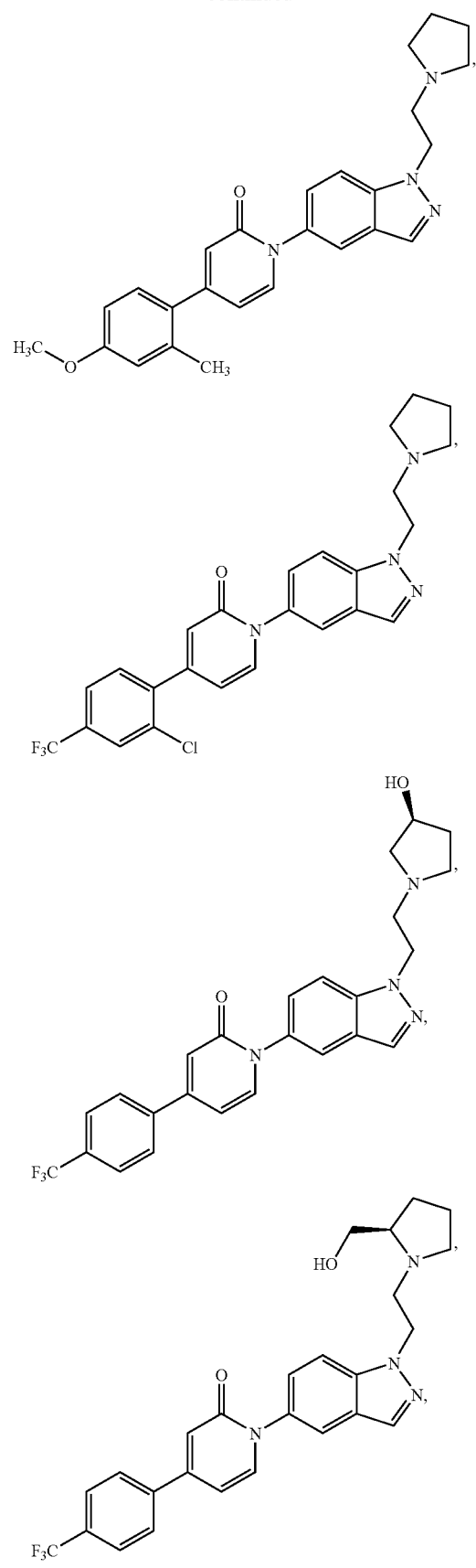

-continued
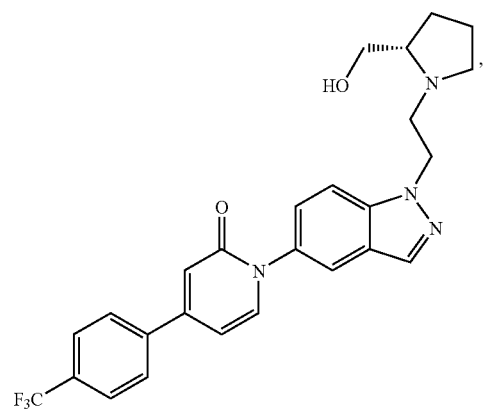
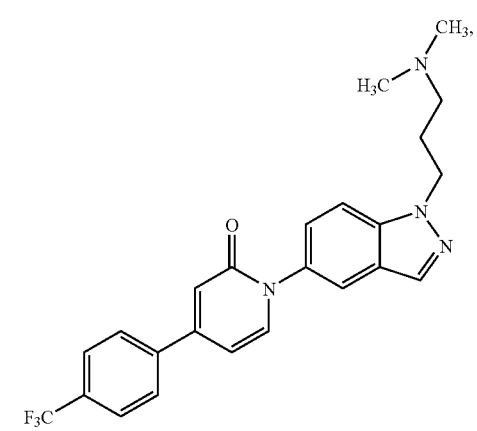
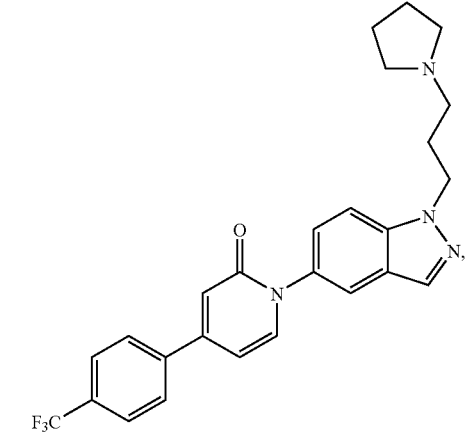
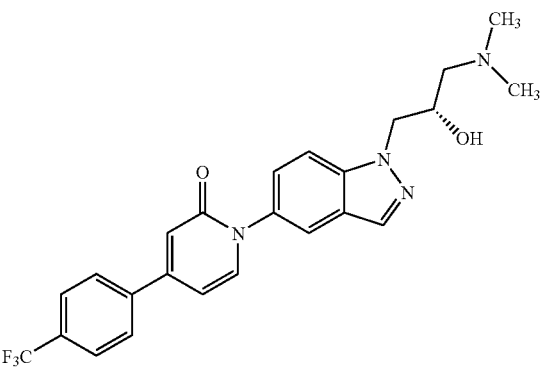
-continued
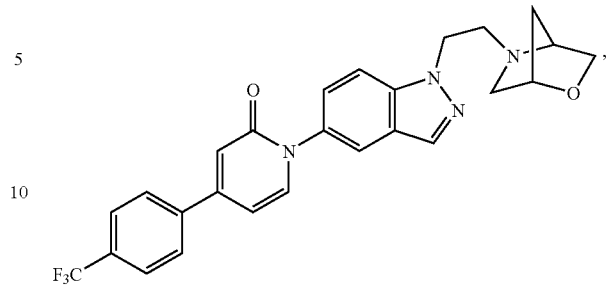
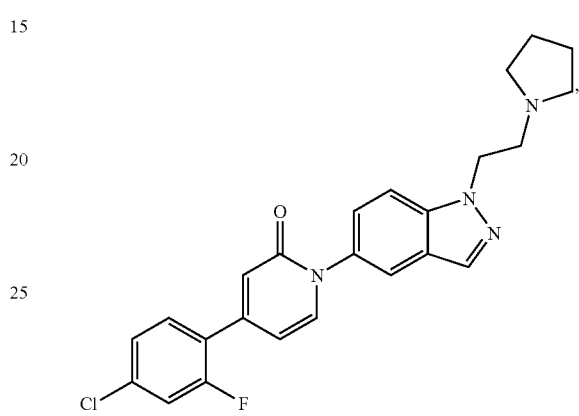
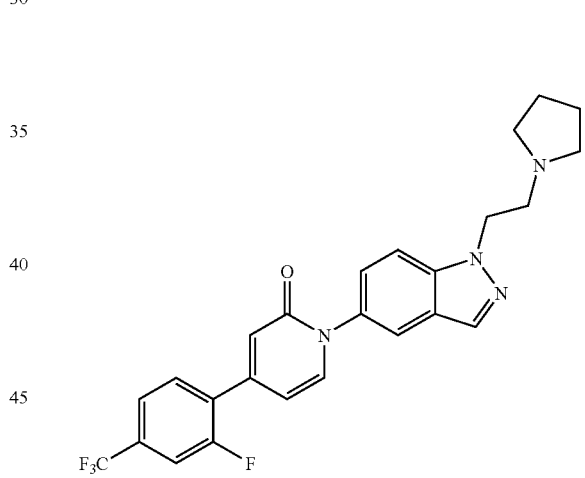
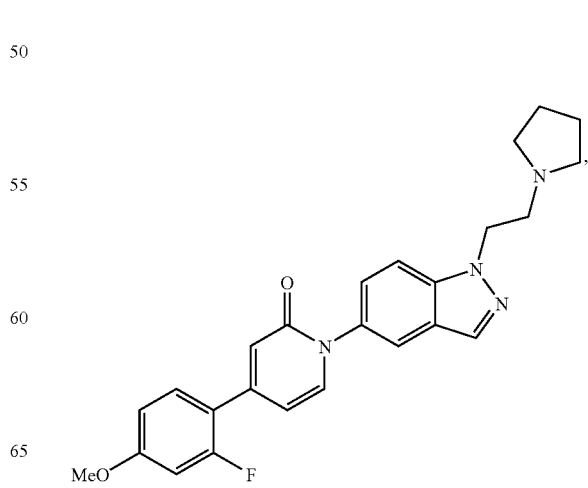

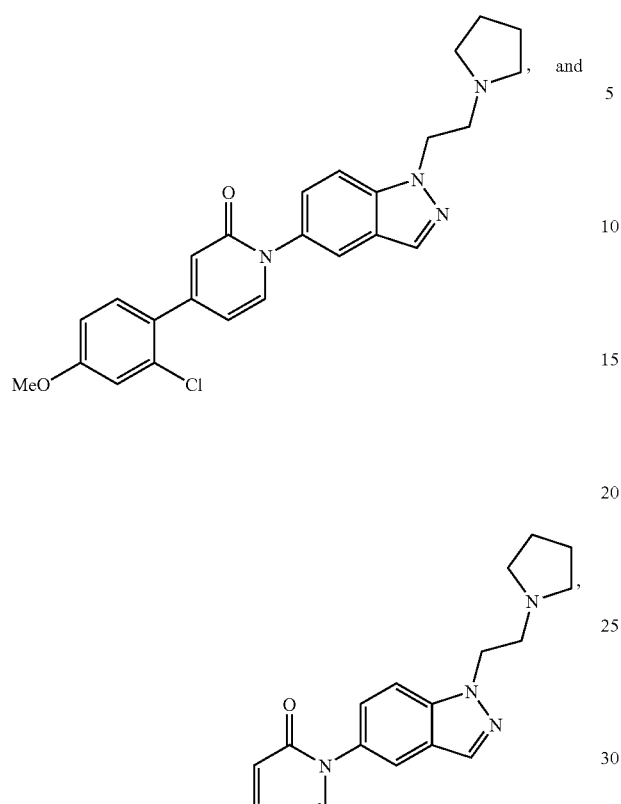
or a pharmaceutically acceptable salt form of the foregoing. In an embodiment of the invention, the pharmaceutically acceptable salt form comprises an HCl salt.
In some embodiments of the invention, the compound is selected from the group comprising:
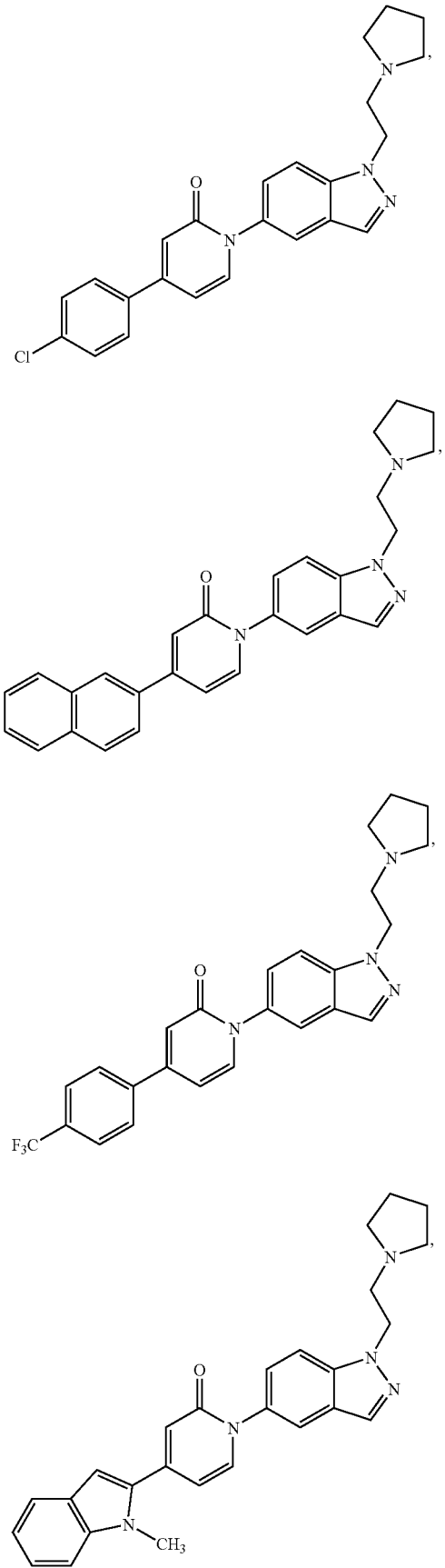

37
-continued
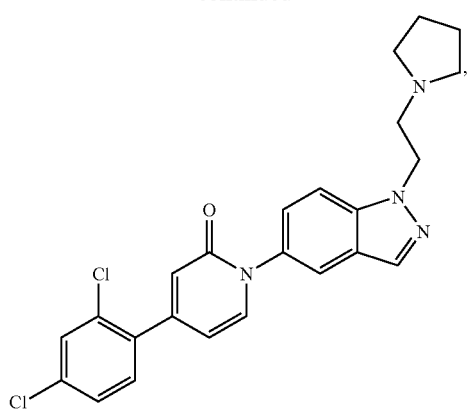
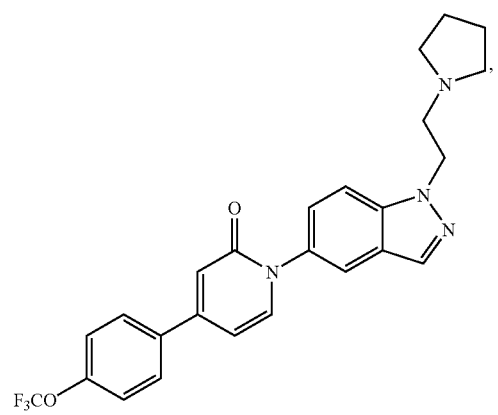
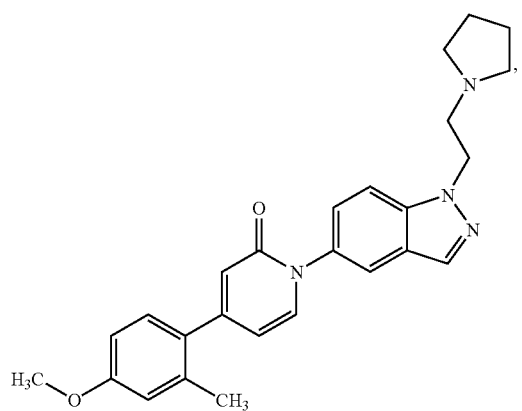
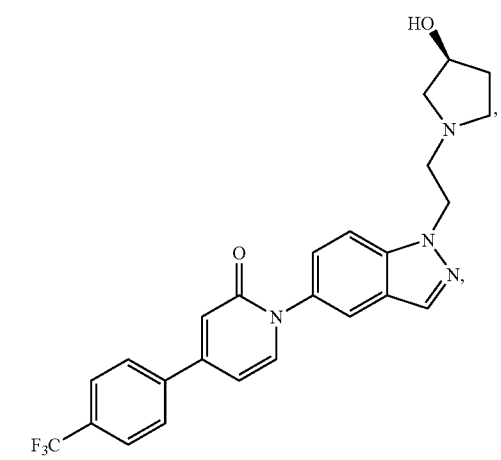
38
-continued
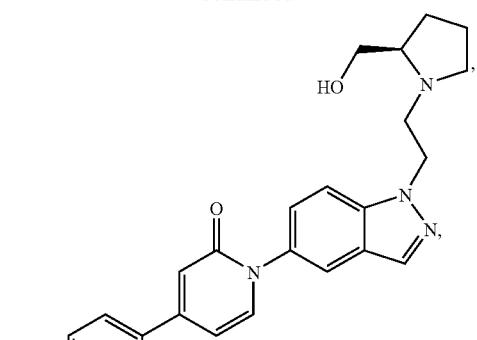
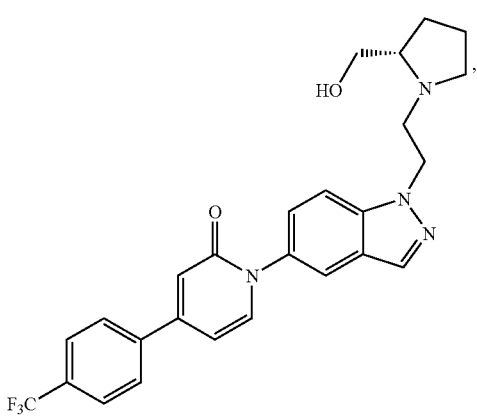
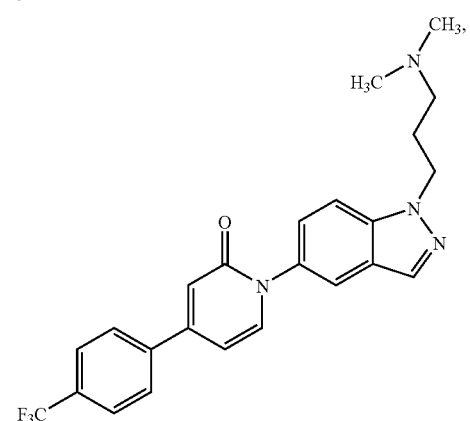
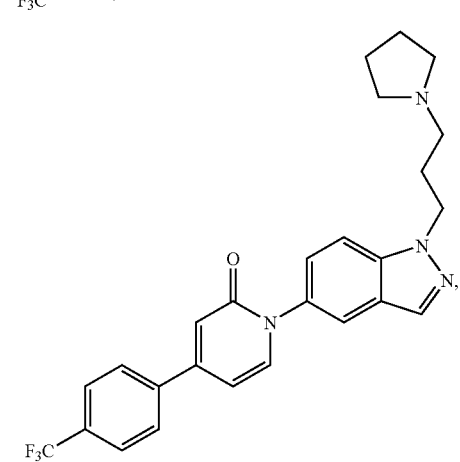

-continued
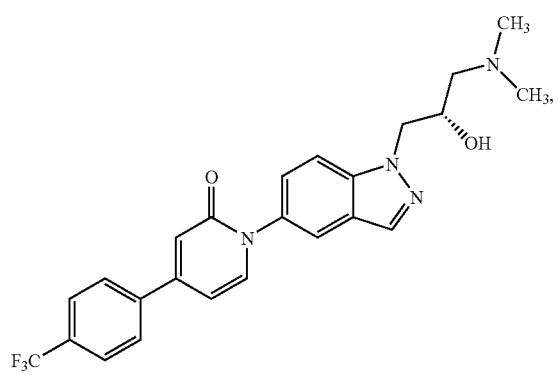
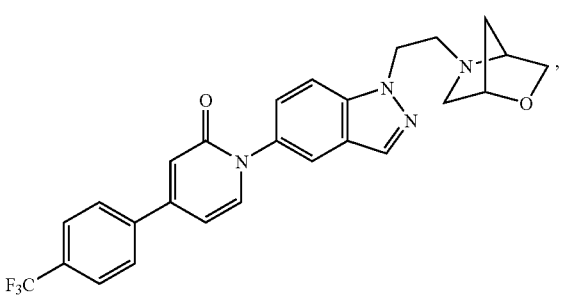
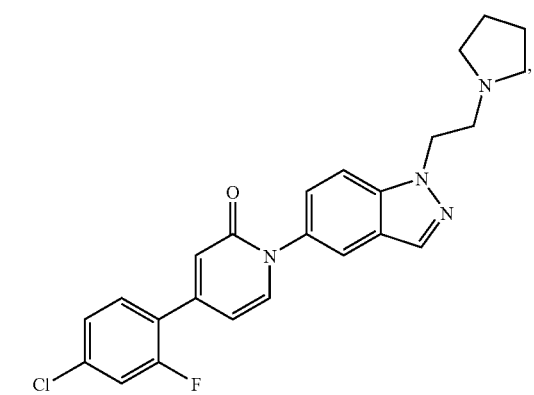
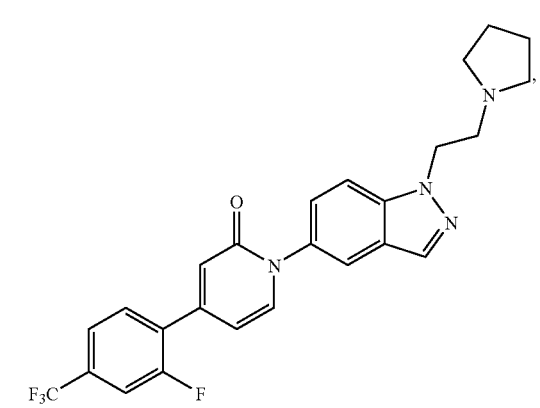
-continued
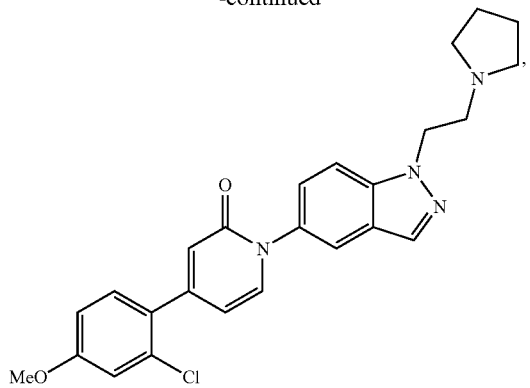
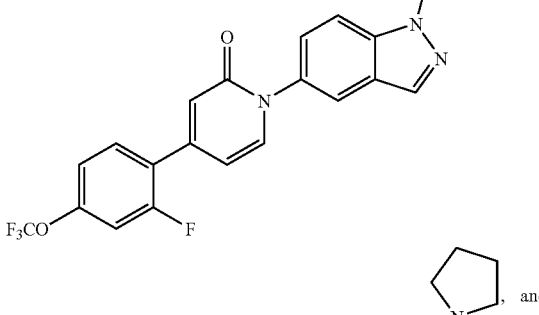
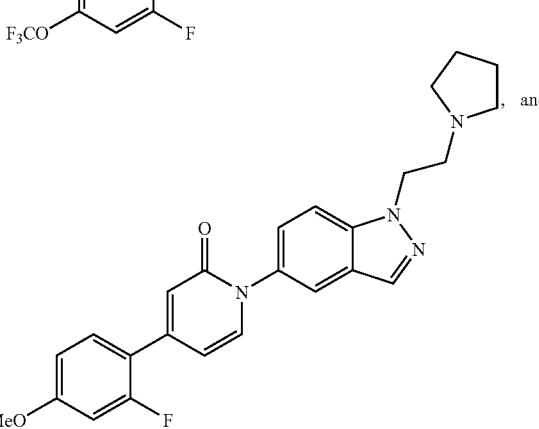
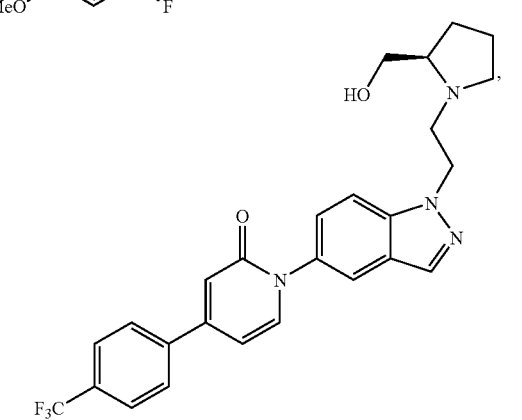
or a pharmaceutically acceptable salt form of the foregoing. In an embodiment of the invention, the pharmaceutically acceptable salt form comprises an HCl salt.
There is also provided, in accordance with embodiments of the invention, a pharmaceutical composition comprising a compound as described herein, and a pharmaceutically acceptable carrier, excipient or diluent therefore.

There is also provided, in accordance with embodiments of the invention, a method of treating obesity, comprising administering to a patient in need of obesity reduction an obesity-reducing effective amount of a compound as described herein.

There is also provided, in accordance with embodiments of the invention, a method of treating anxiety, comprising administering to a patient in need of such treatment an effective amount of a compound as described herein.

There is also provided, in accordance with embodiments of the invention, a method of treating depression, comprising administering to a patient in need of such treatment an effective amount of a compound as described herein.

There is also provided, in accordance with embodiments of the invention, a method of treating a disease or condition which is susceptible to treatment with an MCH$_1$ receptor modulator, comprising administering to a patient in need thereof a therapeutically effective amount of a compound as described herein.

DEFINITIONS

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like. Other examples of cycloalkyl groups include c-propenyl, c-butenyl, c-pentenyl, and c-hexenyl.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

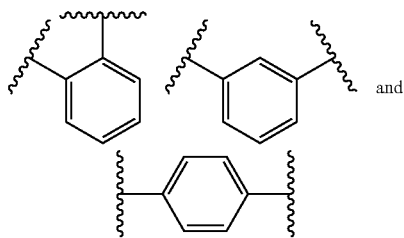 and

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

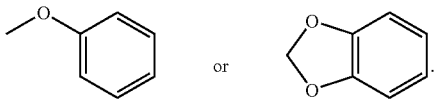

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, iodine and chlorine include $^3$H, $^{14}$C, $^{35}$S, $^{18}$F, $^{32}$P, $^{33}$P, $^{125}$I, and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Throughout this application, various references are referred to. Each of the patents, patent applications, patent publications, and references mentioned herein is hereby incorporated by reference in its entirety.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound" is intended to include salts, solvates and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. In accordance with some embodiments of the invention, the salt is a hydrochloride salt.

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

While it may be possible for compounds of formula I to be administered as the raw chemical, it will often be preferable to present them as part of a pharmaceutical composition. In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, $20^{th}$ Edition, 2000.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasally using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

Table 1 lists compounds representative of embodiments of the invention.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining compounds of formula I are presented below. Other compounds of formula I may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

Scheme 1

Compounds of formula 2 (wherein $Z^1$ is chlorine, bromine or iodine) can be prepared by treating compounds of formula 1 with $NaNO_2$ in acetic acid at room temperature.

Scheme 2

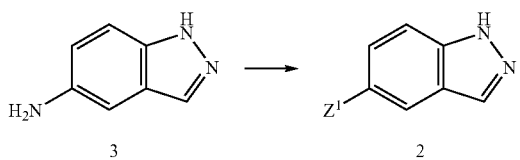

Alternatively, compounds of formula 2 can be prepared by treatment of amino indazoles 3 with NaNO$_2$ and copper halide.

Scheme 3

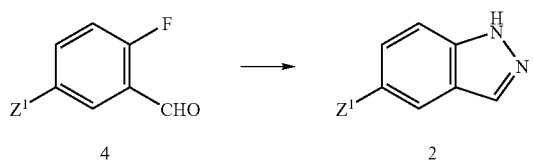

Alternatively, compounds of formula 2 can be prepared by treatment of aldehydes 4 with hydrazine under heated conditions.

Scheme 4

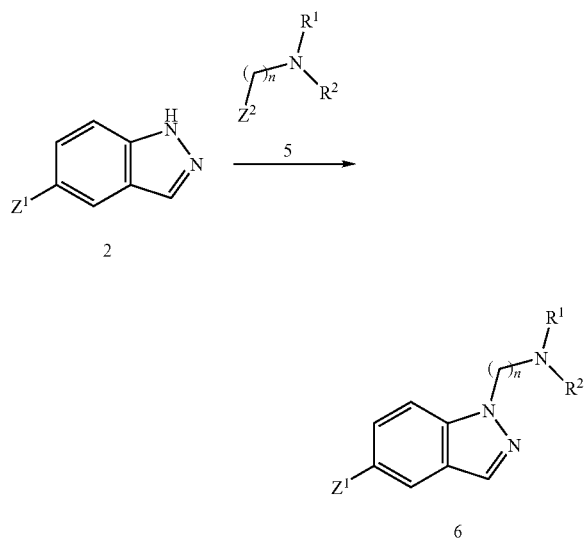

Compounds of formula 2 can be treated with base and compounds of formula 5 (wherein $Z^2$=halogen, methanesulfonate, toluenesulfonate or the like; n=2 or 3) under ambient temperature or heated conditions to give compounds of formula 6. Typical bases include but are not limited to cesium carbonate, potassium carbonate and sodium hydride. Typical solvents include but are not limited to N,N-dimethylformamide (DMF), dimethylsulfoxide (DMSO), acetonitrile and tetrahydrofuran (THF).

Scheme 5

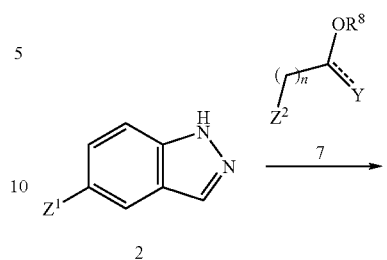

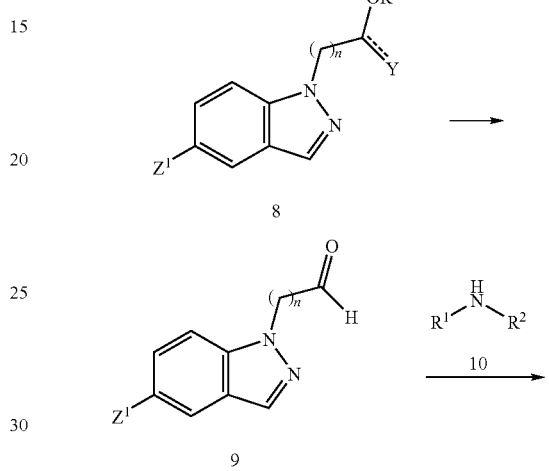

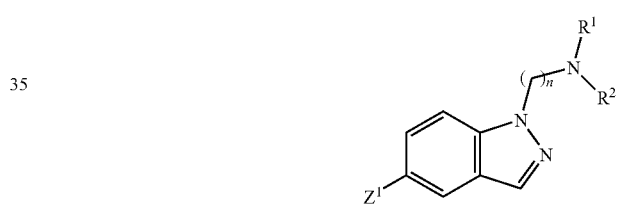

Alternatively, compounds of formula 2 can be treated with base and compounds of formula 7 (wherein $Z^2$=halogen, methanesulfonate, toluenesulfonate or the like; Y=O, OR$^9$ or H; R$^8$=an alkyl group, H or a protecting group such as tert-butyldimethylsilyl; R$^9$=alkyl; n=1 or 2) under ambient temperature or heated conditions to give compounds of formula 8. Typical bases include but are not limited to cesium carbonate, potassium carbonate and sodium hydride. Typical solvents include but are not limited to N,N-dimethylformamide, dimethylsulfoxide, acetonitrile and tetrahydrofuran. In the case where Y=OR$^9$, compounds of formula 8 can be treated under acidic reaction conditions to provide compounds of formula 9. In the case where Y=H and R$^8$=a protecting group, compounds of formula 8 can be treated under appropriate deprotecting conditions to provide compounds of formula 8 wherein R$^8$=H. In the case where Y=H and R$^8$=H, compounds of formula 8 can be treated with an oxidizing agent such as the Dess-Martin periodane or oxalyl chloride and DMSO to give compounds of formula 9. Treatment of compounds 9 with amines 10 and a reducing agent such as sodium borohydride, sodium cyanoborohydride, sodium triacetoxyborohydride, or picoline-borane complex can provide compounds of formula 11.

Scheme 6

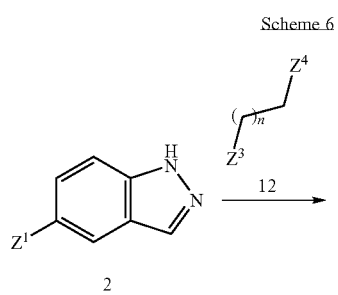

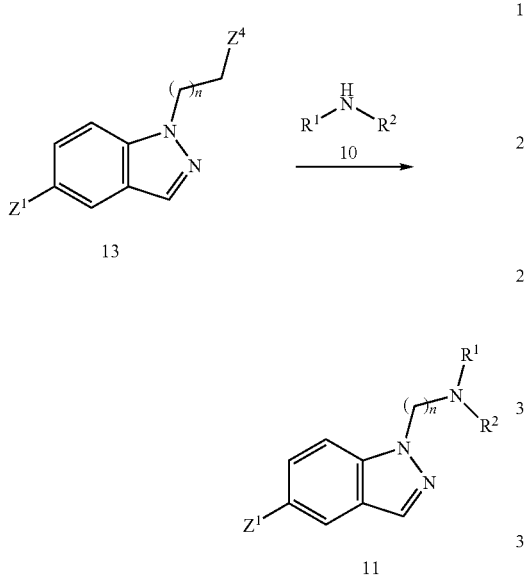

Alternatively, compound 2 can be treated with base and compounds of formula 12 (wherein n=1 or 2 and $Z^3$ and $Z^4$=halogen, methanesulfonate, toluenesulfonate or the like) under ambient temperature or heated conditions to give compounds of formula 13. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds of formula 13 with amines 10 under ambient temperature or heated conditions can provide compounds of formula 11 wherein n=2 or 3.

Scheme 7

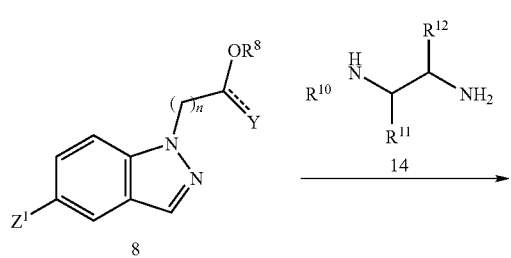

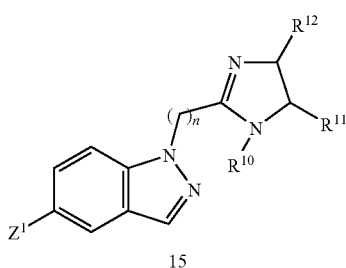

Additionally, in the case where Y=O and $R^8$=alkyl, compounds of formula 8 can be treated with diamines 14 (wherein $R^{10}$, $R^{11}$, $R^{12}$ are each independently H or alkyl) and trimethylaluminum to provide compounds of formula 15.

Scheme 8

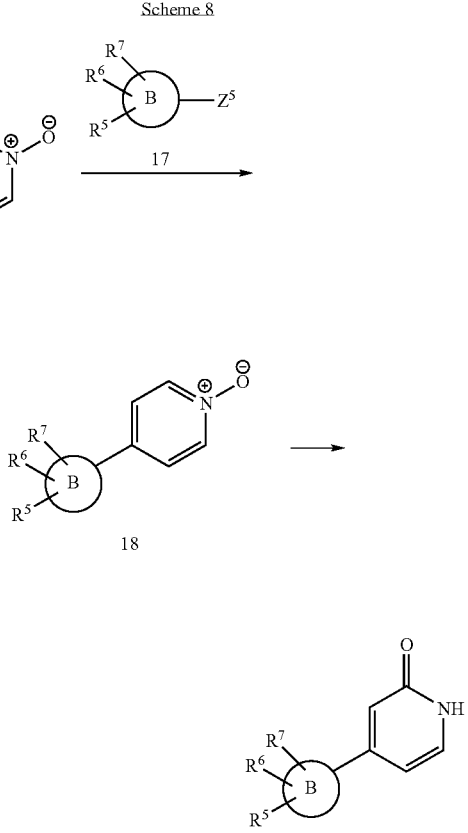

Compounds of formula 19 can be prepared by treating compounds of formula 16 (wherein $X^1$ is chlorine, bromine or iodine) with compounds of formula 17 (wherein $Z^5$=B(OH)$_2$, B(OR$^{13}$)$_2$, SnR$^{13}$$_3$ or the like and $R^{13}$=alkyl), a catalyst such as palladium(0), and a base such as potassium carbonate to give compounds of formula 18. In turn, compounds of formula 18 can be treated with acetic anhydride under heated conditions followed by methanol and water or methanol and sodium hydroxide under ambient to heated conditions to provide compounds of formula 19.

Scheme 9

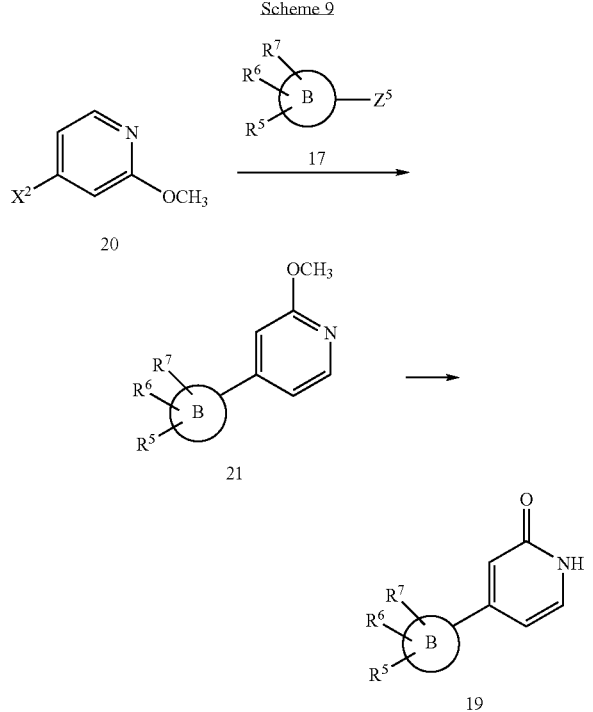

Alternatively, compounds of formula 19 can be prepared by treating compounds of formula 20 (wherein $X^2$ is chlorine, bromine or iodine) with compounds of formula 17 (wherein $Z^5$ is $B(OH)_2$, $B(OR^{13})_2$, $SnR^{13}_3$ or the like and $R^{13}$=alkyl), a catalyst such as palladium(0), and a base such as potassium carbonate to give compounds of formula 21. In turn, compounds of formula 21 can be heated under acid conditions to provide compounds of formula 19.

Scheme 10

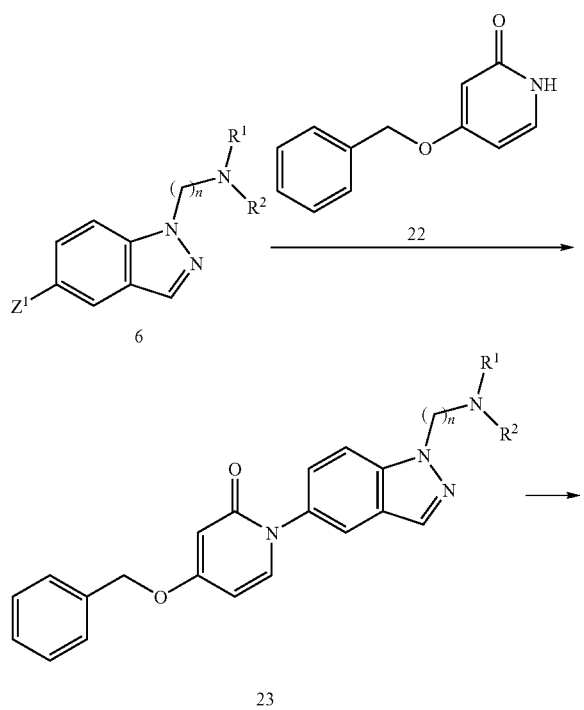

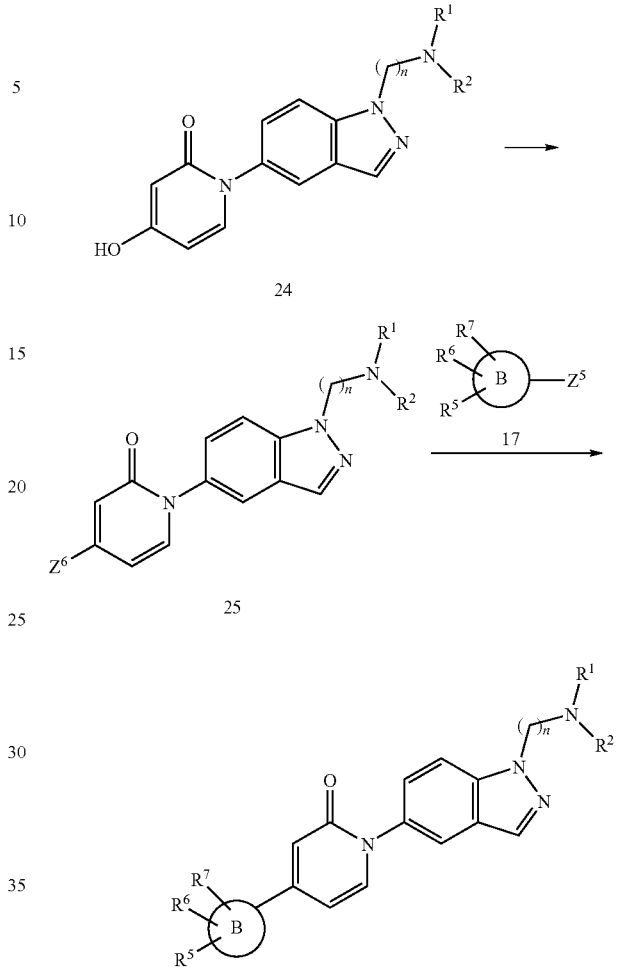

Compounds of formula 6 can be treated under heated conditions with a catalyst such as copper iodide, a ligand such as trans-1,2-diaminocyclohexane or 8-hydroxyquinoline, a base such as potassium carbonate, cesium carbonate or potassium phosphate and 4-(benzyloxy)pyridin-2(1H)-one to give compounds of formula 23. In turn, compounds of formula 23 can be treated with hydrogen and a catalyst such as palladium on carbon to provide compounds of formula 24. The hydroxyl group on compounds of formula 24 can be converted to an appropriate activating group to give compounds of formula 25. In the case where $Z^6$ is triflate, compounds of formula 24 can be treated with trifluoromethylsulfonic anhydride or N-phenyl trifluoromethanesulfonamide and a base such as pyridine or lithium bis(trimethylsilyl)amide under cooled conditions to give compounds of formula 25. In the case where $Z^6$ is trialkylstannane, compounds of formula 25 (wherein $Z^6$ is triflate) can be be treated with hexaalkylditin and palladium(0) under heated conditions to give compounds of formula 25, wherein $Z^6$ is trialkylstannane. Treatment of compounds of formula 25 with compounds of formula 17 (wherein $Z^5$=an appropriately matched activating group, such as $B(OH)_2$, $B(OR^{13})_2$, $SnR^{13}_3$, halogen or the like and $R^{13}$=alkyl), a catalyst such as palladium(0), and a base such as potassium carbonate under heated conditions can provide compounds of formula 26.

Scheme 11

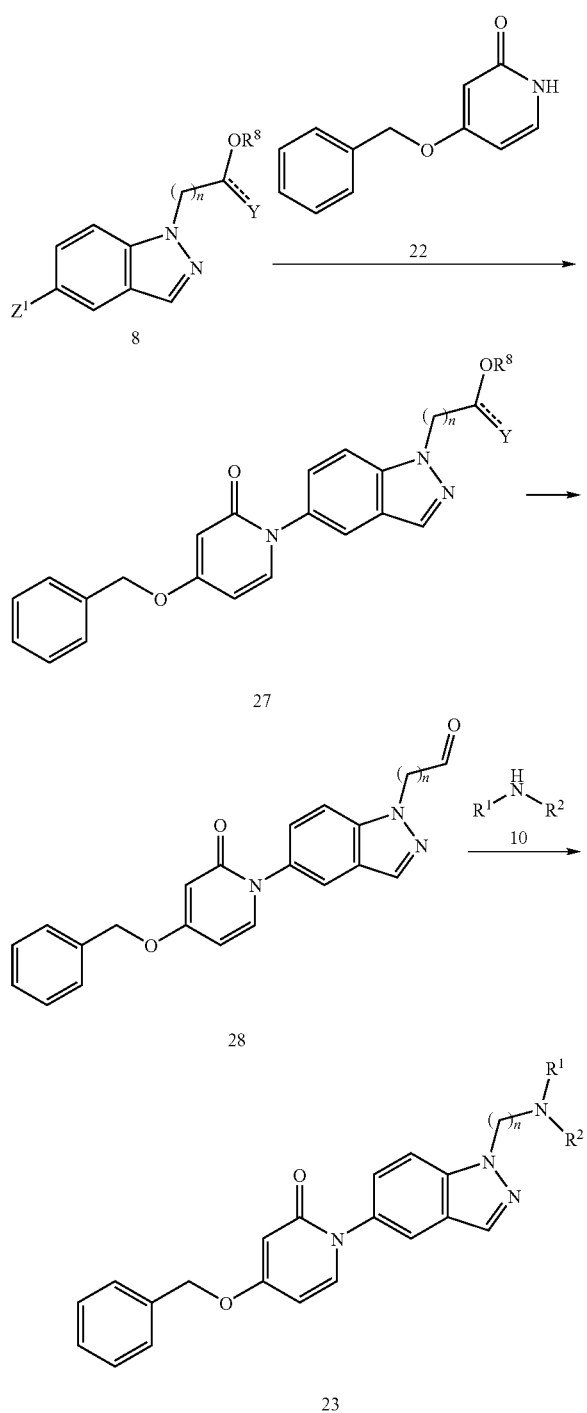

Additionally, compounds of formula 8 can be treated under heated conditions with a catalyst such as copper iodide, a ligand such as trans-1,2-diaminocyclohexane or 8-hydroxyquinoline, a base such as potassium carbonate, cesium carbonate or potassium phosphate and 4-(benzyloxy)pyridin-2(1H)-one to give compounds of formula 27. In the case where Y=$OR^9$, compounds of formula 27 can be treated under acidic reaction conditions to provide compounds of formula 28. In the case where Y=H and $R^8$=a protecting group, compounds of formula 27 can be treated under appropriate deprotecting conditions to provide compounds of formula 27 wherein $R^8$=H. In the case where Y=H and $R^8$=H, compounds of formula 27 can be treated with an oxidizing agent such as the Dess-Martin periodane or oxalyl chloride and DMSO to give compounds of formula 28. Treatment of compounds 28 with amines 10 and a reducing agent such as sodium borohydride, sodium cyanoborohydride, sodium triacetoxyborohydride, or picoline-borane complex can provide compounds of formula 23, which may be converted to compounds of formula 26 as described above.

Scheme 12

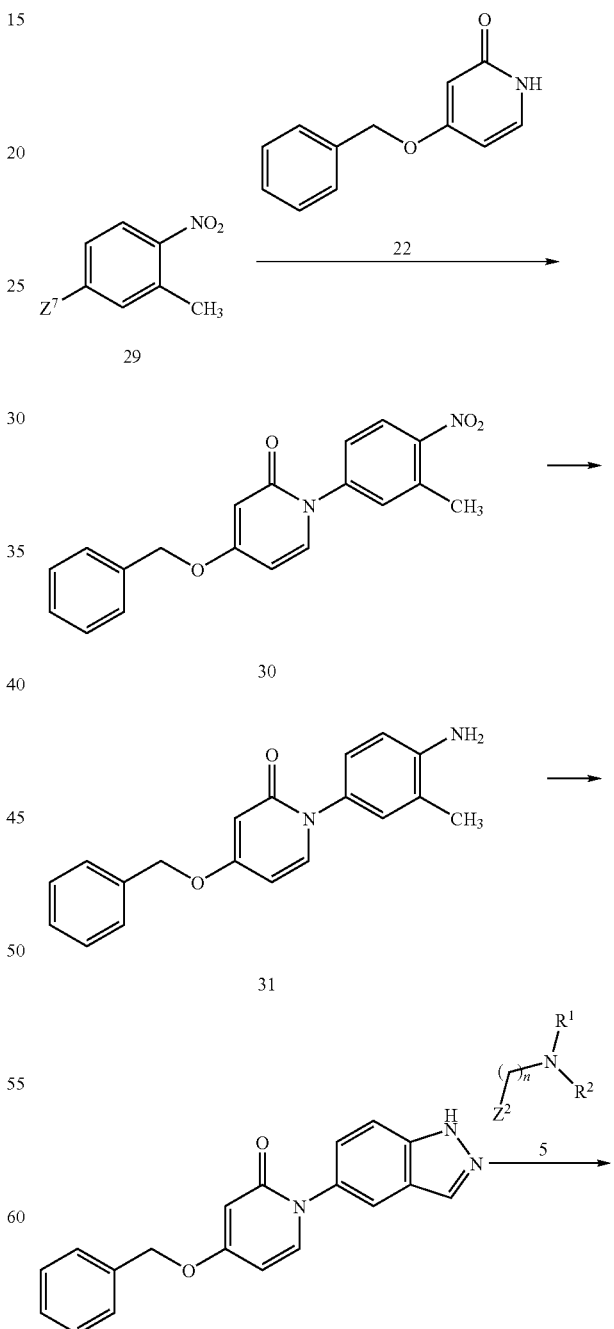

-continued

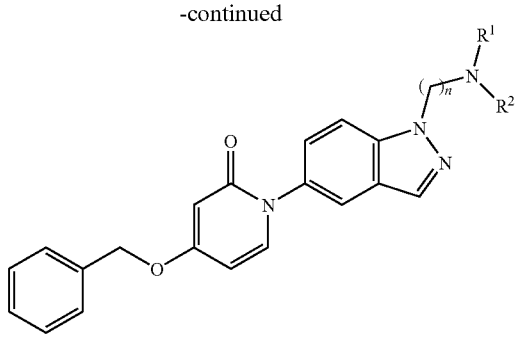

23

Alternatively, compounds of formula 32 can be made starting from compounds of formula 29. Compounds of formula 29 (wherein $Z^7$ is an activating group such as fluorine, chlorine, bromine or iodine) can be treated under heated conditions in a solvent such as DMF with a base such as sodium carbonate or cesium carbonate and 4-(benzyloxy)pyridin-2 (1H)-one to give a compound of formula 30. In turn, compound 30 can be treated under reducing conditions such as $SnCl_2$, iron powder and $NH_4Cl$, or palladium on carbon under a hydrogen atmosphere to provide a compound of formula 31. Treatment of compound 31 with $NaNO_2$ in acetic acid at room temperature can provide a compound of formula 32. Compound 32 can be treated with a base and compounds of formula 5 (wherein $Z^2$=halogen, methanesulfonate, toluenesulfonate or the like; n=2 or 3) under ambient temperature or heated conditions to give compounds of formula 23. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Compounds of formula 23 can be converted to compounds of formula 26 as described above.

Scheme 13

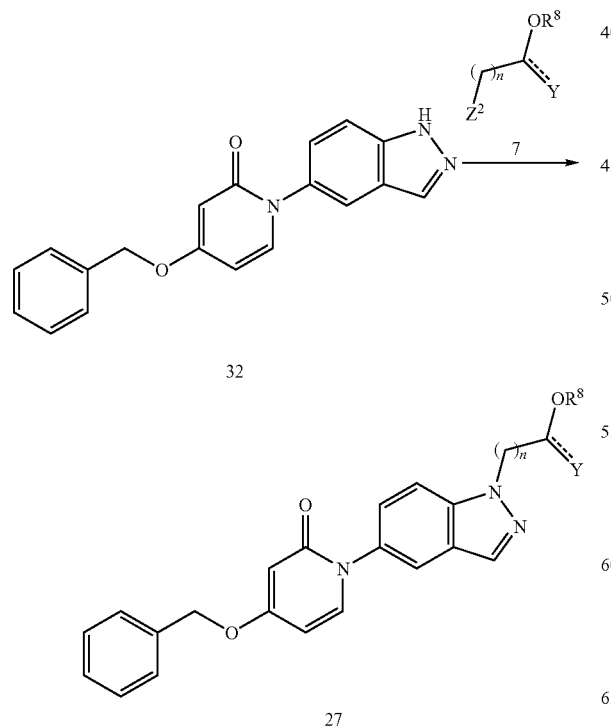

Alternatively, compound 32 can be treated with base and compounds of formula 7 (wherein $Z^2$=halogen, methanesulfonate, toluenesulfonate or the like; Y=O, $OR^9$ or H; $R^8$=an alkyl group, H or a protecting group such as tert-butyldimethylsilyl; $R^9$=alkyl; n=1 or 2) under ambient temperature or heated conditions to give compounds of formula 27. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Compounds of formula 27 can be converted to compounds of formula 26 as described above.

Scheme 14

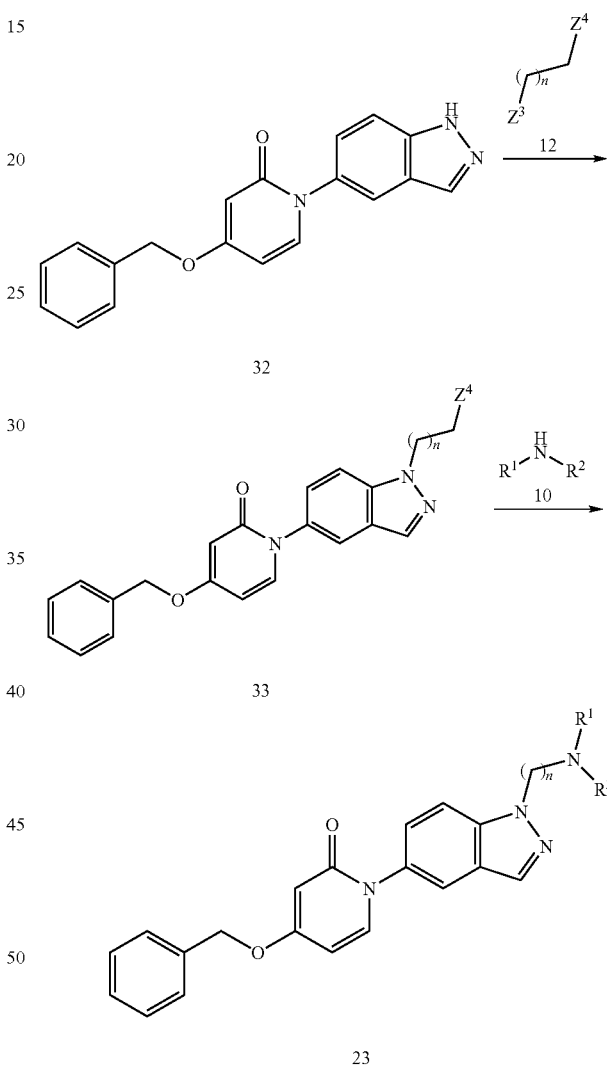

Alternatively, compound 32 can be treated with base and compounds of formula 12 (wherein n=1 or 2 and $Z^3$ and $Z^4$=halogen, methanesulfonate, toluenesulfonate or the like) under ambient temperature or heated conditions to give compounds of formula 33. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds of formula 33 with amines 10 under ambient temperature or heated conditions can provide compounds of formula 23 wherein n=2 or 3, which may be converted to compounds of formula 26 as described above.

Scheme 15

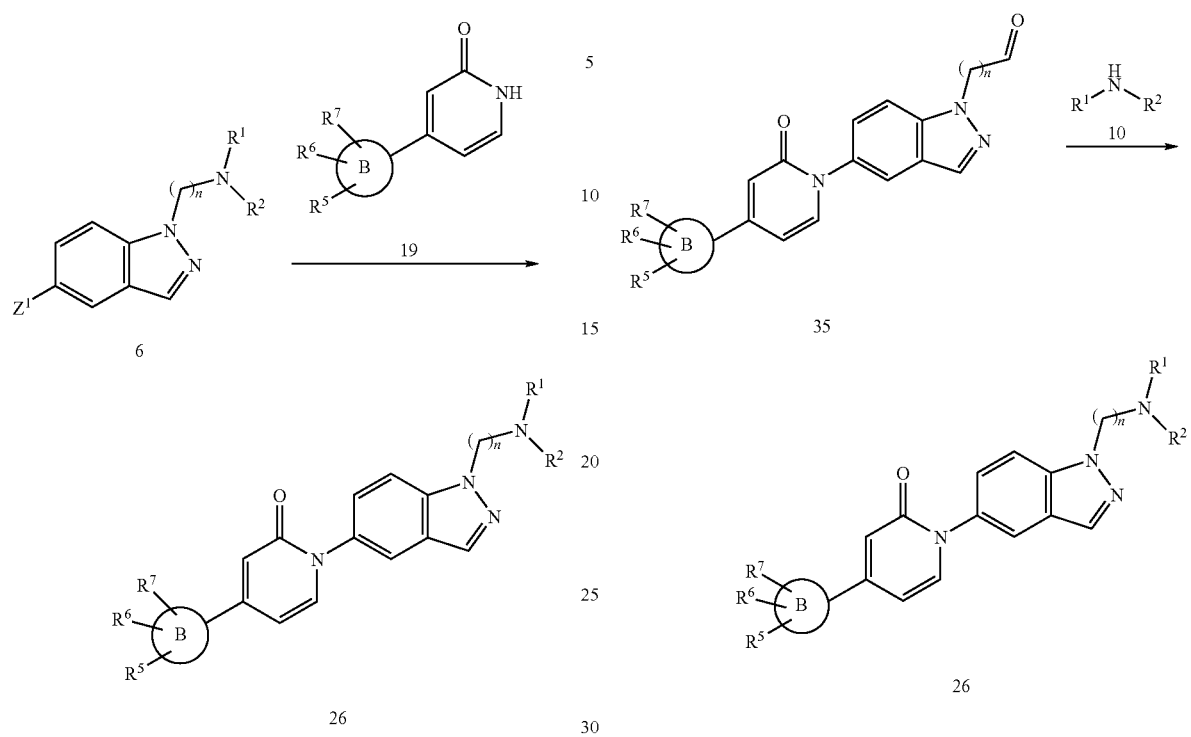

Alternatively, compounds of formula 6 can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 19 to give compounds of formula 26.

Scheme 16

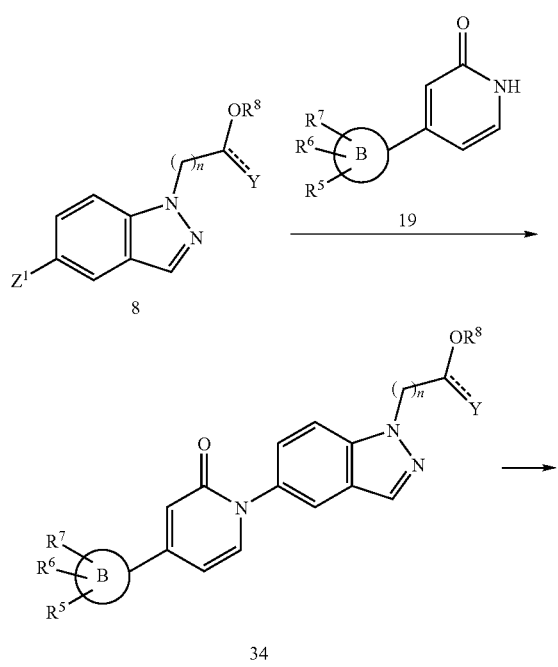

Additionally, compounds of formula 8 can be treated under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 19 to give compounds of formula 34. In the case where $Y=OR^9$, compounds of formula 34 can be treated under acidic reaction conditions to provide compounds of formula 35. In the case where $Y=H$ and $R^8=$a protecting group, compounds of formula 34 can be treated under appropriate deprotecting conditions to provide compounds of formula 34 wherein $R^8=H$. In the case where $Y=H$ and $R^8=H$, compounds of formula 34 can be treated with an oxidizing agent such as the Dess-Martin periodane or oxalyl chloride and DMSO to give compounds of formula 35. Treatment of compounds 35 with amines 10 and a reducing agent such as sodium borohydride, sodium cyanoborohydride, sodium triacetoxyborohydride, or picoline-borane complex can provide compounds of formula 26.

Scheme 17

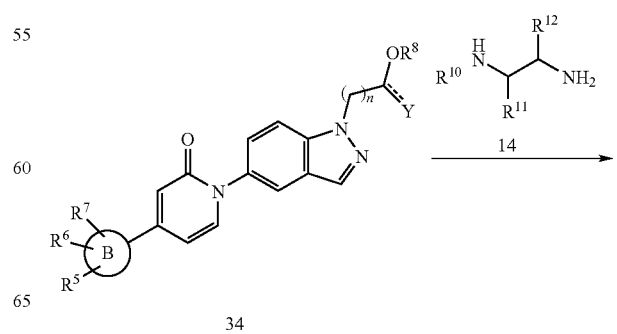

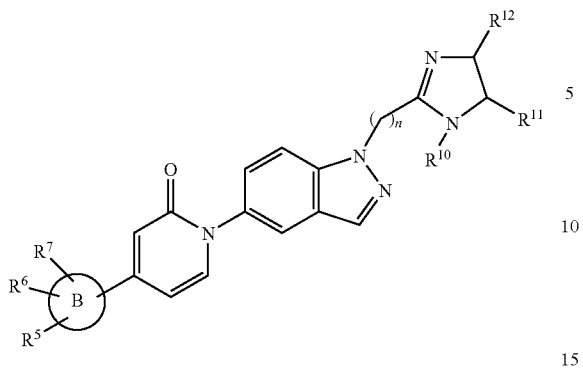

36

Additionally, in the case where Y=O and $R^8$=alkyl, compounds of formula 34 can be treated with diamines 14 (wherein $R^{10}$, $R^{11}$, $R^{12}$ are each independently H or alkyl) and trimethylaluminum to provide compounds of formula 36.

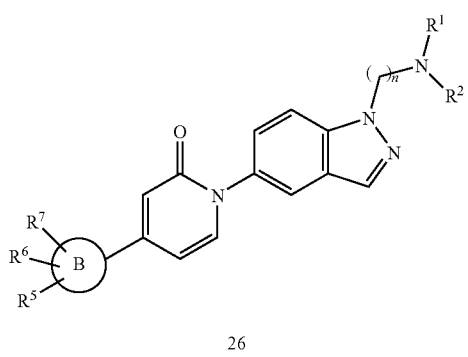

26

Alternatively, compounds of formula 39 can be made starting from compounds of formula 29. Compounds of formula 29 (wherein $Z^7$ is an activating group such as fluorine, chlorine, bromine or iodine) can be treated under heated conditions in a solvent such as DMF with a base such as sodium carbonate and compounds of formula 19 to give compounds of formula 37. In turn, compounds of formula 37 can be treated under reducing conditions such as $SnCl_2$, iron powder and $NH_4Cl$, or palladium on carbon under a hydrogen atmosphere to provide compounds of formula 38. Treatment of compounds of formula 38 with $NaNO_2$ in acetic acid at room temperature can provide compounds of formula 39. Compounds of formula 39 can be treated with base and compounds of formula 5 (wherein $Z^2$=halogen, methanesulfonate, toluenesulfonate or the like; n=2 or 3) under ambient temperature or heated conditions to give compounds of formula 26. Typical bases include but are not limited to cesium carbonate, potassium carbonate and sodium hydride. Typical solvents include but are not limited to N,N-dimethylformamide, dimethylsulfoxide, acetonitrile and tetrahydrofuran.

Scheme 18

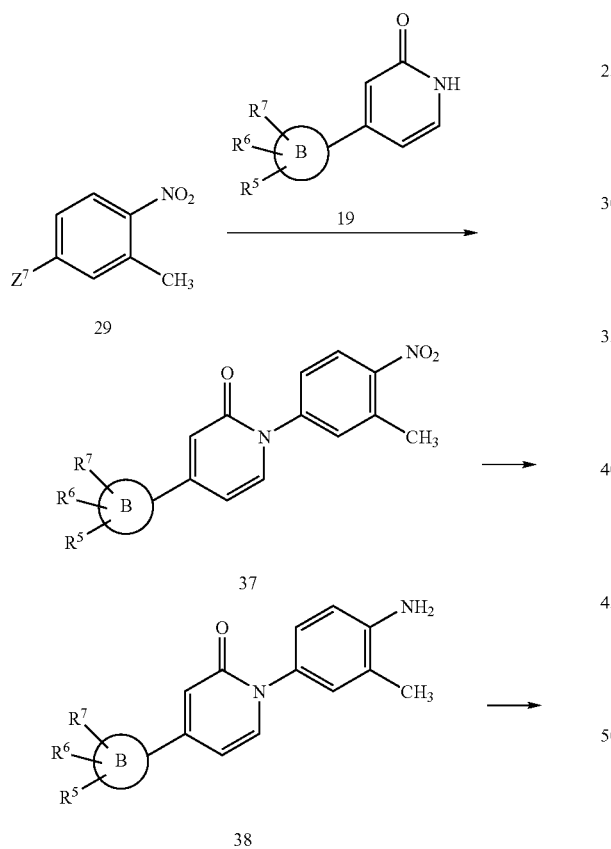

Scheme 19

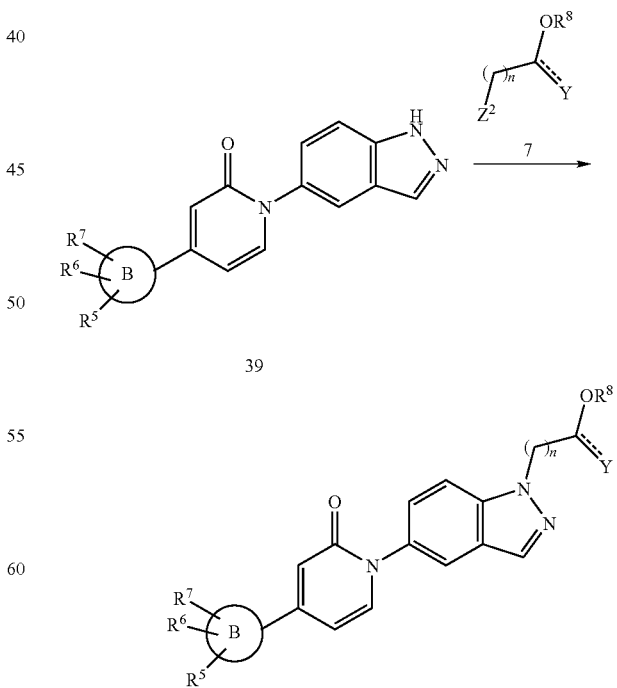

Alternatively, compounds of formula 39 can be treated with base and compounds of formula 7 (wherein $Z^2$=halogen, methanesulfonate, toluenesulfonate or the like; Y=O, $OR^9$ or H; $R^8$=an alkyl group, H or a protecting group such as tert-butyldimethylsilyl; $R^9$=alkyl; n=1 or 2) under ambient temperature or heated conditions to give compounds of formula 34. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Compounds of formula 34 can be converted to compounds of formula 26 as described above.

hydride. Typical solvents include but are not limited to N,N-dimethylformamide, dimethylsulfoxide, acetonitrile and tetrahydrofuran. Treatment of compounds of formula 40 with amines 10 under ambient temperature or heated conditions can provide compounds of formula 26 wherein n=2 or 3.

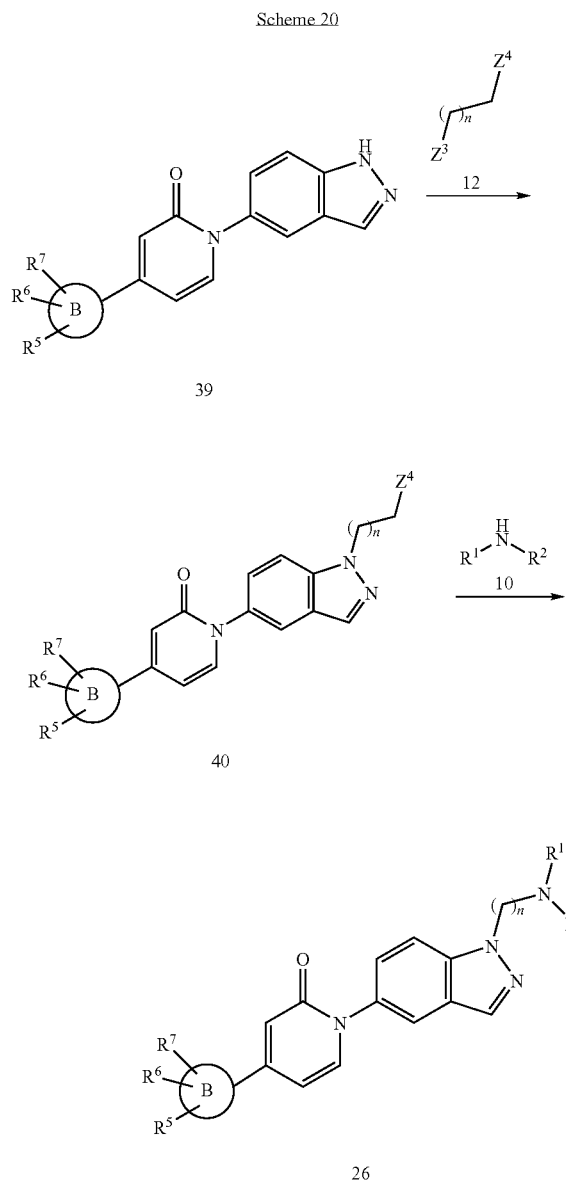

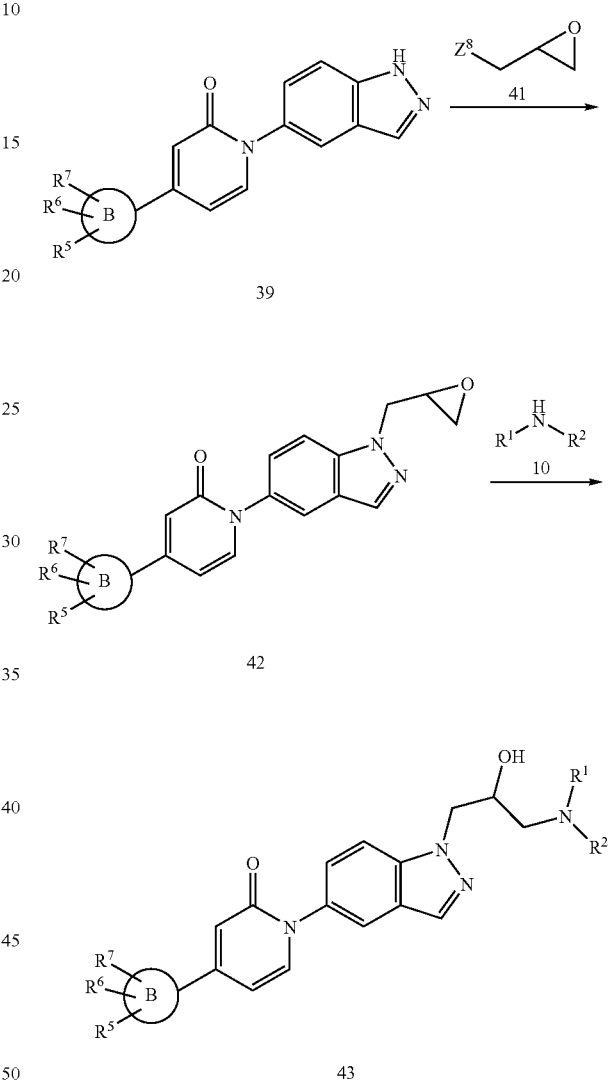

Alternatively, compound 39 can be treated with base and compounds of formula 12 (wherein n=1 or 2 and $Z^3$ and $Z^4$=halogen, methanesulfonate, toluenesulfonate or the like) under ambient temperature or heated conditions to give compounds of formula 40. Typical bases include but are not limited to cesium carbonate, potassium carbonate and sodium Compounds of formula 39 (wherein B is aryl or heteroaryl and $R^5$, $R^6$, $R^7$ are each independently selected from H, —OH, —O-alkyl, alkyl, halo, —$CF_3$, and —CN) can be treated with base and compounds of formula 41 (wherein $Z^8$=halogen, methanesulfonate, toluenesulfonate, 3-nitrobenzenesulfonate or the like) at ambient temperature or under heated conditions to give compounds of formula 42. Typical bases include but are not limited to cesium carbonate, potassium carbonate and sodium hydride. Typical solvents include but are not limited to N,N-dimethylformamide, dimethylsulfoxide, acetonitrile and tetrahydrofuran. Treatment of compounds 42 with amines 10 and a Lewis acid such as lithium perchlorate in a solvent such as tetrahydrofuran can provide compounds of formula 43.

Scheme 22

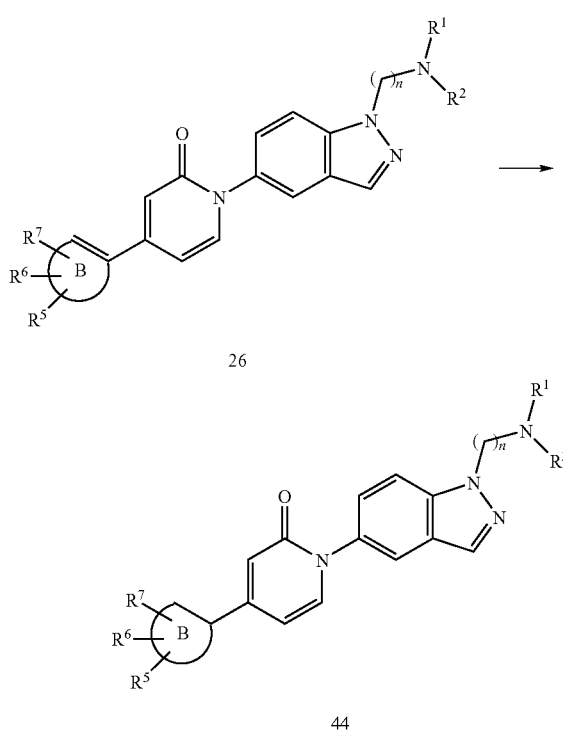

In the case where B contains a single site of unsaturation, compounds of formula 26 can be treated with hydrogen gas and a catalyst such as palladium on carbon to provide compounds of formula 44, wherein B is fully saturated cycloalkyl.

EXAMPLES

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (5 u, 250×4.6 mm, Phenomenex) or a Gemini C18 column (5 u, 250×4.5 mm, Phenomenex) with UV detection at 254 nm using a standard solvent gradient program (Method A, Method B, Method C, Method D, or Method E).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid Method C:

| Time (min) | Flow (mL/min) | % A | % B |
|---|---|---|---|
| 0.0 | 1.0 | 98.0 | 2.0 |
| 20.0 | 1.0 | 10.0 | 90.0 |
| 25.0 | 1.0 | 10.0 | 90.0 |

A = Water with 0.025% Trifluoroacetic Acid
B = Acetonitrile with 0.025% Trifluoroacetic Acid Method D:

| Time (min) | Flow (mL/min) | % A | % B |
|---|---|---|---|
| 0.0 | 1.0 | 98.0 | 2.0 |
| 20.0 | 1.0 | 10.0 | 90.0 |
| 25.0 | 1.0 | 10.0 | 90.0 |

A = Water with 0.05% Trifluoroacetic Acid
B = Acetonitrile with 0.05% Trifluoroacetic Acid Method E:

| Time (min) | Flow (mL/min) | % A | % B |
|---|---|---|---|
| 0.0 | 1.0 | 98.0 | 2.0 |
| 25.0 | 1.0 | 10.0 | 90.0 |
| 30.0 | 1.0 | 10.0 | 90.0 |

A = Water with 0.025% Trifluoroacetic Acid
B = Acetonitrile with 0.025% Trifluoroacetic Acid

Example 1

Preparation of 4-(Phenyl)-1-(1-(2-(pyrrolidin-1-yl)ethyl)-1H-indazol-5-yl)pyridin-2(1H)-one hydrochloride a) 1-(2-(Pyrrolidin-1-yl)ethyl)-1H-indazol-5-amine Beilstein Registry Number 10008406

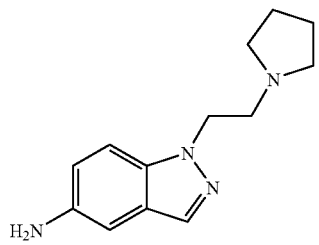

Chemical Formula: $C_{13}H_{18}N_4$
Exact Mass: 230.15
Molecular Weight: 230.31

This compound was prepared in accordance with the procedure of Souers et al., *Bioorg. Med. Chem. Lett.* 2005, 15, 2752-2757.

b) 5-Bromo-1-(2-(pyrrolidin-1-yl)ethyl)-1H-indazole

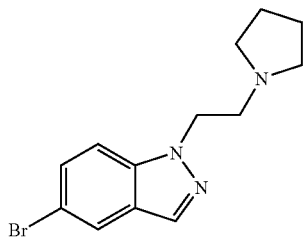

Chemical Formula: $C_{13}H_{16}BrN_3$
Exact Mass: 293.05
Molecular Weight: 294.19

A solution of NaNO$_2$ (0.20 g, 2.8 mmol) in H$_2$O (5 mL) was cooled in a wet ice bath and treated with a solution of 1-(2-(pyrrolidin-1-yl)ethyl)-1H-indazol-5-amine (0.65 g, 2.8 mmol) in 48% aqueous HBr (2 mL). The resulting mixture was added to a pre-heated solution of CuBr (0.49 g, 3.4 mmol) in 48% aqueous HBr (2 mL) at 100° C. After stirring at 100° C. for 15 min, the dark mixture was allowed to cool. The solids were isolated by filtration, washed with 1N NaOH, and dried under vacuum. Purification by flash column chromatography (silica gel, CH$_2$Cl$_2$/MeOH, 95:5 to 90:10 gave the title compound (0.21 g, 25%) as a brown solid: ESI MS m/z 294 [M+H]$^+$.

c) 4-(Benzyloxy)-1-(1-(2-(pyrrolidin-1-yl)ethyl)-1H-indazol-5-yl)pyridin-2(1H)-one

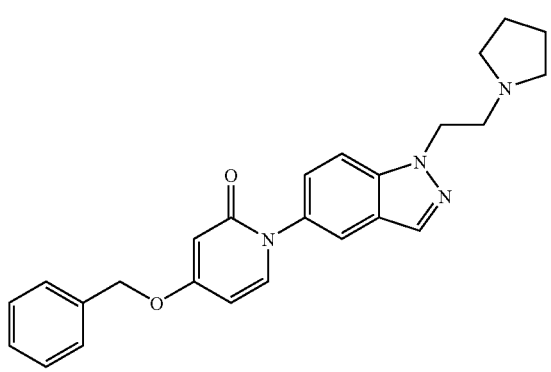

Chemical Formula: $C_{25}H_{26}N_4O_2$
Exact Mass: 414.21
Molecular Weight: 414.5

A suspension of 5-bromo-1-(2-(pyrrolidin-1-yl)ethyl)-1H-indazole (0.21 g, 0.70 mmol) in 1,4-dioxane (10 mL) stirred under nitrogen was treated sequentially with 4-(benzyloxy)pyridin-2(1H)-one (0.14 g, 0.70 mmol), trans-1,2-diaminocyclohexane (0.03 mL, 0.2 mmol), CuI (28 mg, 0.15 mmol) and K$_2$CO$_3$ (0.19 g, 1.4 mmol). After stirring overnight at 110° C., the mixture was allowed to cool to room temperature, diluted with CH$_2$Cl$_2$, washed with brine, dried over Na$_2$SO$_4$, filtered and concentrated to dryness. Purification by flash column chromatography (silica gel, CH$_2$Cl$_2$/MeOH, 95:5 to 90:10 gave the title compound (21 mg, 7%) as an off-white powder: $^1$H NMR (500 MHz, DMSO-d$_6$) δ 8.03 (s, 1H), 7.66 (d, J=1.4 Hz, 1H), 7.53 (d, J=8.8 Hz, 1H), 7.43-7.36 (m, 6H), 7.28 (d, J=7.5 Hz, 1H), 6.09-6.06 (m, 2H), 5.06 (s, 2H), 4.58-4.55 (m, 2H), 3.03 (br s, 2H), 2.61 (br s, 4H), 1.81 (br s, 4H); ESI MS m/z 415 [M+H]$^+$.

d) 4-Hydroxy-1-(1-(2-(pyrrolidin-1-yl)ethyl)-1H-indazol-5-yl)pyridin-2(1H)-one

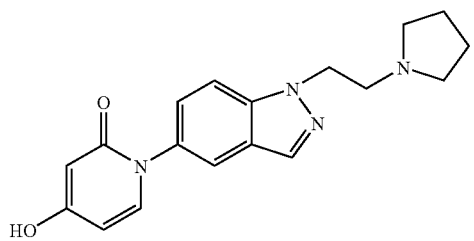

Chemical Formula: $C_{18}H_{20}N_4O_2$
Exact Mass: 324.1586
Molecular Weight: 324.377

To a solution of 4-(benzyloxy)-1-(1-(2-(pyrrolidin-1-yl)ethyl)-1H-indazol-6-yl)pyridin-2(1H)-one (240 mg, 0.58 mmol) in CH$_3$OH was added Pd/C (200 mg) under an Ar atmosphere. The Ar balloon was replaced with a H$_2$ balloon. The reaction was heated to 55° C. overnight and then allowed to cool. The mixture was filtered through a layer of Celite and the filtrate was concentrated. Purification by flash column chromatography (silica gel, CH$_2$Cl$_2$/MeOH, 80:20) gave the title compound as a white solid in 65% yield: $^1$H NMR (500 MHz, CD$_3$OD) δ 8.12 (s, 1H), 7.74 (d, J=2.0 Hz, 1H), 7.71 (d, J=9.0 Hz, 1H), 7.48 (d, J=7.5 Hz, 1H), 7.39 (dd, J=9.0, 2.0 Hz, 1H), 6.12 (d, J=7.5 Hz, 1H), 4.65 (t, J=7.0 Hz, 2H), 3.17 (t, J=7.0 Hz, 2H), 2.72-2.71 (m, 4H), 1.84-1.80 (m, 4H); ESI MS m/z 325 [M+H]$^+$.

e) 1-(2-(Pyrrolidin-1-yl)ethyl)-1H-indazol-5-yl)pyridin-2(1H)-one-4-trifluoromethanesulfonate

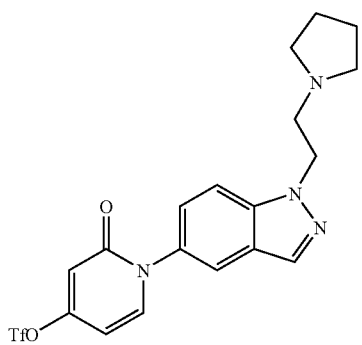

4-Hydroxy-1-(1-(2-(pyrrolidin-1-yl)ethyl)-1H-indazol-5-yl)pyridin-2(1H)-one (900 mg, 2.7 mmol) was suspended in THF (20 mL) under a nitrogen atmosphere and LiN(SiMe$_3$)$_2$ (1M in THF) (4.2 mL, 4.2 mmol) added. After stirring for 1 minute, PhNTf$_2$ (1.48 g, 4.16 mmol) was added in one portion and the mixture was stirred for 2 h. The mixture was concentrated, diluted with methylene chloride (50 mL) and washed successively with saturated NH$_4$Cl and saturated Na$_2$CO$_3$, dried over sodium sulfate and concentrated. The residue was purified by column chromatography (40 g ISCO column eluting with methylene chloride and a methanol/ammonia mixture (10:1); gradient 100% methylene chloride to 80% methylene chloride over 30 min at 40 mL/min) to provide the title compound (780 mg, 60%) as a white solid; $^1$H NMR (500 MHz, CDCl$_3$) δ 8.05 (s, 1H), 7.68 (d, J=1.8 Hz, 1H), 7.57 (d, J=8.9 Hz, 1H), 7.53 (d, J=7.4 Hz, 1H), 7.37-7.35 (dd, J=8.9, 2.0 Hz, 1H), 6.60 (d, J=2.7 Hz, 1H), 6.30-6.28 (dd, J=8.7, 2.5 Hz, 1H), 4.57 (t, J=7.2 Hz, 2H), 3.01 (t, J=7.2 Hz, 2H), 2.60-2.57 (m, 4H), 1.80-1.76 (m, 4H); ESI MS m/z 457 [M+H]$^+$.

f) 4-(Phenyl)-1-(1-(2-(pyrrolidin-1-yl)ethyl)-1H-indazol-5-yl)pyridin-2(1H)-one hydrochloride

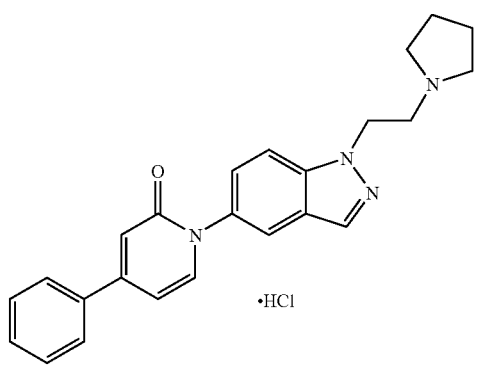

1-(2-(Pyrrolidin-1-yl)ethyl)-1H-indazol-5-yl)pyridin-2 (1H)-one-4-trifluoromethanesulfonate (100 mg, 0.22 mmol), phenylboronic acid (67 mg, 0.55 mmol), K$_2$CO$_3$ (75 mg, 0.55 mmol) and [1,1'-Bis-(diphosphenylphosphino)ferrocene] dichloropalladium(II) (PdCl$_2$dppf) (18 mg, 0.022 mmol) were stirred in DMSO (2 mL) under vacuum for 30 min. The flask was flushed with nitrogen and the mixture was heated to 80° C. for 10 min. Upon cooling, the mixture was diluted with methylene chloride and washed with 5% lithium chloride solution (5×), dried, concentrated and the residue was purified by column chromatography (12 g ISCO column eluting with methylene chloride and a methanol/ammonia mixture (10:1); gradient 100% methylene chloride to 80% methylene chloride over 30 min at 25 mL/min) to provide the free base. This was dissolved in methylene chloride (2 mL) and treated with 1 equivalent of 2 M HCl in Et$_2$O and the mixture was concentrated to provide the title compound (20 mg, 21%) as a yellow solid: melting point (mp) 192-196° C.; $^1$H NMR (500 MHz, CD$_3$OD) δ 8.27 (s, 1H), 7.93 (d, J=1.7 Hz, 1H), 7.86-7.82 (m, 2H), 7.79-7.76 (m, 2H), 7.57-7.52 (m, 4H), 6.97-6.96 (m, 2H), 4.90 (t, J=5.7 Hz, 2H), 3.88 (t, J=5.7 Hz, 2H), 3.74-3.69 (m, 2H), 3.20-3.15 (m, 2H), 2.20-2.14 (m, 2H), 2.06-2.00 (m, 2H); ESI MS m/z 385 [M+H]$^+$; HPLC (Method D)>99% (AUC), t$_R$=13.0 min.

Example 2

Preparation of 4-(4-Chlorophenyl)-1-(1-(2-(pyrrolidin-1-yl)ethyl)-1H-indazol-5-yl)pyridin-2(1H)-one hydrochloride

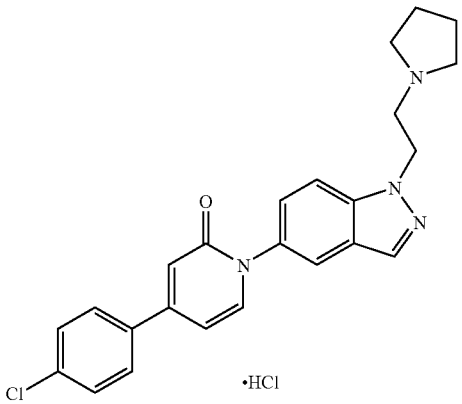

Following the procedure of Example 1, but substituting p-chlorophenylboronic acid for phenylboronic acid, the title compound (26 mg, 24%) was prepared as a yellow solid: mp 255-260° C. (decomposition); $^1$H NMR (500 MHz, CD$_3$OD) δ 8.26 (s, 1H), 7.91 (d, J=1.6 Hz, 1H), 7.86-7.82 (m, 2H), 7.77 (d, J=8.6 Hz, 2H), 7.56-7.53 (m, 3H), 6.95-6.92 (m, 2H), 4.90 (t, J=5.6 Hz, 2H), 3.87 (t, J=5.6 Hz, 2H), 3.73-3.69 (m, 2H), 3.19-3.14 (m, 2H), 2.18-2.15 (m, 2H), 2.03-2.00 (m, 2H); ESI MS m/z 419 [M+H]$^+$; HPLC (Method D)>99% (AUC), t$_R$=13.9 min.

Example 3

Preparation of 4-(Benzo[b]thiophen-2-yl)-1-(1-(2-(pyrrolidin-1-yl)ethyl)-1H-indazol-5-yl)pyridin-2 (1H)-one hydrochloride

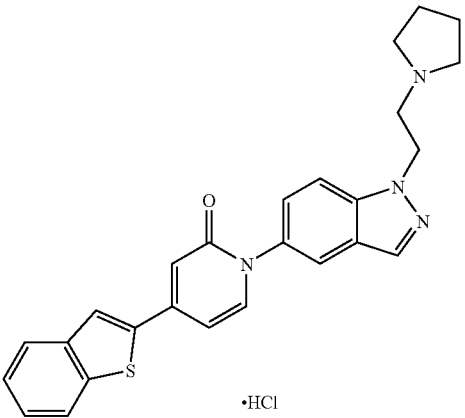

Following the procedure of Example 1, but substituting benzothiophene-2-boronic acid for phenylboronic acid, the title compound (23 mg, 22%) was prepared as a yellow solid: mp 260-264° C.; $^1$H NMR (500 MHz, CD$_3$OD) δ 8.26 (s, 1H), 8.03 (s, 1H), 7.95-7.91 (m, 3H), 7.83 (d, J=8.9 Hz, 1H), 7.77 (d, J=7.1 Hz, 1H), 7.56-7.54 (dd, J=8.9, 1.9 Hz, 1H), 7.46-7.41 (m, 2H), 7.06-7.02 (dd, J=7.2, 2.0 Hz, 1H), 6.97 (d, J=1.8 Hz, 1H), 4.89 (t, J=5.8 Hz, 2H), 3.87 (t, J=5.8 Hz, 2H), 3.73-3.69 (m, 2H), 3.20-3.15 (m, 2H), 2.19-2.16 (m, 2H), 2.04-2.00 (m, 2H); ESI MS m/z 441 [M+H]$^+$; HPLC (Method D)>99% (AUC), t$_R$=14.5 min.

Example 4

Preparation of 4-(Benzofuran-2-yl)-1-(1-(2-(pyrrolidin-1-yl)ethyl)-1H-indazol-5-yl)pyridin-2(1H)-one hydrochloride

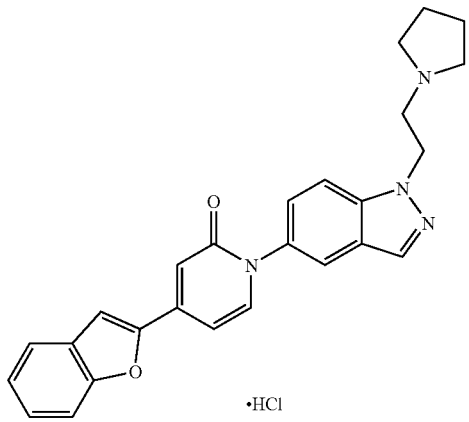

Following the procedure of Example 1, but substituting benzofuran-2-boronic acid for phenylboronic acid, the title compound (21 mg, 21%) was prepared as a brown solid: mp 256-260° C.; $^1$H NMR (500 MHz, CD$_3$OD) δ 8.26 (s, 1H), 7.91 (d, J=1.7 Hz, 1H), 7.85 (d, J=8.9 Hz, 1H), 7.78 (d, J=7.1 Hz, 1H), 7.71 (d, J=7.8 Hz, 1H), 7.61 (d, J=8.3 Hz, 1H), 7.60 (s, 1H), 7.56-7.53 (dd, J=8.9, 1.9 Hz, 1H), 7.45-7.41 (t, J=8.3 Hz, 1H), 7.31 (t, J=7.8 Hz, 1H), 7.15 (d, J=1.8 Hz, 1H), 7.05-7.03 (dd, J=7.1, 1.8 Hz, 1H) 4.91 (t, J=5.3 Hz, 2H), 3.88 (t, J=5.3 Hz, 2H), 3.73-3.69 (m, 2H), 3.20-3.14 (m, 2H), 2.18-2.14 (m, 2H), 2.04-1.99 (m, 2H); ESI MS m/z 425 [M+H]$^+$; HPLC (Method E) 99% (AUC), t$_R$=15.4 min.

Example 5

Preparation of 4-(4-Fluorophenyl)-1-(1-(2-(pyrrolidin-1-yl)ethyl)-1H-indazol-5-yl)pyridin-2(1H)-one hydrochloride

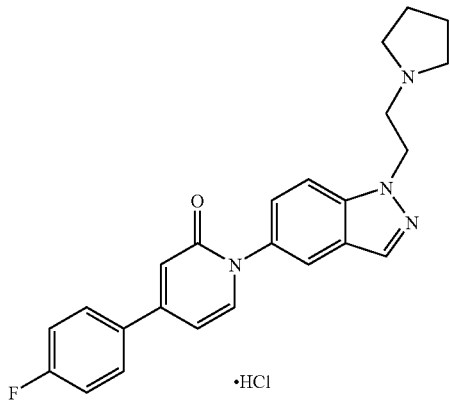

Following the procedure of Example 1, but substituting p-fluorophenylboronic acid for phenylboronic acid, the title compound (18 mg, 19%) was prepared as a yellow solid: mp 115-120° C.; $^1$H NMR (500 MHz, CD$_3$OD) δ 8.26 (s, 1H), 7.91 (d, J=1.4 Hz, 1H), 7.83-7.79 (m, 3H), 7.77 (d, J=7.1 Hz, 1H), 7.55-7.53 (dd, J=8.8, 1.9 Hz, 1H), 7.26-7.25 (m, 2H), 6.89 (d, J=1.8 Hz, 1H), 6.87-6.85 (dd, J=7.2, 2.1 Hz, 1H), 4.87 (t, J=5.7 Hz, 2H), 3.87 (t, J=5.7 Hz, 2H), 3.76-3.69 (m, 2H), 3.20-3.15 (m, 2H), 2.19-2.16 (m, 2H), 2.03-2.00 (m, 2H); ESI MS m/z 403 [M+H]$^+$; HPLC (Method D)>99% (AUC), t$_R$=13.2 min.

Example 6

Preparation of 4-(Naphthalen-2-yl)-1-(1-(2-(pyrrolidin-1-yl)ethyl)-1H-indazol-5-yl)pyridin-2(1H)-one hydrochloride

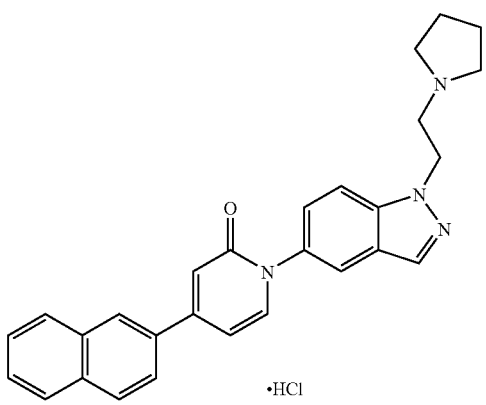

Following the procedure of Example 1, but substituting napthyl-2-boronic acid for phenylboronic acid, the title compound (24 mg, 24%) was prepared as a yellow solid: mp 128-134° C.; $^1$H NMR (500 MHz, CD$_3$OD) δ 8.32 (s, 1H), 8.27 (s, 1H), 8.04-8.01 (m, 2H), 7.95-7.93 (m, 2H), 7.87-7.81 (m, 3H), 7.59-7.56 (m, 3H), 7.07-7.05 (m, 2H), 4.89 (t, J=5.8 Hz, 2H), 3.88 (t, J=5.8 Hz, 2H), 3.74-3.70 (m, 2H), 3.19-3.16 (m, 2H), 2.19-2.16 (m, 2H), 2.04-2.01 (m, 2H); ESI MS m/z 435 [M+H]$^+$; HPLC (Method D)>99% (AUC), t$_R$=14.4 min.

Example 7

Preparation of 4-(3-Chlorophenyl)-1-(1-(2-(pyrrolidin-1-yl)ethyl)-1H-indazol-5-yl)pyridin-2(1H)-one hydrochloride

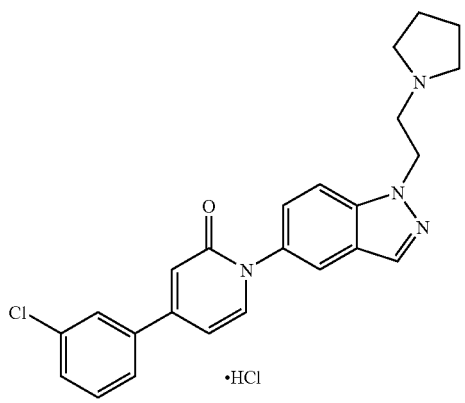

Following the procedure of Example 1, but substituting m-chlorophenylboronic acid for phenylboronic acid, the title compound (20 mg, 21%) was prepared as an orange solid: mp 118-125° C.; $^1$H NMR (500 MHz, CD$_3$OD) δ 8.26 (s, 1H), 7.91 (d, J=1.6 Hz, 1H), 7.83 (d, J=8.9 Hz, 1H), 7.79-7.78 (m, 2H), 7.70-7.68 (m, 1H), 7.55-7.52 (m, 3H), 6.91 (d, J=1.8 Hz, 1H), 6.86-6.84 (dd, J=7.1, 2.0 Hz, 1H), 4.90 (t, J=5.8 Hz, 2H), 3.88-3.86 (m, 2H), 3.76-3.69 (m, 2H), 3.20-3.15 (m, 2H), 2.19-2.16 (m, 2H), 2.03-2.00 (m, 2H); ESI MS m/z 419 [M+H]+; HPLC (Method D) 98.5% (AUC), $t_R$=13.9 min.

Example 8

Preparation of 4-(3-Phenoxyphenyl)-1-(1-(2-(pyrrolidin-1-yl)ethyl)-1H-indazol-5-yl)pyridin-2(1H)-one hydrochloride

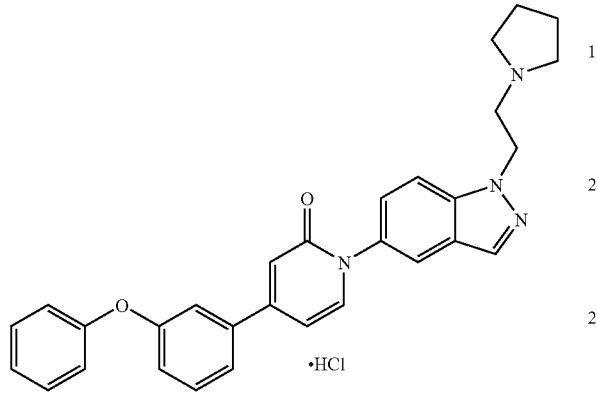

Following the procedure of Example 1, but substituting 3-phenoxyphenylboronic acid for phenylboronic acid, the title compound (18 mg, 16%) was prepared as a yellow-brown solid: $^1$H NMR (500 MHz, CD$_3$OD) δ 8.25 (s, 1H), 7.90 (d, J=1.7 Hz, 1H), 7.82 (d, J=8.9 Hz, 1H), 7.76 (d, J=7.1 1H), 7.54-7.49 (m, 3H), 7.41-7.38 (m, 2H), 7.36-7.35 (m, 1H), 7.16 (t, J=8.5 Hz, 1H), 7.12-7.10 (dt, J=6.7, 2.4 Hz, 1H), 7.07-7.05 (m, 2H), 6.86 (d, J=1.8 Hz, 1H), 6.83-6.81 (dd, J=7.3, 2.0 Hz, 1H), 4.89 (t, J=5.7 Hz, 2H), 3.87 (t, J=5.7 Hz, 2H), 3.73-3.69 (m, 2H), 3.20-3.14 (m, 2H), 2.18-2.15 (m, 2H), 2.04-2.00 (m, 2H); ESI MS m/z 477 [M+H]+; HPLC (Method D)>99% (AUC), $t_R$=15.3 min.

Example 9

Preparation of 1-(1-(2-(Pyrrolidin-1-yl)ethyl)-1H-indazol-5-yl)-4-(4-(trifluoromethyl)phenyl)pyridin-2(1H)-one hydrochloride

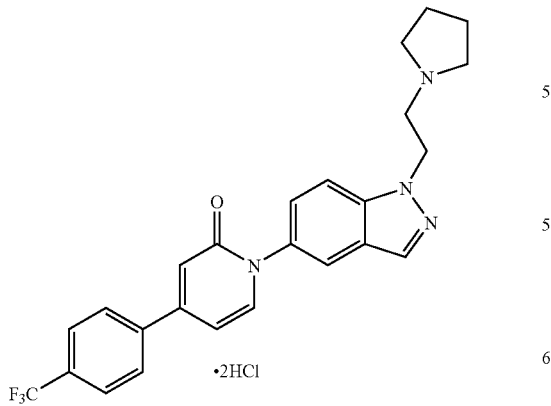

Following the procedure of Example 1, but substituting p-trifluoromethylphenylboronic acid for phenylboronic acid, the title compound (35 mg, 31%) was prepared as a white solid: $^1$H NMR (500 MHz, CD$_3$OD) δ 8.26 (s, 1H), 7.96 (d, J=8.2 Hz, 2H), 7.92 (d, J=1.8 Hz, 1H), 7.85-7.83 (m, 3H), 7.82 (d, J=7.2 Hz, 1H), 7.56-7.54 (dd, J=8.9, 1.9 Hz, 1H), 6.97 (d, J=1.9 Hz, 1H), 6.89-6.87 (dd, J=7.1, 2.0 Hz, 1H), 4.90 (t, J=5.7 Hz, 2H), 3.88 (t, J=5.7 Hz, 2H), 3.74-3.69 (m, 2H), 3.20-3.16 (m, 2H); 2.19-2.16 (m, 2H), 2.04-2.00 (m, 2H); ESI MS m/z 453 [M+H]+; HPLC (Method E)>99% (AUC), $t_R$=13.4 min.

Example 10

Preparation of 1-(1-(2-(Pyrrolidin-1-yl)ethyl)-1H-indazol-5-yl)-4-(3-(trifluoromethyl)phenyl)pyridin-2(1H)-one dihydrochloride

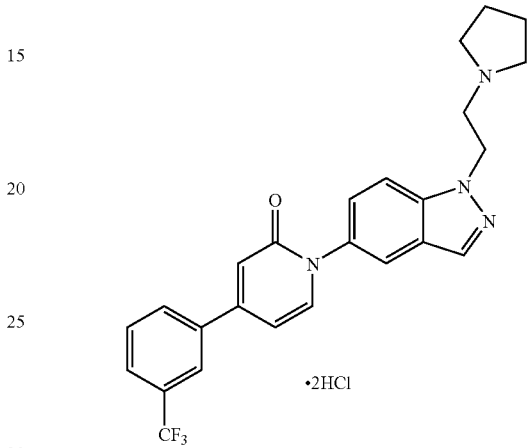

Following the procedure of Example 1, but substituting m-trifluoromethylphenylboronic acid for phenylboronic acid, the title compound (46 mg, 40%) was prepared as a brown solid: $^1$H NMR (500 MHz, CD$_3$OD) δ 8.26 (s, 1H), 8.08-7.99 (br m, 2H), 7.92 (d, J=1.5 Hz, 1H), 7.85-7.81 (m, 3H), 7.75 (t, J=8.0 Hz, 1H), 7.56-7.44 (dd, J=8.9, 1.9 Hz, 1H), 6.96 (d, J=1.8 Hz, 1H), 6.90-6.89 (dd, J=7.1, 1.9 Hz, 1H), 4.90 (t, J=5.8 Hz, 2H), 3.88 (t, J=5.8 Hz, 2H), 3.73-3.69 (m, 2H), 3.20-3.15 (m, 2H), 2.20-2.13 (m, 2H), 2.05-2.00 (m, 2H); ESI MS m/z 453 [M+H]+; HPLC (Method C) 96.9% (AUC), $t_R$=13.3 min.

Example 11

Preparation of 4-(1-Methyl-1H-indol-2-yl)-1-(1-(2-(pyrrolidin-1-yl)ethyl)-1H-indazol-5-yl)pyridin-2(1H)-one dihydrochloride

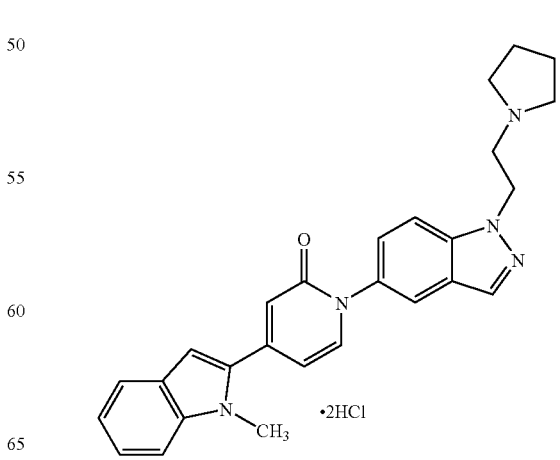

Following the procedure of Example 1, but substituting N-methylindole-2-boronic acid for phenylboronic acid, the title compound (27 mg, 24%) was prepared as a brown solid: $^{1}$H NMR (500 MHz, DMSO-$d_6$) δ 10.71-10.48 (br s, 1H), 8.28 (s, 1H), 7.94 (d, J=6.2 Hz, 1H), 7.92 (s, 1H), 7.82 (d, J=7.2 Hz, 1H), 7.63 (d, J=7.8 Hz, 1H), 7.57 (m, 2H), 7.27 (d, J=8.1 Hz, 1H), 7.11 (t, J=7.0 Hz, 1H), 6.88 (s, 1H), 6.71 (d, J=1.8 Hz, 1H), 6.66-6.63 (dd, J=7.1, 1.9 Hz, 1H), 4.91 (t, J=6.3 Hz, 2H), 3.89 (s, 3H), 3.74 (q, J=6.2 Hz, 2H), 3.53-3.50 (m, 2H), 3.08-3.00 (m, 2H) 1.99-1.83 (m, 4H); ESI MS m/z 438 [M+H]$^{+}$; HPLC (Method C)>99% (AUC), $t_R$=13.2 min.

Example 12

Preparation of 4-(2,4-Dichlorophenyl)-1-(1-(2-(pyrrolidin-1-yl)ethyl)-1H-indazol-5-yl)pyridin-2(1H)-one hydrochloride

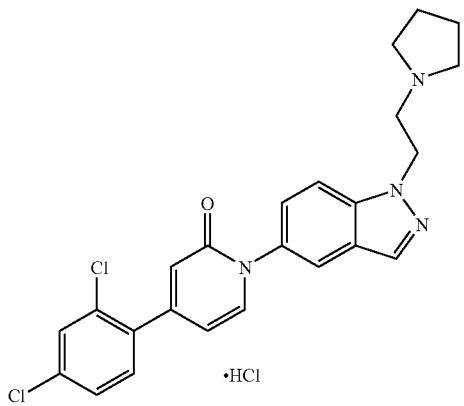

Following the procedure of Example 1, but substituting 2,4-dichlorophenylboronic acid for phenylboronic acid, the title compound (29 mg, 27%) was prepared as a white solid: mp 110-115° C. deliquescent; $^{1}$H NMR (500 MHz, CD$_3$OD) δ 8.26 (s, 1H), 7.92 (d, J=1.5 Hz, 1H), 7.82 (d, J=8.9 Hz, 1H), 7.76 (d, J=7.0 Hz, 1H), 7.65 (s, 1H), 7.56-7.54 (dd, J=8.8, 1.8 Hz, 1H), 7.49 (s, 2H), 6.69 (d, J=1.5 Hz, 1H), 6.22-6.20 (dd, J=7.0, 1.8 Hz, 1H), 4.90 (t, J=5.7 Hz, 2H), 3.87 (t, J=5.7 Hz, 2H), 3.73-3.69 (br m, 2H), 3.20-3.15 (br m, 2H), 2.19-2.16 (m, 2H), 2.03-2.00 (m, 2H); ESI MS m/z 453 [M+H]$^{+}$; HPLC (Method D)>99% (AUC), $t_R$=14.5 min.

Example 13

Preparation of 4-(Naphthalen-1-yl)-1-(1-(2-(pyrrolidin-1-yl)ethyl)-1H-indazol-5-yl)pyridin-2(1H)-one dihydrochloride

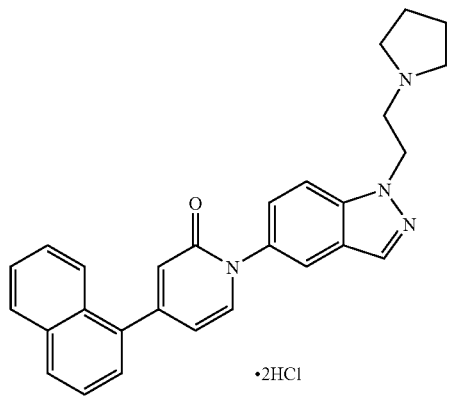

Following the procedure of Example 1, but substituting napthyl-1-boronic acid for phenylboronic acid, the title compound (30.5 mg, 22%) was prepared as orange crystals: mp 128-133° C.; $^{1}$H NMR (500 MHz, CDCl$_3$+CD$_3$OD) δ 8.22 (s, 1H), 8.05-8.03 (m, 1H), 7.99-7.96 (m, 2H), 7.92 (s, 2H), 7.68 (d, J=6.8 Hz, 1H), 7.62-7.54 (m, 5H), 6.86 (s, 1H), 6.70-6.68 (dd, J=5.4, 1.4 Hz, 1H), 4.97-4.96 (br m, 2H), 3.86 (br m, 2H), 3.67-3.66 (br m, 2H), 3.06-2.96 (br m, 2H), 2.13-2.08 (br m, 4H); ESI MS m/z 435 [M+H]$^{+}$. HPLC (Method C) 98.7% (AUC), $t_R$=13.3 min.

Example 14

Preparation of 1-(1-(2-(Pyrrolidin-1-yl)ethyl)-1H-indazol-5-yl)-4-p-tolylpyridin-2(1H)-one hydrochloride

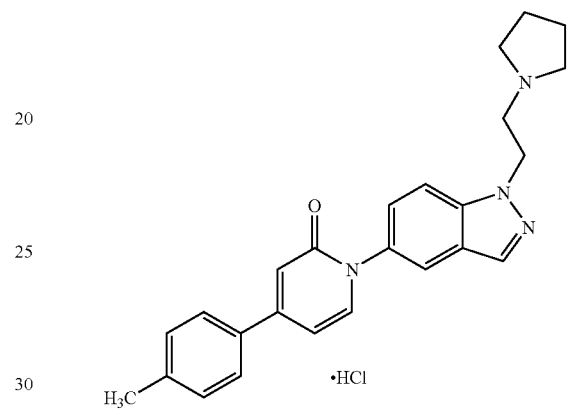

Following the procedure of Example 1, but substituting p-tolylboronic acid for phenylboronic acid, the title compound (52 mg, 55%) was prepared as a brown solid: mp 240-246° C.; $^{1}$H NMR (500 MHz, CD$_3$OD) δ 8.26 (s, 1H), 7.89 (d, J=1.5 Hz, 1H), 7.81 (d, J=8.9 Hz, 1H), 7.32 (d, J=7.3 Hz, 1H), 7.65 (d, J=8.2 Hz, 2H), 7.54-7.52 (dd, J=8.9, 2.0 Hz, 1H), 7.34 (d, J=8.0 Hz, 2H), 6.88 (d, J=1.6 Hz, 1H), 6.86-6.84 (dd, J=7.1, 2.0 Hz, 1H), 4.86 (t, J=5.8 Hz, 2H), 3.81 (t, J=5.8 Hz, 2H), 3.43-3.42 (br m, 4H), 2.41 (s, 3H), 2.12-1.99 (m, 4H); ESI MS m/z 399 [M+H]$^{+}$; HPLC (Method C)>99% (AUC), $t_R$=12.7 min.

Example 15

Preparation of 1-(1-(2-(Pyrrolidin-1-yl)ethyl)-1H-indazol-5-yl)-4-(4-(trifluoromethoxy)phenyl)pyridin-2(1H)-one hydrochloride

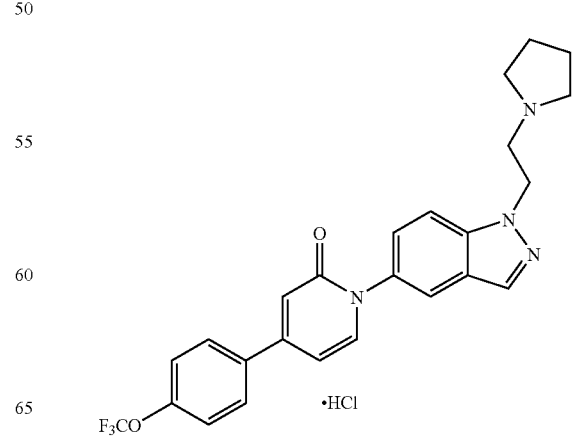

Following the procedure of Example 1, but substituting p-trifluoromethoxyphenylboronic acid for phenylboronic acid, the title compound (51 mg, 46%) was prepared as an orange solid: mp 202-209° C.; $^1$H NMR (500 MHz, CD$_3$OD) δ 8.26 (s, 1H), 7.91 (d, J=1.6 Hz, 1H), 7.88 (d, J=8.7 Hz, 2H), 7.84 (d, J=8.9 Hz, 1H), 7.80 (d, J=7.1 Hz, 1H), 7.55-7.53 (dd, J=8.7 Hz, 1H), 7.45 (d, J=8.3 Hz, 2H), 6.93 (d, J=1.7 Hz, 1H), 6.88-6.86 (dd, J=7.2, 2.0 Hz, 1H), 4.89 (t, J=6.8 Hz, 2H), 3.89 (t, J=6.8 Hz, 2H), 3.74-3.69 (br m, 2H), 3.20-3.15 (br m, 2H), 2.18-2.15 (m, 2H), 2.03-2.00 (m, 2H); ESI MS m/z 469 [M+H]$^+$; HPLC (Method C)>99% (AUC), $t_R$=13.7 min.

Example 16

Preparation of 4-(1-Methyl-1H-indol-5-yL)-1-(1-(2-(pyrrolidin-1-yl)ethyl)-1H-indazol-5-yl)pyridin-2(1H)-one hydrochloride

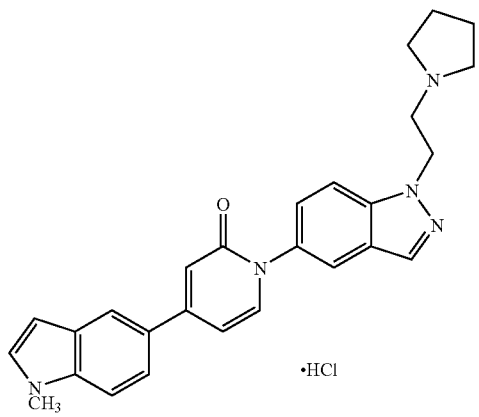

Following the procedure of Example 1, but substituting N-methylindole-5-boronic acid for phenylboronic acid, the title compound (36 mg, 37%) was prepared as a brown solid: $^1$H NMR (500 MHz, CD$_3$OD) δ 8.26 (s, 1H), 8.01 (d, J=1.5 Hz, 1H), 7.91 (d, J=1.5 Hz, 1H), 7.81 (d, J=8.9 Hz, 1H), 7.71 (d, J=7.1 Hz, 1H), 7.60-7.58 (dd, J=8.6, 1.8 Hz, 1H), 7.56-7.54 (dd, J=8.9, 1.9 Hz, 1H), 7.52 (d, J=8.7 Hz, 1H), 7.26 (d, J=3.1 Hz, 1H), 6.97 (dd, J=7.1, 2.0 Hz, 1H), 6.94 (d, J=1.8 Hz, 1H), 6.57 (d, J=3.2 Hz, 1H), 4.88 (t, J=5.7 Hz, 2H), 3.87-3.85 (s overlapping with m, 5H), 3.80-3.10 (br m, 4H), 2.09 (br m, 4H), ESI MS m/z 438 [M+H]$^+$; HPLC (Method C) 98.4% (AUC), $t_R$=12.6 min.

Example 17

Preparation of 4-(4-Cyanophenyl)-1-(1-(2-(pyrrolidin-1-yl)ethyl)-1H-indazol-5-yl)pyridin-2(1H)-one hydrochloride

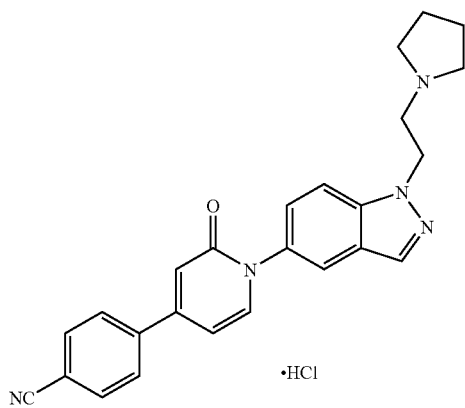

Following the procedure of Example 1, but substituting p-cyanophenylboronic acid for phenylboronic acid, the title compound (23 mg, 23%) was prepared as a yellow solid: mp 92-96° C.; $^1$H NMR (500 MHz, CD$_3$OD) δ 8.23 (s, 1H), 7.94 (d, J=6.6 Hz, 2H), 7.90-7.88 (m, 3H), 7.82 (d, J=2.8 Hz, 1H), 7.80 (s, 1H), 7.53-7.51 (dd, J=8.9, 1.9 Hz, 1H), 6.95 (d, J=1.9 Hz, 1H), 6.86-6.84 (dd, J=7.1, 2.1 Hz, 1H), 4.82 (m, 2H), 3.66 (br m, 2H), 3.26 (br m, 4H), 2.01 (br m, 4H); ESI MS m/z 410 [M+H]; HPLC (Method C)>99% (AUC), $t_R$=11.6 min.

Example 18

Preparation of 4-(4-Methoxyphenyl)-1-(1-(2-(pyrrolidin-1-yl)ethyl)-1H-indazol-5-yl)pyridin-2(1H)-one hydrochloride

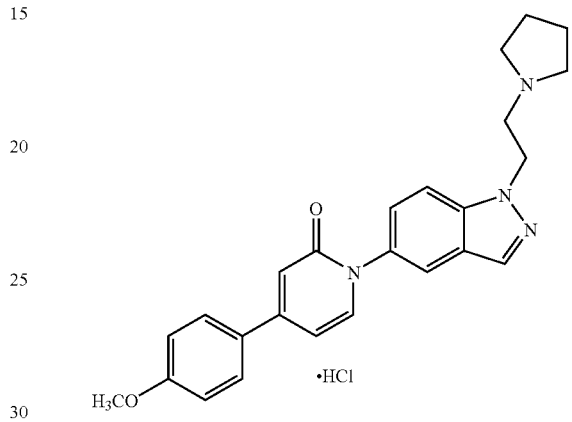

Following the procedure of Example 1, but substituting p-methoxyphenylboronic acid for phenylboronic acid, the title compound (45 mg, 46%) was prepared as an orange solid: mp 105-110° C.; $^1$H NMR (500 MHz, CD$_3$OD) δ 8.26 (s, 1H), 7.91 (d, J=1.5 Hz, 1H), 7.83 (d, J=6.9 Hz, 1H), 7.78-7.43 (m, 3H), 7.56-7.53 (dd, J=8.9 Hz, 1H), 7.09 (d, J=8.9 Hz, 2H), 6.96-6.94 (dd, J=7.1, 2.2 Hz, 1H), 6.93 (d, J=1.7 Hz, 1H), 4.88 (t, J=5.4 Hz, 2H), 3.88-3.86 (s overlapping with m, 5H), 3.73-3.69 (m, 2H), 3.20-3.15 (m, 2H), 2.19-2.14 (m, 2H), 2.03-2.06 (m, 2H); ESI MS m/z 415 [M+H]$^+$; HPLC (Method C)>99% (AUC), $t_R$=12.0 min.

Example 19

Preparation of 4-(4-Fluoro-2-cyanophenyl)-1-(1-(2-(pyrrolidin-1-yl)ethyl)-1H-indazol-5-yl)pyridin-2(1H)-one hydrochloride

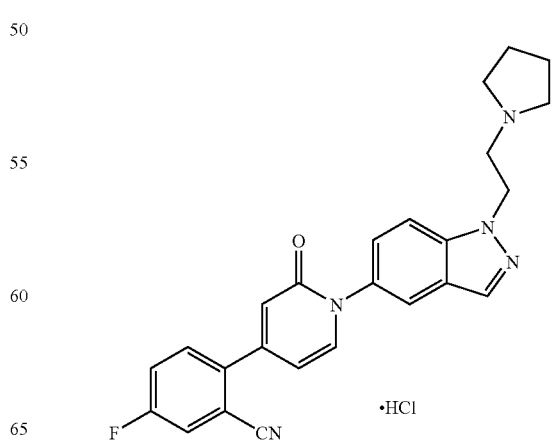

Following the procedure of Example 1, but substituting 2-cyano-4-fluorophenylboronic acid pinacol ester for phenylboronic acid, the title compound (45 mg, 44%) was prepared as a brown solid: mp 81-86° C.; ¹H NMR (500 MHz, CD₃OD) δ 8.26 (s, 1H), 7.94-7.93 (m, 1H), 7.83 (d, J=2.1 Hz, 1H), 7.82 (s, 1H), 7.77-7.74 (m, 2H), 7.63-7.59 (dt, J=8.3, 2.7 Hz, 1H), 7.57-7.53 (dd, J=8.9, 2.0 Hz, 1H), 6.83 (d, J=1.9 Hz, 1H), 6.73-6.70 (dd, J=7.0, 2.0 Hz, 1H), 4.89 (t, J=5.8 Hz, 2H), 3.89-3.86 (t, J=5.8 Hz, 2H), 3.72-3.61 (br m, 2H), 3.26-3.15 (br m, 2H), 2.11-2.05 (m, 4H); ESI MS m/z 428 [M+H]⁺; HPLC (Method C) 98.5% (AUC), $t_R$=11.7 min.

Example 20

Preparation of 4-(2,4-Dimethoxyphenyl)-1-(1-(2-(pyrrolidin-1-yl)ethyl)-1H-indazol-5-yl)pyridin-2(1H)-one hydrochloride

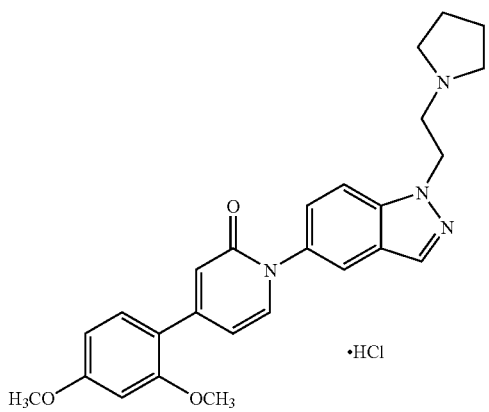

Following the procedure of Example 1, but substituting 2,4-dimethoxyphenylboronic acid for phenylboronic acid, the title compound (29.7 mg, 61%) was prepared as orange crystals: mp 95-115° C.; ¹H NMR (500 MHz, CD₃OD) δ 8.26 (s, 1H), 7.93 (d, J=1.7 Hz, 1H), 7.84 (d, J=8.9 Hz, 1H), 7.73 (d, J=8.1 Hz, 1H), 7.56-7.54 (dd, J=8.9, 2.0 Hz, 1H), 7.45 (d, J=8.4 Hz, 1H) 6.96-6.92 (m, 2H), 6.70-6.67 (m, 2H), 4.89 (t, J=5.8 Hz, 2H), 3.89-3.87 (m, 8H), 3.73-3.69 (br m, 2H), 3.19-3.16 (br m, 2H) 2.17-2.16 (br m, 2H) 2.03-2.01 (br m, 2H); ESI MS m/z 445 [M+H]⁺; HPLC (Method C)>99% (AUC), $t_R$=12.2 min.

Example 21

Preparation of 4-(2,4-Difluorophenyl)-1-(1-(2-(pyrrolidin-1-yl)ethyl)-1H-indazol-5-yl pyridin-2(1H)-one hydrochloride

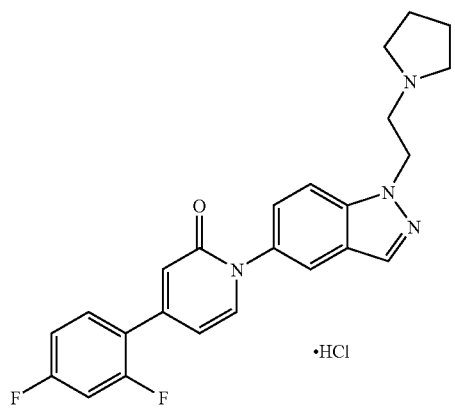

Following the procedure of Example 1, but substituting 2,4-difluorophenylboronic acid for phenylboronic acid, the title compound (20.4 mg, 45%) was prepared as a brown solid: mp 235-255° C.; ¹H NMR (500 MHz, CD₃OD) δ 8.26 (s, 1H), 7.91 (d, J=1.4 Hz, 1H), 7.80 (d, J=8.9 Hz, 1H), 7.75 (d, J=6.9 Hz, 1H), 7.71-7.62 (m, 1H), 7.55-7.53 (dd, J=8.8, 1.9 Hz, 1H), 7.18-7.12 (m, 2H), 6.82 (s, 1H), 6.74-6.71 (dt, J=7.1, 1.9 Hz, 1H), 4.88 (t, J=5.8, 2H), 3.85 (t, J=5.7 Hz, 2H), 3.56-3.32 (br m, 4H), 2.20-1.91 (br m, 4H); ESI MS m/z 421 [M+H]⁺; HPLC (Method C)>99% (AUC), $t_R$=12.3 min.

Example 22

Preparation of 4-(4-Isopropoxyphenyl)-1-(1-(2-(pyrrolidin-1-yl)ethyl)-1H-indazol-5-yl)pyridine-2(1H)-one hydrochloride

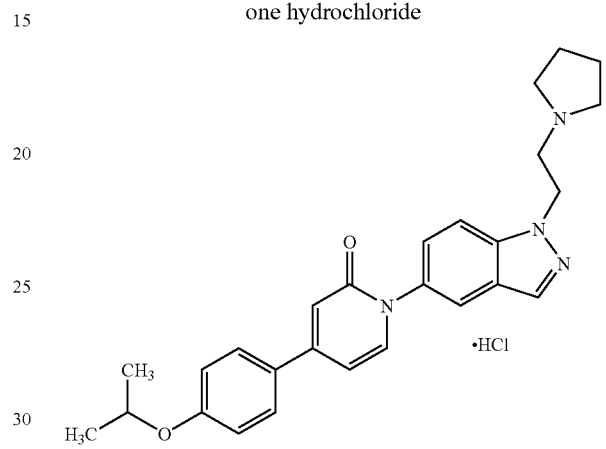

Following the procedure of Example 1, but substituting 4-isopropoxyphenylboronic acid for phenylboronic acid, the title compound (63 mg, 65%) was prepared as gray crystals: mp 235-250° C.; ¹H NMR (500 MHz, CD₃OD) δ 8.25 (s, 1H), 7.89 (d, J=1.4 Hz, 1H), 7.81 (d, J=8.9 Hz, 1H), 7.72-7.69 (m, 3H), 7.54-7.51 (dd, J=8.9, 2.0 Hz, 1H), 7.05-7.02 (d, J=8.8 Hz, 2H), 6.86-6.84 (m, 2H), 4.87 (t, J=5.8 Hz, 2H), 4.72-4.67 (m, 1H), 3.84 (t, J=5.7 Hz, 2H), 3.50-3.32 (br m, 4H), 2.15-2.01 (br m, 4H), 1.35 (d, J=6.0 Hz, 6H); ESI MS m/z 443 [M+H]⁺; HPLC (Method C) 98.3% (AUC), $t_R$=13.2 min.

Example 23

Preparation of 4-(2,4-bis(Trifluoromethyl)phenyl)-1-(1-(2-(pyrrolidin-1-yl)ethyl)-1H-indazol-5-yl)pyridin-2(1H)-one hydrochloride

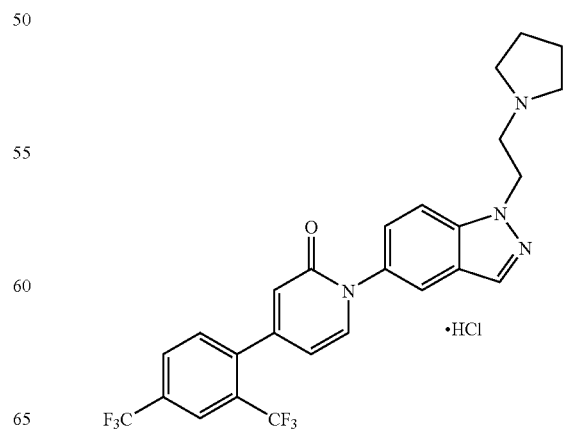

Following the procedure of Example 1, but substituting 2,4-bis(trifluoromethyl)phenylboronic acid for phenylboronic acid, the title compound (24.9 mg, 5%) was prepared as gray crystals: mp 235-245° C.; $^1$H NMR (500 MHz, CD$_3$OD) δ 8.25 (s, 1H), 8.13 (s, 1H) 8.09 (d, J=8.0 Hz, 1H), 7.93 (d, J=1.7, 1H), 7.82 (d, J=9.0 Hz, 1H), 7.78 (d, J=7.0 Hz, 1H), 7.75 (d, J=8.1 Hz, 1H), 7.56-7.54 (dd, J=8.9, 1.9 Hz, 1H), 6.64 (d, J=1.7 Hz, 1H), 6.53-6.51 (dd, J=7.0, 1.8 Hz, 1H), 4.87-4.84 (br m, 2H), 3.81-3.68 (br m, 2H), 3.44-3.34 (br m, 4H), 2.12-1.94 (br m, 4H); ESI MS m/z 521 [M+H]$^+$; HPLC (Method C)>99% (AUC), t$_R$=14.2 min.

Example 24

Preparation of 4-(4-Butoxy-2-methylphenyl)-1-(1-(2-(pyrrolidin-1-yl)ethyl)-1H-indazol-5-yl)pyridin-2(1H)-one hydrochloride

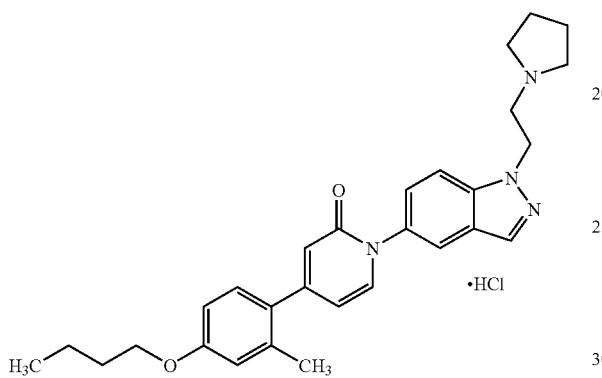

Following the procedure of Example 1, but substituting 4-(butyloxy)-2-methylphenylboronic acid for phenylboronic acid, the title compound (82.3 mg, 24%) was prepared as brown crystals: mp 80-95° C.; $^1$H NMR (500 MHz, CD$_3$OD) δ 8.26 (s, 1H), 7.92 (d, J=1.4 Hz, 1H), 7.82 (d, J=8.9 Hz, 1H), 7.70 (d, J=6.9 Hz, 1H), 7.56-7.54 (dd, J=8.9, 2.0 Hz, 1H), 7.24 (d, J=8.4 Hz, 1H), 6.88 (d, J=2.4 Hz, 1H), 6.86-6.84 (dd, J=8.4, 2.6, 1H), 6.58-6.56 (m, 2H), 4.89 (t, J=5.8 Hz, 2H), 4.02 (t, J=6.7 Hz, 2H), 3.87 (t, J=5.8 Hz, 2H), 3.74-3.69 (br m, 2H), 3.20-3.15 (br m, 2H), 2.39 (s, 3H), 2.19-2.16 (br m, 2H), 2.04-2.00 (br m, 2H), 1.80-1.75 (m, 2H), 1.55-1.49 (m, 2H), 1.00 (t, J=7.4 Hz, 3H); ESI MS m/z 471 [M+H]$^+$; HPLC (Method C) 94.6% (AUC), t$_R$=14.8 min.

Example 25

Preparation of 1-(1-(2-(Pyrrolidin-1-yl)ethyl)-1H-indazol-5-yl)-4-o-tolylpyridin-2(1H)-one hydrochloride

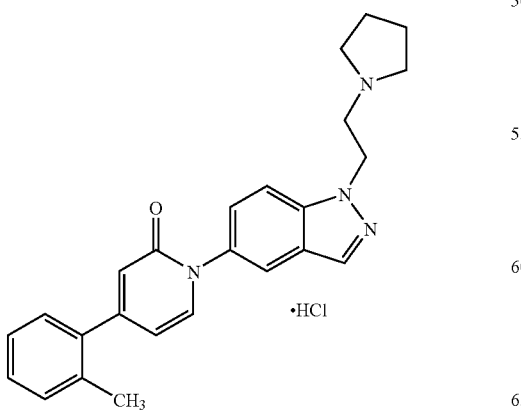

Following the procedure of Example 1, but substituting o-tolylboronic acid for phenylboronic acid, the title compound (34.3 mg, 79%) was prepared as orange crystals: mp 80-95° C.; $^1$H NMR (500 MHz, CD$_3$OD) δ 8.26 (s, 1H), 7.93 (d, J=1.5 Hz, 1H) 7.82 (d, J=8.9 Hz, 1H), 7.72 (d, J=7.0 Hz, 1H), 7.57 (dd, J=8.9, 2.1 Hz, 1H), 7.35-7.33 (m, 2H), 7.30-7.29 (m, 2H), 6.58 (d, J=1.4 Hz, 1H), 6.55-6.53 (dd, J=7.0, 2.2 Hz, 1H), 4.89 (t, J=5.7 Hz, 2H), 3.87 (t, J=5.7 Hz, 2H), 3.76-3.67 (br m, 2H), 3.19-3.15 (br m, 2H), 2.39 (s, 3H) 2.22-2.11 (br m, 2H), 2.03-2.01 (br m, 2H); ESI MS m/z 399 [M+H]$^+$; HPLC (Method C)>99% (AUC), t$_R$=12.4 min.

Example 26

Preparation of 4-(4-(Benzyloxy)-2-methylphenyl)-1-(1-(2-(pyrrolidin-1-yl)ethyl)-1H-indazol-5-yl)pyridin-2(1H)-one hydrochloride

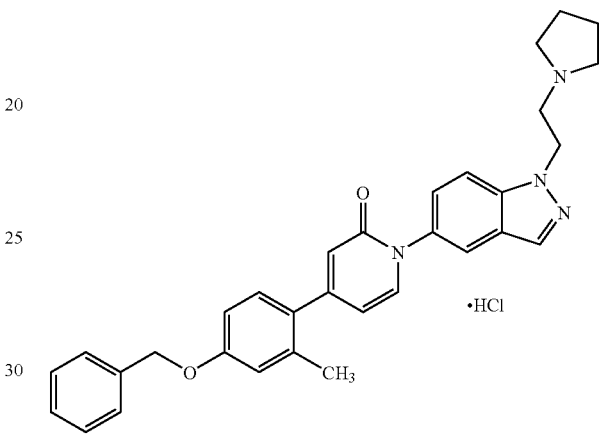

Following the procedure of Example 1, but substituting 4-(benzyloxy)-2-methylphenylboronic acid for phenylboronic acid, the title compound (45.5 mg, 51%) was prepared as orange crystals: mp 75-85° C.; $^1$H NMR (500 MHz, CD$_3$OD) δ 8.25 (s, 1H), 7.91 (d, J=1.8 Hz, 1H), 7.81 (d, J=8.9 Hz, 1H), 7.69 (d, J=6.9 Hz, 1H), 7.55-7.53 (dd, J=8.9, 1.9 Hz, 1H), 7.45 (d, J=7.3 Hz, 2H), 7.38 (t, J=7.5 Hz 2H), 7.32 (d, J=5.3, 1H), 7.25 (d, J=8.5 Hz, 1H), 6.98 (d, J=2.5 Hz, 1H), 6.95-6.93 (dd, J=8.4, 2.6 Hz, 1H), 6.56 (d, J=1.7 Hz, 1H), 6.55-6.53 (dd, J=6.9, 1.9 Hz, 1H), 5.13 (s, 2H), 4.87 (t, J=5.8 Hz, 2H), 3.88-3.79 (br m, 2H), 3.34-3.32 (br m, 4H), 2.38 (s, 3H) 2.16-2.00 (br m, 4H); ESI MS m/z 505 [M+H]$^+$. HPLC (Method C)>99% (AUC), t$_R$=14.7 min.

Example 27

Preparation of 4-(4-Chloro-2-methoxyphenyl)-1-(1-(2-(pyrrolidin-1-yl)ethyl)-1H-indazol-5-yl)pyridin-2(1H)-one hydrochloride

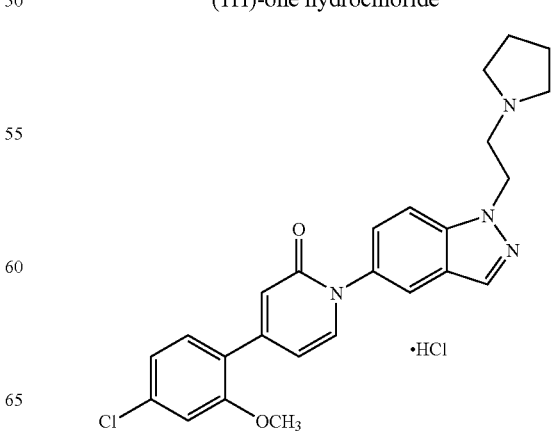

Following the procedure of Example 1, but substituting 4-chloro-2-methoxyphenylboronic acid for phenylboronic acid, the title compound (22.1 mg, 30%) was prepared as a white powder: mp 248-256° C.; $^1$H NMR (500 MHz, CD$_3$OD) δ 8.25 (s, 1H), 7.90 (d, J=1.4 Hz, 1H), 7.81 (d, J=8.9 Hz, 1H), 7.66 (d, J=7.1 Hz, 1H), 7.54-7.52 (dd, J=8.9, 1.9 Hz, 1H), 7.42 (d, J=8.2 Hz, 1H) 7.19 (d, J=1.8 Hz, 1H), 7.11-7.09 (dd, J=8.2, 1.9 Hz, 1H), 6.78 (t, J=1.5 Hz 2H), 4.88 (t, J=5.6 Hz, 2H), 3.89 (s, 3H), 3.85 (t, J=5.7, 2H), 3.80-3.33 (br m, 4H), 2.17-2.00 (br m, 4H); ESI MS m/z 449 [M+H]$^+$; HPLC (Method C) 99.9% (AUC), $t_R$=13.1 min.

Example 28

Preparation of 4-(Benzo[d][1,3]dioxol-5-yl)-1-(1-(2-(pyrrolidin-1-yl)ethyl)-1H-indazol-5-yl)pyridin-2(1H)-one hydrochloride

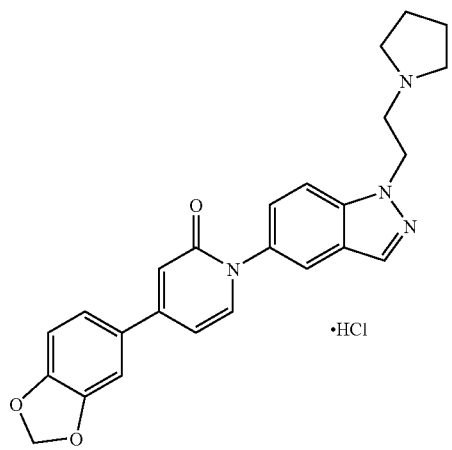

Following the procedure of Example 1, but substituting 3,4-methylenedioxyphenylboronic acid for phenylboronic acid, the title compound (24.1 mg, 52%) was prepared as orange-brown crystals: mp 75-85° C.; $^1$H NMR (500 MHz, CD$_3$OD) δ 8.25 (s, 1H), 7.90 (d, J=1.4 Hz, 1H) 7.82 (d, J=8.9 Hz, 1H), 7.73-7.71 (dd, J=5.1, 2.7 Hz, 1H), 7.54-7.52 (d, J=7.9, 1H), 7.32-7.30 (dd, J=8.1, 1.9 Hz, 1H), 7.27 (d, J=1.8, 1H), 6.97 (d, J=8.1 Hz, 1H), 6.85-6.83 (m, 2H), 6.05 (s, 2H), 4.88 (t, J=5.8 Hz, 2H), 3.87 (t, J=5.8 Hz, 2H), 3.74-3.69 (br m, 2H), 3.20-3.15 (br m, 2H) 2.19-2.16 (br m, 2H), 2.03-2.00 (br m, 2H); ESI MS m/z 429 [M+H]$^+$; HPLC (Method C) 97.7% (AUC), $t_R$=11.7 min.

Example 29

Preparation of 4-(4-Methoxy-2-methylphenyl)-1-(1-(2-(pyrrolidin-1-yl)ethyl)-1H-indazol-5-yl)pyridin-2(1H)-one hydrochloride

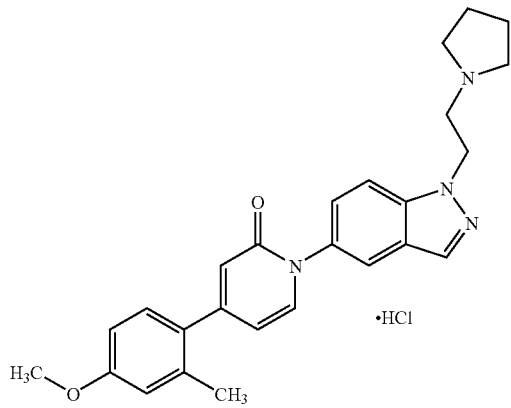

Following the procedure of Example 1, but substituting 4-methoxy-2-methylphenylboronic acid for phenylboronic acid, the title compound (10.3 mg, 20%) was prepared as orange-brown crystals: mp 205-215° C.; $^1$H NMR (500 MHz, CD$_3$OD) δ 8.26 (s, 1H), 7.91 (s, 1H), 7.82 (d, J=8.6 Hz, 1H), 7.69 (d, J=6.9 Hz, 1H), 7.55 (d, J=8.5 Hz, 1H), 7.25 (d, J=8.5 Hz, 1H), 6.90-6.86 (m, 2H), 6.56-6.53 (m, 2H), 4.92-4.85 (br m, 2H), 3.90-3.79 (br m, 5H), 3.75-3.32 (br m, 4H), 2.39 (s, 3H), 2.16-2.01 (br m, 4H); ESI MS m/z 429 [M+H]$^+$; HPLC (Method D) 98.6% (AUC), $t_R$=14.2 min.

Example 30

Preparation of 4-(5-Methylpyridin-2-yl)-1-(1-(2-(pyrrolidin-1-yl)ethyl)-1H-indazol-5-yl)pyridin-2(1H)-one hydrochloride a) 1-(1-(2-(Pyrrolidin-1-yl)ethyl)-1H-indazol-5-yl)-4-(trimethylstannyl)pyridin-2(1H)-one

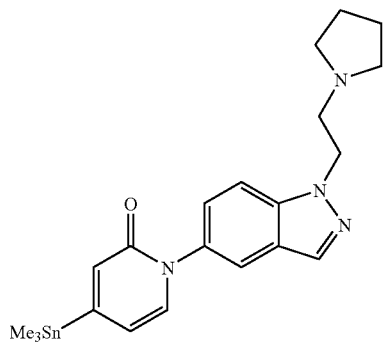

1-(2-(Pyrrolidin-1-yl)ethyl)-1H-indazol-5-yl)pyridin-2(1H)-one-4-trifluoromethanesulfonate (250 mg, 0.54 mmol) and hexamethylditin (360 mg, 1.1 mmol) were stirred in dry toluene (5 mL)/DMSO (1 mL) and degassed with a nitrogen stream as the temperature was increased to 100° C. Palladium tetrakistriphenylphosphine (62 mg, 0.054 mmol) was added and the reaction was maintained at 100° C. under a nitrogen atmosphere for 2 h. Upon cooling, the mixture was purified by Combiflash chromatography (12 g ISCO column eluting with methylene chloride and methanol/ammonia (10:1); 100% methylene chloride to 20% methanol/ammonia over 30 min at 25 mL/min). Concentration of the appropriate fractions provided the desired stannane (143 mg, 56%) as a colorless oil; $^1$H NMR (500 MHz, CDCl$_3$) δ 8.03 (s, 1H), 7.67 (d, J=1.5 Hz, 1H), 7.52 (d, J=8.9 Hz, 1H), 7.41-7.39 (dd, J=8.9, 1.0 Hz, 1H), 7.29 (d, J=6.6 Hz, 1H), 6.84 (s, 1H), 6.32-6.30 (dd, J=6.6, 0.9 Hz, 1H), 4.55 (t, J=7.3 Hz, 2H), 3.00 (t, J=7.3 Hz, 2H), 2.60-2.57 (m, 4H), 1.80-1.77 (m, 4H), 0.34 (s, 9H).

b) 4-(5-Methylpyridin-2-yl)-1-(1-(2-(pyrrolidin-1-yl)ethyl)-1H-indazol-5-yl)pyridin-2(1H)-one hydrochloride

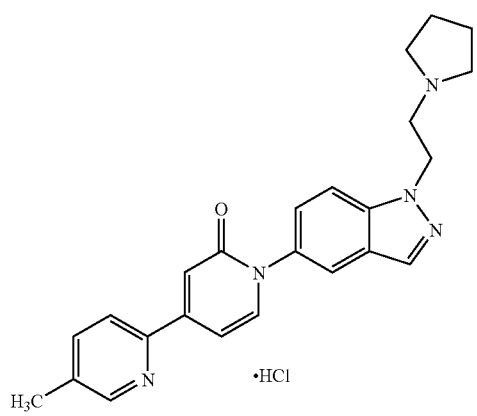

1-(1-(2-(Pyrrolidin-1-yl)ethyl)-1H-indazol-5-yl)-4-(trimethylstannyl)pyridin-2(1H)-one (47 mg, 0.11 mmol) and 2-bromo-5-methylpyridine (94 mg, 0.55 mmol) were stirred dry toluene (3 mL)/DMSO (1 mL) and degassed with a nitrogen stream as the temperature was increased to 100° C. Palladium tetrakistriphenylphosphine (13 mg, 0.011 mmol) was added and the reaction was maintained at 100° C. under a nitrogen atmosphere for 16 h. Upon cooling, the mixture was purified by Combiflash chromatography (12 g ISCO column eluting with methylene chloride and methanol/ammonia (10: 1); 100% methylene chloride to 20% methanol/ammonia over 30 min at 40 mL/min). Concentration of the appropriate fractions provided the free base. Conversion to the hydrochloride salt as in Example 1 gave the title compound (48 mg, 51%) as a white solid: mp 230-234° C.; $^1$H NMR (500 MHz, CD$_3$OD) δ 8.56 (s, 1H), 8.23 (s, 1H), 7.91-7.89 (m, 2H), 7.81-7.76 (m, 3H), 7.54-7.51 (dd, J=8.9, 2.0 Hz, 1H), 7.24 (s, 1H) 7.17-7.15 (dd, J=7.5, 1.9 Hz, 1H), 4.92-4.84 (br m, 2H), 3.74-3.55 (br m, 2H), 3.25-3.06 (br m, 4H), 2.43 (s, 3H), 2.09-1.88 (br m, 4H); ESI MS m/z 400 [M+H]$^+$; HPLC (Method C)>99% (AUC), t$_R$=10.3 min.

Example 31

Preparation of 4-(2-Chloro-4-(trifluoromethyl)phenyl)-1-(1-(2-(pyrrolidin-1-yl)ethyl)-1H-indazol-5-yl)pyridin-2(1H)-one hydrochloride

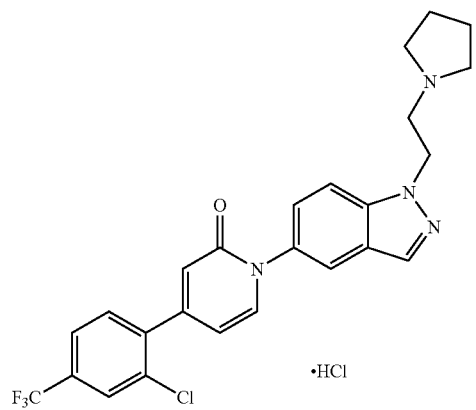

Following the procedure of Example 30, but substituting 2-chloro-5-(trifluoromethyl)iodobenzene for 2-bromo-5-methylpyridine, the title compound (21 mg, 38%) was prepared as a white solid: $^1$H NMR (500 MHz, CD$_3$OD) δ 8.26 (s, 1H), 7.94-7.91 (m, 2H), 7.83 (d, J=8.9 Hz, 1H), 7.80-7.77 (m, 2H), 7.70 (d, J=8.0 Hz, 1H), 7.57-7.55 (dd, J=8.9, 1.9 Hz, 1H), 6.72 (d, J=1.5 Hz, 1H), 6.63-6.62 (dd, J=7.0, 1.8 Hz, 1H), 4.89 (t, J=5.6, 2H), 3.87 (t, J=5.6, 2H), 3.80-3.57 (br m, 2H), 3.20-3.02 (br m, 2H), 2.23-194 (br m, 4H); ESI MS m/z 487 [M+H]$^+$; HPLC (Method C) 98.4% (AUC), t$_R$=13.9 min.

Example 32

Preparation of 1-(1-(2-(Pyrrolidin-1-yl)ethyl)-1H-indazol-5-yl)-4-(quinolin-2-yl)pyridin-2(1H)-one trihydrochloride

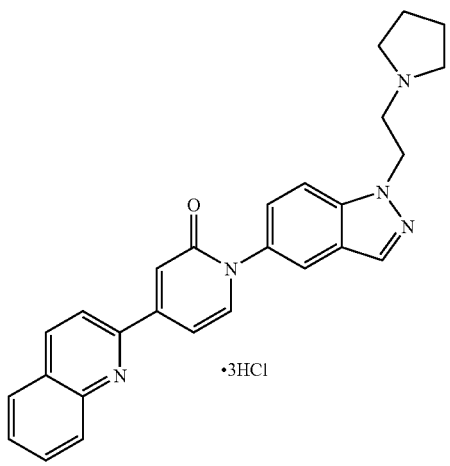

Following the procedure of Example 30, but substituting 2-chloroquinoline for 2-bromo-5-methylpyridine, the title compound (12 mg, 21%) was prepared as a yellow solid: mp 220-225° C.; $^1$H NMR (500 MHz, CD$_3$OD) δ 8.97 (d, J=8.6 Hz, 1H), 8.33 (d, J=8.6 Hz, 1H), 8.30 (d, J=8.1 Hz, 1H), 8.28 (s, 1H), 8.25 (d, J=8.1 Hz, 1H), 8.10-8.07 (m, 1H), 7.98-7.96 (m, 2H), 7.91 (d, J=8.0 Hz, 1H), 7.87 (d, J=7.0 Hz, 1H), 7.60-7.58 (dd, J=8.9, 2.0 Hz, 1H), 7.40 (d, J=1.9 Hz, 1H), 7.25-7.23 (dd, J=7.1, 2.0 Hz, 1H), 4.91 (t, J=5.9, 2H), 3.88 (t, J=5.9, 2H), 3.75-3.70 (m, 2H), 3.21-3.15 (m, 2H), 2.19-2.16 (m, 2H), 2.05-2.01 (m, 2H); ESI MS m/z 436 [M+H]$^+$; HPLC (Method C)>99% (AUC), t$_R$=12.1 min.

Example 33

Preparation of 4-(5-Chloropyridin-2-yl)-1-(1-(2-(pyrrolidin-1-yl)ethyl)-1H-indazol-5-yl)pyridin-2(1H)-one trihydrochloride

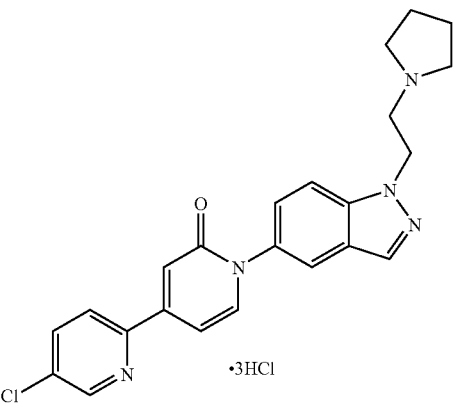

Following the procedure of Example 30, but substituting 2-bromo-5-chloropyridine for 2-bromo-5-methylpyridine, the title compound (14 mg, 26%) was prepared as a yellow solid: $^1$H NMR (500 MHz, CD$_3$OD) δ 8.77-8.69 (m, 1H), 8.28 (d, J=1.7 Hz, 1H), 8.05 (d, J=8.5 Hz, 1H), 8.03-8.01 (dd, J=8.5, 2.4 Hz, 1H), 7.93 (d, J=1.4 Hz, 1H), 7.84 (d, J=8.9 Hz, 1H), 7.81 (d, J=7.1 Hz, 1H), 7.57-7.55 (dd, J=8.9, 1.9 Hz, 1H), 7.33 (d, J=1.6 Hz, 1H), 7.24-7.22 (dd, J=7.2, 2.0 Hz, 1H), 4.90 (t, J=5.8, 2H), 3.89 (t, J=5.8, 2H), 3.75-3.71 (m, 2H), 3.22-3.12 (m, 2H), 2.21-2.16 (m, 2H), 2.05-2.02 (m, 2H); ESI MS m/z 420 [M+H]$^+$; HPLC (Method C)>99% (AUC), $t_R$=11.6 min.

Example 34

Preparation of 1-(1-(2-(Pyrrolidin-1-yl)ethyl)-1H-indazol-5-yl)-4-(5-(trifluoromethyl)pyridin-2-yl)pyridin-2(1H)-one trihydrochloride

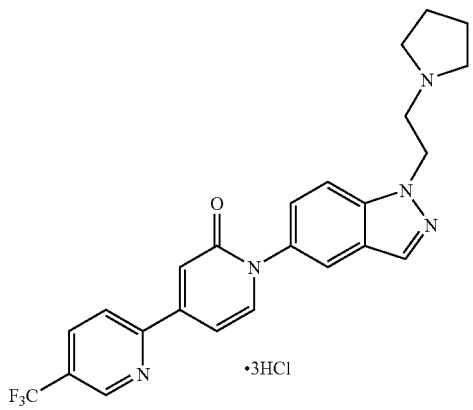

Following the procedure of Example 30, but substituting 2-bromo-5-trifluoromethylpyridine for 2-bromo-5-methylpyridine, the title compound (10 mg, 16%) was prepared as a yellow solid: $^1$H NMR (500 MHz, CD$_3$OD) δ 9.05 (s, 1H), 8.29-8.27 (dd, J=8.4, 2.2 Hz, 1H), 8.27 (s, 1H), 8.22 (d, J=8.4 Hz, 1H), 7.93 (d, J=1.6 Hz, 1H), 7.84-7.82 (2 overlapping d, J=8.9, 7.0 Hz, 2H) 7.57-7.55 (dd, J=8.9, 1.9 Hz, 1H), 7.40 (d, J=1.8 Hz, 1H), 7.27-7.25 (dd, J=7.1, 1.9 Hz, 1H), 4.89 (t, J=5.8, 2H), 3.87 (t, J=5.8, 2H), 3.74-3.70 (m, 2H), 3.21-3.15 (m, 2H), 2.19-2.15 (m, 2H), 2.04-2.00 (m, 2H); ESI MS m/z 454 [M+H]$^+$; HPLC (Method C)>99% (AUC), $t_R$=12.4 min.

Example 35

Preparation of 1-(1-(2-(Pyrrolidin-1-yl)ethyl)-1H-indazol-5-yl)-4-(quinazolin-2-yl)pyridin-2(1H)-one dihydrochloride

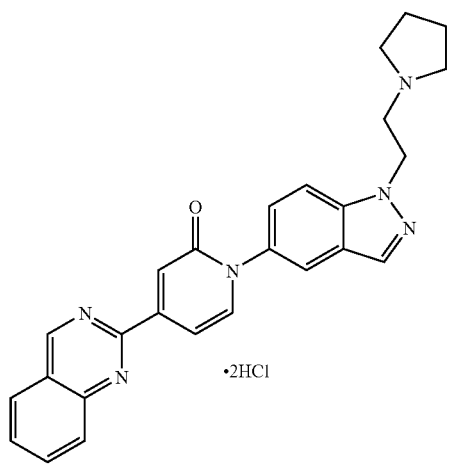

Following the procedure of Example 30, but substituting 2-chloroquinazoline for 2-bromo-5-methylpyridine, the title compound (12 mg, 23%) was prepared as a green solid: $^1$H NMR (500 MHz, CD$_3$OD) δ 9.66 (s, 1H), 8.27 (s, 1H), 8.19-8.15 (m, 2H), 8.09-8.06 (m, 1H), 7.95 (d, J=1.6 Hz, 1H), 7.91 (d, J=1.6 Hz, 1H) 7.86-7.81 (m, 3H), 7.69-7.67 (dd, J=7.1, 1.8 Hz, 1H), 7.60-7.57 (dd, J=8.9, 2.0 Hz, 1H), 4.90 (t, J=5.8, 2H), 3.88 (t, J=5.9, 2H), 3.75-3.70 (m, 2H), 3.21-3.16 (br m, 2H), 2.20-2.17 (m, 2H), 2.04-2.00 (m, 2H); ESI MS m/z 437 [M+H]$^+$; HPLC (Method C)>99% (AUC), $t_R$=11.6 min.

Example 36

Preparation of 1-(1-(2-(Pyrrolidin-1-yl)ethyl)-1H-indazol-5-yl)-4-(6-(trifluoromethyl)pyridazin-3-yl)pyridin-2(1H)-one hydrochloride

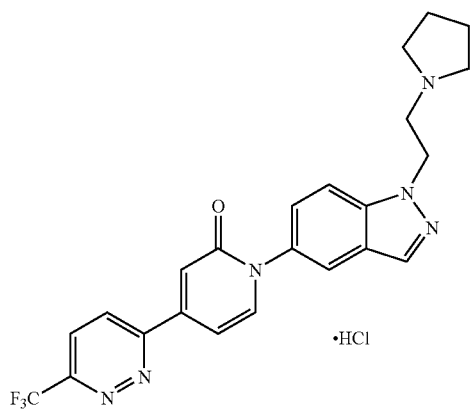

Following the procedure of Example 30, but substituting 3-chloro-6-(trifluoromethyl)pyridazine for 2-bromo-5-methylpyridine, the title compound (14 mg, 26%) was prepared as a yellow solid: $^1$H NMR (500 MHz, CD$_3$OD) δ 8.53 (d, J=8.9 Hz, 1H), 8.28-8.26 (m, 2H), 7.95 (d, J=1.6 Hz, 1H), 7.91 (d, J=7.0 Hz, 1H), 7.86 (d, J=8.9 Hz, 1H), 7.58-7.56 (dd, J=8.9, 1.9 Hz, 1H) 7.44 (d, J=1.6 Hz, 1H), 7.36-7.34 (dd, J=7.1, 2.0 Hz, 1H), 4.89 (t, J=5.9, 2H), 3.88 (t, J=5.9, 2H), 3.72-3.70 (br m, 2H), 3.21-3.15 (br m, 2H), 2.19-2.17 (m, 2H), 2.09-2.07 (m, 2H); ESI MS m/z 455 [M+H]$^+$; HPLC (Method C) 97.7% (AUC), $t_R$=11.6 min.

Example 37

Preparation of 1-(1-(2-Morpholinoethyl)-1H-indazol-5-yl)-4-(4-(trifluoromethyl)phenyl)pyridin-2(1H)-one hydrochloride a) 5-Iodo-1H-indazole

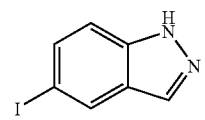

Chemical Formula: C$_7$H$_5$IN$_2$
Exact Mass: 243.95
Molecular Weight: 244.03

A solution of 4-iodo-2-methylaniline (10.0 g, 42.9 mmol) in glacial acetic acid (400 mL) was treated with a solution of NaNO$_2$ (2.96 g, 42.9 mmol) in water (10 mL). After stirring for 6 hours, the mixture was concentrated to dryness and dissolved in ethyl acetate (EtOAc). Filtration through a pad of silica gel (EtOAc) provided the title compound (10.4 g, 99%) as a deep purple solid: ESI MS m/z 245 [M+H]$^+$.

b) 1-(2,2-Dimethoxyethyl)-5-iodo-1H-indazole

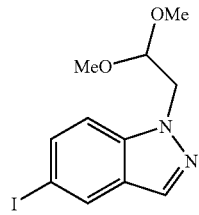

Chemical Formula: C$_{11}$H$_{13}$IN$_2$O$_2$
Exact Mass: 332
Molecular Weight: 332.14

To a solution of 5-iodio-1H-indazole (8.28 g, 33.9 mmol) in DMSO (104 mL) was added 2-bromoacetaldehyde dimethyl acetal (7.9 mL, 68 mmol) and Cs$_2$CO$_3$ (44.1 g, 136 mmol). The reaction was stirred at 40° C. for 18 h; then the reaction was diluted with H$_2$O (100 mL) and EtOAc (175 mL). The partitioned material was extracted with EtOAc (4×175 mL). The organics were washed with brine (2×100 mL), dried (Na$_2$SO$_4$), filtered, and concentrated. Purification by flash chromatography (silica gel, hexanes with 0.1% Et$_3$N/EtOAc with 0.1% Et$_3$N, 100:0 to 90:10) gave the title compound (4.49 g, 46%) as a light orange powder: $^1$H NMR (500 MHz, CDCl$_3$) δ 8.07 (d, J=1.0 Hz, 1H), 7.92 (d, J=0.5 Hz, 1H), 7.60 (dd, J=9.0, 1.5 Hz, 1H), 7.28 (d, J=9.0 Hz, 1H), 4.71 (t, J=5.5 Hz, 1H), 4.44 (d, J=5.5 Hz, 2H), 3.33 (s, 6H).

c) 4-(4-(Trifluoromethyl)phenyl)pyridine 1-oxide

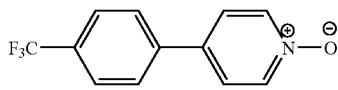

Chemical Formula: C$_{12}$H$_8$F$_3$NO
Exact Mass: 239.06
Molecular Weight: 239.19

A solution of 4-(trifluoromethyl)phenylboronic acid (1.78 g, 9.37 mmol) in DME (10 mL) and aqueous K$_2$CO$_3$ (12 mL, 1.8 M) was degassed with argon for 20 minutes. Triphenylphosphine (797 mg, 3.04 mmol), palladium(II)acetate (174 mg, 0.775 mmol), and 4-chloropyridine 1-oxide (1.00 g, 7.72 mmol) were added sequentially, and the mixture was heated to reflux under an argon atmosphere. After stirring at reflux for 14 h, the mixture was allowed to cool and then filtered. The filtrate was diluted with H$_2$O (25 mL) and extracted with EtOAc (3×25 mL). The organics were dried over Na$_2$SO$_4$, filtered and concentrated to dryness. Purification by flash column chromatography (silica gel, CH$_2$Cl$_2$/MeOH, 95:5) gave the title compound (465 mg, 25%) as white crystals: $^1$H NMR (500 MHz, CDCl$_3$) δ 8.29 (d, J=7.2 Hz, 2H), 7.75 (d, J=8.3 Hz, 2H), 7.69 (d, J=8.2 Hz, 2H), 7.52 (d, J=7.2 Hz, 2H); ESI MS m/z 240 [M+H]$^+$.

d) 4-(4-(Trifluoromethyl)phenyl)pyridin-2(1H)-one

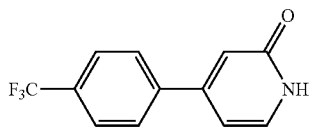

Chemical Formula: C$_{12}$H$_8$F$_3$NO
Exact Mass: 239.06
Molecular Weight: 239.19

A stirred solution of 4-(4-(trifluoromethyl)phenyl)pyridine 1-oxide (465 mg, 1.94 mmol) in Ac$_2$O (10 mL) under nitrogen atmosphere was heated from 110 to 130° C. over 4.5 h. Then the mixture was heated at reflux for 2 h and then allowed to cool. The mixture was concentrated to dryness and then treated with MeOH and water (10 mL, 1:1). After stirring at room temperature for 6 h, the mixture was heated to reflux for 2.5 h. The mixture was allowed to cool and was concentrated to dryness. Purification by flash column chromatography (silica gel, CH$_2$Cl$_2$/MeOH, 95:5) gave the title compound (336 mg, 72%) as a light brown powder: $^1$H NMR (500 MHz, CDCl$_3$) δ 12.67 (br s, 1H), 7.76 (d, J=8.2 Hz, 2H), 7.69 (d, J=8.3 Hz, 2H), 7.47 (d, J=6.8 Hz, 1H), 6.80 (d, J=1.6 Hz, 1H), 6.54 (dd, J=6.8, 1.8 Hz, 1H); ESI MS m/z 240 [M+H]$^+$.

e) 1-(1-(2,2-Dimethoxyethyl)-1H-indazol-5-yl)-4-(4-(trifluoromethyl)phenyl)pyridin-2(1H)-one

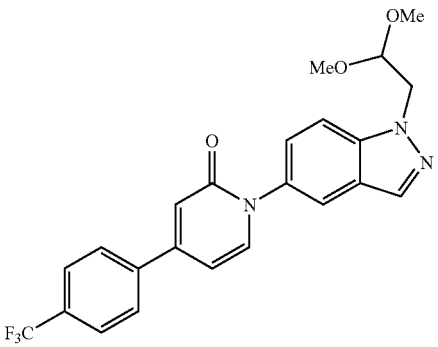

Chemical Formula: C$_{23}$H$_{20}$F$_3$N$_3$O$_3$
Exact Mass: 443.15
Molecular Weight: 443.42

A suspension of 1-(2,2-dimethoxyethyl)-5-iodo-1H-indazole (458 mg, 1.38 mmol), 4-(4-(trifluoromethyl)phenyl)pyridin-2(1H)-one (330 mg, 1.38 mmol), Cs$_2$CO$_3$ (997 mg, 3.06 mmol), 8-hydroxyquinoline (42 mg, 0.29 mmol) and CuI (311 g, 163 mmol) in DMSO (5 mL) was evacuated for 30 minutes under high vacuum then backfilled with argon. The mixture was stirred under argon at 115° C. for 15 h and then allowed to cool. The mixture was diluted with 10% NH$_4$OH in H$_2$O (40 mL) and extracted with EtOAc (4×50 mL). The organics were washed with brine (50 mL), dried over Na$_2$SO$_4$, filtered and concentrated to dryness. Purification by flash chromatography (silica gel, CH$_2$Cl$_2$/MeOH, 95:5) followed by a second purification by flash chromatography (silica gel, CH$_2$Cl$_2$/MeOH, 97.5:2.5) gave the title compound (482 mg, 79%) as a light brown solid: $^1$H NMR (500 MHz, CDCl₃) δ 8.08 (s, 1H), 7.75-7.73 (m, 5H), 7.61 (d, J=8.9 Hz, 1H), 7.52 (d, J=7.1 Hz, 1H), 7.45 (dd, J=8.9, 1.8 Hz, 1H), 6.92 (d, J=1.8 Hz, 1H), 6.52 (dd, J=7.1, 1.9 Hz, 1H), 4.78 (t, J=5.3 Hz, 1H), 4.52 (d, J=5.3 Hz, 2H), 3.39 (s, 6H); ESI MS m/z 444 [M+H]⁺.

f) 2-(5-(2-Oxo-4-(4-(trifluoromethyl)phenyl)pyridin-1(2H)-yl)-1H-indazol-1-yl)acetaldehyde

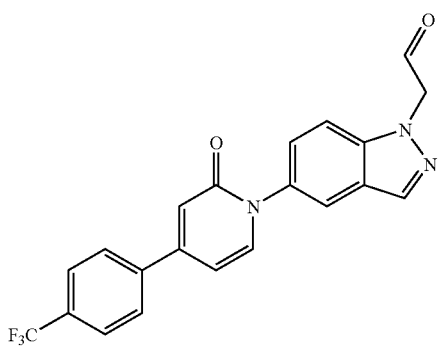

Chemical Formula: C₂₁H₁₄F₃N₃O₂
Exact Mass: 397.1
Molecular Weight: 397.35

A solution of 1-(1-(2,2-dimethoxyethyl)-1H-indazol-5-yl)-4-(4-(trifluoromethyl)-phenyl)pyridin-2(1H)-one (480 mg, 1.08 mmol) in THF (10 mL) was treated with aqueous HCl (9 mL, 2.0 M). The solution was heated to reflux for 1 h, allowed to cool and then treated with H₂O (100 mL). The resulting solids were isolated by filtration, washed with H₂O and dried under high vacuum for 16 h to give the title compound (1.00 g, 64%) as a light brown solid: ESI MS m/z 398 [M+H]⁺.

g) 1-(1-(2-Morpholinoethyl)-1H-indazol-5-yl)-4-(4-(trifluoromethyl)phenyl)pyridin-2(1H)-one

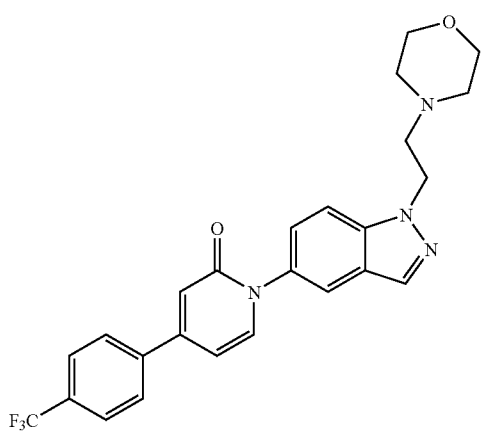

Chemical Formula: C₂₅H₂₃F₃N₄O₂
Exact Mass: 468.18
Molecular Weight: 468.47

To a solution of 2-(5-(2-oxo-4-(4-(trifluoromethyl)phenyl)pyridin-1(2H)-yl)-1H-indazol-1-yl)acetaldehyde (84 mg, 0.21 mmol) in CH₂Cl₂ (4.0 mL), MeOH (1.0 mL) and AcOH (0.50 mL) was added morpholine (0.06 mL, 0.7 mmol) and picoline-borane complex (25 mg, 0.23 mmol). After stirring at ambient temperature under nitrogen atmosphere for 1.5 h, the solution was treated with 1 N HCl (10.0 mL) and stirred vigorously for 30 minutes. The mixture was made basic with saturated aqueous NaHCO₃ (25 mL) and extracted with CH₂Cl₂ (3×25 mL). The organics were dried over Na₂SO₄, filtered and concentrated to dryness. Purification by flash chromatography (silica gel, CH₂Cl₂/MeOH, 97:3) gave the title compound (33 mg, 33%) as an off-white solid: ¹H NMR (500 MHz, CDCl₃) δ 8.14 (d, J=0.7 Hz, 1H), 7.95 (d, J=8.1 Hz, 2H), 7.85-7.77 (m, 5H), 7.48 (dd, J=8.9, 1.9 Hz, 1H), 6.95 (d, J=1.8 Hz, 1H), 6.85 (dd, J=7.1, 2.0 Hz, 1H), 4.63 (t, J=6.5 Hz, 2H), 3.64-3.62 (m, 4H), 2.91 (t, J=6.5 Hz, 2H), 2.54-2.52 (m, 4H); ESI MS m/z 469 [M+H]⁺.

h) 1-(1-(2-Morpholinoethyl)-1H-indazol-5-yl)-4-(4-(trifluoromethyl)phenyl)pyridin-2(1H)-one hydrochloride

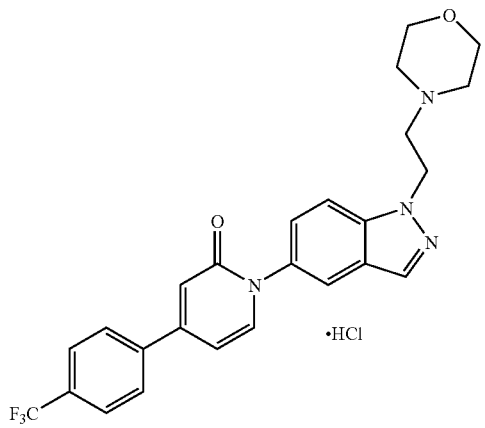

Chemical Formula: C₂₅H₂₃F₃N₄O₂
Exact Mass: 468.18
Molecular Weight: 468.47

A solution of 1-(1-(2-morpholinoethyl)-1H-indazol-5-yl)-4-(4-(trifluoro-methyl)-phenyl)pyridin-2(1H)-one (32 mg, 0.068 mmol) in CH₂Cl₂ (2 mL) was treated with anhydrous HCl in diethyl ether (0.07 mL, 0.07 mmol, 1.0 M). After stirring at ambient temperature for 15 min, the reaction mixture was diluted with Et₂O (20 mL). The resulting solids were collected by filtration and dried in a vacuum oven to yield the title compound (24 mg, 69%) as an off-white powder: mp 248-250° C. (decomposition); ¹H NMR (500 MHz, DMSO-d₆) δ 10.58 (br s, 1H), 8.28 (s, 1H), 8.02 (d, J=8.0 Hz, 2H), 7.92-7.84 (m, 5H), 7.55 (d, J=9.0 Hz, 1H), 6.90 (d, J=2.0 Hz, 1H), 6.75 (dd, J=7.0, 2.0 Hz, 1H), 4.95 (br, 2H), 4.02-3.99 (m, 2H), 3.72-3.70 (m, 4H), 3.56-3.54 (m, 2H), 3.20 (br, 2H); ESI MS m/z 469 [M+H]⁺; HPLC (Method B) 98.9% (AUC), t_R=14.8 min.

Example 38

Preparation of (S)-1-(1-(2-(3-hydroxypyrrolidin-1-yl)ethyl)-1H-indazol-5-yl)-4-(4-(trifluoromethyl)phenyl)pyridin-2(1H)-one hydrochloride

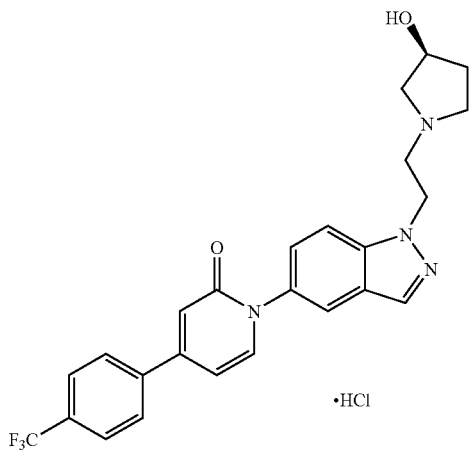

Chemical Formula: $C_{25}H_{23}F_3N_4O_2$
Exact Mass: 468.18
Molecular Weight: 468.47

Following the procedure of Example 37, but substituting (S)-pyrrolidin-3-ol for morpholine, the title compound (10 mg, 10%) was prepared as an off-white powder: $^1$H NMR (500 MHz, DMSO-d$_6$) δ 10.65 (br s, 0.4H), 10.41 (br s, 0.6H), 8.28 (br s, 1H), 8.02 (d, J=8.0 Hz, 2H), 7.94-7.85 (m, 5H), 7.54 (d, J=9.0 Hz, 1H), 6.90 (d, J=2.0 Hz, 1H), 6.75 (dd, J=7.5, 2.0 Hz, 1H), 5.49 (br s, 1H), 4.90-4.88 (m, 2H), 4.43-4.37 (m, 1H), 3.78-3.71 (m, 2H), 3.60 (br, 1H), 3.41-3.34 (m, 1H), 3.17-3.13 (m, 1H), 2.99-2.97 (m, 1H), 2.25-2.22 (m, 1H), 1.95-1.81 (m, 1H); ESI MS m/z 469 [M+H]$^+$; HPLC (Method B) 98.2% (AUC), t$_R$=15.7 min; Optical Rotation [α]$^{23.5}_D$ −4.3° (c 1.00, Methanol).

Example 39

Preparation of (R)-1-(1-(2-(3-hydroxypyrrolidin-1-yl)ethyl)-1H-indazol-5-yl)-4-(4-(trifluoromethyl)phenyl)pyridin-2(1H)-one hydrochloride

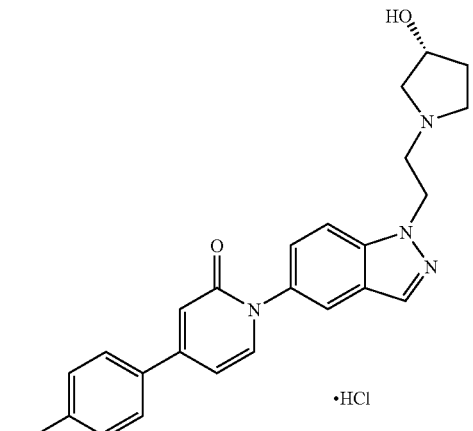

Chemical Formula: $C_{25}H_{23}F_3N_4O_2$
Exact Mass: 468.18
Molecular Weight: 468.47

Following the procedure of Example 37, but substituting (R)-pyrrolidin-3-ol for morpholine, the title compound (23 mg, 22%) was prepared as an off-white powder: $^1$H NMR (500 MHz, DMSO-d$_6$) δ 10.40 (br s, 0.3H), 10.31 (br s, 0.5H), 8.28 (d, J=6.5 Hz, 1H), 8.02 (d, J=8.0 Hz, 2H), 7.93-7.84 (m, 5H), 7.54 (d, J=8.0 Hz, 1H), 6.90 (s, 1H), 6.75 (d, J=7.0 Hz, 1H), 5.50 (br s, 1H), 4.90-4.88 (m, 2H), 4.44-4.38 (m, 1H), 3.79-3.72 (m, 2H), 3.61-3.60 (m, 1H), 3.42-3.40 (m, 1H), 3.14-3.13 (m, 1H), 3.01-2.99 (m, 1H), 2.25-2.24 (m, 1H), 1.95-1.81 (m, 1H); ESI MS m/z 469 [M+H]$^+$; HPLC (Method B) 96.7% (AUC), t$_R$=13.9 min; Optical Rotation [α]$^{23.5}_D$ +3.7° (c 1.00, Methanol).

Example 40

Preparation of (R)-1-(1-(2-(2-(Hydroxymethyl)pyrrolidin-1-yl)ethyl)-1H-indazol-5-yl)-4-(4-(trifluoromethyl)phenyl)pyridin-2(1H)-one hydrochloride

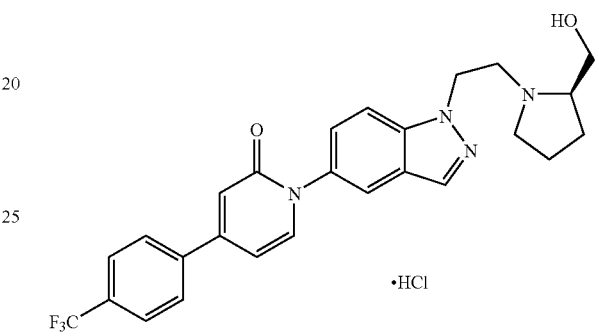

Chemical Formula: $C_{26}H_{26}ClF_3N_4O_2$·
Exact Mass: 518.17
Molecular Weight: 518.96

Following the procedure of Example 37, but substituting (R)-pyrrolidin-2-ylmethanol for morpholine, the title compound (88 mg, 58%) was prepared as a yellow powder: $^1$H NMR (500 MHz, DMSO-d$_6$) δ 9.85 (s, 1H), 8.28 (s, 1H), 8.04-8.01 (m, 2H), 7.93-7.85 (m, 5H), 7.54 (dd, J=8.8, 2.0 Hz, 1H), 6.90 (d, J=1.9 Hz, 1H), 6.75 (dd, J=7.2, 2.0 Hz, 1H), 4.95-4.85 (m, 2H), 3.97-3.93 (m, 1H), 3.81-3.76 (m, 1H), 3.71-3.63 (m, 3H), 3.58-3.52 (m, 1H), 3.16-3.10 (m, 1H), 2.14-2.05 (m, 1H), 2.04-1.97 (m, 1H), 1.89-1.81 (m, 1H), 1.78-1.70 (m, 1H); ESI MS m/z 483 [M+H]$^+$; HPLC (Method B) 96.4% (AUC), t$_R$=15.0 min.

Example 41

Preparation of (S)-1-(1-(2-(2-(Hydroxymethyl)pyrrolidin-1-yl)ethyl)-1H-indazol-5-yl)-4-(4-(trifluoromethyl)phenyl)pyridin-2(1H)-one hydrochloride

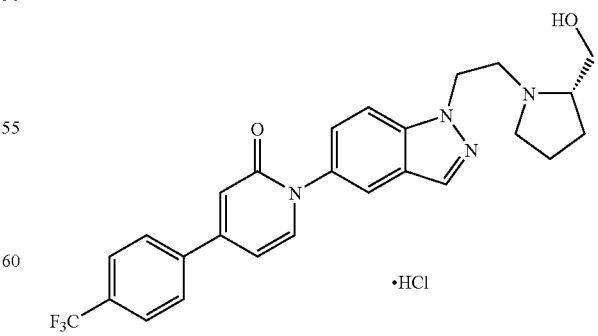

Chemical Formula: $C_{26}H_{26}ClF_3N_4O_2$·
Exact Mass: 518.17
Molecular Weight: 518.96

Following the procedure of Example 37, but substituting (S)-pyrrolidin-2-ylmethanol for morpholine, the title compound (76 mg, 50%) was prepared as a yellow powder: $^1$H NMR (500 MHz, DMSO-d$_6$) δ 9.88 (s, 1H), 8.28 (s, 1H), 8.04-8.00 (m, 2H), 7.92-7.83 (m, 5H), 7.54 (dd, J=9.0, 1.9 Hz, 1H), 6.90 (d, J=2.0 Hz, 1H), 6.75 (dd, J=7.2, 2.0 Hz, 1H), 4.95-4.85 (m, 2H), 3.98-3.91 (m, 1H), 3.82-3.75 (m, 1H), 3.70-3.63 (m, 3H), 3.58-3.52 (m, 1H), 3.15-3.09 (m, 1H), 2.12-2.05 (m, 1H), 2.03-1.97 (m, 1H), 1.92-1.82 (m, 1H), 1.78-1.71 (m, 1H); ESI MS m/z 483 [M+H]$^+$; HPLC (Method B) 96.4% (AUC), t$_R$=16.0 min.

Example 42

Preparation of 1-(1-(2-Dimethylamino)ethyl)-1H-indazol-5-yl)-4-(4-(trifluoromethyl)phenyl)pyridin-2(1H)-one hydrochloride

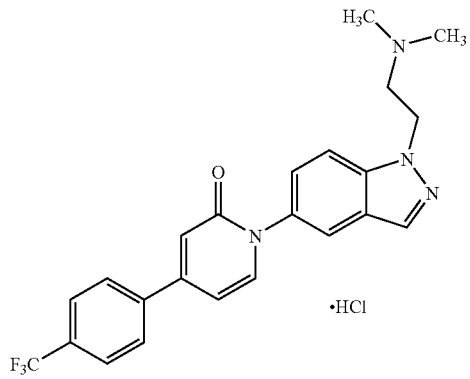

Chemical Formula: C$_{23}$H$_{22}$ClF$_3$N$_4$O
Exact Mass: 462.14
Molecular Weight: 462.90

Following the procedure of Example 37, but substituting dimethylamine for morpholine, the title compound (45 mg, 100%) was prepared as a white powder: mp 222-224° C.; $^1$H NMR (500 MHz, DMSO-d$_6$) δ 9.76 (br s, 1H), 8.28 (s, 1H), 8.02-8.01 (m, 2H), 7.92-7.84 (m, 5H), 7.55-7.53 (m, 1H), 6.89 (d, J=2.0 Hz, 1H), 6.76-6.74 (m, 1H), 4.89 (t, J=6.0 Hz, 2H), 3.65-3.64 (m, 2H), 2.86 (s, 6H); ESI MS m/z 427 [M+H]$^+$; HPLC (Method B)>99% (AUC), t$_R$=14.8 min.

Example 43

Preparation of 1-(1-(2-(piperazin-1-yl)ethyl)-1H-indazol-5-yl)-4-(4-(trifluoromethyl)phenyl)pyridin-2(1H)-one hydrochloride a) 1-(3-Methyl-4-nitrophenyl)-4-(4-(trifluoromethyl)phenyl)pyridin-2(1H)-one

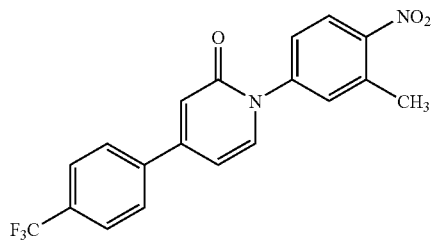

Chemical Formula: C$_{19}$H$_{13}$F$_3$N$_2$O$_3$
Exact Mass: 374.09
Molecular Weight: 374.31

To a solution of 5-fluoro-2-nitrotoluene (0.27 g, 2.25 mmol) in DMF (4.0 mL) was added 4-(4-(trifluoromethyl)phenyl-pyridin-2(1H)-one (0.45 g, 1.87 mmol) and Cs$_2$CO$_3$ (0.67 g, 2.1 mmol), and the reaction was heated to 85° C. for 18 h. The reaction mixture was cooled, H$_2$O (20 mL) was added, and the mixture was stirred for 20 min. The resulting solids were collected by filtration and washed with H$_2$O (10 mL). Flash chromatography (silica gel, hexanes/EtOAc, 10:1 to 3:1) yielded the title compound (0.45 g, 65%) as a yellow solid: $^1$H NMR (300 MHz, DMSO-d$_6$) δ 8.33 (d, J=5.4 Hz, 1H), 8.12-7.89 (m, 5H), 7.65-7.60 (m, 2H), 7.33-7.22 (m, 2H), 2.55 (s, 3H).

b) 1-(4-Amino-3-methylphenyl)-4-(4-(trifluoromethyl)phenyl)pyridin-2(1H)-one

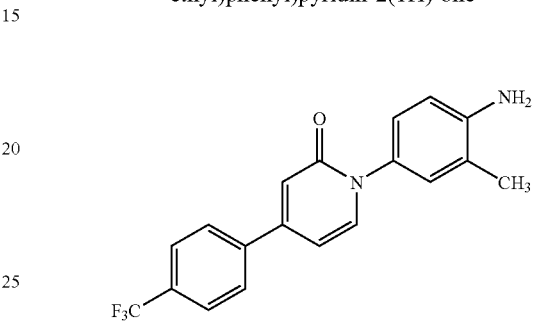

Chemical Formula: C$_{19}$H$_{15}$F$_3$N$_2$O
Exact Mass: 344.11
Molecular Weight: 344.33

A solution of 1-(3-methyl-4-nitrophenyl)-4-(4-(trifluoromethyl)phenyl)pyridin-2(1H)-one (0.46 g, 1.2 mmol) in 9:1 EtOH/H$_2$O (20 mL) was treated with iron powder (0.62 g, 11.1 mmol) and NH$_4$Cl (33 mg, 0.61 mmol), and the resulting suspension was heated at reflux for 18 h. The reaction mixture was filtered, while hot, through Celite® with portions of CH$_2$Cl$_2$ (2×25 mL) and MeOH (2×25 mL). The filtrates were combined and made basic with 1 N NaOH (10 mL). The solution was extracted with CH$_2$Cl$_2$ (2×40 mL) and the combined organic extracts were dried over Na$_2$SO$_4$, filtered and concentrated to provide the title compound (0.409 g, 100%) as a yellow solid: $^1$H NMR (500 MHz, DMSO-d$_6$) δ 7.97 (d, J=8.0 Hz, 2H), 7.85 (d, J=8.5 Hz, 2H), 7.68 (d, J=7.0 Hz, 1H), 6.96 (s, 1H), 6.92 (dd, J=8.5, 2.0 Hz, 1H), 6.80 (d, J=1.5 Hz, 1H), 6.67 (d, J=8.0 Hz, 1H), 6.63 (dd, J=7.0, 2.0 Hz, 1H), 5.11 (s, 2H), 2.09 (s, 3H).

c) 1-(1H-Indazol-5-yl)-4-(4-(trifluoromethyl)phenyl)pyridin-2(1H)-one

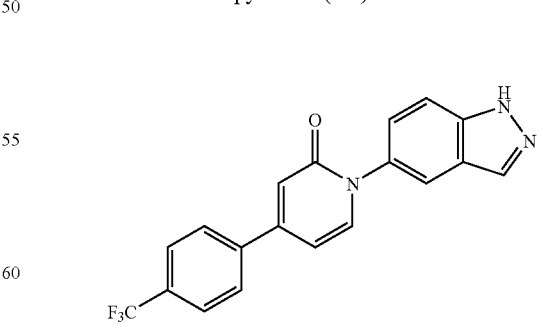

Chemical Formula: C$_{19}$H$_{12}$F$_3$N$_3$O
Exact Mass: 355.09
Molecular Weight: 355.31

A solution of 1-(4-amino-3-methylphenyl)-4-(4-(trifluoromethyl)phenyl)pyridin-2(1H)-one (0.405 g, 1.22 mmol) in AcOH (12.5 mL) was treated with a solution of NaNO$_2$ (84.0 mg, 1.22 mmol) in H$_2$O (0.4 mL) and stirred at ambient temperature for 18 h. The reaction mixture was concentrated. Flash chromatography (silica gel, CH$_2$Cl$_2$/MeOH/NH$_4$OH, 90:9:1) yielded the title compound (0.330 g, 76%) as a yellow solid: $^1$H NMR (500 MHz, DMSO-d$_6$) δ 13.28 (s, 1H), 8.17 (s, 1H), 8.01 (d, J=8.0 Hz, 2H), 7.88-7.85 (m, 4H), 7.64 (d, J=8.8 Hz, 1H), 7.39 (dd, J=8.8, 2.0 Hz, 1H), 6.89 (d, J=2.0 Hz, 1H), 6.72 (dd, J=7.0, 2.0 Hz, 1H).

d) 1-(1-(2-Chloroethyl)-1H-indazol-5-yl)-4-(4-(trifluoromethyl)phenyl)pyridin-2(1H)-one

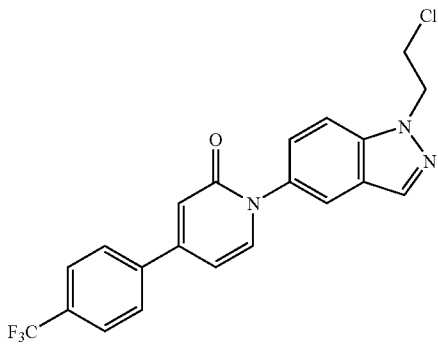

Chemical Formula: C$_{21}$H$_{15}$ClF$_3$N$_3$O
Exact Mass: 417.09
Molecular Weight: 417.81

To a solution of 1-(1H-indazol-5-yl)-4-(4-(trifluoromethyl)phenyl)pyridin-2(1H)-one (120 mg, 0.338 mmol) in DMSO (2.0 mL) was added 2-bromo-1-chloroethane (485 mg, 3.38 mmol) and Cs$_2$CO$_3$ (330 mg, 1.01 mmol), and the reaction was stirred at ambient temperature for 3 h. The reaction was diluted with H$_2$O (25 mL) and extracted with EtOAc (3×25 mL). The extracts were washed with brine (25 mL), dried over Na$_2$SO$_4$, and concentrated. Flash chromatography (Biotage 25+M column, CH$_2$Cl$_2$/MeOH, 99:1 to 98:2) yielded the title compound (72 mg, 51%): $^1$H NMR (500 MHz, CDCl$_3$) δ 8.11 (s, 1H), 7.76-7.73 (m, 5H), 7.59-7.47 (m, 3H), 6.92-6.91 (m, 1H), 6.53-6.51 (m, 1H), 4.74-4.71 (m, 2H), 4.00-3.98 (m, 2H).

e) 1-(1-(2-(piperazin-1-yl)ethyl)-1H-indazol-5-yl)-4-(4-(trifluoromethyl)phenyl)pyridin-2(1H)-one

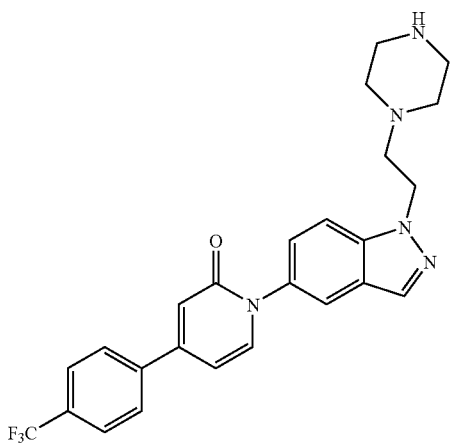

Chemical Formula: C$_{25}$H$_{24}$F$_3$N$_5$O
Exact Mass: 467.19
Molecular Weight: 467.49

To a solution of 1-(1-(2-chloroethyl)-1H-indazol-5-yl)-4-(4-(trifluoromethyl)phenyl)pyridin-2(1H)-one (72 mg, 0.17 mmol) in DMF (2.0 mL) was added K$_2$CO$_3$ (0.12 g, 0.86 mmol), piperazine (0.29 g, 3.4 mmol) and KI (29 mg, 0.17 mmol), and the reaction was heated to 50° C. for 3 h. The reaction was cooled, diluted with H$_2$O (25 mL) and extracted with EtOAc (3×25 mL). The combined organic extracts were washed with brine (25 mL), dried over Na$_2$SO$_4$, filtered and concentrated. Flash chromatography (silica gel, CH$_2$Cl$_2$/MeOH/NH$_4$OH, 30:1:0 to 10:1:0.2) provided the title compound (65 mg, 80%): $^1$H NMR (500 MHz, CDCl$_3$) δ 8.05 (s, 1H), 7.75-7.74 (m, 5H), 7.57-7.76 (m, 3H), 6.92 (d, J=2.0 Hz, 1H), 6.52 (d, J=7.0 Hz, 1H), 4.55 (t, J=7.0 Hz, 2H), 2.89-2.87 (m, 6H), 2.51-2.50 (m, 4H).

f) 1-(1-(2-(piperazin-1-yl)ethyl)-1H-indazol-5-yl)-4-(4-(trifluoromethyl)phenyl)pyridin-2(1H)-one hydrochloride

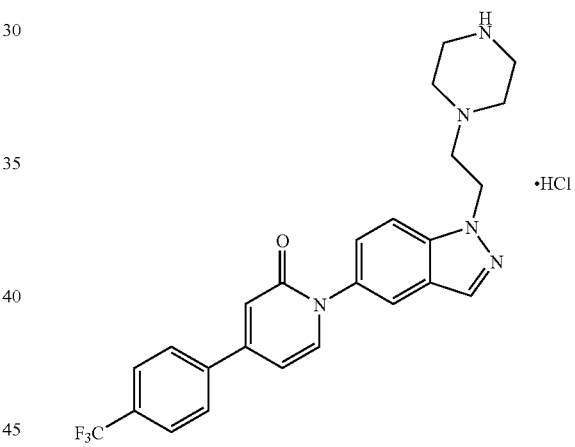

Chemical Formula: C$_{25}$H$_{25}$ClF$_3$N$_5$O
Exact Mass: 503.17
Molecular Weight: 503.95

According to the procedure of Example 37 step h, except substituting 1-(1-(2-(piperazin-1-yl)ethyl)-1H-indazol-5-yl)-4-(4-(trifluoromethyl)phenyl)pyridin-2(1H)-one for 1-(1-(2-morpholinoethyl)-1H-indazol-5-yl)-4-(4-(trifluoromethyl)-phenyl)pyridin-2(1H)-one, the title compound (32 mg, 83%) was prepared as a white solid: mp 222-224° C. (decomposition); $^1$H NMR (500 MHz, DMSO-d$_6$) δ 8.24 (s, 1H), 8.02-8.01 (m, 2H), 7.92-7.85 (m, 5H), 7.51 (d, J=8.6 Hz, 1H), 6.89 (d, J=2.0 Hz, 1H), 6.75 (dd, J=7.1, 1.8 Hz, 1H), 4.87-4.85 (m, 2H), 3.71-3.60 (m, 6H), 3.38-3.31 (m, 4H); ESI MS m/z 468 [M+H]$^+$; HPLC (Method B) 96.2% (AUC), t$_R$=13.9 min.

Example 44

Preparation of 1-(1-(3-(Dimethylamino)propyl)-1H-indazol-5-yl)-4-(4-(trifluoromethyl)phenyl)pyridin-2(1H)-one hydrochloride a) 1-(1-(3-(Dimethylamino)propyl)-1H-indazol-5-yl)-4-(4-(trifluoromethyl)phenyl)pyridin-2(1H)-one

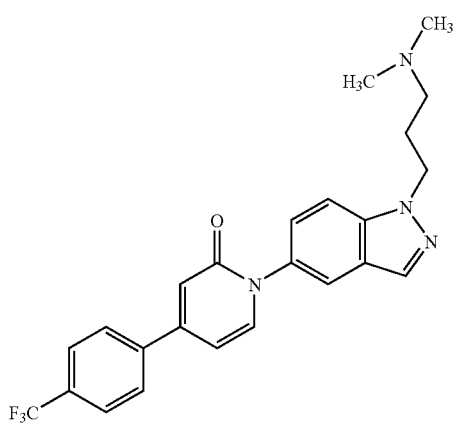

Chemical Formula: $C_{24}H_{23}F_3N_4O$
Exact Mass: 440.18
Molecular Weight: 440.46

To a solution of 1-(1H-indazol-5-yl)-4-(4-(trifluoromethyl)phenyl)pyridin-2(1H)-one (278 mg, 0.783 mmol) in DMSO (4.0 mL) was added 3-bromo-1-chloropropane (1.23 g, 7.83 mmol) and $Cs_2CO_3$ (765 mg, 2.35 mmol), and the reaction was stirred at ambient temperature for 18 h. The reaction was diluted with $H_2O$ (25 mL) and extracted with EtOAc (3×25 mL). The extracts were washed with brine (25 mL), dried over $Na_2SO_4$, and concentrated. Flash chromatography (silica gel, $CH_2Cl_2$/MeOH, 100:1) yielded 1-(1-(3-chloropropyl)-1H-indazol-5-yl)-4-(4-(trifluoromethyl)phenyl)pyridin-2(1H)-one. To a solution of 1-(1-(3-chloropropyl)-1H-indazol-5-yl)-4-(4-(trifluoromethyl)phenyl)pyridin-2(1H)-one (84 mg, 0.19 mmol) in DMF (1.0 mL) was added $K_2CO_3$ (0.13 g, 0.97 mmol), dimethylamine (1.94 mL, 3.88 mmol, 2.0 M in THF) and KI (32 mg, 0.19 mmol), and the reaction was heated to 45° C. for 18 h. The reaction mixture was cooled, diluted with $H_2O$ (25 mL) and extracted with EtOAc (3×25 mL). The combined organic extracts were washed with brine (25 mL), dried over $Na_2SO_4$, filtered and concentrated. Flash chromatography (Biotage 25+M column, $CH_2Cl_2$/MeOH/$NH_4OH$, 50:1:0 to 20:1:0.1) provided the title compound (54 mg, 63%): $^1$H NMR (500 MHz, $CDCl_3$) δ 8.06 (s, 1H), 7.75-7.70 (m, 5H), 7.60-7.43 (m, 3H), 6.92-6.91 (m, 1H), 6.53-6.51 (m, 1H), 4.49 (t, J=6.8 Hz, 2H), 2.29 (t, J=6.8 Hz, 2H), 2.23 (s, 6H), 2.13-2.08 (m, 2H).

b) 1-(1-(3-(Dimethylamino)propyl)-1H-indazol-5-yl)-4-(4-(trifluoromethyl)phenyl)pyridine-2(1H)-one hydrochloride

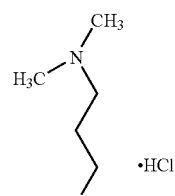

Chemical Formula: $C_{24}H_{24}ClF_3N_4O$
Exact Mass: 476.16
Molecular Weight: 476.92

According to the procedure of Example 37 step h, except substituting 1-(1-(3-(dimethylamino)propyl)-1H-indazol-5-yl)-4-(4-(trifluoromethyl)phenyl)pyridin-2(1H)-one for 1-(1-(2-morpholinoethyl)-1H-indazol-5-yl)-4-(4-(trifluoromethyl)-phenyl)pyridin-2(1H)-one, the title compound (48 mg, 79%) was prepared as a white solid: mp 209-211° C.; $^1$H NMR (500 MHz, DMSO-$d_6$) δ 9.85 (br s, 1H), 8.21 (s, 1H), 8.01 (d, J=8.0 Hz, 2H), 7.88-7.84 (m, 5H), 7.50-7.48 (m, 1H), 6.89-6.88 (m, 1H), 6.74 (dd, J=7.0, 1.7 Hz, 1H), 4.57 (t, J=6.5 Hz, 2H), 3.10 (t, J=7.5 Hz, 2H), 2.75 (s, 6H), 2.26-2.22 (m, 2H); ESI MS m/z 441 [M+H]$^+$; HPLC (Method B) 98.9% (AUC), $t_R$=15.4 min.

Example 45

Preparation of 1-(1-(2-(piperazin-1-yl)ethyl)-1H-indazol-5-yl)-4-(4-(trifluoromethyl)phenyl)pyridin-2(1H)-one hydrochloride a) 1-(1-(3-(Pyrrolidin-1-yl)propyl)-1H-indazol-5-yl)-4-(4(trifluoromethyl)phenyl)pyridin-2(1H)-one

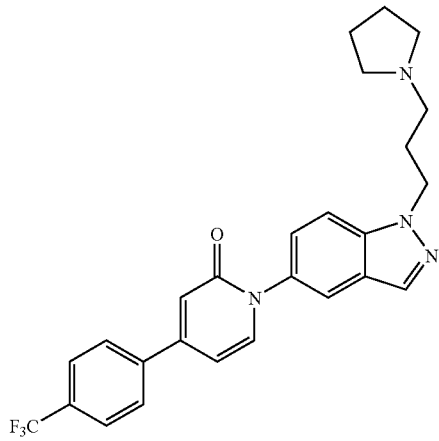

Chemical Formula: $C_{26}H_{25}F_3N_4O$
Exact Mass: 466.20
Molecular Weight: 466.50

To a solution of 1-(1H-indazol-5-yl)-4-(4-(trifluoromethyl)phenyl)pyridin-2(1H)-one (278 mg, 0.783 mmol) in DMSO (4.0 mL) was added 3-bromo-1-chloropropane (1.23 g, 7.83 mmol) and $Cs_2CO_3$ (765 mg, 2.35 mmol), and the reaction was stirred at ambient temperature for 18 h. The reaction mixture was diluted with $H_2O$ (25 mL) and extracted with EtOAc (3×25 mL). The extracts were washed with brine (25 mL), dried over $Na_2SO_4$, and concentrated. Flash chromatography (silica gel, $CH_2Cl_2$/MeOH, 100:1) yielded the intermediate 1-(1-(3-chloropropyl)-1H-indazol-5-yl)-4-(4-(trifluoromethyl)phenyl)pyridin-2(1H)-one. To a solution of 1-(1-(3-chloropropyl)-1H-indazol-5-yl)-4-(4-(trifluoromethyl)phenyl)pyridin-2(1H)-one (78 mg, 0.18 mmol) in DMF (1.0 mL) was added $K_2CO_3$ (0.12 g, 0.90 mmol), pyrrolidine (130 mg, 1.8 mmol) and KI (30 mg, 0.18 mmol), and the reaction was heated to 50° C. for 18 h. The reaction mixture was cooled and diluted with $H_2O$ (25 mL). The resulting solids were collected by filtration and washed with $H_2O$ (10 mL). The collected solid was dissolved in EtOAc (20 mL) and washed with brine (10 mL). The washed organic solution was dried over $Na_2SO_4$, filtered and concentrated to provide the title compound (77 mg, 91%): $^1$H NMR (500 MHz, $CDCl_3$) δ 8.05 (s, 1H), 7.77-7.74 (m, 5H), 7.60-7.42 (m, 3H), 6.92 (d, J=2.0 Hz, 1H), 6.53-6.51 (m, 1H), 4.51 (t, J=7.0 Hz, 2H), 2.48-2.44 (m, 6H), 2.16-2.12 (m, 2H), 1.79-1.77 (m, 4H).

b) 1-(1-(3-(Pyrrolidin-1-yl)propyl)-1H-indazol-5-yl)-4-(4-(trifluoromethyl)phenyl)pyridine-2(1H)-one hydrochloride

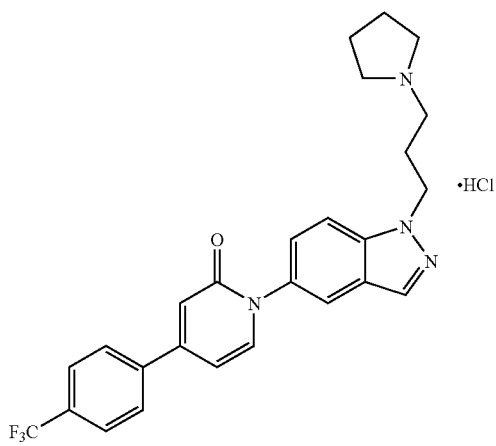

Chemical Formula: $C_{26}H_{26}ClF_3N_4O$
Exact Mass: 502.17
Molecular Weight: 502.96

According to the procedure of Example 37 step h, except substituting 1-(1-(3-(pyrrolidin-1-yl)propyl)-1H-indazol-5-yl)-4-(4-(trifluoromethyl)phenyl)pyridin-2(1H)-one for 1-(1-(2-morpholinoethyl)-1H-indazol-5-yl)-4-(4-(trifluoromethyl)-phenyl)pyridin-2(1H)-one, the title compound (54 mg, 67%) was prepared as a yellow solid: $^1$H NMR (500 MHz, DMSO-$d_6$) δ 10.26 (br s, 1H), 8.21 (s, 1H), 8.01 (d, J=8.1 Hz, 2H), 7.88-7.84 (m, 5H), 7.49 (dd, J=8.8, 1.9 Hz, 1H), 6.89 (d, J=1.9 Hz, 1H), 6.74 (dd, J=7.1, 2.0 Hz, 1H), 4.59 (t, J=7.0 Hz, 2H), 3.54-3.51 (m, 2H), 3.19-3.15 (m, 2H), 2.99-2.93 (m, 2H), 2.30-2.24 (m, 2H), 2.01-1.95 (m, 2H), 1.89-1.84 (m, 2H); ESI MS m/z 467 [M+H]$^+$; HPLC (Method B) 96.8% (AUC), $t_R$=15.9 min.

Example 46

Preparation of 1-(1-(3-(Amino)propyl)-1H-indazol-5-yl)-4-(4-(trifluoromethyl)phenyl)pyridin-2(1H)-one hydrochloride a) 1-(1-(3-Aminopropyl)-1H-indazol-5-yl)-4-(4-(trifluoromethyl)phenyl)pyridin-2(1H)-one

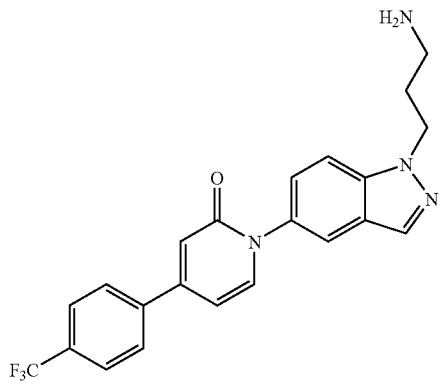

Chemical Formula: $C_{22}H_{19}F_3N_4O$
Exact Mass: 412.15
Molecular Weight: 412.41

To a solution of 1-(1H-indazol-5-yl)-4-(4-(trifluoromethyl)phenyl)pyridin-2(1H)-one (278 mg, 0.783 mmol) in DMSO (4.0 mL) was added 3-bromo-1-chloropropane (1.23 g, 7.83 mmol) and $Cs_2CO_3$ (765 mg, 2.35 mmol), and the reaction was stirred at ambient temperature for 18 h. The reaction was diluted with $H_2O$ (25 mL) and extracted with EtOAc (3×25 mL). The extracts were washed with brine (25 mL), dried over $Na_2SO_4$, and concentrated. Flash chromatography (silica gel, $CH_2Cl_2$/MeOH, 100:1) yielded 1-(1-(3-chloropropyl)-1H-indazol-5-yl)-4-(4-(trifluoromethyl)phenyl)pyridin-2(1H)-one. To a solution of 1-(1-(3-chloropropyl)-1H-indazol-5-yl)-4-(4-(trifluoromethyl)phenyl)pyridin-2(1H)-one (84 g, 0.20 mmol) in DMF (1.5 mL) was added potassium phthalimide (41 mg, 0.22 mmol) and the reaction was heated to 100° C. for 4 h. The reaction was allowed to cool, diluted with $H_2O$ (20 mL) and extracted with $CH_2Cl_2$ (3×25 mL). The combined organic extracts were washed with brine (25 mL), dried over $Na_2SO_4$, and concentrated. Flash chromatography (Biotage 25+M column, $CH_2Cl_2$/MeOH, 50:1 to 40:1) yielded 2-(3-(5-(2-oxo-4-(4-(trifluoromethyl)phenyl)pyridin-1(2H)-yl)-1H-indazol-1-yl)propyl)isoindoline-1,3-dione. 2-(3-(5-(2-oxo-4-(4-(trifluoromethyl)phenyl)pyridin-1(2H)-yl)-1H-indazol-1-yl)propyl)isoindoline-1,3-dione (73 mg, 0.13 mmol) was dissolved in ethanolamine (1.0 mL) and stirred at ambient temperature for 18 h. The reaction was concentrated. Flash column chromatography (Biotage 25+M column, $CH_2Cl_2$/MeOH/$NH_4OH$, 30:1:0.1 to 10:1:0.2) yielded 1-(1-(3-aminopropyl)-1H-indazol-5-yl)-4-(4-(trifluoromethyl)phenyl)pyridin-2(1H)-one. 1-(1-(3-aminopropyl)-1H-indazol-5-yl)-4-(4-(trifluoromethyl)phenyl)pyridin-2(1H)-one was dissolved in $CH_2Cl_2$ (1.0 mL) and $Et_3N$ (30 μL, 0.22 mmol), and di-tert-butyl dicarbonate (26 mg, 0.12 mmol) were added. The resulting solution was stirred at ambient temperature for 18 h. The reaction was concentrated. Flash column chromatography (silica gel, $CH_2Cl_2$/MeOH, 40:1) afforded tert-butyl-3-(5-(2-oxo-4-(4-(trifluoromethyl)phenyl)pyridin-1(2H)-yl)-1H-indazol-1-yl)propylcarbamate. Tert-butyl-3-(5-(2-oxo-4-(4-(trifluoromethyl)phenyl)pyridin-1(2H)-yl)-1H-indazol-1-yl)propylcarbamate was dissolved in $CH_2Cl_2$ (1.0 mL) and TFA (25 μL, 0.33 mmol). The resulting solution was stirred at ambient temperature for 18 h. The reaction was diluted with $CH_2Cl_2$ (10 mL) and washed with saturated $NaHCO_3$. The organic solution was dried over $Na_2SO_4$, filtered and concentrated. Flash column chromatography (silica gel, $CH_2Cl_2$/MeOH/$NH_4OH$, 30:1:0.1 to 20:1:0.1) yielded the title compound (16 mg, 29%): $^1H$ NMR (500 MHz, $CDCl_3$) δ 8.03 (s, 1H), 7.77-7.74 (m, 5H), 7.58-7.44 (m, 3H), 6.92 (d, J=1.5 Hz, 1H), 6.53 (dd, J=7.5, 2.0 Hz, 1H), 4.54 (t, J=7.0 Hz, 2H), 2.70 (t, J=7.0 Hz, 2H), 2.10-2.04 (m, 2H).

b) 1-(1-(3-Aminopropyl)-1H-indazol-5-yl)-4-(4-(trifluoromethyl)phenyl)pyridin-2(1H)-one hydrochloride

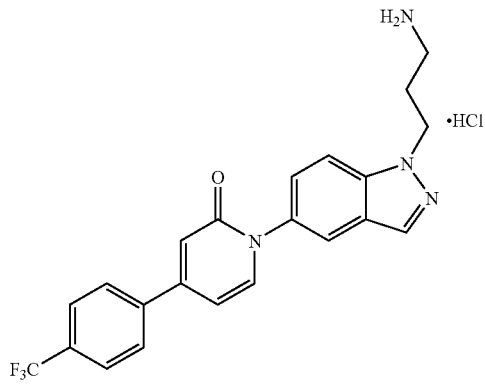

Chemical Formula: $C_{22}H_{20}ClF_3N_4O$
Exact Mass: 448.13
Molecular Weight: 448.87

According to the procedure of Example 37 step h, except substituting 1-(1-(3-aminopropyl)-1H-indazol-5-yl)-4-(4-(trifluoromethyl)phenyl)pyridin-2(1H)-one for 1-(1-(2-morpholinoethyl)-1H-indazol-5-yl)-4-(4-(trifluoromethyl)-phenyl)pyridin-2(1H)-one, the title compound (8.4 mg, 52%) was prepared as a yellow powder: mp 222-224° C. (decomposition); $^1H$ NMR (500 MHz, DMSO-$d_6$) δ 8.21 (s, 1H), 8.01 (d, J=8.5 Hz, 2H), 7.89-7.80 (m, 8H), 7.50-7.48 (m, 1H), 6.89 (d, J=1.5 Hz, 1H), 6.74 (dd, J=7.0, 2.0 Hz, 1H), 4.58 (t, J=6.5 Hz, 2H), 2.84-2.80 (m, 2H), 2.16-2.12 (m, 2H); ESI MS m/z 413 [M+H]$^+$; HPLC (Method B) 97.0% (AUC), $t_R$=14.9 min.

Example 47

Preparation of (S)-1-(1-(Pyrrolidin-2-ylmethyl)-1H-indazol-5-yl)-4-(4-(trifluoromethyl)phenyl)pyridin-2(1H)-one hydrochloride

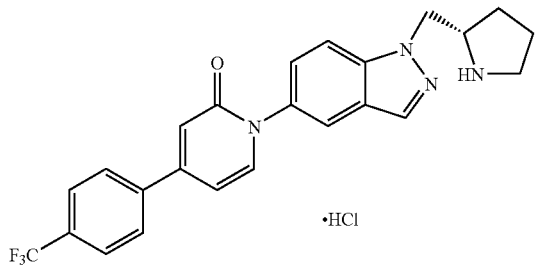

Chemical Formula: $C_{24}H_{22}ClF_3N_4O$
Exact Mass: 474.14
Molecular Weight: 474.91

A mixture of 1-(1H-indazol-5-yl)-4-(4-(trifluoromethyl)phenyl)pyridin-2(1H)-one (200 mg, 0.56 mmol), (S)-tert-butyl 2-(bromomethyl)pyrrolidine-1-carboxylate (GRA-B-188) (298 mg, 1.12 mmol), and cesium carbonate (732 mg, 2.25 mmol) in methyl sulfoxide (5 mL) was stirred overnight at ambient temperature. The reaction mixture was diluted with water (20 mL) and extracted with dichloromethane (2×30 mL). The combined organic extracts were washed with brine (20 mL), dried ($Na_2SO_4$), and concentrated under reduced pressure. Isolation of the desired regioisomer was performed by column chromatography (silica gel, $Et_2O$ to 9:1 $Et_2O$/MeOH/90:9:1 $Et_2O$/MeOH/concd $NH_4OH$). To the desired regioisomer (100 mg, 0.18 mmol) was added dichloromethane (10 mL) and trifluoroacetic acid (2 mL). After stirring at ambient temperature for 2 h, the reaction was brought to pH=9 with 1N NaOH. The organic layer was washed with brine (10 mL), dried ($Na_2SO_4$), and concentrated under reduced pressure. The dried residue (87 mg, 0.20 mmol) was dissolved in dichloromethane (10 mL) and HCl (1.25 M solution in methanol, 0.22 mL, 0.17 mmol) was added. The mixture was concentrated under reduced pressure and then triturated with dichloromethane/hexanes and the obtained solid was triturated with diethyl ether. The solid was dried to afford the title compound (43 mg, 16%) as an off-white solid: mp 241-245° C.; $^1H$ NMR (500 MHz, DMSO-$d_6$) δ 9.05 (br s, 2H), 8.28 (s, 1H), 8.03-7.85 (m, 7H), 7.51 (d, J=8.5 Hz, 1H), 6.89 (s, 1H), 6.75 (d. J=7.0 Hz, 1H), 4.80 (d, J=6.0 Hz, 2H), 3.99-3.95 (m, 1H), 3.30-3.23 (m, 1H), 3.16-3.10 (m, 1H), 2.08-2.03 (m, 1H), 1.99-1.96 (m, 1H), 1.91-1.85 (m, 1H), 1.74-1.70 (m, 1H); ESI MS m/z 439 [M+H]$^+$; HPLC (Method B) 98.7% (AUC), $t_R$=15.5 min; $[α]^{23}_D$ +20.5° (c 0.13, Methanol).

Example 48

Preparation of (R)-1-(1-(3-(Dimethylamino)-2-hydroxypropyl)-1H-indazol-5-yl)-4-(4-(trifluoromethyl)phenyl)pyridin-2(1H)-one hydrochloride a) (S)-1-(1-(Oxiran-2-ylmethyl)-1H-indazol-5-yl)-4-(4-(trifluoromethyl)phenyl)pyridin-2(1H)-one

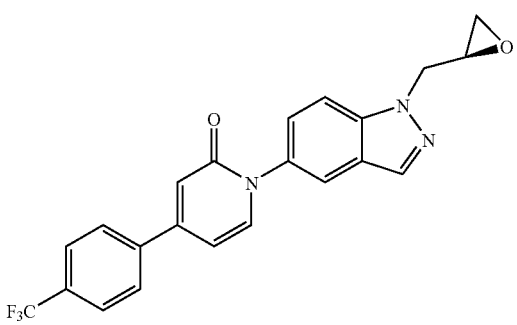

Chemical Formula: $C_{22}H_{16}F_3N_3O_2$
Exact Mass: 411.12
Molecular Weight: 411.38

A mixture of 1-(1H-indazol-5-yl)-4-(4-(trifluoromethyl)phenyl)pyridin-2(1H)-one (750 mg, 2.11 mmol), (R)-(−)-glycidyl nosylate (657 mg, 2.53 mmol) and cesium carbonate (1.03 g, 3.17 mmol) in methyl sulfoxide (6 mL) was stirred at ambient temperature overnight. The reaction mixture was diluted with water (20 mL) and extracted with ethyl acetate (2×50 mL). The combined organic extracts were washed with brine (20 mL), dried ($Na_2SO_4$), and concentrated under reduced pressure. Purification by column chromatography (silica gel, ethyl acetate) gave the title compound (480 mg, 55%) as a yellow solid: $^1$H NMR (300 MHz, $CDCl_3$) δ 8.09 (d, J=0.9 Hz, 1H), 7.76-7.72 (m, 5H), 7.65 (d, J=9.0 Hz, 1H), 7.52 (d, J=7.2 Hz, 1H), 7.47 (dd, J=9.0, 2.1 Hz, 1H), 6.92 (d, J=1.8 Hz, 1H), 6.53 (dd, J=6.9, 1.8 Hz, 1H), 4.79 (dd, J=15, 3.0 Hz, 1H), 4.48 (dd, J=15.3, 5.7 hz, 1H), 3.41-3.37 (m, 1H), 2.88 (app t, J=4.5 Hz, 1H), 2.60 (dd, J=4.5, 2.4 Hz, 1H).

b) (R)-1-(1-(3-(Dimethylamino)-2-hydroxypropyl)-1H-indazol-5-yl)-4-(4-(trifluoromethyl)phenyl)pyridin-2(1H)-one hydrochloride

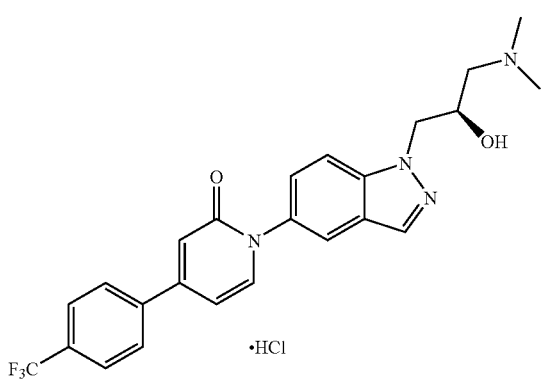

Chemical Formula: $C_{24}H_{24}ClF_3N_4O_2$
Exact Mass: 492.15
Molecular Weight: 492.92

To (S)-1-(1-(oxiran-2-ylmethyl)-1H-indazol-5-yl)-4-(4-(trifluoromethyl)phenyl)-pyridin-2(1H)-one (200 mg, 0.48 mmol) in tetrahydrofuran (5 mL) was added $LiClO_4$ (775 mg, 7.3 mmol) followed by dimethylamine (2.4 ml of a 2 M solution in tetrahydrofuran, 4.9 mmol). The reaction mixture was heated in a 45° C. oil bath for 4.5 h. The reaction mixture was cooled to ambient temperature, diluted with dichloromethane (50 ml), washed with water (25 mL) and brine (25 mL), dried ($Na_2SO_4$), and concentrated under reduced pressure. The material was purified by column chromatography (silica gel, 9:1 $CH_2Cl_2$/MeOH to 90:9:1 $CH_2Cl_2$/MeOH/conc. $NH_4OH$). The dried residue (160 mg, 0.35 mmol) was dissolved in dichloromethane (10 mL) and HCl (1.25 M solution in methanol, 0.31 mL, 0.43 mmol) was added. The mixture was concentrated under reduced pressure and dried to afford the title compound (190 mg, 80%) as a yellow solid: mp 210-213° C.; $^1$H NMR (500 MHz, DMSO-$d_6$) δ 9.50 (br s, 1H), 8.22 (s, 1H), 8.02-8.00 (m, 2H), 7.89-7.84 (m, 5H), 7.48 (dd, J=9.0, 2.0 Hz, 1H), 6.89 (d, J=2.0 Hz, 1H), 6.74 (dd, J=7.0 Hz, 2.0 Hz, 1H), 6.01 (br s, 1H), 4.58-4.49 (m, 2H), 4.40 (br s, 1H), 3.28-3.24 (m, 1H), 3.15-3.10 (m, 1H), 2.81 (d, J=4.5 Hz, 3H), 2.78 (d, J=4.5 Hz, 3H); ESI MS m/z 457 [M+H]$^+$; HPLC (Method B) 96.5% (AUC), $t_R$=14.4 min; $[α]^{23}_D$ +10.4° (c 0.11, Methanol).

Example 49

Preparation of (R)-1-(1-(2-Hydroxy-3-(pyrrolidin-1-yl)propyl)-1H-indazol-5-yl)-4-(4-(trifluoromethyl)phenyl)pyridin-2(1H)-one hydrochloride

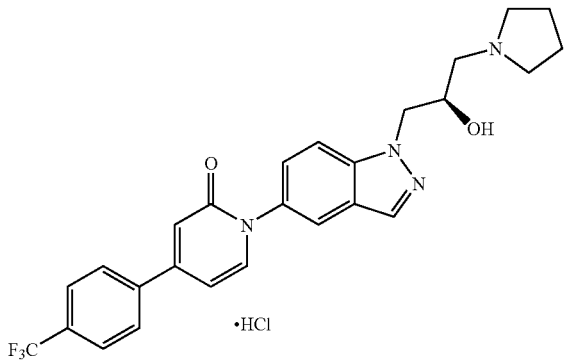

Chemical Formula: $C_{26}H_{26}ClF_3N_4O_2$
Exact Mass: 518.17
Molecular Weight: 518.96

To (S)-1-(1-(oxiran-2-ylmethyl)-1H-indazol-5-yl)-4-(4-(trifluoromethyl)phenyl)-pyridin-2(1H)-one (200 mg, 0.48 mmol) in tetrahydrofuran (5 mL) was added $LiClO_4$ (775 mg, 7.28 mmol) followed by pyrrolidine (0.41 mL, 4.9 mmol). The reaction mixture was heated in a 45° C. oil bath for 4.5 h. The reaction mixture was cooled to ambient temperature, diluted with dichloromethane (50 ml), washed with water (25 mL) and brine (25 mL), dried ($Na_2SO_4$), and concentrated under reduced pressure. The material was purified by column chromatography (silica gel, 9:1 $CH_2Cl_2$/MeOH to 90:9:1 $CH_2Cl_2$/MeOH/conc. $NH_4OH$). The dried residue (197 mg, 0.41 mmol) was dissolved in dichloromethane (10 mL) and HCl (1.25 M solution in methanol, 0.36 mL, 0.45 mmol) was added. The mixture was concentrated under reduced pressure and dried to afford the title compound (194 mg, 78%) as a yellow solid: mp 116-119° C.; $^1$H NMR (500 MHz, DMSO-$d_6$) δ 9.65 (br s, 1H), 8.21 (s, 1H), 8.02-8.00 (m, 2H), 7.89-7.82 (m, 5H), 7.47 (dd, J=9.0, 2.0 Hz, 1H), 6.89 (d, J=2.0 Hz, 1H), 6.74 (dd, J=7.0, 2.0 Hz, 1H), 5.75 (br s, 1H), 4.57-4.47 (m, 2H), 4.33 (br s, 1H), 3.56-2.90 (br m, 6H), 1.89 (br s, 4H); ESI MS m/z 483 [M+H]$^+$; HPLC (Method B)>99% (AUC), $t_R$=14.5 min; $[α]^{23}_D$ +10.8° (c 0.11, Methanol).

Example 50

Preparation of (S)-1-(1-(3-(Dimethylamino)-2-hydroxypropyl)-1H-indazol-5-yl)-4-(4-(trifluoromethyl)phenyl)pyridin-2(1H)-one hydrochloride a) (R)-1-(1-(Oxiran-2-ylmethyl)-1H-indazol-5-yl)-4-(4-(trifluoromethyl)phenyl)pyridin-2(1H)-one

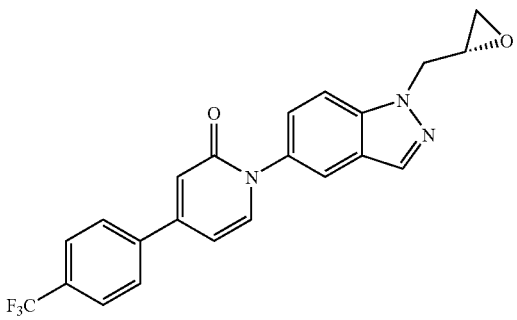

Chemical Formula: $C_{22}H_{16}F_3N_3O_2$
Exact Mass: 411.12
Molecular Weight: 411.38

A mixture of 1-(1H-indazol-5-yl)-4-(4-(trifluoromethyl)phenyl)pyridin-2(1H)-one (1.1 g, 3.1 mmol), (S)-(+)-glycidyl nosylate (0.96 g, 3.7 mmol) and cesium carbonate (1.5 g, 4.6 mmol) in methyl sulfoxide (10 mL) was stirred at ambient temperature overnight. The reaction mixture was diluted with water (20 mL) and extracted with ethyl acetate (2×50 mL). The combined organic extracts were washed with brine (20 mL), dried (Na$_2$SO$_4$), and concentrated under reduced pressure. Purification by column chromatography (silica gel, ethyl acetate) gave the title compound (510 mg, 40%) as a yellow solid: $^1$H NMR (500 MHz, CDCl$_3$) δ 8.08 (s, 1H), 7.76-7.73 (m, 5H), 7.64 (d, J=9.0 Hz, 1H), 7.51 (d, J=7.0 Hz, 1H), 7.47 (dd, J=9.0, 2.0 Hz, 1H), 6.92 (d, J=2.0 Hz, 1H), 6.52 (dd, J=7.5, 2.0 Hz, 1H), 4.78 (dd, J=15.5, 3.5 Hz, 1H), 4.48 (dd, J=15.0, 5.5 Hz, 1H), 3.41-3.38 (m, 1H), 2.88 (app t, J=4.5 Hz, 1H), 2.60 (dd, J=5.0, 3.0 Hz, 1H).

b) (S)-1-(1-(3-(Dimethylamino)-2-hydroxypropyl)-1H-indazol-5-yl)-4-(4-(trifluoromethyl)phenyl)pyridin-2(1H)-one hydrochloride

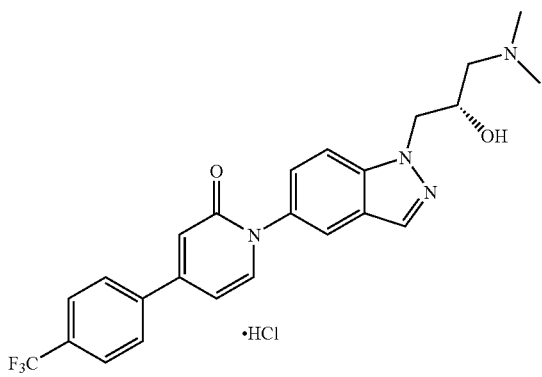

Chemical Formula: C$_{24}$H$_{24}$ClF$_3$N$_4$O$_2$
Exact Mass: 492.15
Molecular Weight: 492.92

To (R)-1-(1-(oxiran-2-ylmethyl)-1H-indazol-5-yl)-4-(4-(trifluoromethyl)-phenyl)pyridin-2(1H)-one (230 mg, 0.56 mmol) in tetrahydrofuran (5 mL) was added LiClO$_4$ (892 mg, 8.38 mmol) followed by dimethylamine (2.8 ml of a 2 M solution in tetrahydrofuran, 5.6 mmol). The reaction mixture was heated in a 45° C. oil bath for 3.75 h. The reaction mixture was cooled to ambient temperature, diluted with dichloromethane (50 ml), washed with water (25 mL) and brine (25 mL), dried (Na$_2$SO$_4$), and concentrated under reduced pressure. The material was purified by column chromatography (silica gel, 9:1 CH$_2$Cl$_2$/MeOH to 90:9:1 CH$_2$Cl$_2$/MeOH/conc. NH$_4$OH). The dried residue (198 mg, 0.43 mmol) was dissolved in dichloromethane (2 mL), and HCl (1.25 M solution in methanol, 0.38 mL, 0.47 mmol) was added. The mixture was concentrated under reduced pressure and dried to afford the title compound (198 mg, 71%) as a yellow solid: $^1$H NMR (500 MHz, DMSO-d$_6$) δ 9.42 (br s, 1H), 8.20 (s, 1H), 8.02-8.00 (m, 2H), 7.88-7.80 (m, 5H), 7.46 (dd, J=8.5, 1.5 Hz, 1H), 6.89 (d, J=2.0 Hz, 1H), 6.74 (dd, J=7.0, 2.0 Hz, 1H), 5.60 (br s, 1H), 4.56-4.52 (m, 1H), 4.48-4.44 (m, 1H), 4.27 (br s, 1H), 2.92-2.88 (br m, 2H), 2.58 (br s, 6H); ESI MS m/z 457 [M+H]$^+$; HPLC (Method B)>99% (AUC), t$_R$=14.5 min; [α]$^{23}$$_D$ –9.5° (c 0.14, Methanol).

Example 51

Preparation of (S)-1-(1-(2-Hydroxy-3-(pyrrolidin-1-yl)propyl)-1H-indazol-5-yl)-4-(4-(trifluoromethyl)phenyl)pyridin-2(1H)-one hydrochloride

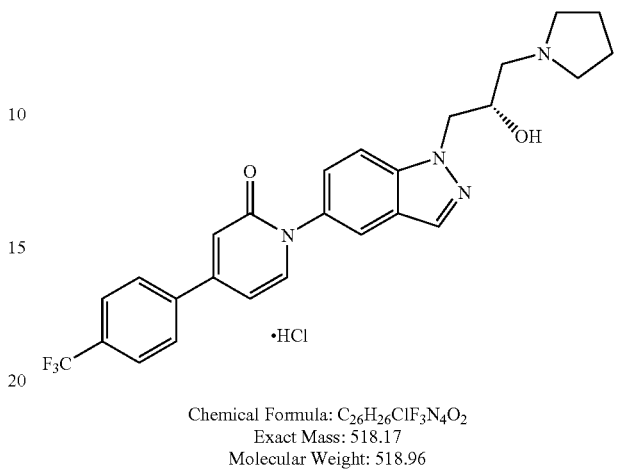

Chemical Formula: C$_{26}$H$_{26}$ClF$_3$N$_4$O$_2$
Exact Mass: 518.17
Molecular Weight: 518.96

To (R)-1-(1-(oxiran-2-ylmethyl)-1H-indazol-5-yl)-4-(4-(trifluoromethyl)phenyl)-pyridin-2(1H)-one (250 mg, 0.61 mmol) in tetrahydrofuran (5 mL) was added LiClO$_4$ (969 mg, 9.11 mmol) followed by pyrrolidine (0.51 mL, 6.1 mmol). The reaction mixture was heated in a 45° C. oil bath for 3.75 h. The reaction mixture was cooled to ambient temperature, diluted with dichloromethane (50 ml) and washed with water (25 mL), brine (25 mL), dried (Na$_2$SO$_4$), and concentrated under reduced pressure. The material was purified by column chromatography (silica gel, 9:1 CH$_2$Cl$_2$/MeOH to 90:9:1 CH$_2$Cl$_2$/MeOH/conc. NH$_4$OH). The dried residue (233 mg, 0.48 mmol) was dissolved in dichloromethane (2 mL), and HCl (1.25 M solution in methanol, 0.42 mL, 0.53 mmol) was added. The mixture was concentrated under reduced pressure and dried to afford the title compound (240 mg, 76%) as a yellow solid: $^1$H NMR (500 MHz, DMSO-d$_6$) δ 9.60 (br s, 1H), 8.20 (s, 1H), 8.02-8.00 (m, 2H), 7.89-7.80 (m, 5H), 7.46 (dd, J=8.5, 1.5 Hz, 1H), 6.89 (d, J=2.0 Hz, 1H), 6.74 (dd, J=7.5, 2.0 Hz, 1H), 4.57-4.53 (m, 1H), 4.49-4.46 (m, 1H), 4.27 (br s, 1H), 3.25-2.75 (br m, 6H), 1.85 (br s, 4H); ESI MS m/z 483 [M+H]$^+$; HPLC (Method B)>99% (AUC), t$_R$=15.1 min; [α]$^{23}$$_D$ –11.3° (c 0.11, Methanol).

Example 52

Preparation of (+)-1-(1-(2-((1S,4S)-2-Oxa-5-azabicyclo[2.2.1]heptan-5-yl)ethyl)-1H-indazol-5-yl)-4-(4-(trifluoromethyl)phenyl)pyridin-2(1H)-one hydrochloride a) 5-Bromo-1-(2-chloroethyl)-1H-indazole

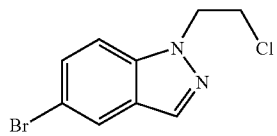

Chemical Formula: C$_9$H$_8$BrClN$_2$
Exact Mass: 257.96
Molecular Weight: 259.53

1-Bromo-2-chloroethane (2.9 mL, 35 mmol) was added to a suspension of 5-bromo-1H-indazole (4.302 g, 21.95 mmol) and $Cs_2CO_3$ (28.56 g, 87.81 mmol) in DMSO (50 mL) under $N_2$. The resulting suspension was stirred at 25° C. for 6 h. $H_2O$ (50 mL) was added, and the resulting suspension was cooled in an ice bath. The suspension was filtered, and the solid was dried under reduced pressure to afford a pink powder. Flash chromatography on silica gel (19:1 to 5:2 hexanes/EtOAc) gave the title compound (3.094 g, 54%) as a white solid: $^1$H NMR (500 MHz, $CDCl_3$) δ 8.00 (br s, 1H), 7.90 (d, J=1.5 Hz, 1H), 7.50 (dd, J=9.0, 1.5 Hz, 1H), 7.38 (d, J=9.0 Hz, 1H), 4.68 (t, J=6.3 Hz, 2H), 3.98 (t, J=6.3 Hz, 2H).

b) 5-(2-(5-Bromo-1H-indazol-1-yl)ethyl)-(1S,4S)-2-oxa-5-azabicyclo[2.2.1]heptane

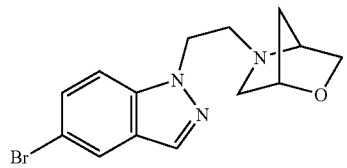

Chemical Formula: $C_{14}H_{16}BrN_3O$
Exact Mass: 321.05
Molecular Weight: 322.20

5-Bromo-1-(2-chloroethyl)-1H-indazole (183 mg, 0.703 mmol) was added to a suspension of (1S,4S)-(+)-5-aza-2-oxabicyclo[2.2.1]heptane hydrochloride (286 mg, 2.11 mmol), $K_2CO_3$ (485 mg, 3.52 mmol) and KI (117 mg, 0.703 mmol) in DMF (10 mL) under $N_2$. The resulting suspension was stirred at 90° C. for 19 h. The suspension was cooled, and $H_2O$ (10 mL) was added. The aqueous solution was extracted with EtOAc, and the combined organic extracts were washed with brine. The organic solution was dried over $Na_2SO_4$ and concentrated under reduced pressure to afford clear viscous oil. Flash chromatography on silica gel (100:0 to 0:100 hexanes/(9:0.9:0.1 $CH_2Cl_2$/MeOH/$NH_4OH$)) gave the title compound (88 mg, 39%) as a clear oil: $^1$H NMR (300 MHz, $CDCl_3$) δ 7.95-7.92 (m, 1H), 7.87-7.84 (m, 1H), 7.45 (dd, J=8.7, 1.8 Hz, 1H), 7.34 (d, J=8.7 Hz, 1H), 4.43 (t, J=6.7 Hz, 2H), 4.34 (br s, 1H), 3.92 (d, J=7.8 Hz, 1H), 3.56 (dd, J=7.8, 1.5 Hz, 1H), 3.34 (br s, 1H), 3.15-3.01 (m, 2H), 2.92 (d, J=21.9 Hz, 1H), 2.81 (dd, J=9.9, 1.5 Hz, 1H), 2.47 (br d, J=9.9 Hz, 1H), 1.79-1.60 (m, 1H).

c) (+)-1-(1-(2-((1S,4S)-2-Oxa-5-azabicyclo[2.2.1]heptan-5-yl)ethyl)-1H-indazol-5-yl)-4-(4-(trifluoromethyl)phenyl)pyridin-2(1H)-one hydrochloride

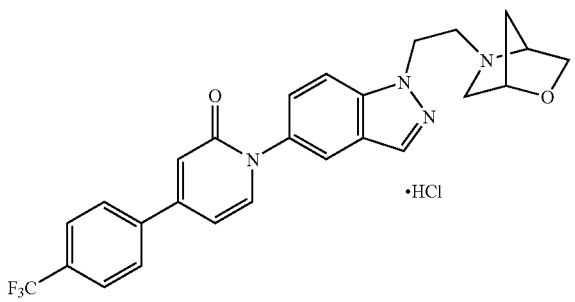

Chemical Formula: $C_{26}H_{24}ClF_3N_4O_2$
Exact Mass: 516.15
Molecular Weight: 516.94

A suspension of 4-(4-(trifluoromethyl)phenyl)pyridin-2(1H)-one (54 mg, 0.23 mmol), 5-(2-(5-bromo-1H-indazol-1-yl)ethyl)-(1S,4S)-2-oxa-5-azabicyclo[2.2.1]heptane (88 mg, 0.27 mmol), CuI (52 mg, 0.27 mmol), 8-hydroxyquinoline (7.0 mg, 0.045 mmol) and $Cs_2SO_4$ (81 mg, 0.25 mmol) in DMSO (5 mL) was degassed under reduced pressure for 45 min. The suspension was put under Ar and heated at 130° C. with stirring for 22 h. The suspension was cooled, $NH_4OH$ was added and the resulting suspension was stirred at 25° C. for 30 min. The suspension was passed through a plug of silica gel with 4:1 $CH_2Cl_2$/(9:1 MeOH/$NH_4OH$). The phases of the filtrate were separated and the aqueous phase was extracted with $CH_2Cl2$. The combined organic extracts were washed with brine, dried over $Na_2SO_4$ and concentrated under reduced pressure to afford a viscous oil. Flash chromatography on silica gel (hexanes/(9:0.9:0.1 $CH_2Cl_2$/MeOH/$NH_4OH$) 100:0 to 9:1) gave 13 mg of a viscous oil. 1.0 M HCl in $Et_2O$ (0.03 mL, 0.03 mmol) was added to a solution of the viscous oil in $CH_2Cl_2$ (10 mL) under $N_2$, and the mixture was stirred at 25° C. for 1 h. The solution was concentrated to afford the title compound (14 mg, 12%) as an off-white powder: mp 148-150° C.; $^1$H NMR (500 MHz, DMSO-$d_6$) δ 10.62-10.50 (m, 0.4H), 10.21-10.09 (m, 0.6H), 8.28 (s, 1H), 8.02 (d, J=8.0 Hz, 2H), 7.96-7.80 (m, 5H), 7.55 (d, J=9.0 Hz, 1H), 6.90 (s, 1H), 6.75 (dd, J=7.0, 1.5 Hz, 1H), 4.93-4.86 (m, 2H), 4.70 (s, 0.6H), 4.61-4.52 (m, 1.4H), 4.22 (d, J=11.0 Hz, 0.4H), 4.07-4.01 (m, 0.6H), 3.92-3.79 (m, 1.2H), 3.77 (d, J=8.5 Hz, 0.6H), 3.71-3.60 (m, 0.8H), 3.59-3.54 (m, 0.6H), 3.51-3.43 (m, 0.4H), 3.22 (d, J=12.0 Hz, 0.6H), 2.64 (s, 0.4H), 2.39-2.36 (m, 1H), 2.12 (d, J=11.5 Hz, 0.4H), 2.05-1.99 (m, 1H); ESI MS m/z 481 [M+H]$^+$; [α]$^{24}_D$ +15.0° (c 1.00, MeOH).

Example 53

Preparation of 4-(4-Chloro-2-fluorophenyl)-1-(1-(2-(pyrrolidin-1-yl)ethyl)-1H-indazol-5-yl)pyridin-2(1H)-one hydrochloride

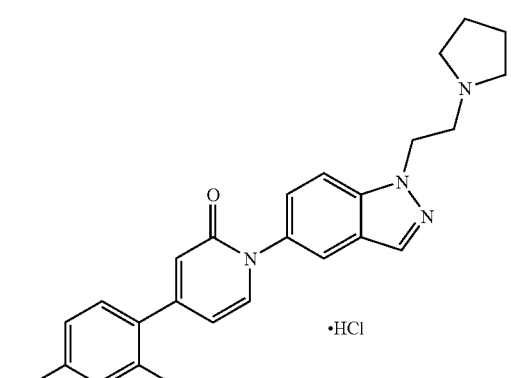

Chemical Formula: $C_{24}H_{23}Cl_2FN_4O$
Exact Mass: 472.12
Molecular Weight: 473.37

Following the procedure of Example 1, but substituting 2-fluoro-4-chlorophenylboronic acid for phenylboronic acid, the title compound (26.7 mg, 28%) was prepared as orange solid: mp 215-230° C.; $^1$H NMR (500 MHz, $CD_3OD$) δ 8.26 (s, 1H), 7.92 (d, J=1.8 Hz, 1H), 7.83 (d, J=8.9 Hz, 1H), 7.77 (d, J=8.9 Hz, 1H), 7.65 (t, J=8.2 Hz, 1H), 7.56-7.53 (dd, J=8.9, 1.9 Hz, 1H), 7.65 (m, 2H), 6.85 (m, 1H), 6.76-6.73 (dd, J=7.1, 1.8 Hz, 1H), 4.89 (t, J=5.7 Hz, 2H), 3.88 (t, J=5.7 Hz, 2H), 3.74-3.70 (m, 2H), 3.20-3.15 (m, 2H), 2.19-2.16 (m, 2H), 2.04-2.01 (m, 2H); ESI MS m/z 437 [M+H]$^+$; HPLC (Method C)>99% (AUC), $t_R$=13.1 min.

Example 54

Preparation of 4-(4-(Trifluoromethyl)-2-fluorophenyl)-1-(1-(2-(pyrrolidin-1-yl)ethyl)-1H-indazol-5-yl)pyridin-2(1H)-one hydrochloride

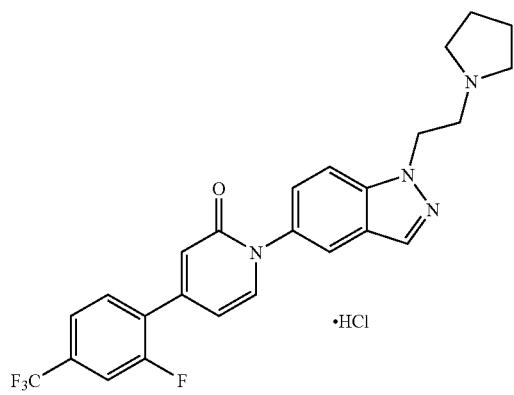

Chemical Formula: $C_{25}H_{23}ClF_4N_4O$
Exact Mass: 506.15
Molecular Weight: 506.92

Following the procedure of Example 1, but substituting 2-fluoro-4-methoxyphenylboronic acid for phenylboronic acid, the title compound (40.8 mg, 40%) was prepared as a brown solid: mp 80-95° C.; $^1$H NMR (500 MHz, CD$_3$OD) δ 8.27 (d, J=0.5 Hz, 1H), 7.93 (d, J=1.7 Hz, 1H), 7.86-7.79 (m, 3H), 7.68-7.65 (m, 2H), 7.57-7.54 (dd, J=8.9, 1.9 Hz, 1H), 6.89 (s, 1H), 6.77-6.75 (m, 1H), 4.89 (t, J=5.7 Hz, 2H), 3.88 (t, J=5.7 Hz, 2H), 3.73-3.69 (m, 2H), 3.21-3.15 (m, 2H), 2.20-2.13 (m, 2H), 2.06-2.00 (m, 2H); ESI MS m/z 471 [M+H]$^+$; HPLC (Method C) 96.1% (AUC), $t_R$=13.6 min.

Example 55

Preparation of 4-(4-Methoxy-2-fluorophenyl)-1-(1-(2-(pyrrolidin-1-yl)ethyl)-1H-indazol-5-yl)pyridin-2(1H)-one hydrochloride

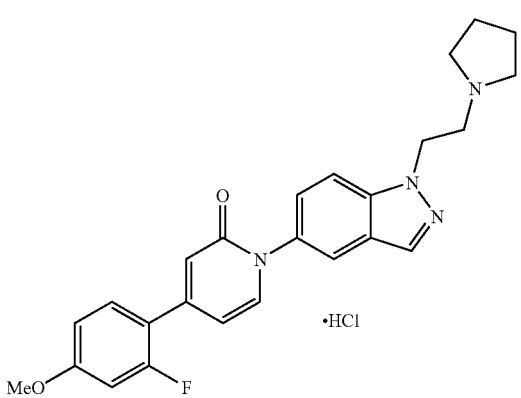

Chemical Formula: $C_{25}H_{26}ClFN_4O_2$
Exact Mass: 468.17
Molecular Weight: 468.95

Following the procedure of Example 1, but substituting 2-fluoro-4-methoxyphenylboronic acid for phenylboronic acid, the title compound (82.4 mg, 86%) was prepared as a brown-orange solid: mp 230-240° C.; $^1$H NMR (500 MHz, CD$_3$OD) δ 8.26 (d, J=0.7 Hz, 1H), 7.91 (d, J=1.6 Hz, 1H), 7.82 (d, J=8.9 Hz, 1H), 7.72 (d, J=7.2 Hz, 1H), 7.58 (t, J=8.9 Hz, 1H), 7.55-7.53 (dd, J=8.9, 1.9 Hz, 1H), 6.93-6.91 (dd, J=8.7, 2.4 Hz, 1H), 6.88-6.86 (dd, J=13.2, 2.4 Hz, 1H), 6.83 (s, 1H), 6.77-6.75 (m, 1H), 4.89 (t, J=5.7 Hz, 2H), 3.88 (m, 5H), 3.73-3.69 (m, 2H), 3.20-3.14 (m, 2H), 2.19-2.13 (m, 2H), 2.05-2.01 (m, 2H); ESI MS m/z 433 [M+H]$^+$; HPLC (Method C)>99% (AUC), $t_R$=12.6 min.

Example 56

Preparation of 4-(4-Methoxy-2-chlorophenyl)-1-(1-(2-(pyrrolidin-1-yl)ethyl)-1H-indazol-5-yl)pyridin-2(1H)-one hydrochloride

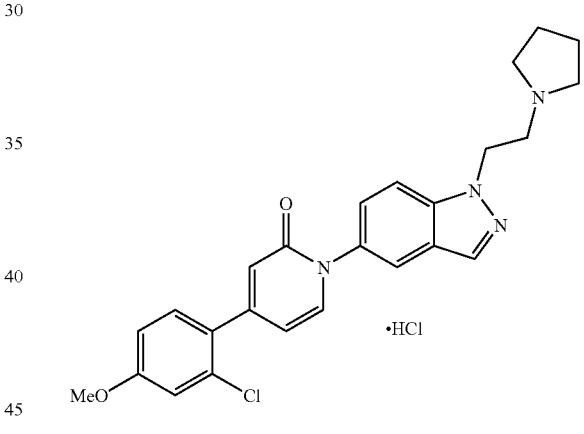

Chemical Formula: $C_{25}H_{26}Cl_2N_4O_2$
Exact Mass: 484.14
Molecular Weight: 485.41

Following the procedure in Example 1, but substituting 2-chloro-4-methoxyphenylboronic acid for phenylboronic acid, the title compound (67.3 mg, 37%) was prepared as a brown-orange solid: mp 225-235° C.; $^1$H NMR (500 MHz, CD$_3$OD) δ 8.26 (s, 1H), 7.92 (d, J=1.8 Hz, 1H), 7.82 (d, J=8.9 Hz, 1H), 7.71 (d, J=7.0 Hz, 1H), 7.56-7.54 (dd, J=8.9, 1.9 Hz, 1H), 7.42 (d, J=8.6, Hz, 1H), 7.14 (d, J=2.5 Hz, 1H), 7.04-7.02 (dd, J=8.6, 2.5 Hz, 1H), 6.68 (d, J=1.8 Hz, 1H), 6.65-6.63 (dd, J=7.0, 1.9 Hz, 1H), 4.89 (t, J=5.7 Hz, 2H), 3.88-3.87 (m, 5H), 3.72-3.69 (m, 2H), 3.20-3.15 (m, 2H), 2.21-2.13 (m, 2H), 2.06-2.01 (m, 2H); ESI MS m/z 449 [M+H]$^+$; HPLC (Method C)>99% (AUC), $t_R$=12.9 min.

Example 57

Preparation of 4-(4-Ethoxyphenyl)-1-(1-(2-(pyrrolidin-1-yl)ethyl)-1H-indazol-5-yl)pyridin-2(1H)-one hydrochloride

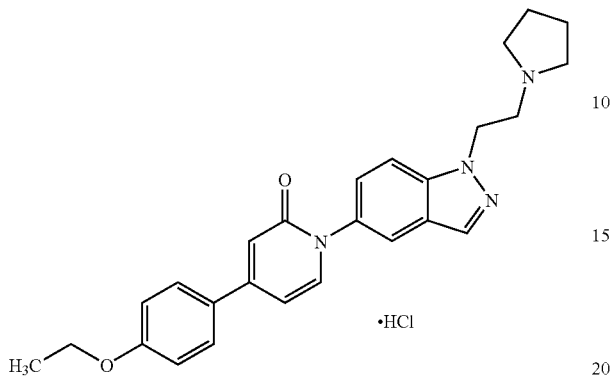

Chemical Formula: C$_{26}$H$_{29}$ClN$_4$O$_2$
Exact Mass: 464.20
Molecular Weight: 464.99

Following the procedure in Example 1, but substituting 4-ethoxyphenylboronic acid for phenylboronic acid, the title compound (54.5 mg, 23%) was prepared as a orange solid: mp 255-265° C.; $^1$H NMR (500 MHz, CD$_3$OD) δ 8.25 (s, 1H), 7.90 (d, J=1.9 Hz, 1H), 7.82 (d, J=8.9 Hz, 1H), 7.74-7.72 (m, 3H), 7.55-7.52 (dd, J=8.9, 1.9 Hz, 1H), 7.07-7.04 (m, 2H), 6.90-6.88 (m, 2H), 4.89 (t, J=5.7 Hz, 2H), 4.12 (q, J=7.0 Hz, 2H), 3.88 (t, J=5.7 Hz, 2H), 3.73-3.69 (m, 2H), 3.20-3.15 (m, 2H), 2.19-2.14 (m, 2H), 2.04-2.00 (m, 2H), 1.43 (t, J=7.0 Hz, 3H); ESI MS m/z 429 [M+H]$^+$; HPLC (Method C)>99% (AUC), t$_R$=13.1 min.

Example 58

Preparation of 4-(4-(Trifluoromethoxy)-2-fluorophenyl)-1-(1-(2-(pyrrolidin-1-yl)ethyl)-1H-indazol-5-yl)pyridin-2(1H)-one hydrochloride

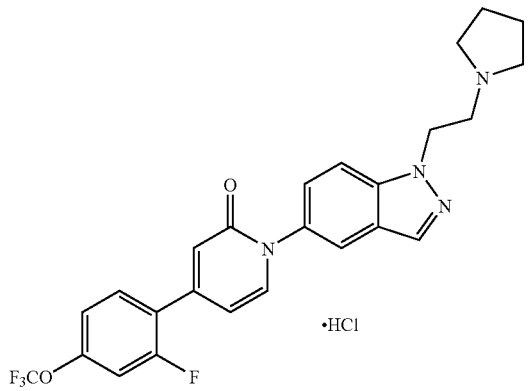

Chemical Formula: C$_{25}$H$_{23}$ClF$_4$N$_4$O$_2$
Exact Mass: 522.14
Molecular Weight: 522.92

Following the procedure in Example 30, but substituting 1-bromo-2-fluoro-4-(trifluoromethoxy)benzene for 2-bromo-5-methylpyridine, the title compound (24.1 mg, 19%) was prepared as a yellow solid: mp 215-225° C.; $^1$H NMR (500 MHz, CD$_3$OD) δ 8.26 (d, J=0.4 Hz, 1H), 7.92 (d, J=1.8 Hz, 1H), 7.82 (d, J=8.9 Hz, 1H), 7.78-7.75 (m, 2H), 7.56-7.54 (dd, J=8.9, 1.9 Hz, 1H), 7.33-7.30 (m, 2H), 6.86 (s, 1H), 6.75-6.73 (m, 1H), 4.89 (t, J=5.8, 2H), 3.87 (t, J=5.8, 2H), 3.71 (m, 2H), 3.19 (m, 2H), 2.16-2.04 (m, 4H); ESI MS m/z 487 [M+H]$^+$; HPLC (Method C)>99% (AUC), t$_R$=14.3 min.

Example 59

Preparation of 4-(4-(Trifluoromethoxy)-2-methylphenyl)-1-(1-(2-(pyrrolidin-1-yl)ethyl)-1H-indazol-5-yl)pyridin-2(1H)-one hydrochloride

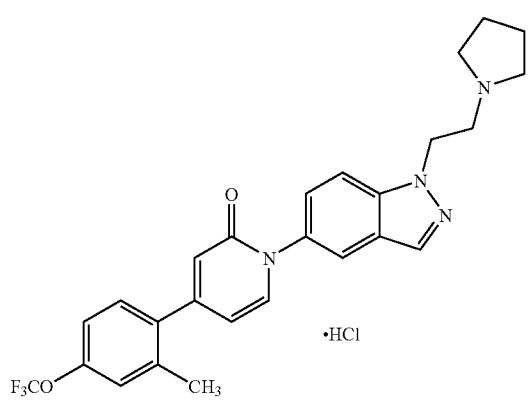

Chemical Formula: C$_{26}$H$_{26}$ClF$_3$N$_4$O$_2$
Exact Mass: 518.17
Molecular Weight: 518.96

Following the procedure in Example 30, but substituting 1-bromo-2-fluoro-4-(trifluoromethoxy)benzene for 2-bromo-5-methylpyridine, the title compound (49.0 mg, 21%) was prepared as a orange solid: mp 185-195° C.; $^1$H NMR (500 MHz, CD$_3$OD) δ 8.27 (s, 1H), 7.93 (d, J=1.7 Hz, 1H), 7.83 (d, J=8.9 Hz, 1H), 7.75 (d, J=7.0 Hz, 1H), 7.57-7.55 (dd, J=8.9, 1.9 Hz, 1H), 7.41 (d, J=8.4 Hz, 1H), 7.27 (s, 1H), 7.23 (d, J=8.4 Hz, 1H), 6.61 (d, J=1.7 Hz, 1H), 6.56-6.54 (dd, J=7.0, 1.8 Hz, 1H), 4.90 (t, J=5.7, 2H), 3.88 (t, J=5.7, 2H), 3.74-3.69 (m, 2H), 3.21-3.15 (m, 2H), 2.43 (s, 3H), 2.19-2.16 (m, 2H) 2.04-2.00 (m, 2H); ESI MS m/z 483 [M+H]$^+$; HPLC (Method C)>99% (AUC), t$_R$=14.7 min.

Example 60

Preparation of 4-(1-Methyl-1H-indazol-5-yl)-1-(1-(2-(pyrrolidin-1-yl)ethyl)-1H-indazol-5-yl)pyridine 2(1H)-one hydrochloride a) 5-Bromo-1-methyl-1H-indazole Beilstein Registry Number 127881

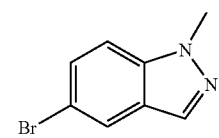

Chemical Formula: C$_8$H$_7$BrN$_2$
Exact Mass: 209.98
Molecular Weight: 211.06

To a solution of 5-bromo-1H-indazole (1.0 g, 5.07 mmol) in DMSO (15 mL) was added iodomethane (0.41 mL, 6.6 mmol) and $K_2CO_3$ (3.4 g, 25 mmol). The reaction was stirred at room temperature for 3 h; then the reaction was diluted with methylene chloride (100 mL) and washed with a 5% LiCl solution (4×). The organics were washed with brine (50 mL), dried ($Na_2SO_4$), filtered, and concentrated. Purification by flash chromatography (40 g ISCO column, hexanes/EtOAc, 100:0 to 70:30) gave the title compound (532 mg, 50%) as a white powder: $^1$H NMR (500 MHz, $CDCl_3$) δ 7.91 (s, 1H), 7.87 (d, J=1.7 Hz, 1H), 7.47-7.44 (dd, J=8.9, 1.7 Hz, 1H), 7.28 (d, J=8.8 Hz, 1H), 4.06 (s, 3H).

b) 4-(1-Methyl-1H-indazol-5-yl)-1-(1-(2-(pyrrolidin-1-yl)ethyl)-1H-indazol-5-yl)pyridine 2(1H)-one hydrochloride

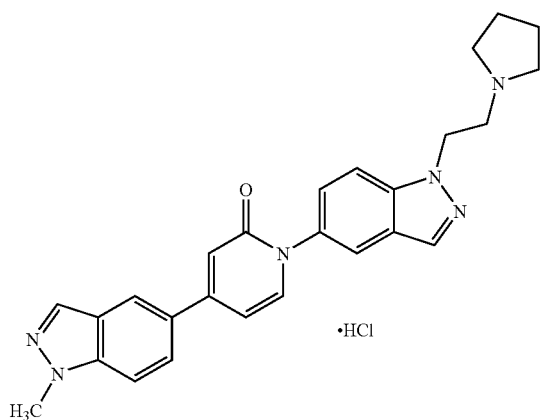

Chemical Formula: $C_{26}H_{27}ClN_6O$
Exact Mass: 474.19
Molecular Weight: 474.99

Following the procedure in Example 30, but substituting 5-bromo-1-methyl-1H-indazole for 2-bromo-5-methylpyridine, the title compound (18.0 mg, 11%) was prepared as a orange solid: mp 55-65° C.; $^1$H NMR (500 MHz, $CD_3OD$) δ 8.27 (d, J=0.9 Hz, 1H), 8.23 (d, J=0.9 Hz, 1H), 8.14 (d, J=0.9 Hz, 1H), 7.93 (d, J=1.4 Hz, 1H), 7.84 (t, J=8.9 Hz, 2H), 7.80-7.78 (dd, J=5.8, 1.9 Hz, 1H), 7.72 (d, J=8.9 Hz, 1H), 7.58-7.55 (dd, J=8.9, 1.9 Hz, 1H), 7.01-6.99 (m, 2H), 4.90 (t, J=5.7, 2H), 4.12 (s, 3H), 3.88 (t, J=5.7, 2H), 3.74-3.70 (m, 2H), 3.21-3.16 (m, 2H), 2.21-2.14 (m, 2H) 2.07-1.99 (m, 2H); ESI MS m/z 439 [M+H]$^+$; HPLC (Method C) 96.5% (AUC), $t_R$=11.0 min.

Example 61

1-(1-(3-(Pyrrolidin-1-yl)propyl)-1H-indazol-5-yl)-4-(5-(trifluoromethyl)pyridin-2-yl)pyridin-2(1H)-one hydrochloride a) 2'-Methoxy-5-(trifluoromethyl)-2,4'-bipyridine

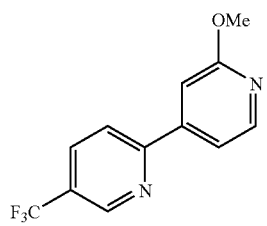

Chemical Formula: $C_{12}H_9F_3N_2O$
Exact Mass: 254.07
Molecular Weight: 254.21

2-Bromo-5-trifluoromethylpyridine (410 mg, 2.13 mmol), 2-methoxy-4-(4,4,5,5-tetramethyl-1,3,2-dioxaborolan-2-yl)pyridine (500 mg, 1.81 mmol), $K_2CO_3$ (749 mg, 5.43 mmol) and [1,1'-Bis-(diphosphenylphosphino)ferrocene]dichloropalladium(II) ($PdCl_2dppf$) (74 mg, 0.091 mmol) were stirred in DMSO (2 mL) under vacuum for 30 min. The flask was flushed with nitrogen and the mixture was heated to 90° C. for 30 min. Upon cooling, the mixture was diluted with methylene chloride and washed with 5% lithium chloride solution (5×), dried, concentrated, and the residue was purified by column chromatography (silica gel, hexanes/ethyl acetate, 97:3 to 75:25) provide the title compound (337 mg, 62%) as a white solid: $^1$H NMR (300 MHz, $CDCl_3$) δ 8.96 (s, 1H), 8.31 (d, J=5.4 Hz, 1H), 8.06-8.02 (dd, J=8.3, 2.1 Hz, 1H), 7.87 (d, J=8.3 Hz, 1H), 7.52-7.49 (dd, J=5.4, 1.4 Hz, 1H), 7.36 (s, 1H), 3.52 (s, 3H).

b) 4-(5-(Trifluoromethyl)pyridin-2-yl)pyridin-2(1H)-one

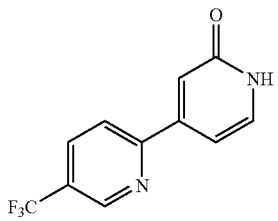

Chemical Formula: $C_{11}H_7F_3N_2O$
Exact Mass: 240.05
Molecular Weight: 240.18

2'-Methoxy-5-(trifluoromethyl)-2,4'-bipyridine (337 mg, 1.32 mmol) was stirred in concentrated hydrochloric acid (200 mL) at 120° C. for 18 h and then concentrated. The residue was dissolved in MeOH (100 mL) and made basic with 6 N NaOH and re-concentrated until most of the solvent had been removed. The solids were filtered off, washed with water and dried under vacuum to provide the title compound (289 mg, 89%) as a white solid: $^1$H NMR (300 MHz, DMSO-d$_6$) δ 11.08 (s, 1H) 9.10 (s, 1H), 8.36-8.33 (dd, J=8.4, 2.1 Hz, 1H), 8.25 (d, J=8.3 Hz, 1H), 7.53 (d, J=6.8, 1H), 7.09 (d, J=1.3 Hz, 1H), 6.90 (dd, J=6.8, 1.6 Hz, 1H).

c) 5-Bromo-1-(3-chloropropyl)-1H-indazole

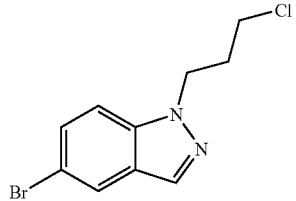

Chemical Formula: C$_{10}$H$_{10}$BrClN$_2$
Exact Mass: 271.97
Molecular Weight: 273.56

To a solution of 5-bromo-1H-indazole (3.0 g, 15 mmol) in DMSO (15 mL) was added 1-bromo-3-chloropropane (2.0 mL, 20 mmol) and K$_2$CO$_3$ (6.33 g, 45.9 mmol). The reaction was stirred at room temperature for 72 h; then the reaction was diluted with methylene chloride (100 mL) and washed with a 5% LiCl solution (4×). The organics were washed with brine (50 mL), dried (Na$_2$SO$_4$), filtered, and concentrated. Purification by flash chromatography (40 g ISCO column, hexanes/EtOAc, 95:5 to 65:35) gave the title compound (2.14 g, 51%) as a white powder: $^1$H NMR (500 MHz, CDCl$_3$) δ 7.95 (d, J=0.5, 1H), 7.87 (d, J=1.5 Hz, 1H), 7.48-7.45 (dd, J=8.9, 1.8 Hz, 1H), 7.38 (d, J=8.9 Hz, 1H), 4.54 (t, J=6.4 Hz, 2H) 3.47 (t, J=6.0 Hz, 2H) 2.42-2.37 (m, 2H); ESI MS m/z 273 [M+H]$^+$.

d) 5-Bromo-1-(3-(pyrrolidin-1-yl)propyl)-1H-indazole

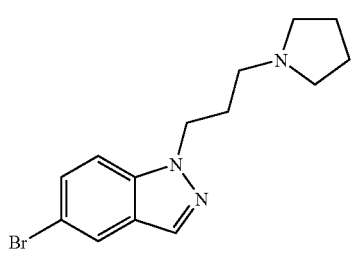

Chemical Formula: C$_{14}$H$_{18}$BrN$_3$
Exact Mass: 307.07
Molecular Weight: 308.22

To a solution of 5-bromo-1-(3-chloropropyl)-1H-indazole (2.14 g, 7.84 mmol) in DMF (40 mL) was added potassium iodide (1.3 mg, 7.8 mmol) and K$_2$CO$_3$ (5.40 g, 39.2 mmol) under N$_2$ (g). Then pyrrolidine (17.2 ml, 26.6 mmol) was added. The reaction was heated to 50° C. for 20 h. The reaction was diluted with EtOAc (100 mL) and washed with a 5% LiCl solution (4×). The organics were dried (Na$_2$SO$_4$), filtered, and concentrated to give the title compound (2.48 g, quant.) as a brown oil: $^1$H NMR (300 MHz, CDCl$_3$) δ 7.93 (s, 1H), 7.85 (d, J=1.2 Hz, 1H), 7.45-7.41 (dd, J=8.9, 1.7 Hz, 1H), 7.36 (d, J=8.9 Hz, 1H), 4.45 (t, J=6.7 Hz, 1H), 2.44-2.36 (m, 6H), 2.15-2.07 (m, 2H), 1.78-1.74 (m, 4H); ESI MS m/z 308 [M+H]$^+$.

e) 1-(1-(3-(Pyrrolidin-1-yl)propyl)-1H-indazol-5-yl)-4-(5-(trifluoromethyl)pyridin-2-yl)pyridin-2(1H)-one hydrochloride

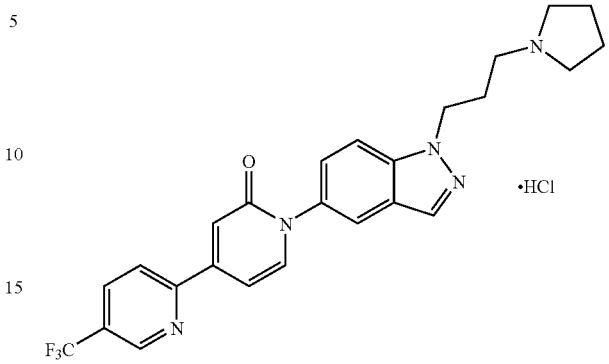

Chemical Formula: C$_{25}$H$_{25}$ClF$_3$N$_5$O
Exact Mass: 503.17
Molecular Weight: 503.95

5-Bromo-1-(3-(pyrrolidin-1-yl)propyl)-1H-indazole (137 mg, 0.444 mmol) and 4-(5-(trifluoromethyl)pyridin-2-yl)pyridin-2(1H)-one (82 mg, 0.342 mmol) were reacted according to Example 37 (steps e and h) to provide the title compound (57.9 mg, 29%) as a yellow solid: mp 110-120° C.; $^1$H NMR (500 MHz, CD$_3$OD) δ 9.05 (s, 1H), 8.29-8.27 (dd, J=8.4, 2.1 Hz, 1H), 8.22 (d, J=8.4 Hz, 1H), 8.20 (s, 1H), 7.90 (d, J=1.8 Hz, 1H), 7.83 (d, J=7.2 Hz, 1H), 7.79 (d, J=8.9 Hz, 1H), 7.53-7.51 (dd, J=8.9, 1.9 Hz, 1H), 7.40 (d, J=1.7 Hz, 1H), 7.27-7.25 (dd, J=7.2, 1.9 Hz, 1H), 4.63 (t, J=6.5, 2H), 3.67-3.63 (m, 2H), 3.27-3.24 (m, 2H), 3.08-3.03 (m, 2H), 2.43-2.36 (m, 2H), 2.16-2.12 (m, 2H) 2.03-1.99 (m, 2H); ESI MS m/z 468 [M+H]$^+$; HPLC (Method D)>99% (AUC), t$_R$=18.0 min.

Example 62

Preparation of 4-(4-(Piperidin-1-yl)phenyl)-1-(1-(2-(pyrrolidin-1-yl)ethyl)-1H-indazol-5-yl)pyridin-2(1H)-one hydrochloride a) 1-(4-(4,4,5,5-Tetramethyl-1,3,2-dioxaborolan-2-yl)phenyl)piperidine

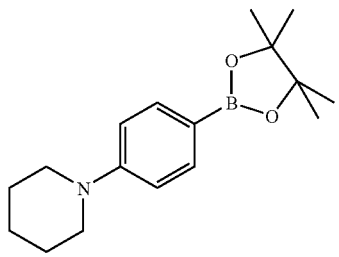

Chemical Formula: C$_{17}$H$_{26}$BNO$_2$
Exact Mass: 287.21
Molecular Weight: 287.20

To a solution of 1-(4-bromophenyl)piperidine (250 mg, 1.04 mmol) in DMSO (6 mL) was added bis-pinacolatodiboron (314 mg, 1.24 mmol) and KOAc (306 mg, 3.12 mmol). The reaction was degassed under vacuum for 30 min. then the flask was flushed N$_2$ (g). PdCl$_2$dppf (85 mg, 0.104 mmol) was added, then the reaction was heated to 60° C. for 20 h. Upon cooling, the reaction was then diluted with methylene chloride (50 mL) and washed with a 5% LiCl solution (4×). The organics were dried (Na$_2$SO$_4$), filtered, and concentrated. Purification by flash chromatography (12 g ISCO column, methylene chloride/[MeOH/NH$_4$OH 10:1)], 100:0 to 85:15) gave the title compound (262 mg, 86%) as a white powder: ESI MS m/z 288 [M+H]$^+$.

b) 4-(4-(Piperidin-1-yl)phenyl)-1-(1-(2-(pyrrolidin-1-yl)ethyl)-1H-indazol-5-yl)pyridin-2(1H)-one hydrochloride

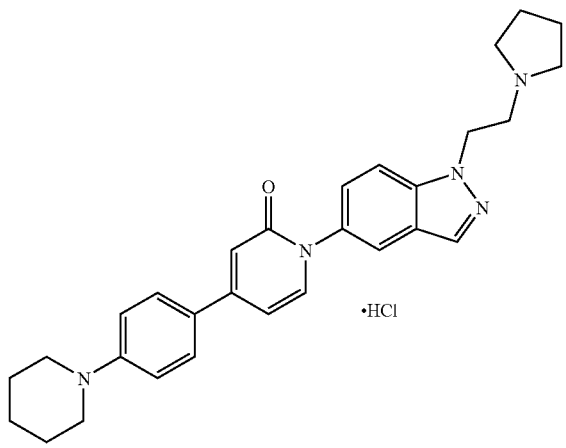

Chemical Formula: C$_{29}$H$_{34}$ClN$_5$O
Exact Mass: 503.25
Molecular Weight: 504.07

Following the procedure in Example 1, but substituting 1-(4-(4,4,5,5-tetramethyl-1,3,2-dioxaborolan-2-yl)phenyl) piperidine (268 mg, 0.434 mmol) for phenylboronic acid, the title compound (54.5 mg, 23%) was prepared as a orange solid: melting point (mp) 80-90° C.; $^1$H NMR (500 MHz, CD$_3$OD) δ 8.26 (s, 1H), 7.98 (d, J=8.7 Hz, 2H), 7.91 (d, J=1.8 Hz, 1H), 7.84-7.76 (m, 4H), 7.55-7.53 (dd, J=9.0, 1.9 Hz, 1H), 6.93 (d, J=1.9 Hz, 1H), 6.87-6.85 (dd, J=7.2, 2.0 Hz, 1H), 4.89 (t, J=5.7 Hz, 2H), 3.88 (t, J=5.7 Hz, 2H), 3.72-3.66 (m, 6H), 3.19-3.15 (m, 2H), 2.18-2.16 (m, 2H), 2.06-2.01 (m, 6H), 1.83 (m, 2H); ESI MS m/z 468 [M+H]$^+$; HPLC (Method C) 97.1% (AUC), t$_R$=10.2 min.

Example 63

Preparation of 4-(5-Methylbenzo[d]oxazol-2-yl)-1-(1-(2-(pyrrolidin-1-yl)ethyl)-1H-indazol-5-yl)pyridin-2(1H)-one hydrochloride a) 5-Methyl-2-(methylthio)benzo[d]oxazole Beilstein Registry Number 4849575

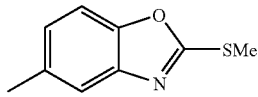

Chemical Formula: C$_9$H$_9$NOS
Exact Mass: 179.04
Molecular Weight: 179.24

To a solution of 5-methylbenzoxazoline-2-thione (1.0 g, 6.2 mmol) in Acetone (50 mL) was added iodomethane (0.6 mL, 9.9 mmol) and K$_2$CO$_3$ (3.4 mg, 24.8 mmol). The flask was flushed with N$_2$ (g), and the mixture was stirred at room temperature for 20 h. The reaction was then filtered through celite, rinsed with acetone, and then the organics were concentrated. The resulting solid was dissolved in EtOAc and washed with water (3×). The organics were dried (Na$_2$SO$_4$), filtered, and concentrated. Purification by flash chromatography (12 g ISCO column, hexanes/EtOAc, 95:5 to 70:30) gave the title compound (1.04 g, 93%) as a white powder: $^1$H NMR (300 MHz, CDCl$_3$) δ 7.39 (s, 1H), 7.30 (d, J=8.3 Hz, 1H), 7.06-7.02 (dd, J=8.3, 0.9 Hz, 1H), 2.75 (s, 3H), 2.44 (s, 3H); ESI MS m/z 180 [M+H]$^+$.

b) 4-(5-Methylbenzo[d]oxazol-2-yl)-1-(1-(2-(pyrrolidin-1-yl)ethyl)-1H-indazol-5-yl)pyridin-2(1H)-one hydrochloride

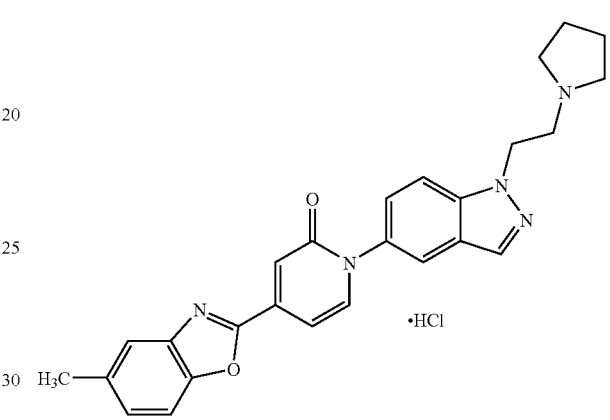

Chemical Formula: C$_{26}$H$_{26}$ClN$_5$O$_2$
Exact Mass: 475.18
Molecular Weight: 475.97

1-(1-(2-(Pyrrolidin-1-yl)ethyl)-1H-indazol-5-yl)-4-(trimethylstannyl)pyridin-2(1H)-one (prepared according to Example 30, step a) (250 mg, 0.530 mmol), 5-methyl-2-(methylthio)benzo[d]oxazole (198 mg, 1.11 mmol), copper (II) bromide (331 mg, 1.16 mmol) and palladium tetrakistriphenylphosphine (61 mg, 0.053 mmol) were stirred in dry THF (6 mL) under a nitrogen atmosphere. The mixture was heated to 70° C. for 20 h. Upon cooling, the mixture was diluted with THF, filtered through celite and rinsed with THF/methylene chloride. The organics were concentrated and purified by flash chromatography (40 g ISCO column eluting with methylene chloride and methanol/ammonia (10:1); 100% methylene chloride to 15% methanol/ammonia over 35 min at 40 mL/min) then further purified by Preparatory HPLC. The appropriate fractions were concentrated and partitioned between methylene chloride and Na$_2$CO$_3$. The organics were dried with Na$_2$SO$_4$, filtered, and concentrated to provide the free base. This was dissolved in methylene chloride (2 mL) and treated with 1 equivalent of 2 M HCl in Et$_2$O, and the mixture was concentrated to provide the title compound (55.8 mg, 24%) as a yellow solid: mp 270-280° C.; $^1$H NMR (500 MHz, CD$_3$OD) δ 8.27 (s, 1H), 7.94 (d, J=1.7 Hz, 1H), 7.88 (d, J=7.1 Hz, 1H), 7.83 (d, J=8.9 Hz, 1H), 7.64-7.61 (m, 2H), 7.58-7.55 (dd, J=8.9, 1.9 Hz, 1H), 7.44 (d, J=1.7 Hz, 1H), 7.37 (d, J=8.4 Hz, 1H), 7.24-7.22 (dd, J=7.1, 1.9 Hz, 1H), 4.89 (t, J=5.7, 2H), 3.88 (t, J=5.7, 2H), 3.74-3.70 (m, 2H), 3.21-3.16 (m, 2H), 2.51 (s, 3H), 2.20-2.16 (m, 2H) 2.04-2.01 (m, 2H); ESI MS m/z 440 [M+H]$^+$; HPLC (Method C) 98.7% (AUC), t$_R$=13.1 min.

Example 64

Preparation of 4-(5-Methoxy-1H-indol-2-yl)-1-(1-(2-(pyrrolidin-1-yl)ethyl)-1H-indazol-5-yl)pyridin-2(1H)-one hydrochloride

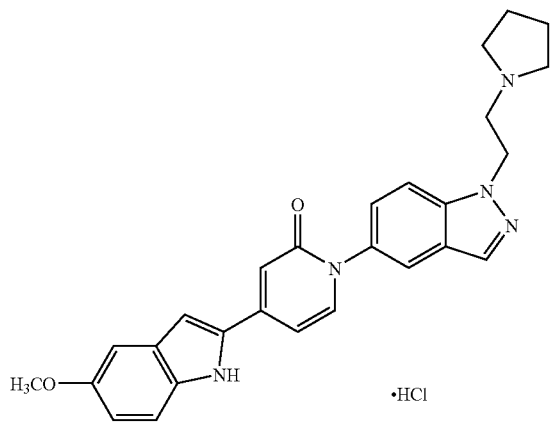

Chemical Formula: $C_{27}H_{28}ClN_5O_2$
Exact Mass: 489.19
Molecular Weight: 490.00

Following the procedure of Example 1, but substituting 5-methoxyindole-2-boronic acid for phenylboronic acid, the title compound (67 mg, 68%) was prepared as a yellow solid: mp 275-280° C.; $^1$H NMR (500 MHz, CD$_3$OD) δ 8.25 (s, 1H), 7.90 (d, J=1.6 Hz, 1H), 7.80 (d, J=8.9 Hz, 1H), 7.68-7.67 (dd, J=6.9, 1.2 Hz, 1H), 7.55-7.52 (dd, J=8.8, 1.9 Hz, 1H), 7.33 (d, J=8.9 Hz, 1H), 7.08 (d, J=2.2 Hz, 1H), 7.06 (s, 1H), 6.98-6.95 (m, 2H), 6.90-6.88 (dd, J=8.9, 2.5 Hz, 1H), 4.88 (t, J=5.8 Hz, 2H), 3.87 (t, J=5.8 Hz, 2H), 3.83 (s, 3H), 3.77-3.67 (br m, 2H), 3.22-3.12 (br m, 2H), 2.20-2.11 (br m, 2H), 2.08-1.97 (br m, 2H); ESI MS m/z 454 [M+H]$^+$; HPLC (Method C)>99% (AUC), $t_R$=12.4 min.

Example 65

Preparation of 4-(5-Methoxy-1-methyl-1H-indol-2-yl)-1-(1-(2-(pyrrolidin-1-yl)ethyl)-1H-indazol-5-yl)pyridin-2(1H)-one dihydrochloride

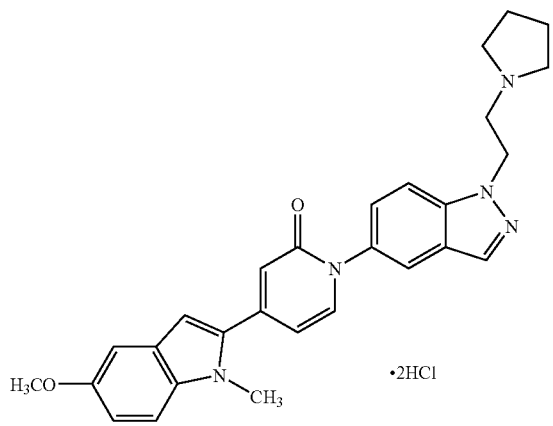

Chemical Formula: $C_{28}H_{31}Cl_2N_5O_2$
Exact Mass: 539.19
Molecular Weight: 540.48

Under a nitrogen atmosphere 4-(5-methoxy-1H-indol-2-yl)-1-(1-(2-(pyrrolidin-1-yl)ethyl)-1H-indazol-5-yl)pyridin-2(1H)-one (47 mg, 0.10 mmol) was dissolved in DMF (5 mL) and NaH (60% dispersion, 5 mg, 0.12 mmol) was added. After 20 minutes MeI (21 mg, 9.3 µL, 0.15 mmol) was added and the mixture was stirred overnight. The solid was filtered off, purified by prep HPLC and converted to the dihydrochloride as in Example 1 to provide the title compound (10 mg, 18%) as a yellow solid: $^1$H NMR (500 MHz, CD$_3$OD) δ 8.27 (s, 1H), 7.92 (d, J=1.7 Hz, 1H), 7.82 (d, J=8.8 Hz, 1H), 7.75 (d, J=6.6 Hz, 1H), 7.57-7.55 (dd, J=8.9, 1.9 Hz, 1H), 7.37 (d, J=8.9 Hz, 1H), 7.11 (d, J=2.4 Hz, 1H), 6.96-6.94 (dd, J=8.9, 2.4 Hz, 1H), 6.80-6.78 (m, 3H), 4.89 (t, J=5.7 Hz, 2H), 3.88 (s, 3H), 3.87 (t, J=5.7 Hz, 2H), 3.83 (s, 3H), 3.72 (br m, 2H), 3.18 (br m, 2H), 2.17 (br m, 2H), 2.03 (br m, 2H); ESI MS m/z 468 [M+H]$^+$; HPLC (Method C) 98.8% (AUC), $t_R$=12.8 min.

Example 66

Preparation of 4-(4-(1H-Pyrazol-1-yl)phenyl)-1-(1-(2-(pyrrolidin-1-yl)ethyl)-1H-indazol-5-yl)pyridin-2(1H)-one hydrochloride

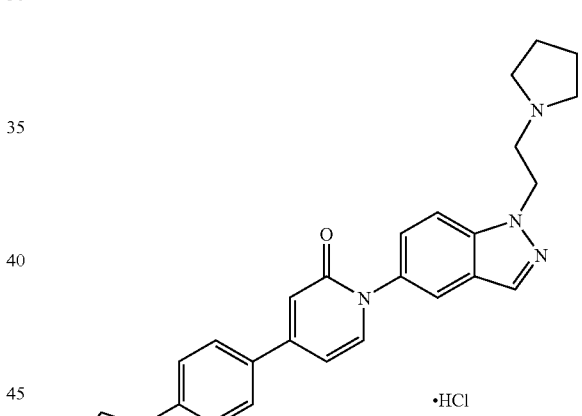

Chemical Formula: $C_{27}H_{27}ClN_6O$
Exact Mass: 486.19
Molecular Weight: 487.00

Following the procedure of Example 1, but substituting 4-(1H-pyrazol-1-yl)phenylboronic acid for phenylboronic acid, the title compound (64 mg, 60%) was prepared as a brown solid: mp 271-275° C.; $^1$H NMR (500 MHz, CD$_3$OD) δ 8.34 (d, J=2.5 Hz, 1H), 8.26 (s, 1H), 7.95-7.90 (m, 5H), 7.83 (d, J=8.9 Hz, 1H), 7.78-7.76 (m, 2H), 7.56-7.54 (d, J=8.9, 1.9 Hz, 1H), 6.95 (d, J=1.9 Hz, 1H), 6.90 (dd, J=7.1, 2.0 Hz, 1H), 6.58 (t, J=1.9 Hz, 1H), 4.89 (t, J=5.8 Hz, 2H), 3.89 (t, J=5.8 Hz, 2H), 3.76-3.68 (br m, 2H), 3.21-3.13 (br m, 2H), 2.22-2.12 (br m, 2H), 2.08-1.96 (br m, 2H); ESI MS m/z 451 [M+H]$^+$; HPLC (Method C) 95.1% (AUC), $t_R$=11.7 min.

Example 67

Preparation of 4-(4-Methylcyclohex-1-enyl)-1-(1-(2-(pyrrolidin-1-yl)ethyl)-1H-indazol-5-yl)pyridin-2(1H)-one hydrochloride

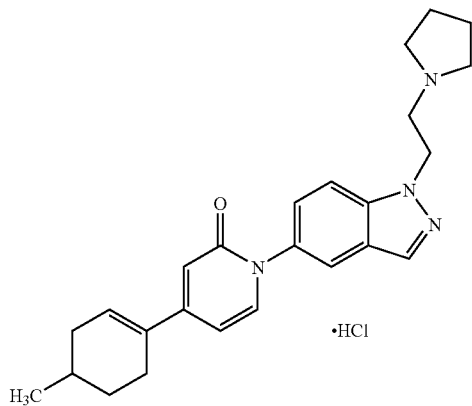

Following the procedure of Example 1, but substituting 4-methylcyclohex-1-enylboronic acid for phenylboronic acid, the title compound (76 mg, 54%) was prepared as an orange solid: mp 256-260° C.; $^1$H NMR (500 MHz, CD$_3$OD) δ 8.23 (s, 1H), 7.84 (d, J=1.4 Hz, 1H), 7.78 (d, J=8.9 Hz, 1H), 7.55 (d, J=7.2 Hz, 1H), 7.49-7.47 (dd, J=8.9, 1.9 Hz, 1H), 6.70-6.68 (dd, J=7.3, 1.9 Hz, 1H), 6.57-6.54 (m, 2H), 4.87 (t, J=5.7 Hz, 2H), 3.86 (t, J=5.7 Hz, 2H), 3.73-3.69 (m, 2H), 3.20-3.13 (m, 2H), 2.46-2.36 (m, 3H), 2.21-2.12 (m, 2H), 2.05-1.97 (m, 2H), 1.96-1.85 (m, 2H), 1.79-1.71 (m, 1H), 1.44-1.34 (m, 1H), 1.03 (d, J=6.6 Hz, 3H); ESI MS m/z 403 [M+H]$^+$; HPLC (Method C)>99% (AUC), t$_R$=13.4 min.

Example 68

Preparation of 4-(4-Methylcyclohexyl)-1-(1-(2-(pyrrolidin-1-yl)ethyl)-1H-indazol-5-yl)pyridin-2(1H)-one hydrochloride

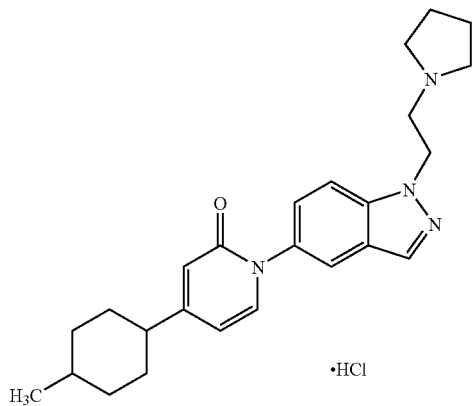

Chemical Formula: C$_{25}$H$_{33}$ClN$_4$O
Exact Mass: 440.23
Molecular Weight: 441.01

4-(4-Methylcyclohex-1-enyl)-1-(1-(2-(pyrrolidin-1-yl)ethyl)-1H-indazol-5-yl)pyridin-2(1H)-one (50 mg, 0.12 mmol) was reacted following the procedure of Example 1 (step d) to provide the title compound (mixture of E and Z isomers) (31 mg, 60%) as a white solid: mp 80-85° C.; $^1$H NMR (500 MHz, CD$_3$OD) δ 8.21 (s, 1H), 7.82 (s, 1H), 7.77 (d, J=8.8 Hz, 1H), 7.57-7.56 (m, 1H), 7.47-7.44 (m, 1H), 6.54-6.45 (m, 2H), 4.82 (m, 2H), 3.71-3.64 (br m, 2H), 3.29-3.28 (br m, 3H), 2.61-2.55 (t, J=8.5, 0.6 Hz, 0.6H), 2.48-2.41 (t, J=13.2 Hz, 0.4H), 2.02 (s, 4H), 1.97-1.67 (m, 6H), 1.59-1.42 (m, 3H), 1.34 (q, J=13.1 Hz, 1H), 1.05 (d, J=7.3 Hz, 2H), 0.92 (d, J=7.0 Hz, 1H); ESI MS m/z 405 [M+H]$^+$; HPLC (Method C) 98.6% (AUC), t$_R$=13.4 min.

Binding Assay I for Human Melanin-Concentrating Hormone (MCH$_1$) Receptor

Evaluation of the affinity of compounds for the human MCH$_1$ receptor was accomplished in transfected Chinese Hamster Ovary (CHO) cells determined in a radioligand binding assay, as described in MacDonald et al., "Molecular characterization of the melanin-concentrating hormone/receptor complex: identification of critical residues involved in binding and activation", Mol Pharmacol., 58:217 (2000). Cell membrane homogenates (5 μg protein) were incubated for 60 min at 22° C. with 0.1 nM [$^{125}$I][Phe$^{13}$,Tyr$^{19}$]-MCH in the absence or presence of the test compound in a buffer containing 25 mM Hepes/Tris (pH 7.4), 5 mM MgCl$_2$, 1 mM CaCl$_2$ and 0.5% bovine serum albumin (BSA). Nonspecific binding was determined in the presence of 0.1 μM MCH. Following incubation, the samples were filtered rapidly under vacuum through glass fiber filters (GF/B, Packard) and rinsed several times with an ice-cold buffer containing 25 mM Hepes/Tris (pH 7.4), 500 mM NaCl, 5 mM MgCl$_2$, 1 mM CaCl$_2$ and 0.1% BSA using a 96-sample cell harvester (Unifilter, Packard). The filters were dried, then counted for radioactivity in a scintillation counter (Topcount, Packard) using a scintillation cocktail (Microscint 0, Packard).

The results are expressed as a percent inhibition of the control radioligand specific binding. The IC$_{50}$ value (concentration causing a half-maximal inhibition of control specific binding) and Hill coefficient (n$_H$) were determined by non-linear regression analysis of the competition curve using Hill equation curve fitting. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor).

Binding Assay II for Human Melanin-Concentrating Hormone (MCH$_1$) Receptor

Evaluation of the affinity of compounds for the human MCH$_1$ receptor was accomplished using tri-[$^3$H]-labeled 4-(benzyloxy)-1-(1-(2-(pyrrolidin-1-yl)ethyl)-1H-indazol-5-yl)pyridin-2(1H)-one and membranes prepared from stable CHO-K1 cells expressing the human MCH$_1$ receptor obtained from Euroscreen (Batch 1138). Cell membrane homogenates (8.92 μg protein) were incubated for 60 min at 25° C. with 1.44 nM of the [$^3$H]-labeled compound in the absence or presence of the test compound in 50 mM Tris-HCl buffer, pH 7.4. Nonspecific binding was determined in the presence of 50 μM 1-(5-(4-cyanophenyl)bicyclo [3.1.0] hexan-2-yl)-3-(4-fluoro-3-(trifluoromethyl)phenyl)-1-(3-(4-methylpiperazin-1-yl)propyl)urea. Following incubation, the samples were filtered rapidly under vacuum through Skatron 11731 filters, pre-soaked in 0.5% polyethylenimine, and washed with ice-cold 50 mM Tris-HCl buffer, pH 7.4, (wash setting 9,9,0) using a Skatron cell harvester. The filters were counted for radioactivity in a liquid scintillation counter (Tri-Carb 2100TR, Packard) using a scintillation cocktail (Ultima Gold MV, Perkin Elmer).

The results are expressed as a percent inhibition of the control radioligand specific binding. The IC$_{50}$ value (concentration causing a half-maximal inhibition of control specific binding) and Hill coefficient (n$_H$) were determined by non-linear regression analysis of the competition curve using Hill equation curve fitting. The inhibition constant ($K_i$) was calculated from the Cheng Prusoff equation: ($K_i=IC_{50}/(1+(L/K_D))$), where L=concentration of radioligand in the assay, and $K_D$=affinity of the radioligand for the receptor.

By methods described above, the compounds listed in Table 1 were synthesized and tested for biological activity. All of the compounds in Table 1 exhibited $K_i$ of less than or equal to 3.5 μM in the MCH$_1$ binding assay I or II.

| Ex. No. | Structure | Mass Spec | $^1$H NMR Data |
|---|---|---|---|
| 1 | 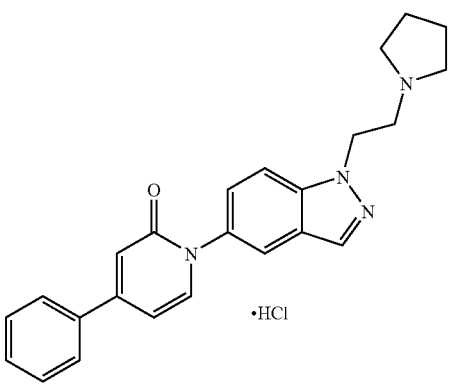 | 385 | $^1$H NMR (500 MHz, CD$_3$OD) δ 8.27 (s, 1H), 7.93 (d, J = 1.7 Hz, 1H), 7.86-7.82 (m, 2H), 7.79-7.76 (m, 2H), 7.57-7.52 (m, 4H), 6.97-6.96 (m, 2H), 4.90 (t, J = 5.7 Hz, 2H), 3.88 (t, J = 5.7 Hz, 2H), 3.74-3.69 (m, 2H), 3.20-3.15 (m, 2H), 2.20-2.14 (m, 2H), 2.06-2.00 (m, 2H) |
| 2 | 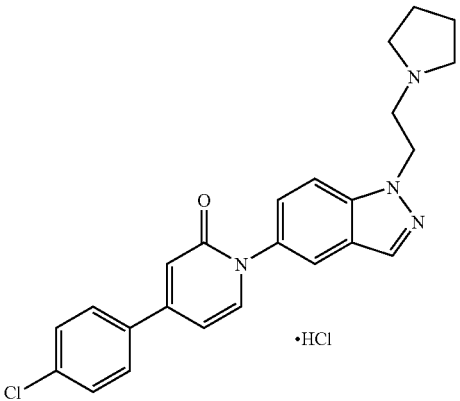 | 419 | $^1$H NMR (500 MHz, CD$_3$OD) δ 8.26 (s, 1H), 7.91 (d, J = 1.6 Hz, 1H), 7.86-7.82 (m, 2H), 7.77 (d, J = 8.6 Hz, 2H), 7.56-7.53 (m, 3H), 6.95-6.92 (m, 2H), 4.90 (t, J = 5.6 Hz, 2H), 3.87 (t, J = 5.6 Hz, 2H), 3.73-3.69 (m, 2H), 3.19-3.14 (m, 2H), 2.18-2.15 (m, 2H), 2.03-2.00 (m, 2H) |
| 3 | 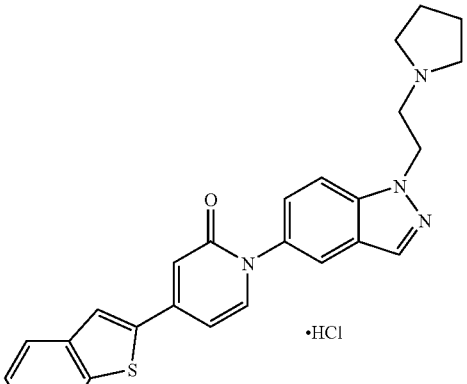 | 441 | $^1$H NMR (500 MHz, CD$_3$OD) δ 8.26 (s, 1H), 8.03 (s, 1H), 7.95-7.91 (m, 3H), 7.83 (d, J = 8.9 Hz, 1H), 7.77 (d, J = 7.1 Hz, 1H), 7.56-7.54 (dd, J = 8.9, 1.9 Hz, 1H), 7.46-7.41 (m, 2H), 7.06-7.02 (dd, J = 7.2, 2.0 Hz, 1H), 6.97 (d, J = 1.8 Hz, 1H), 4.89 (t, J = 5.8 Hz, 2H), 3.87 (t, J = 5.8 Hz, 2H), 3.73-3.69 (m, 2H), 3.20-3.15 (m, 2H), 2.19-2.16 (m, 2H), 2.04-2.00 (m, 2H) |

| Ex. No. | Structure | Mass Spec | ¹H NMR Data |
|---|---|---|---|
| 4 | 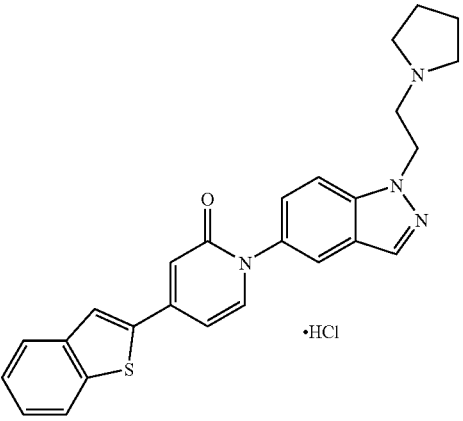 •HCl | 425 | ¹H NMR (500 MHz, CD$_3$OD) δ 8.26 (s, 1H), 7.91 (d, J = 1.7 Hz, 1H), 7.85 (d, J = 8.9 Hz, 1H), 7.78 (d, J = 7.1 Hz, 1H), 7.71 (d, J = 7.8 Hz, 1H), 7.61 (d, J = 8.3 Hz, 1H), 7.60 (s, 1H), 7.56-7.53 (dd, J = 8.9, 1.9 Hz, 1H), 7.45-7.41 (t, J = 8.3 Hz, 1H), 7.31 (t, J = 7.8 Hz, 1H), 7.15 (d, J = 1.8 Hz, 1H), 7.05-7.03 (dd, J = 7.1, 1.8 Hz, 1H) 4.91 (t, J = 5.3 Hz, 2H), 3.88 (t, J = 5.3 Hz, 2H), 3.73-3.69 (m, 2H), 3.20-3.14 (m, 2H), 2.18-2.14 (m, 2H), 2.04-1.99 (m, 2H) |
| 5 | 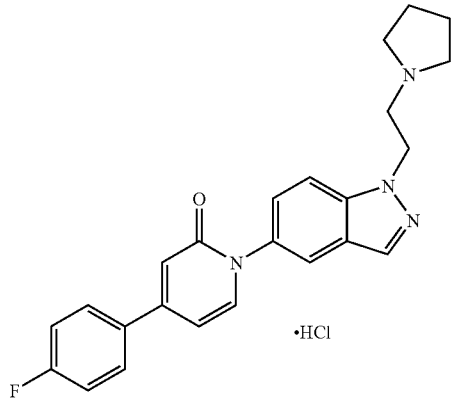 •HCl | 403 | ¹H NMR (500 MHz, CD$_3$OD) δ 8.26 (s, 1H), 7.91 (d, J = 1.4 Hz, 1H), 7.83-7.79 (m, 3H), 7.77 (d, J = 7.1 Hz, 1H), 7.55-7.53 (dd, J = 8.8, 1.9 Hz, 1H), 7.26-7.25 (m, 2H), 6.89 (d, J = 1.8 Hz, 1H), 6.87-6.85 (dd, J = 7.2, 2.1 Hz, 1H), 4.87 (t, J = 5.7 Hz, 2H), 3.87 (t, J = 5.7 Hz, 2H), 3.76-3.69 (m, 2H), 3.20-3.15 (m, 2H), 2.19-2.16 (m, 2H), 2.03-2.00 (m, 2H) |
| 6 | 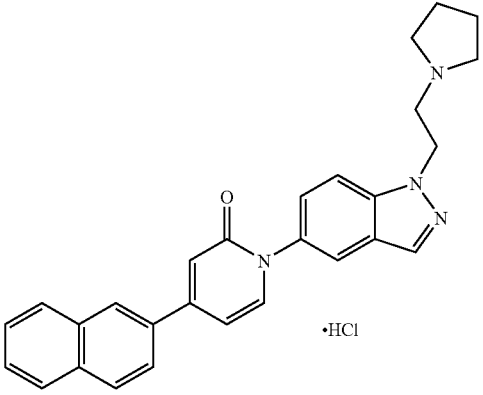 •HCl | 435 | ¹H NMR (500 MHz, CD$_3$OD) δ 8.32 (s, 1H), 8.27 (s, 1H), 8.04-8.01 (m, 2H), 7.95-7.93 (m, 2H), 7.87-7.81 (m, 3H), 7.59-7.56 (m, 3H), 7.07-7.05 (m, 2H), 4.89 (t, J = 5.8 Hz, 2H), 3.88 (t, J = 5.8 Hz, 2H), 3.74-3.70 (m, 2H), 3.19-3.16 (m, 2H), 2.19-2.16 (m, 2H), 2.04-2.01 (m, 2H) |

-continued
| Ex. No. | Structure | Mass Spec | ¹H NMR Data |
|---|---|---|---|
| 7 | 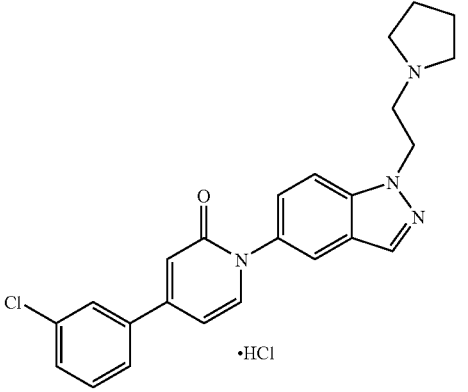 •HCl | 419 | ¹H NMR (500 MHz, CD₃OD) δ 8.26 (s, 1H), 7.91 (d, J = 1.6 Hz, 1H), 7.83 (d, J = 8.9 Hz, 1H), 7.79-7.78 (m, 2H), 7.70-7.68 (m, 1H), 7.55-7.52 (m, 3H), 6.91 (d, J = 1.8 Hz, 1H), 6.86-6.84 (dd, J = 7.1, 2.0 Hz, 1H), 4.90 (t, J = 5.8 Hz, 2H), 3.88-3.86 (m, 2H), 3.76-3.69 (m, 2H), 3.20-3.15 (m, 2H), 2.19-2.16 (m, 2H), 2.03-2.00 (m, 2H) |
| 8 | 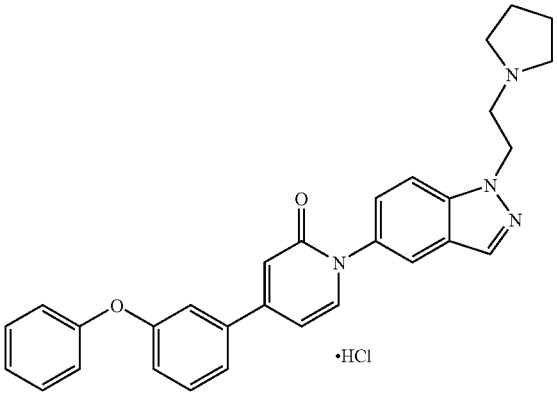 •HCl | 477 | ¹H NMR (500 MHz, CD₃OD) δ 8.25 (s, 1H), 7.90 (d, J = 1.7 Hz, 1H), 7.82 (d, J = 8.9 Hz, 1H), 7.76 (d, J = 7.1 1H), 7.54-7.49 (m, 3H), 7.41-7.38 (m, 2H), 7.36-7.35 (m, 1H), 7.16 (t, J = 8.5 Hz, 1H), 7.12-7.10 (dt, J = 6.7, 2.4 Hz, 1H), 7.07-7.05 (m, 2H), 6.86 (d, J = 1.8 Hz, 1H), 6.83-6.81 (dd, J = 7.3, 2.0 Hz, 1H), 4.89 (t, J = 5.7 Hz, 2H), 3.87 (t, J = 5.7 Hz, 2H), 3.73-3.69 (m, 2H), 3.20-3.14 (m, 2H), 2.18-2.15 (m, 2H), 2.04-2.00 (m, 2H) |
| 9 | 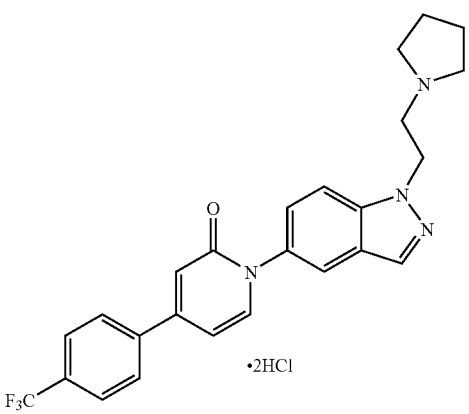 •2HCl | 453 | ¹H NMR (500 MHz, CD₃OD) δ 8.26 (s, 1H), 7.96 (d, J = 8.2 Hz, 2H), 7.92 (d, J = 1.8 Hz, 1H), 7.85-7.83 (m, 3H), 7.82 (d, J = 7.2 Hz, 1H), 7.56-7.54 (dd, J = 8.9, 1.9 Hz, 1H), 6.97 (d, J = 1.9 Hz, 1H), 6.89-6.87 (dd, J = 7.1, 2.0 Hz, 1H), 4.90 (t, J = 5.7 Hz, 2H), 3.88 (t, J = 5.7 Hz, 2H), 3.74-3.69 (m, 2H), 3.20-3.16 (m, 2H); 2.19-2.16 (m, 2H), 2.04-2.00 (m, 2H) |

| Ex. No. | Structure | Mass Spec | ¹H NMR Data |
|---|---|---|---|
| 10 | (structure: 4-(3-trifluoromethylphenyl)-1-[1-(2-pyrrolidin-1-ylethyl)-1H-indazol-5-yl]pyridin-2(1H)-one · 2HCl) | 453 | ¹H NMR (500 MHz, CD₃OD) δ 8.26 (s, 1H), 8.08-7.99 (br m, 2H), 7.92 (d, J = 1.5 Hz, 1H), 7.85-7.81 (m, 3H), 7.75 (t, J = 8.0 Hz, 1H), 7.56-7.44 (dd, J = 8.9, 1.9 Hz, 1H), 6.96 (d, J = 1.8 Hz, 1H), 6.90-6.89 (dd, J = 7.1, 1.9 Hz, 1H), 4.90 (t, J = 5.8 Hz, 2H), 3.88 (t, J = 5.8 Hz, 2H), 3.73-3.69 (m, 2H), 3.20-3.15 (m, 2H), 2.20-2.13 (m, 2H), 2.05-2.00 (m, 2H) |
| 11 | (structure: 4-(1-methyl-1H-indol-2-yl)-1-[1-(2-pyrrolidin-1-ylethyl)-1H-indazol-5-yl]pyridin-2(1H)-one · 2HCl) | 438 | ¹H NMR (500 MHz, DMSO-d₆) δ 10.71-10.48 (br s, 1H), 8.28 (s, 1H), 7.94 (d, J = 6.2 Hz, 1H), 7.92 (s, 1H), 7.82 (d, J = 7.2 Hz, 1H), 7.63 (d, J = 7.8 Hz, 1H), 7.57 (m, 2H), 7.27 (d, J = 8.1 Hz, 1H), 7.11 (t, J = 7.0 Hz, 1H), 6.88 (s, 1H), 6.71 (d, J = 1.8 Hz, 1H), 6.66-6.63 (dd, J = 7.1, 1.9 Hz, 1H), 4.91 (t, J = 6.3 Hz, 2H), 3.89 (s, 3H), 3.74 (q, J = 6.2 Hz, 2H), 3.53-3.50 (m, 2H), 3.08-3.00 (m, 2H) 1.99-1.83 (m, 4H) |
| 12 | (structure: 4-(2,4-dichlorophenyl)-1-[1-(2-pyrrolidin-1-ylethyl)-1H-indazol-5-yl]pyridin-2(1H)-one · HCl) | 453 | ¹H NMR (500 MHz, CD₃OD) δ 8.26 (s, 1H), 7.92 (d, J = 1.5 Hz, 1H), 7.82 (d, J = 8.9 Hz, 1H), 7.76 (d, J = 7.0 Hz, 1H), 7.65 (s, 1H), 7.56-7.54 (dd, J = 8.8, 1.8 Hz, 1H), 7.49 (s, 2H), 6.69 (d, J = 1.5 Hz, 1H), 6.22-6.20 (dd, J = 7.0, 1.8 Hz, 1H), 4.90 (t, J = 5.7 Hz, 2H), 3.87 (t, J = 5.7 Hz, 2H), 3.73-3.69 (br m, 2H), 3.20-3.15 (br m, 2H), 2.19-2.16 (m, 2H), 2.03-2.00 (m, 2H) |

| Ex. No. | Structure | Mass Spec | ¹H NMR Data |
|---|---|---|---|
| 13 | (naphthalen-1-yl pyridinone - indazole - pyrrolidinylethyl) ·2HCl | 435 | ¹H NMR (500 MHz, CDCl₃ + CD₃OD) δ 8.22 (s, 1H), 8.05-8.03 (m, 1H), 7.99-7.96 (m, 2H), 7.92 (s, 2H), 7.68 (d, J = 6.8 Hz, 1H), 7.62-7.54 (m, 5H), 6.86 (s, 1H), 6.70-6.68 (dd, J = 5.4, 1.4 Hz, 1H), 4.97-4.96 (br m, 2H), 3.86 (br m, 2H), 3.67-3.66 (br m, 2H), 3.06-2.96 (br m, 2H), 2.13-2.08 (br m, 4H) |
| 14 | (p-tolyl pyridinone - indazole - pyrrolidinylethyl) ·HCl | 399 | ¹H NMR (500 MHz, CD₃OD) δ 8.26 (s, 1H), 7.89 (d, J = 1.5 Hz, 1H), 7.81 (d, J = 8.9 Hz, 1H), 7.32 (d, J = 7.3 Hz, 1H), 7.65 (d, J = 8.2 Hz, 2H), 7.54-7.52 (dd, J = 8.9, 2.0 Hz, 1H), 7.34 (d, J = 8.0 Hz, 2H), 6.88 (d, J = 1.6 Hz, 1H), 6.86-6.84 (dd, J = 7.1, 2.0 Hz, 1H), 4.86 (t, J = 5.8 Hz, 2H), 3.81 (t, J = 5.8 Hz, 2H), 3.43-3.42 (br m, 4H), 2.41 (s, 3H), 2.12-1.99 (m, 4H) |
| 15 | (4-trifluoromethoxyphenyl pyridinone - indazole - pyrrolidinylethyl) ·HCl | 469 | ¹H NMR (500 MHz, CD₃OD) δ 8.26 (s, 1H), 7.91 (d, J = 1.6 Hz, 1H), 7.88 (d, J = 8.7 Hz, 2H), 7.84 (d, J = 8.9 Hz, 1H), 7.80 (d, J = 7.1 Hz, 1H), 7.55-7.53 (dd, J = 8.7 Hz, 1H), 7.45 (d, J = 8.3 Hz, 2H), 6.93 (d, J = 1.7 Hz, 1H), 6.88-6.86 (dd, J = 7.2, 2.0 Hz, 1H), 4.89 (t, J = 6.8 Hz, 2H), 3.89 (t, J = 6.8 Hz, 2H), 3.74-3.69 (br m, 2H), 3.20-3.15 (br m, 2H), 2.18-2.15 (m, 2H), 2.03-2.00 (m, 2H) |

-continued

| Ex. No. | Structure | Mass Spec | $^1$H NMR Data |
|---|---|---|---|
| 16 | 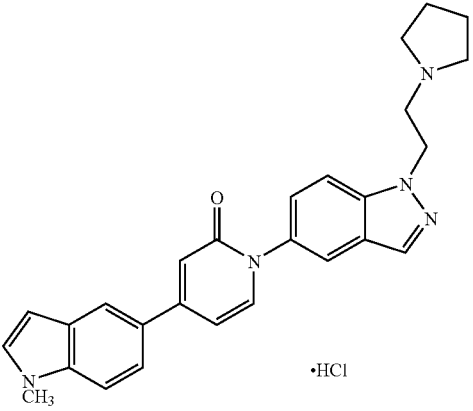 ·HCl | 438 | $^1$H NMR (500 MHz, CD$_3$OD) δ 8.26 (s, 1H), 8.01 (d, J = 1.5 Hz, 1H), 7.91 (d, J = 1.5 Hz, 1H), 7.81 (d, J = 8.9 Hz, 1H), 7.71 (d, J = 7.1 Hz, 1H), 7.60-7.58 (dd, J = 8.6, 1.8 Hz, 1H), 7.56-7.54 (dd, J = 8.9, 1.9 Hz, 1H), 7.52 (d, J = 8.7 Hz, 1H), 7.26 (d, J = 3.1 Hz, 1H), 6.97 (dd, J = 7.1, 2.0 Hz, 1H), 6.94 (d, J = 1.8 Hz, 1H), 6.57 (d, J = 3.2 Hz, 1H), 4.88 (t, J = 5.7 Hz, 2H), 3.87-3.85 (s overlapping with m, 5H), 3.80-3.10 (br m, 4H), 2.09 (br m, 4H) |
| 17 | 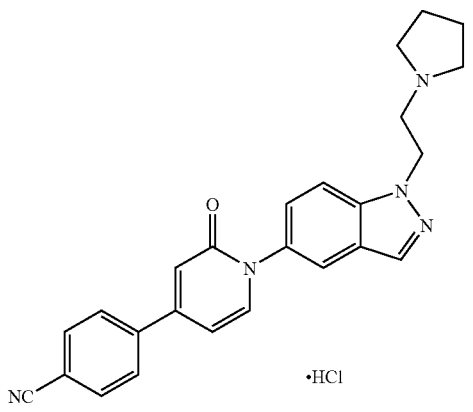 ·HCl | 410 | $^1$H NMR (500 MHz, CD$_3$OD) δ 8.23 (s, 1H), 7.94 (d, J = 6.6 Hz, 2H), 7.90-7.88 (m, 3H), 7.82 (d, J = 2.8 Hz, 1H), 7.80 (s, 1H), 7.53-7.51 (dd, J = 8.9, 1.9 Hz, 1H), 6.95 (d, J = 1.9 Hz, 1H), 6.86-6.84 (dd, J = 7.1, 2.1 Hz, 1H), 4.82 (m, 2H), 3.66 (br m, 2H), 3.26 (br m, 4H), 2.01 (br m, 4H) |
| 18 | 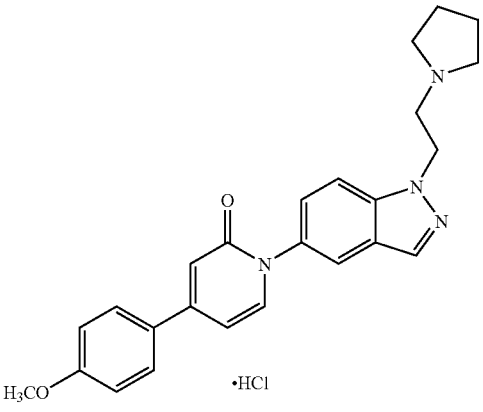 ·HCl | 415 | $^1$H NMR (500 MHz, CD$_3$OD) δ 8.26 (s, 1H), 7.91 (d, J = 1.5 Hz, 1H), 7.83 (d, J = 6.9 Hz, 1H), 7.78-7.43 (m, 3H), 7.56-7.53 (dd, J = 8.9 Hz, 1H), 7.09 (d, J = 8.9 Hz, 2H), 6.96-6.94 (dd, J = 7.1, 2.2 Hz, 1H), 6.93 (d, J = 1.7 Hz, 1H), 4.88 (t, J = 5.4 Hz, 2H), 3.88-3.86 (s overlapping with m, 5H), 3.73-3.69 (m, 2H), 3.20-3.15 (m, 2H), 2.19-2.14 (m, 2H), 2.03-2.06 (m, 2H) |

| Ex. No. | Structure | Mass Spec | ¹H NMR Data |
|---|---|---|---|
| 19 | 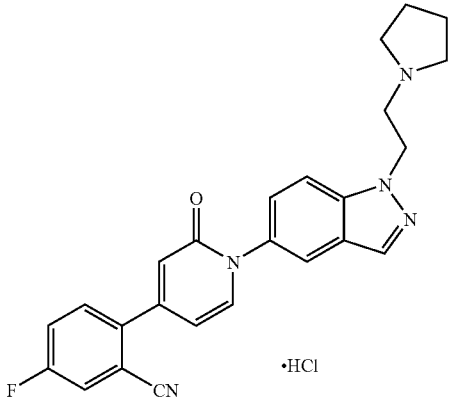 | 428 | ¹H NMR (500 MHz, CD₃OD) δ 8.26 (s, 1H), 7.94-7.93 (m, 1H), 7.83 (d, J = 2.1 Hz, 1H), 7.82 (s, 1H), 7.77-7.74 (m, 2H), 7.63-7.59 (dt, J = 8.3, 2.7 Hz, 1H), 7.57-7.53 (dd, J = 8.9, 2.0 Hz, 1H), 6.83 (d, J = 1.9 Hz, 1H), 6.73-6.70 (dd, J = 7.0, 2.0 Hz, 1H), 4.89 (t, J = 5.8 Hz, 2H), 3.89-3.86 (t, J = 5.8 Hz, 2H), 3.72-3.61 (br m, 2H), 3.26-3.15 (br m, 2H), 2.11-2.05 (m, 4H) |
| 20 | 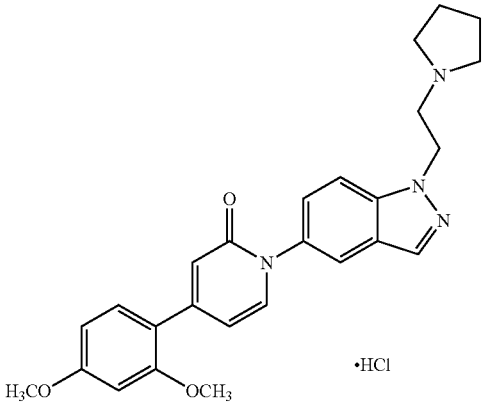 | 445 | ¹H NMR (500 MHz, CD₃OD) δ 8.26 (s, 1H), 7.93 (d, J = 1.7 Hz, 1H), 7.84 (d, J = 8.9 Hz, 1H), 7.73 (d, J = 8.1 Hz, 1H), 7.56-7.54 (dd, J = 8.9, 2.0 Hz, 1H), 7.45 (d, J = 8.4 Hz, 1H) 6.96-6.92 (m, 2H), 6.70-6.67 (m, 2H), 4.89 (t, J = 5.8 Hz, 2H), 3.89-3.87 (m, 8H), 3.73-3.69 (br m, 2H), 3.19-3.16 (br m, 2H) 2.17-2.16 (br m, 2H) 2.03-2.01 (br m, 2H) |
| 21 | 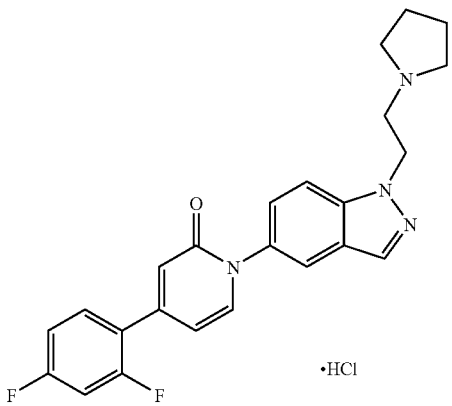 | 421 | ¹H NMR (500 MHz, CD₃OD) δ 8.26 (s, 1H), 7.91 (d, J = 1.4 Hz, 1H), 7.80 (d, J = 8.9 Hz, 1H), 7.75 (d, J = 6.9 Hz, 1H), 7.71-7.62 (m, 1H), 7.55-7.53 (dd, J = 8.8, 1.9 Hz, 1H), 7.18-7.12 (m, 2H), 6.82 (s, 1H), 6.74-6.71 (dt, J = 7.1, 1.9 Hz, 1H), 4.88 (t, J = 5.8 Hz, 2H), 3.85 (t, J = 5.7 Hz, 2H), 3.56-3.32 (br m, 4H), 2.20-1.91 (br m, 4H) |

| Ex. No. | Structure | Mass Spec | ¹H NMR Data |
|---|---|---|---|
| 22 | (structure) ·HCl | 443 | ¹H NMR (500 MHz, CD$_3$OD) δ 8.25 (s, 1H), 7.89 (d, J = 1.4 Hz, 1H), 7.81 (d, J = 8.9 Hz, 1H), 7.72-7.69 (m, 3H), 7.54-7.51 (dd, J = 8.9, 2.0 Hz, 1H), 7.05-7.02 (d, J = 8.8 Hz, 2H), 6.86-6.84 (m, 2H), 4.87 (t, J = 5.8 Hz, 2H), 4.72-4.67 (m, 1H), 3.84 (t, J = 5.7 Hz, 2H), 3.50-3.32 (br m, 4H), 2.15-2.01 (br m, 4H), 1.35 (d, J = 6.0 Hz, 6H) |
| 23 | (structure) ·HCl | 521 | ¹H NMR (500 MHz, CD$_3$OD) δ 8.25 (s, 1H), 8.13 (s, 1H) 8.09 (d, J = 8.0 Hz, 1H), 7.93 (d, J = 1.7, 1H), 7.82 (d, J = 9.0 Hz, 1H), 7.78 (d, J = 7.0 Hz, 1H), 7.75 (d, J = 8.1 Hz, 1H), 7.56-7.54 (dd, J = 8.9, 1.9 Hz, 1H), 6.64 (d, J = 1.7 Hz, 1H), 6.53-6.51 (dd, J = 7.0, 1.8 Hz, 1H), 4.87-4.84 (br m, 2H), 3.81-3.68 (br m, 2H), 3.44-3.34 (br m, 4H), 2.12-1.94 (br m, 4H) |
| 24 | (structure) ·HCl | 471 | ¹H NMR (500 MHz, CD$_3$OD) δ 8.26 (s, 1H), 7.92 (d, J = 1.4 Hz, 1H), 7.82 (d, J = 8.9 Hz, 1H), 7.70 (d, J = 6.9 Hz, 1H), 7.56-7.54 (dd, J = 8.9, 2.0 Hz, 1H), 7.24 (d, J = 8.4 Hz, 1H), 6.88 (d, J = 2.4 Hz, 1H), 6.86-6.84 (dd, J = 8.4, 2.6, 1H), 6.58-6.56 (m, 2H), 4.89 (t, J = 5.8 Hz, 2H), 4.02 (t, J = 6.7 Hz, 2H), 3.87 (t, J = 5.8 Hz, 2H), 3.74-3.69 (br m, 2H), 3.20-3.15 (br m, 2H), 2.39 (s, 3H), 2.19-2.16 (br m, 2H), 2.04-2.00 (br m, 2H), 1.80-1.75 (m, 2H), 1.55-1.49 (m, 2H), 1.00 (t, J = 7.4 Hz, 3H) |

-continued

| Ex. No. | Structure | Mass Spec | ¹H NMR Data |
|---|---|---|---|
| 25 | (structure: 4-(2-methylphenyl)-1-[1-(2-pyrrolidin-1-ylethyl)-1H-indazol-5-yl]pyridin-2(1H)-one · HCl) | 399 | ¹H NMR (500 MHz, CD₃OD) δ 8.26 (s, 1H), 7.93 (d, J = 1.5 Hz, 1H) 7.82 (d, J = 8.9 Hz, 1H), 7.72 (d, J = 7.0 Hz, 1H), 7.57 (dd, J = 8.9, 2.1 Hz, 1H), 7.35-7.33 (m, 2H), 7.30-7.29 (m, 2H), 6.58 (d, J = 1.4 Hz, 1H), 6.55-6.53 (dd, J = 7.0, 2.2 Hz, 1H), 4.89 (t, J = 5.7 Hz, 2H), 3.87 (t, J = 5.7 Hz, 2H), 3.76-3.67 (br m, 2H), 3.19-3.15 (br m, 2H), 2.39 (s, 3H) 2.22-2.11 (br m, 2H), 2.03-2.01 (br m, 2H) |
| 26 | (structure: 4-(4-benzyloxy-2-methylphenyl)-1-[1-(2-pyrrolidin-1-ylethyl)-1H-indazol-5-yl]pyridin-2(1H)-one · HCl) | 505 | ¹H NMR (500 MHz, CD₃OD) δ 8.25 (s, 1H), 7.91 (d, J = 1.8 Hz, 1H), 7.81 (d, J = 8.9 Hz, 1H), 7.69 (d, J = 6.9 Hz, 1H), 7.55-7.53 (dd, J = 8.9, 1.9 Hz, 1H), 7.45 (d, J = 7.3 Hz, 2H), 7.38 (t, J = 7.5 Hz 2H), 7.32 (d, J = 5.3, 1H), 7.25 (d, J = 8.5 Hz, 1H), 6.98 (d, J = 2.5 Hz, 1H), 6.95-6.93 (dd, J = 8.4, 2.6 Hz, 1H), 6.56 (d, J = 1.7 Hz, 1H), 6.55-6.53 (dd, J = 6.9, 1.9 Hz, 1H), 5.13 (s, 2H), 4.87 (t, J = 5.8 Hz, 2H), 3.88-3.79 (br m, 2H), 3.34-3.32 (br m, 4H), 2.38 (s, 3H) 2.16-2.00 (br m, 4H) |
| 27 | (structure: 4-(4-chloro-2-methoxyphenyl)-1-[1-(2-pyrrolidin-1-ylethyl)-1H-indazol-5-yl]pyridin-2(1H)-one · HCl) | 449 | ¹H NMR (500 MHz, CD₃OD) δ 8.25 (s, 1H), 7.90 (d, J = 1.4 Hz, 1H), 7.81 (d, J = 8.9 Hz, 1H), 7.66 (d, J = 7.1 Hz, 1H), 7.54-7.52 (dd, J = 8.9, 1.9 Hz, 1H), 7.42 (d, J = 8.2 Hz, 1H) 7.19 (d, J = 1.8 Hz, 1H), 7.11-7.09 (dd, J = 8.2, 1.9 Hz, 1H), 6.78 (t, J = 1.5 Hz 2H), 4.88 (t, J = 5.6 Hz, 2H), 3.89 (s, 3H), 3.85 (t, J = 5.7 Hz, 2H), 3.80-3.33 (br m, 4H), 2.17-2.00 (br m, 4H) |

| Ex. No. | Structure | Mass Spec | $^1$H NMR Data |
| --- | --- | --- | --- |
| 28 | 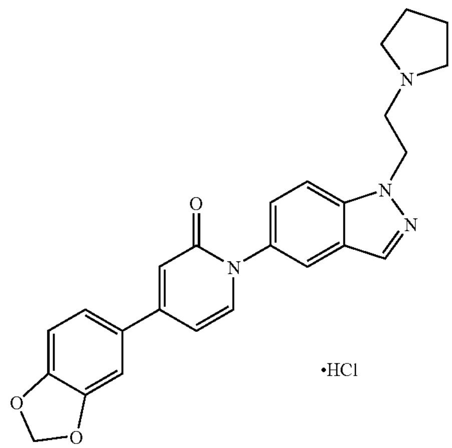 | 429 | $^1$H NMR (500 MHz, CD$_3$OD) δ 8.25 (s, 1H), 7.90 (d, J = 1.4 Hz, 1H) 7.82 (d, J = 8.9 Hz, 1H), 7.73-7.71 (dd, J = 5.1, 2.7 Hz, 1H), 7.54-7.52 (d, J = 7.9, 1H), 7.32-7.30 (dd, J = 8.1, 1.9 Hz, 1H), 7.27 (d, J = 1.8, 1H), 6.97 (d, J = 8.1 Hz, 1H), 6.85-6.83 (m, 2H), 6.05 (s, 2H), 4.88 (t, J = 5.8 Hz, 2H), 3.87 (t, J = 5.8 Hz, 2H), 3.74-3.69 (br m, 2H), 3.20-3.15 (br m, 2H) 2.19-2.16 (br m, 2H), 2.03-2.00 (br m, 2H) |
| 29 | 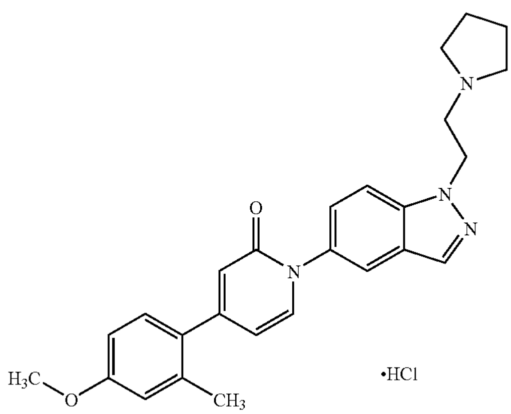 | 429 | $^1$H NMR (500 MHz, CD$_3$OD) δ 8.26 (s, 1H), 7.91 (s, 1H), 7.82 (d, J = 8.6 Hz, 1H), 7.69 (d, J = 6.9 Hz, 1H), 7.55 (d, J = 8.5 Hz, 1H), 7.25 (d, J = 8.5 Hz, 1H), 6.90-6.86 (m, 2H), 6.56-6.53 (m, 2H), 4.92-4.85 (br m, 2H), 3.90-3.79 (br m, 5H), 3.75-3.32 (br m, 4H), 2.39 (s, 3H), 2.16-2.01 (br m, 4H) |
| 30 | 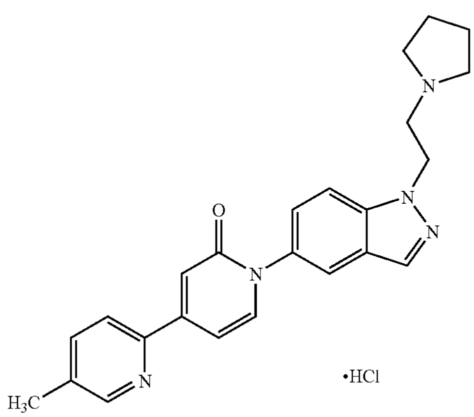 | 400 | $^1$H NMR (500 MHz, CD$_3$OD) δ 8.56 (s, 1H), 8.23 (s, 1H), 7.91-7.89 (m, 2H), 7.81-7.76 (m, 3H), 7.54-7.51 (dd, J = 8.9, 2.0 Hz, 1H), 7.24 (s, 1H) 7.17-7.15 (dd, J = 7.5, 1.9 Hz, 1H), 4.92-4.84 (br m, 2H), 3.74-3.55 (br m, 2H), 3.25-3.06 (br m, 4H), 2.43 (s, 3H), 2.09-1.88 (br m, 4H) |

-continued

| Ex. No. | Structure | Mass Spec | ¹H NMR Data |
|---|---|---|---|
| 31 | (structure: 4-(2-chloro-4-trifluoromethylphenyl)-1-[1-(2-pyrrolidin-1-ylethyl)-1H-indazol-5-yl]pyridin-2(1H)-one · HCl) | 487 | ¹H NMR (500 MHz, CD₃OD) δ 8.26 (s, 1H), 7.94-7.91 (m, 2H), 7.83 (d, J = 8.9 Hz, 1H), 7.80-7.77 (m, 2H), 7.70 (d, J = 8.0 Hz, 1H), 7.57-7.55 (dd, J = 8.9, 1.9 Hz, 1H), 6.72 (d, J = 1.5 Hz, 1H), 6.63-6.62 (dd, J = 7.0, 1.8 Hz, 1H), 4.89 (t, J = 5.6, 2H), 3.87 (t, J = 5.6, 2H), 3.80-3.57 (br m, 2H), 3.20-3.02 (br m, 2H), 2.23-194 (br m, 4H) |
| 32 | (structure: 4-(quinolin-2-yl)-1-[1-(2-pyrrolidin-1-ylethyl)-1H-indazol-5-yl]pyridin-2(1H)-one · 3HCl) | 436 | ¹H NMR (500 MHz, CD₃OD) δ 8.97 (d, J = 8.6 Hz, 1H), 8.33 (d, J = 8.6 Hz, 1H), 8.30 (d, J = 8.1 Hz, 1H), 8.28 (s, 1H), 8.25 (d, J = 8.1 Hz, 1H), 8.10-8.07 (m, 1H), 7.98-7.96 (m, 2H), 7.91 (d, J = 8.0 Hz, 1H), 7.87 (d, J = 7.0 Hz, 1H), 7.60-7.58 (dd, J = 8.9, 2.0 Hz, 1H), 7.40 (d, J = 1.9 Hz, 1H), 7.25-7.23 (dd, J = 7.1, 2.0 Hz, 1H), 4.91 (t, J = 5.9, 2H), 3.88 (t, J = 5.9, 2H), 3.75-3.70 (m, 2H), 3.21-3.15 (m, 2H), 2.19-2.16 (m, 2H), 2.05-2.01 (m, 2H) |
| 33 | (structure: 4-(5-chloropyridin-2-yl)-1-[1-(2-pyrrolidin-1-ylethyl)-1H-indazol-5-yl]pyridin-2(1H)-one · 3HCl) | 420 | ¹H NMR (500 MHz, CD₃OD) δ 8.77-8.69 (m, 1H), 8.28 (d, J = 1.7 Hz, 1H), 8.05 (d, J = 8.5 Hz, 1H), 8.03-8.01 (dd, J = 8.5, 2.4 Hz, 1H), 7.93 (d, J = 1.4 Hz, 1H), 7.84 (d, J = 8.9 Hz, 1H), 7.81 (d, J = 7.1 Hz, 1H), 7.57-7.55 (dd, J = 8.9, 1.9 Hz, 1H), 7.33 (d, J = 1.6 Hz, 1H), 7.24-7.22 (dd, J = 7.2, 2.0 Hz, 1H), 4.90 (t, J = 5.8, 2H), 3.89 (t, J = 5.8, 2H), 3.75-3.71 (m, 2H), 3.22-3.12 (m, 2H), 2.21-2.16 (m, 2H), 2.05-2.02 (m, 2H) |

| Ex. No. | Structure | Mass Spec | ¹H NMR Data |
|---|---|---|---|
| 34 | •3HCl | 454 | ¹H NMR (500 MHz, CD₃OD) δ 9.05 (s, 1H), 8.29-8.27 (dd, J = 8.4, 2.2 Hz, 1H), 8.27 (s, 1H), 8.22 (d, J = 8.4 Hz, 1H), 7.93 (d, J = 1.6 Hz, 1H), 7.84-7.82 (2 overlapping d, J = 8.9, 7.0 Hz, 2H) 7.57-7.55 (dd, J = 8.9, 1.9 Hz, 1H), 7.40 (d, J = 1.8 Hz, 1H), 7.27-7.25 (dd, J = 7.1, 1.9 Hz, 1H), 4.89 (t, J = 5.8, 2H), 3.87 (t, J = 5.8, 2H), 3.74-3.70 (m, 2H), 3.21-3.15 (m, 2H), 2.19-2.15 (m, 2H), 2.04-2.00 (m, 2H) |
| 35 | •2HCl | 437 | ¹H NMR (500 MHz, CD₃OD) δ 9.66 (s, 1H), 8.27 (s, 1H), 8.19-8.15 (m, 2H), 8.09-8.06 (m, 1H), 7.95 (d, J = 1.6 Hz, 1H), 7.91 (d, J = 1.6 Hz, 1H) 7.86-7.81 (m, 3H), 7.69-7.67 (dd, J = 7.1, 1.8 Hz, 1H), 7.60-7.57 (dd, J = 8.9, 2.0 Hz, 1H), 4.90 (t, J = 5.8, 2H), 3.88 (t, J = 5.9, 2H), 3.75-3.70 (m, 2H), 3.21-3.16 (br m, 2H), 2.20-2.17 (m, 2H), 2.04-2.00 (m, 2H) |
| 36 | •HCl | 455 | ¹H NMR (500 MHz, CD₃OD) δ 8.53 (d, J = 8.9 Hz, 1H), 8.28-8.26 (m, 2H), 7.95 (d, J = 1.6 Hz, 1H), 7.91 (d, J = 7.0 Hz, 1H), 7.86 (d, J = 8.9 Hz, 1H), 7.58-7.56 (dd, J = 8.9, 1.9 Hz, 1H) 7.44 (d, J = 1.6 Hz, 1H), 7.36-7.34 (dd, J = 7.1, 2.0 Hz, 1H), 4.89 (t, J = 5.9, 2H), 3.88 (t, J = 5.9, 2H), 3.72-3.70 (br m, 2H), 3.21-3.15 (br m, 2H), 2.19-2.17 (m, 2H), 2.09-2.07 (m, 2H) |

-continued
| Ex. No. | Structure | Mass Spec | ¹H NMR Data |
|---|---|---|---|
| 37 | 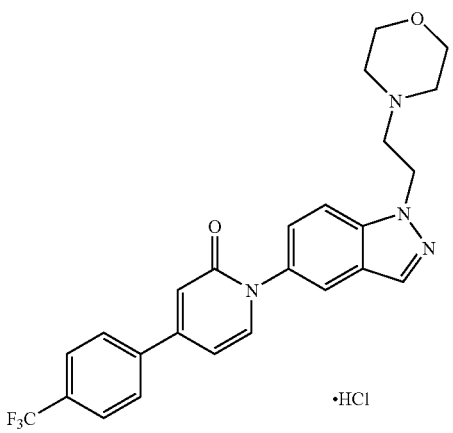 •HCl | 469 | ¹H NMR (500 MHz, DMSO-d₆) δ 10.58 (br s, 1H), 8.28 (s, 1H), 8.02 (d, J = 8.0 Hz, 2H), 7.92-7.84 (m, 5H), 7.55 (d, J = 9.0 Hz, 1H), 6.90 (d, J = 2.0 Hz, 1H), 6.75 (dd, J = 7.0, 2.0 Hz, 1H), 4.95 (br, 2H), 4.02-3.99 (m, 2H), 3.72-3.70 (m, 4H), 3.56-3.54 (m, 2H), 3.20 (br, 2H) |
| 38 | 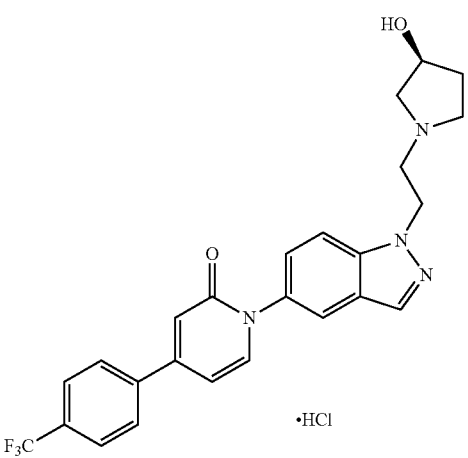 •HCl | 469 | ¹H NMR (500 MHz, DMSO-d₆) δ 10.65 (br s, 0.4H), 10.41 (br s, 0.6H), 8.28 (br s, 1H), 8.02 (d, J = 8.0 Hz, 2H), 7.94-7.85 (m, 5H), 7.54 (d, J = 9.0 Hz, 1H), 6.90 (d, J = 2.0 Hz, 1H), 6.75 (dd, J = 7.5, 2.0 Hz, 1H), 5.49 (br s, 1H), 4.90-4.88 (m, 2H), 4.43-4.37 (m, 1H), 3.78-3.71 (m, 2H), 3.60 (br, 1H), 3.41-3.34 (m, 1H), 3.17-3.13 (m, 1H), 2.99-2.97 (m, 1H), 2.25-2.22 (m, 1H), 1.95-1.81 (m, 1H) |
| 39 | 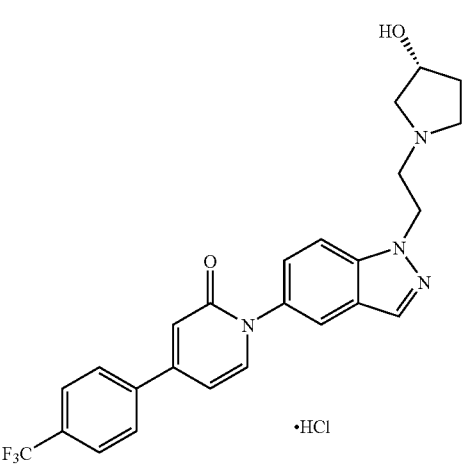 •HCl | 469 | ¹H NMR (500 MHz, DMSO-d₆) δ 10.40 (br s, 0.3H), 10.31 (br s, 0.5H), 8.28 (d, J = 6.5 Hz, 1H), 8.02 (d, J = 8.0 Hz, 2H), 7.93-7.84 (m, 5H), 7.54 (d, J = 8.0 Hz, 1H), 6.90 (s, 1H), 6.75 (d, J = 7.0 Hz, 1H), 5.50 (br s, 1H), 4.90-4.88 (m, 2H), 4.44-4.38 (m, 1H), 3.79-3.72 (m, 2H), 3.61-3.60 (m, 1H), 3.42-3.40 (m, 1H), 3.14-3.13 (m, 1H), 3.01-2.99 (m, 1H), 2.25-2.24 (m, 1H), 1.95-1.81 (m, 1H) |

| Ex. No. | Structure | Mass Spec | ¹H NMR Data |
|---|---|---|---|
| 40 | 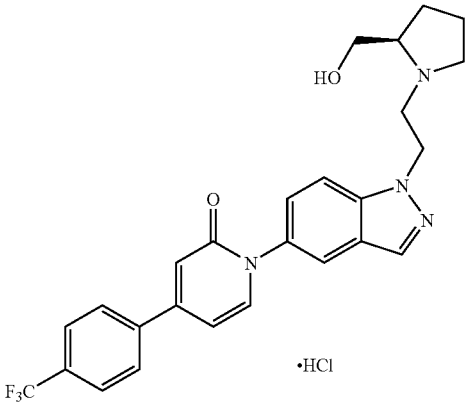 | 483 | ¹H NMR (500 MHz, DMSO-$d_6$) δ 9.85 (s, 1H), 8.28 (s, 1H), 8.04-8.01 (m, 2H), 7.93-7.85 (m, 5H), 7.54 (dd, J = 8.8, 2.0 Hz, 1H), 6.90 (d, J = 1.9 Hz, 1H), 6.75 (dd, J = 7.2, 2.0 Hz, 1H), 4.95-4.85 (m, 2H), 3.97-3.93 (m, 1H), 3.81-3.76 (m, 1H), 3.71-3.63 (m, 3H), 3.58-3.52 (m, 1H), 3.16-3.10 (m, 1H), 2.14-2.05 (m, 1H), 2.04-1.97 (m, 1H), 1.89-1.81 (m, 1H), 1.78-1.70 (m, 1H) |
| 41 | 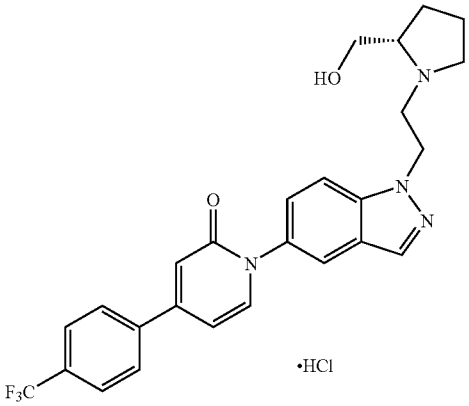 | 483 | ¹H NMR (500 MHz, DMSO-$d_6$) δ 9.88 (s, 1H), 8.28 (s, 1H), 8.04-8.00 (m, 2H), 7.92-7.83 (m, 5H), 7.54 (dd, J = 9.0, 1.9 Hz, 1H), 6.90 (d, J = 2.0 Hz, 1H), 6.75 (dd, J = 7.2, 2.0 Hz, 1H), 4.95-4.85 (m, 2H), 3.98-3.91 (m, 1H), 3.82-3.75 (m, 1H), 3.70-3.63 (m, 3H), 3.58-3.52 (m, 1H), 3.15-3.09 (m, 1H), 2.12-2.05 (m, 1H), 2.03-1.97 (m, 1H), 1.92-1.82 (m, 1H), 1.78-1.71 (m, 1H) |
| 42 | 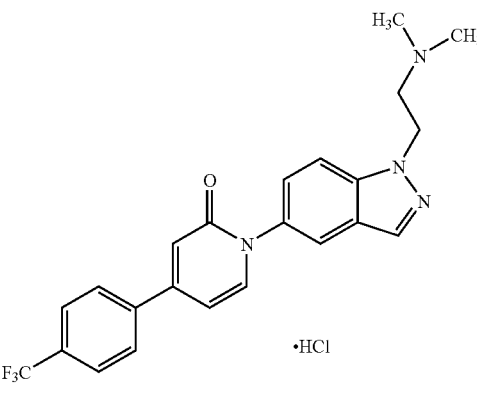 | 427 | ¹H NMR (500 MHz, DMSO-$d_6$) δ 9.76 (br s, 1H), 8.28 (s, 1H), 8.02-8.01 (m, 2H), 7.92-7.84 (m, 5H), 7.55-7.53 (m, 1H), 6.89 (d, J = 2.0 Hz, 1H), 6.76-6.74 (m, 1H), 4.89 (t, J = 6.0 Hz, 2H), 3.65-3.64 (m, 2H), 2.86 (s, 6H) |

-continued
| Ex. No. | Structure | Mass Spec | ¹H NMR Data |
|---|---|---|---|
| 43 | 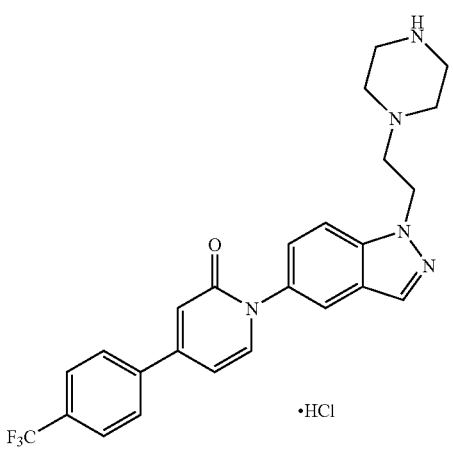 •HCl | 468 | ¹H NMR (500 MHz, DMSO-$d_6$) δ 8.24 (s, 1H), 8.02-8.01 (m, 2H), 7.92-7.85 (m, 5H), 7.51 (d, J = 8.6 Hz, 1H), 6.89 (d, J = 2.0 Hz, 1H), 6.75 (dd, J = 7.1, 1.8 Hz, 1H), 4.87-4.85 (m, 2H), 3.71-3.60 (m, 6H), 3.38-3.31 (m, 4H) |
| 44 | 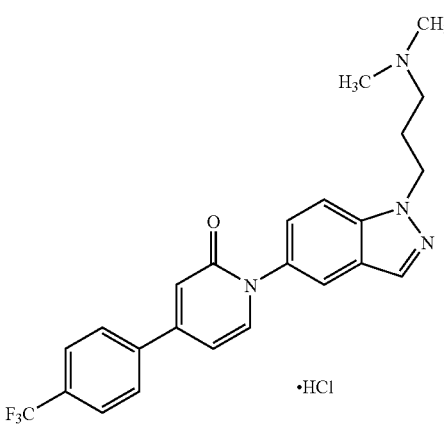 •HCl | 441 | ¹H NMR (500 MHz, DMSO-$d_6$) δ 9.85 (br s, 1H), 8.21 (s, 1H), 8.01 (d, J = 8.0 Hz, 2H), 7.88-7.84 (m, 5H), 7.50-7.48 (m, 1H), 6.89-6.88 (m, 1H), 6.74 (dd, J = 7.0, 1.7 Hz, 1H), 4.57 (t, J = 6.5 Hz, 2H), 3.10 (t, J = 7.5 Hz, 2H), 2.75 (s, 6H), 2.26-2.22 (m, 2H) |
| 45 | 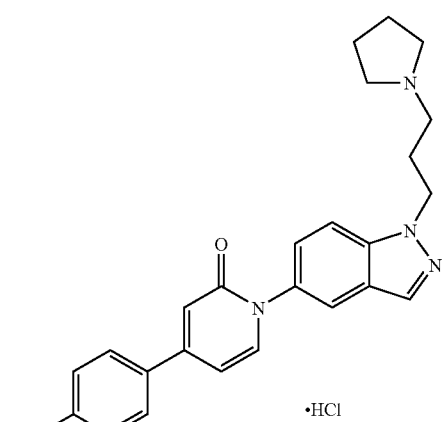 •HCl | 467 | ¹H NMR (500 MHz, DMSO-$d_6$) δ 10.26 (br s, 1H), 8.21 (s, 1H), 8.01 (d, J = 8.1 Hz, 2H), 7.88-7.84 (m, 5H), 7.49 (dd, J = 8.8, 1.9 Hz, 1H), 6.89 (d, J = 1.9 Hz, 1H), 6.74 (dd, J = 7.1, 2.0 Hz, 1H), 4.59 (t, J = 7.0 Hz, 2H), 3.54-3.51 (m, 2H), 3.19-3.15 (m, 2H), 2.99-2.93 (m, 2H), 2.30-2.24 (m, 2H), 2.01-1.95 (m, 2H), 1.89-1.84 (m, 2H) |

| Ex. No. | Structure | Mass Spec | ¹H NMR Data |
|---|---|---|---|
| 46 | (structure with H₂N-propyl chain, indazole, pyridinone, 4-trifluoromethylphenyl, ·HCl) | 413 | ¹H NMR (500 MHz, DMSO-d₆) δ 8.21 (s, 1H), 8.01 (d, J = 8.5 Hz, 2H), 7.89-7.80 (m, 8H), 7.50-7.48 (m, 1H), 6.89 (d, J = 1.5 Hz, 1H), 6.74 (dd, J = 7.0, 2.0 Hz, 1H), 4.58 (t, J = 6.5 Hz, 2H), 2.84-2.80 (m, 2H), 2.16-2.12 (m, 2H) |
| 47 | (structure with pyrrolidinylmethyl, indazole, pyridinone, 4-trifluoromethylphenyl, ·HCl) | 439 | ¹H NMR (500 MHz, DMSO-d₆) δ 9.05 (br s, 2H), 8.28 (s, 1H), 8.03-7.85 (m, 7H), 7.51 (d, J = 8.5 Hz, 1H), 6.89 (s, 1H), 6.75 (d, J = 7.0 Hz, 1H), 4.80 (d, J = 6.0 Hz, 2H), 3.99-3.95 (m, 1H), 3.30-3.23 (m, 1H), 3.16-3.10 (m, 1H), 2.08-2.03 (m, 1H), 1.99-1.96 (m, 1H), 1.91-1.85 (m, 1H), 1.74-1.70 (m, 1H) |
| 48 | (structure with N,N-dimethylamino-hydroxypropyl, indazole, pyridinone, 4-trifluoromethylphenyl, ·HCl) | 457 | ¹H NMR (500 MHz, DMSO-d₆) δ 9.50 (br s, 1H), 8.22 (s, 1H), 8.02-8.00 (m, 2H), 7.89-7.84 (m, 5H), 7.48 (dd, J = 9.0, 2.0 Hz, 1H), 6.89 (d, J = 2.0 Hz, 1H), 6.74 (dd, J = 7.0, 2.0 Hz, 1H), 6.01 (br s, 1H), 4.58-4.49 (m, 2H), 4.40 (br s, 1H), 3.28-3.24 (m, 1H), 3.15-3.10 (m, 1H), 2.81 (d, J = 4.5 Hz, 3H), 2.78 (d, J = 4.5 Hz, 3H) |
| 49 | (structure with pyrrolidinyl-hydroxypropyl, indazole, pyridinone, 4-trifluoromethylphenyl, ·HCl) | 483 | ¹H NMR (500 MHz, DMSO-d₆) δ 9.65 (br s, 1H), 8.21 (s, 1H), 8.02-8.00 (m, 2H), 7.89-7.82 (m, 5H), 7.47 (dd, J = 9.0, 2.0 Hz, 1H), 6.89 (d, J = 2.0 Hz, 1H), 6.74 (dd, J = 7.0, 2.0 Hz, 1H), 5.75 (br s, 1H), 4.57-4.47 (m, 2H), 4.33 (br s, 1H), 3.56-2.90 (br m, 6H), 1.89 (br s, 4H) |

-continued

| Ex. No. | Structure | Mass Spec | ¹H NMR Data |
|---|---|---|---|
| 50 | (structure) ·HCl | 457 | ¹H NMR (500 MHz, DMSO-d₆) δ 9.42 (br s, 1H), 8.20 (s, 1H), 8.02-8.00 (m, 2H), 7.88-7.80 (m, 5H), 7.46 (dd, J = 8.5, 1.5 Hz, 1H), 6.89 (d, J = 2.0 Hz, 1H), 6.74 (dd, J = 7.0, 2.0 Hz, 1H), 5.60 (br s, 1H), 4.56-4.52 (m, 1H), 4.48-4.44 (m, 1H), 4.27 (br s, 1H), 2.92-2.88 (br m, 2H), 2.58 (br s, 6H) |
| 51 | (structure) ·HCl | 483 | ¹H NMR (500 MHz, DMSO-d₆) δ 9.60 (br s, 1H), 8.20 (s, 1H), 8.02-8.00 (m, 2H), 7.89-7.80 (m, 5H), 7.46 (dd, J = 8.5, 1.5 Hz, 1H), 6.89 (d, J = 2.0 Hz, 1H), 6.74 (dd, J =7.5, 2.0 Hz, 1H), 4.57-4.53 (m, 1H), 4.49-4.46 (m, 1H), 4.27 (br s, 1H), 3.25-2.75 (br m, 6H), 1.85 (br s, 4H) |
| 52 | (structure) ·HCl | 481 | ¹H NMR (500 MHz, DMSO-d₆) δ 10.62-10.50 (m, 0.4H), 10.21-10.09 (m, 0.6H), 8.28 (s, 1H), 8.02 (d, J = 8.0 Hz, 2H), 7.96-7.80 (m, 5H), 7.55 (d, J = 9.0 Hz, 1H), 6.90 (s, 1H), 6.75 (dd, J = 7.0, 1.5 Hz, 1H), 4.93-4.86 (m, 2H), 4.70 (s, 0.6H), 4.61-4.52 (m, 1.4H), 4.22 (d, J = 11.0 Hz, 0.4H), 4.07-4.01 (m, 0.6H), 3.92-3.79 (m, 1.2H), 3.77 (d, J = 8.5 Hz, 0.6H), 3.71-3.60 (m, 0.8H), 3.59-3.54 (m, 0.6H), 3.51-3.43 (m, 0.4H), 3.22 (d, J = 12.0 Hz, 0.6 H), 2.64 (s, 0.4H), 2.39-2.36 (m, 1H), 2.12 (d, J = 11.5 Hz, 0.4H), 2.05-1.99 (m, 1H) |
| 53 | (structure) ·HCl | 437 | ¹H NMR (500 MHz, CD₃OD) δ 8.26 (s, 1H), 7.92 (d, J = 1.8 Hz, 1H), 7.83 (d, J = 8.9 Hz, 1H), 7.77 (d, J = 8.9 Hz, 1H), 7.65 (t, J = 8.2 Hz, 1H), 7.56-7.53 (dd, J = 8.9, 1.9 Hz, 1H), 7.65 (m, 2H), 6.85 (m, 1H), 6.76-6.73 (dd, J = 7.1, 1.8 Hz, 1H), 4.89 (t, J = 5.7 Hz, 2H), 3.88 (t, J = 5.7 Hz, 2H), 3.74-3.70 (m, 2H), 3.20-3.15 (m, 2H), 2.19-2.16 (m, 2H), 2.04-2.01 (m, 2H) |

| Ex. No. | Structure | Mass Spec | ¹H NMR Data |
|---|---|---|---|
| 54 | (structure with pyrrolidinylethyl-indazole-pyridinone-2-fluoro-4-trifluoromethylphenyl) ·HCl | 471 | ¹H NMR (500 MHz, CD₃OD) δ 8.27 (d, J = 0.5 Hz, 1H), 7.93 (d, J = 1.7 Hz, 1H), 7.86-7.79 (m, 3H), 7.68-7.65 (m, 2H), 7.57-7.54 (dd, J = 8.9, 1.9 Hz, 1H), 6.89 (s, 1H), 6.77-6.75 (m, 1H), 4.89 (t, J = 5.7 Hz, 2H), 3.88 (t, J = 5.7 Hz, 2H), 3.73-3.69 (m, 2H), 3.21-3.15 (m, 2H), 2.20-2.13 (m, 2H), 2.06-2.00 (m, 2H) |
| 55 | (structure with pyrrolidinylethyl-indazole-pyridinone-2-fluoro-4-methoxyphenyl) ·HCl | 433 | ¹H NMR (500 MHz, CD₃OD) δ 8.26 (d, J = 0.7 Hz, 1H), 7.91 (d, J = 1.6 Hz, 1H), 7.82 (d, J = 8.9 Hz, 1H), 7.72 (d, J = 7.2 Hz, 1H), 7.58 (t, J = 8.9 Hz, 1H), 7.55-7.53 (dd, J = 8.9, 1.9 Hz, 1H), 6.93-6.91 (dd, J = 8.7, 2.4 Hz, 1H), 6.88-6.86 (dd, J = 13.2, 2.4 Hz, 1H), 6.83 (s, 1H), 6.77-6.75 (m, 1H), 4.89 (t, J = 5.7 Hz, 2H), 3.88 (m, 5H), 3.73-3.69 (m, 2H), 3.20-3.14 (m, 2H), 2.19-2.13 (m, 2H), 2.05-2.01 (m, 2H) |
| 56 | (structure with pyrrolidinylethyl-indazole-pyridinone-2-chloro-4-methoxyphenyl) ·HCl | 449 | ¹H NMR (500 MHz, CD₃OD) δ 8.26 (s, 1H), 7.92 (d, J = 1.8 Hz, 1H), 7.82 (d, J = 8.9 Hz, 1H), 7.71 (d, J = 7.0 Hz, 1H), 7.56-7.54 (dd, J = 8.9, 1.9 Hz, 1H), 7.42 (d, J = 8.6 Hz, 1H), 7.14 (d, J = 2.5 Hz, 1H), 7.04-7.02 (dd, J = 8.6, 2.5 Hz, 1H), 6.68 (d, J = 1.8 Hz, 1H), 6.65-6.63 (dd, J = 7.0, 1.9 Hz, 1H), 4.89 (t, J = 5.7 Hz, 2H), 3.88-3.87 (m, 5H), 3.72-3.69 (m, 2H), 3.20-3.15 (m, 2H), 2.21-2.13 (m, 2H), 2.06-2.01 (m, 2H) |
| 57 | (structure with pyrrolidinylethyl-indazole-pyridinone-4-ethoxyphenyl) ·HCl | 429 | ¹H NMR (500 MHz, CD₃OD) δ 8.25 (s, 1H), 7.90 (d, J = 1.9 Hz, 1H), 7.82 (d, J = 8.9 Hz, 1H), 7.74-7.72 (m, 3H), 7.55-7.52 (dd, J = 8.9, 1.9 Hz, 1H), 7.07-7.04 (m, 2H), 6.90-6.88 (m, 2H), 4.89 (t, J = 5.7 Hz, 2H), 4.12 (q, J = 7.0 Hz, 2H), 3.88 (t, J = 5.7 Hz, 2H), 3.73-3.69 (m, 2H), 3.20-3.15 (m, 2H), 2.19-2.14 (m, 2H), 2.04-2.00 (m, 2H), 1.43 (t, J = 7.0 Hz, 3H) |

-continued

| Ex. No. | Structure | Mass Spec | ¹H NMR Data |
|---|---|---|---|
| 58 | 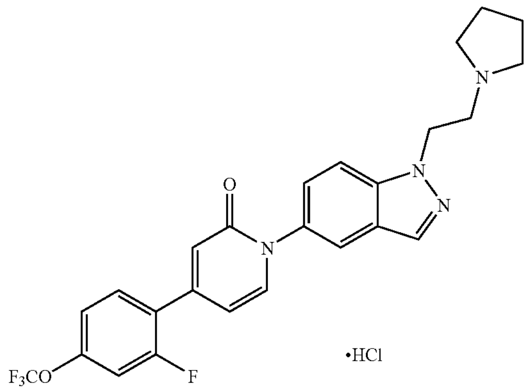 | 487 | ¹H NMR (500 MHz, CD₃OD) δ 8.26 (d, J = 0.4 Hz, 1H), 7.92 (d, J = 1.8 Hz, 1H), 7.82 (d, J = 8.9 Hz, 1H), 7.78-7.75 (m, 2H), 7.56-7.54 (dd, J = 8.9, 1.9 Hz, 1H), 7.33-7.30 (m, 2H), 6.86 (s, 1H), 6.75-6.73 (m, 1H), 4.89 (t, J = 5.8, 2H), 3.87 (t, J = 5.8, 2H), 3.71 (m, 2H), 3.19 (m, 2H), 2.16-2.04 (m, 4H) |
| 59 | 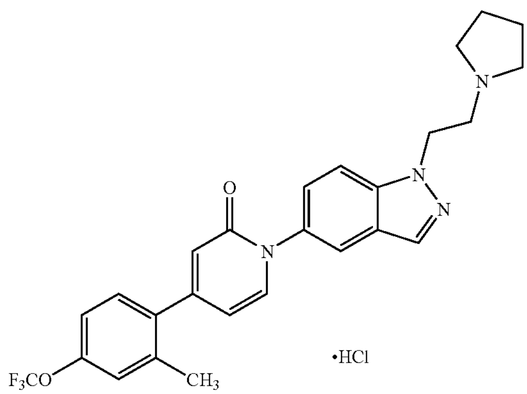 | 483 | ¹H NMR (500 MHz, CD₃OD) δ 8.27 (s, 1H), 7.93 (d, J = 1.7 Hz, 1H), 7.83 (d, J = 8.9 Hz, 1H), 7.75 (d, J = 7.0 Hz, 1H), 7.57-7.55 (dd, J = 8.9, 1.9 Hz, 1H), 7.41 (d, J = 8.4 Hz, 1H), 7.27 (s, 1H), 7.23 (d, J = 8.4 Hz, 1H), 6.61 (d, J = 1.7 Hz, 1H), 6.56-6.54 (dd, J = 7.0, 1.8 Hz, 1H), 4.90 (t, J = 5.7, 2H), 3.88 (t, J = 5.7, 2H), 3.74-3.69 (m, 2H), 3.21-3.15 (m, 2H), 2.43 (s, 3H), 2.19-2.16 (m, 2H) 2.04-2.00 (m, 2H) |
| 60 | 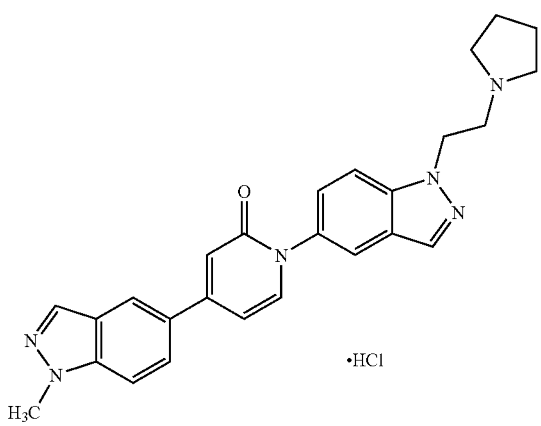 | 439 | ¹H NMR (500 MHz, CD₃OD) δ 8.27 (d, J = 0.9 Hz, 1H), 8.23 (d, J = 0.9 Hz, 1H), 8.14 (d, J = 0.9 Hz, 1H), 7.93 (d, J = 1.4 Hz, 1H), 7.84 (t, J = 8.9 Hz, 2H), 7.80-7.78 (dd, J = 5.8, 1.9 Hz, 1H), 7.72 (d, J = 8.9 Hz, 1H), 7.58-7.55 (dd, J = 8.9, 1.9 Hz, 1H), 7.01-6.99 (m, 2H), 4.90 (t, J = 5.7, 2H), 4.12 (s, 3H), 3.88 (t, J = 5.7, 2H), 3.74-3.70 (m, 2H), 3.21-3.16 (m, 2H), 2.21-2.14 (m, 2H) 2.07-1.99 (m, 2H) |
| 61 | 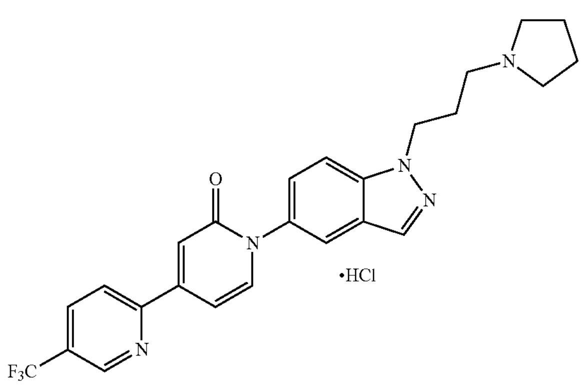 | 468 | ¹H NMR (500 MHz, CD₃OD) δ 9.05 (s, 1H), 8.29-8.27 (dd, J = 8.4, 2.1 Hz, 1H), 8.22 (d, J = 8.4 Hz, 1H), 8.20 (s, 1H), 7.90 (d, J = 1.8 Hz, 1H), 7.83 (d, J = 7.2 Hz, 1H), 7.79 (d, J = 8.9 Hz, 1H), 7.53-7.51 (dd, J = 8.9, 1.9 Hz, 1H), 7.40 (d, J = 1.7 Hz, 1H), 7.27-7.25 (dd, J = 7.2, 1.9 Hz, 1H), 4.63 (t, J = 6.5, 2H), 3.67-3.63 (m, 2H), 3.27-3.24 (m, 2H), 3.08-3.03 (m, 2H), 2.43-2.36 (m, 2H), 2.16-2.12 (m, 2H) 2.03-1.99 (m, 2H) |

| Ex. No. | Structure | Mass Spec | ¹H NMR Data |
|---|---|---|---|
| 62 | (piperidinyl-phenyl-pyridinone-indazole-ethyl-pyrrolidine) ·HCl | 468 | ¹H NMR (500 MHz, CD₃OD) δ 8.26 (s, 1H), 7.98 (d, J = 8.7 Hz, 2H), 7.91 (d, J = 1.8 Hz, 1H), 7.84-7.76 (m, 4H), 7.55-7.53 (dd, J = 9.0, 1.9 Hz, 1H), 6.93 (d, J = 1.9 Hz, 1H), 6.87-6.85 (dd, J = 7.2, 2.0 Hz, 1H), 4.89 (t, J = 5.7 Hz, 2H), 3.88 (t, J = 5.7 Hz, 2H), 3.72-3.66 (m, 6H), 3.19-3.15 (m, 2H), 2.18-2.16 (m, 2H), 2.06-2.01 (m, 6H), 1.83 (m, 2H) |
| 63 | (methyl-benzoxazole-pyridinone-indazole-ethyl-pyrrolidine) ·HCl | 440 | ¹H NMR (500 MHz, CD₃OD) δ 8.27 (s, 1H), 7.94 (d, J = 1.7 Hz, 1H), 7.88 (d, J = 7.1 Hz, 1H), 7.83 (d, J = 8.9 Hz, 1H), 7.64-7.61 (m, 2H), 7.58-7.55 (dd, J = 8.9, 1.9 Hz, 1H), 7.44 (d, J = 1.7 Hz, 1H), 7.37 (d, J = 8.4 Hz, 1H), 7.24-7.22 (dd, J = 7.1, 1.9 Hz, 1H), 4.89 (t, J = 5.7 Hz, 2H), 3.88 (t, J = 5.7 Hz, 2H), 3.74-3.70 (m, 2H), 3.21-3.16 (m, 2H), 2.51 (s, 3H), 2.20-2.16 (m, 2H) 2.04-2.01 (m, 2H) |
| 64 | (methoxy-indole-pyridinone-indazole-ethyl-pyrrolidine) ·HCl | 454 | ¹H NMR (500 MHz, CD₃OD) δ 8.25 (s, 1H), 7.90 (d, J = 1.6 Hz, 1H), 7.80 (d, J = 8.9 Hz, 1H), 7.68-7.67 (dd, J = 6.9, 1.2 Hz, 1H), 7.55-7.52 (dd, J = 8.8, 1.9 Hz, 1H), 7.33 (d, J = 8.9 Hz, 1H), 7.08 (d, J = 2.2 Hz, 1H), 7.06 (s, 1H), 6.98-6.95 (m, 2H), 6.90-6.88 (dd, J = 8.9, 2.5 Hz, 1H), 4.88 (t, J = 5.8 Hz, 2H), 3.87 (t, J = 5.8 Hz, 2H), 3.83 (s, 3H), 3.77-3.67 (br m, 2H), 3.22-3.12 (br m, 2H), 2.20-2.11 (br m, 2H), 2.08-1.97 (br m, 2H) |

| Ex. No. | Structure | Mass Spec | ¹H NMR Data |
|---|---|---|---|
| 65* | 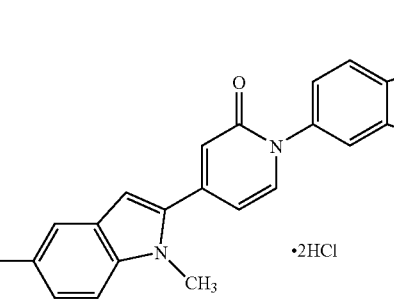 •2HCl | 468 | ¹H NMR (500 MHz, CD₃OD) δ 8.27 (s, 1H), 7.92 (d, J = 1.7 Hz, 1H), 7.82 (d, J = 8.8 Hz, 1H), 7.75 (d, J = 6.6 Hz, 1H), 7.57-7.55 (dd, J = 8.9, 1.9 Hz, 1H), 7.37 (d, J = 8.9 Hz, 1H), 7.11 (d, J = 2.4 Hz, 1H), 6.96-6.94 (dd, J = 8.9, 2.4 Hz, 1H), 6.80-6.78 (m, 3H), 4.89 (t, J = 5.7 Hz, 2H), 3.88 (s, 3H), 3.87 (t, J = 5.7 Hz, 2H), 3.83 (s, 3H), 3.72 (br m, 2H), 3.18 (br m, 2H), 2.17 (br m, 2H), 2.03 (br m, 2H) |
| 66 | 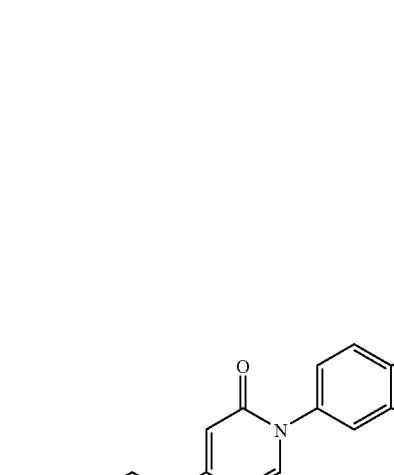 •HCl | 451 | ¹H NMR (500 MHz, CD₃OD) δ 8.34 (d, J = 2.5 Hz, 1H), 8.26 (s, 1H), 7.95-7.90 (m, 5H), 7.83 (d, J = 8.9 Hz, 1H), 7.78-7.76 (m, 2H), 7.56-7.54 (d, J = 8.9, 1.9 Hz, 1H), 6.95 (d, J = 1.9 Hz, 1H), 6.90 (dd, J = 7.1, 2.0 Hz, 1H), 6.58 (t, J = 1.9 Hz, 1H), 4.89 (t, J = 5.8 Hz, 2H), 3.89 (t, J = 5.8 Hz, 2H), 3.76-3.68 (br m, 2H), 3.21-3.13 (br m, 2H), 2.22-2.12 (br m, 2H), 2.08-1.96 (br m, 2H) |
| 67 | 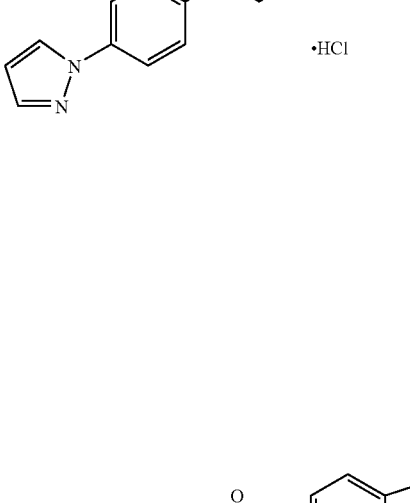 •HCl | 403 | ¹H NMR (500 MHz, CD₃OD) δ 8.23 (s, 1H), 7.84 (d, J = 1.4 Hz, 1H), 7.78 (d, J = 8.9 Hz, 1H), 7.55 (d, J = 7.2 Hz, 1H), 7.49-7.47 (dd, J = 8.9, 1.9 Hz, 1H), 6.70-6.68 (dd, J = 7.3, 1.9 Hz, 1H), 6.57-6.54 (m, 2H), 4.87 (t, J = 5.7 Hz, 2H), 3.86 (t, J = 5.7 Hz, 2H), 3.73-3.69 (m, 2H), 3.20-3.13 (m, 2H), 2.46-2.36 (m, 3H), 2.21-2.12 (m, 2H), 2.05-1.97 (m, 2H), 1.96-1.85 (m, 2H), 1.79-1.71 (m, 1H), 1.44-1.34 (m, 1H), 1.03 (d, J = 6.6 Hz, 3H) |

| Ex. No. | Structure | Mass Spec | $^1$H NMR Data |
|---|---|---|---|
| 68 | 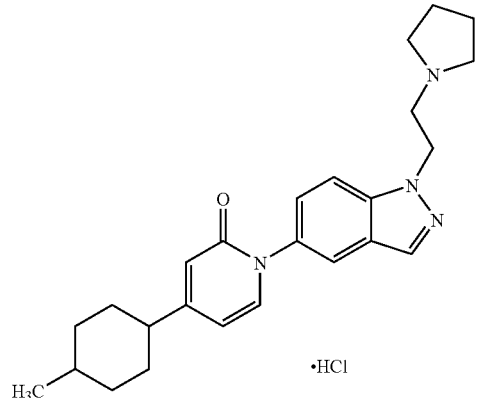 | 405 | $^1$H NMR (500 MHz, CD$_3$OD) δ 8.21 (s, 1H), 7.82 (s, 1H), 7.77 (d, J = 8.8 Hz, 1H), 7.57-7.56 (m, 1H), 7.47-7.44 (m, 1H), 6.54-6.45 (m, 2H), 4.82 (m, 2H), 3.71-3.64 (br m, 2H), 3.29-3.28 (br m, 3H), 2.61-2.55 (t, J = 8.5, 0.6 Hz, 0.6H), 2.48-2.41 (t, J = 13.2 Hz, 0.4H), 2.02 (s, 4H), 1.97-1.67 (m, 6H), 1.59-1.42 (m, 3H), 1.34 (q, J = 13.1 Hz, 1H), 1.05 (d, J = 7.3 Hz, 2H), 0.92 (d, J = 7.0 Hz, 1H) |

*$K_i$ for IC$_{50}$ is estimated to be around 3 micromolar based on the measured percent inhibition.

The present invention is not limited to the compounds found in the above examples, and many other compounds falling within the scope of the invention may also be prepared using the procedures set forth in the above synthetic schemes. The preparation of additional compounds of formula I using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

What is claimed is:

1. A compound of formula I:

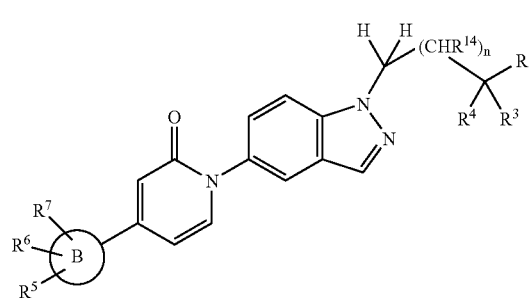

wherein
n is 0 or 1;
R is an optionally substituted pyrrolidin-1-yl;
R$^3$ and R$^4$ are each independently H or alkyl;
B is selected from aryl, and cycloalkyl;
R$^5$, R$^6$, R$^7$ are each independently selected from H, —OH, —O-alkyl, alkyl, halo, —CF$_3$, —CN, and —O-aryl; and
R$^{14}$ is H or —OH;
wherein optional substituents are selected from the group consisting of alkyl, halogen, haloalkyl, hydroxy, lower alkoxy, carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, and heteroaryloxy; and
provided that when n is 0, R$^3$ and R$^4$ are H and R is pyrrolidin-1-yl, then
when B is phenyl which is substituted at the 2-position by methoxy or at the 3-position by methyl, there is at least one additional substituent on the phenyl ring;
or pharmaceutically acceptable salt thereof.

2. A compound according to claim 1, wherein R is selected from the group consisting of pyrrolidin-1-yl, 3-hydroxypyrrolidin-1-yl, and 3-hydroxymethylpyrrolidin-1-yl.

3. A compound according to claim 1, wherein R is selected from S-3-hydroxypyrrolidin-1-yl, R-3-hydroxypyrrolidin-1-yl, S-3-hydroxymethylpyrrolidin-1-yl, and R-3-hydroxymethylpyrrolidin-1-yl.

4. A compound according to claim 3, wherein R$^3$ and R$^4$ are both H.

5. A compound according to claim 1, wherein B, taken together with R$^5$, R$^6$ and R$^7$, is 4-trifluoromethylphenyl and n is 1.

6. A compound according to claim 5, wherein R$^{14}$ is —OH.

7. A compound according to claim 1, wherein n is 0.

8. A compound according to claim 1, wherein n is 1.

9. A compound according to claim 1, wherein B is phenyl.

10. A compound according to claim 9, wherein B, taken together with R$^5$, R$^6$ and R$^7$, is selected from the group consisting of phenyl, 4-chlorophenyl, 4-fluorophenyl, 3-chlorophenyl, 3-phenoxyphenyl, 4-trifluoromethylphenyl, 3-trifluoromethylphenyl, 2,4-dichlorophenyl, 4-methylphenyl, 4-trifluoromethoxyphenyl, 4-cyanophenyl, 4-methoxyphenyl, 2-cyano-4-fluorophenyl, 2,4-dimethoxyphenyl, 2,4-difluorophenyl, 4-isopropoxyphenyl, 2,4-di-trifluoromethylphenyl, 4-n-butoxy-2-methylphenyl, 2-methylphenyl, 4-benzyloxy-2-methylphenyl, 4-chloro-2-methoxyphenyl, 4 methoxy-2-methylphenyl, 2-chloro-4-trifluoromethylphenyl, 4-chloro-2-fluorophenyl, 4-trifluoromethyl-2-fluorophenyl, 4-methoxy-2-fluorophenyl, 4-methoxy-2-chlorophenyl, 4-ethoxyphenyl, 4-trifluoromethoxy-2-fluorophenyl, and 4-trifluoromethoxy-2-methylphenyl.

11. A compound according to claim 1, wherein B, taken together with R$^5$, R$^6$ and R$^7$, is selected from napthalen-1-yl and naphthalen-2-yl.

12. A compound according to claim 1, wherein B, taken together with R$^5$, R$^6$ and R$^7$, is selected from 4-methylcyclohex-1-enyl.

13. A compound according to claim 1, wherein B, taken together with R$^5$, R$^6$ and R$^7$, is selected from 4-methylcyclohex-1-yl.

14. A compound according to claim 1, wherein the compound is selected from the group consisting of:
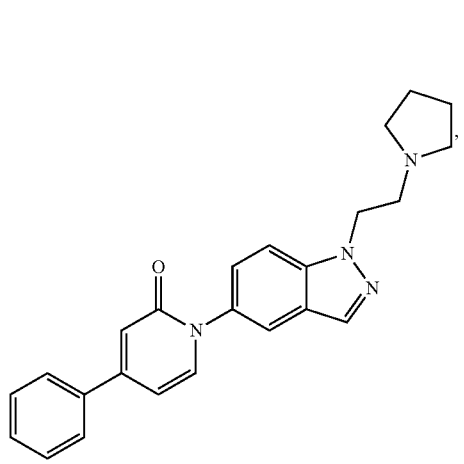
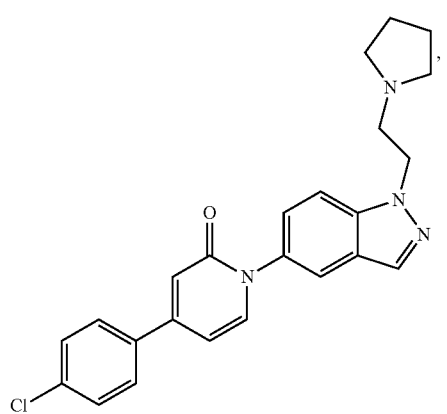
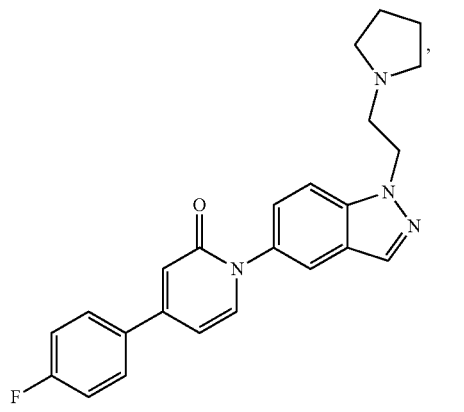
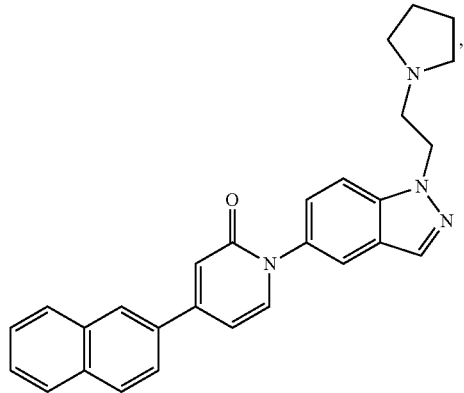
-continued
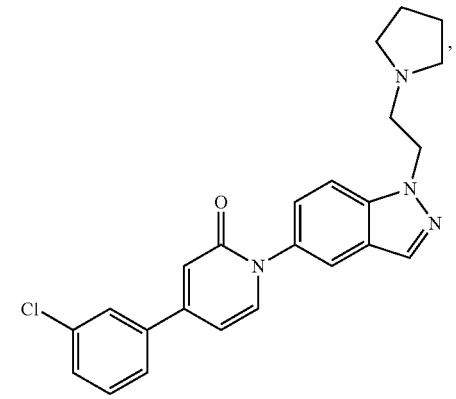
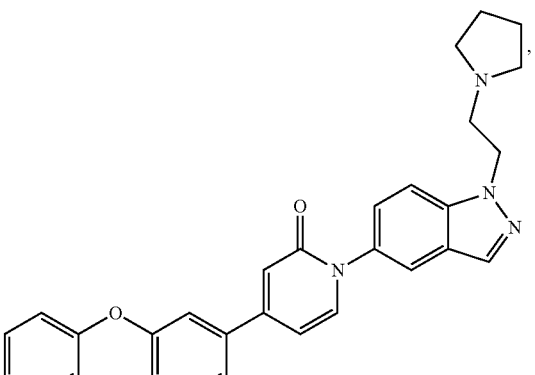
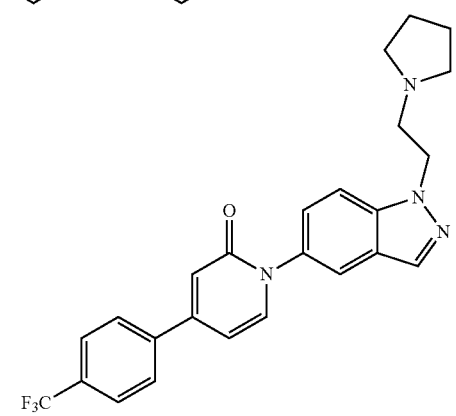
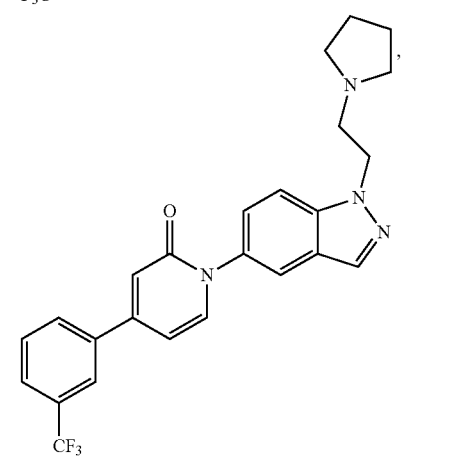

171
-continued
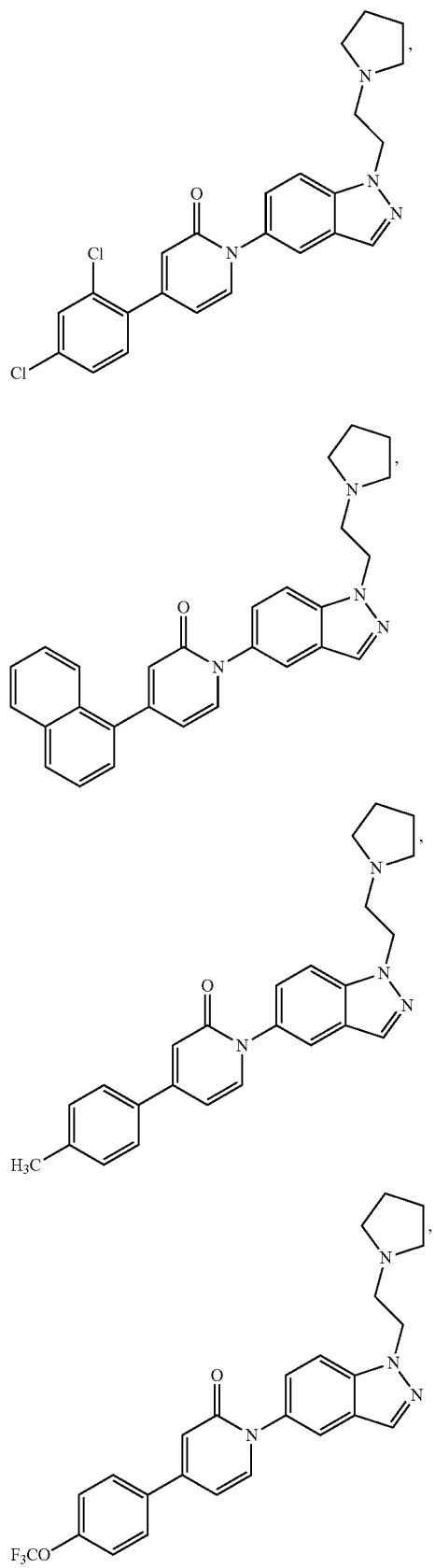
172
-continued
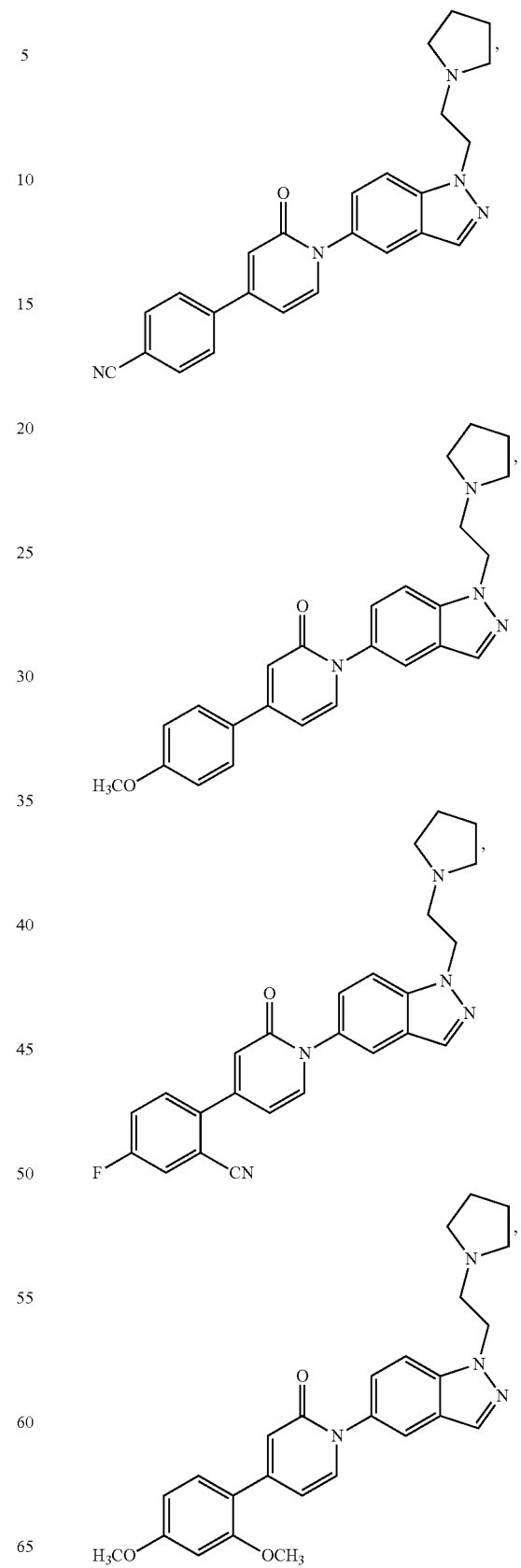

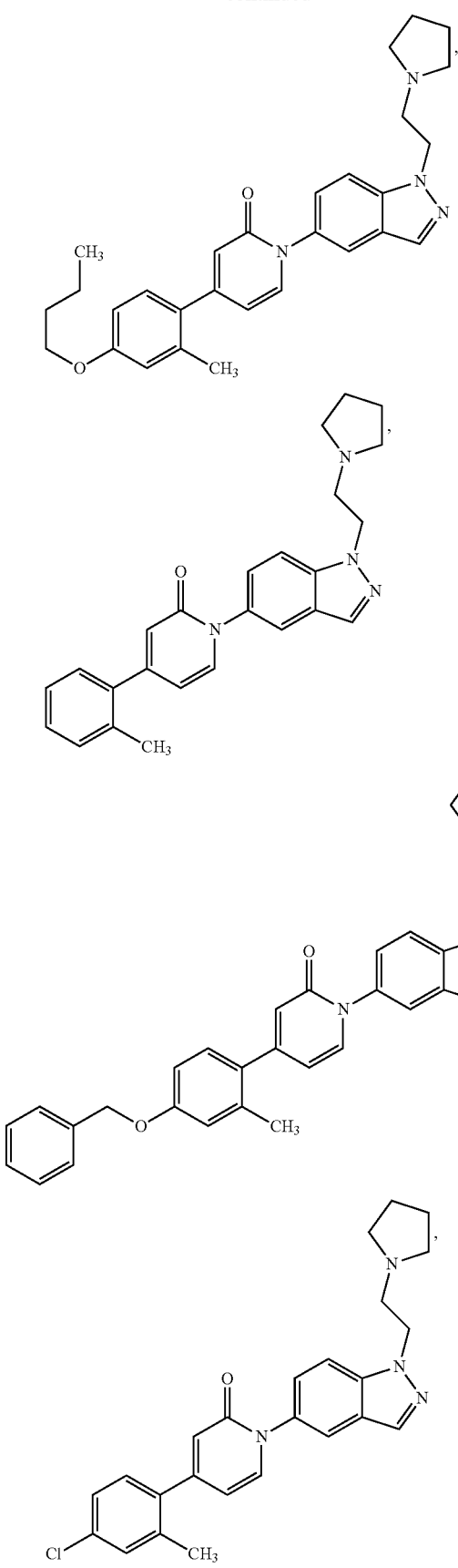
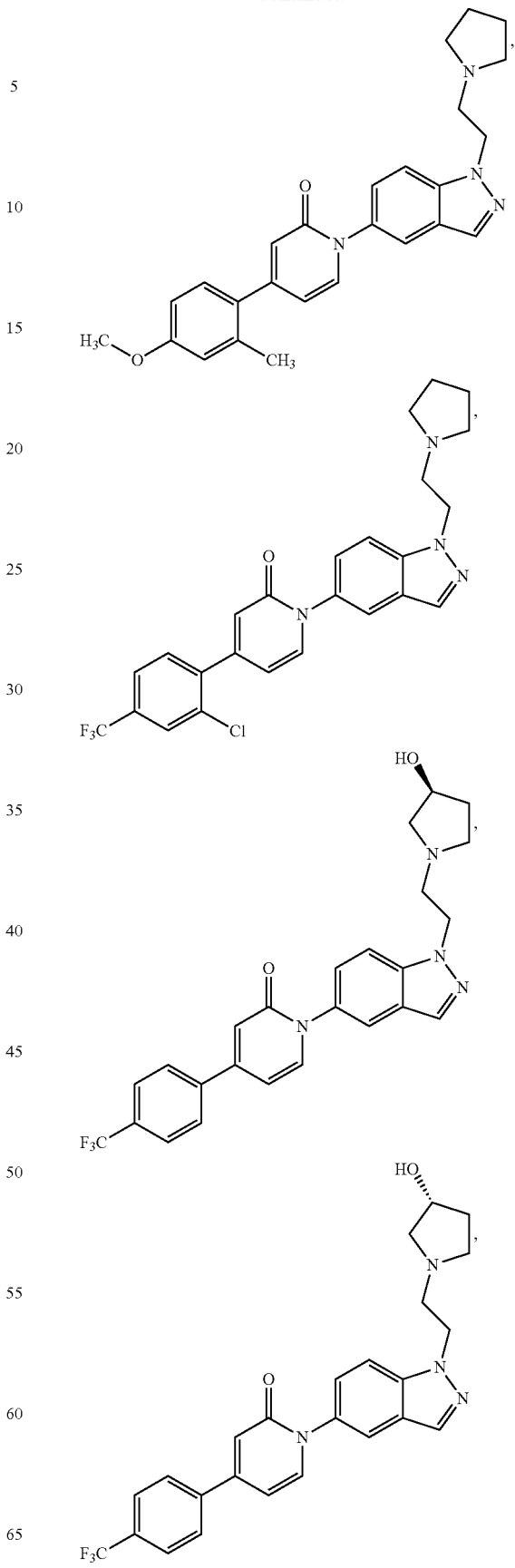

175
-continued
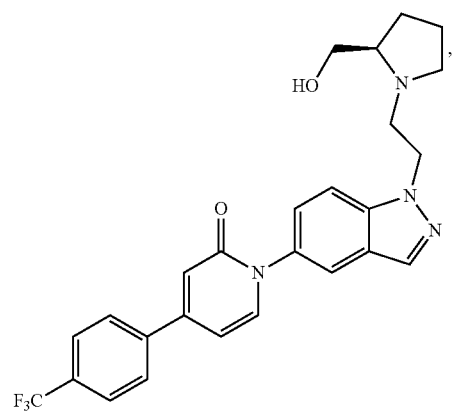
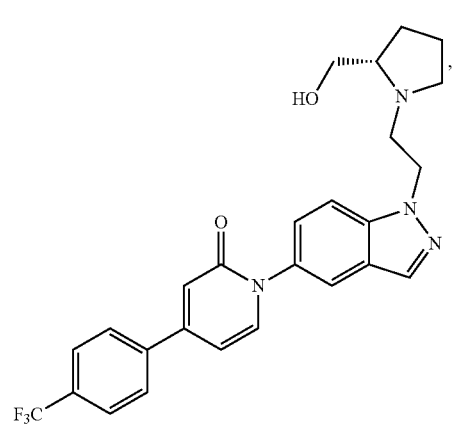
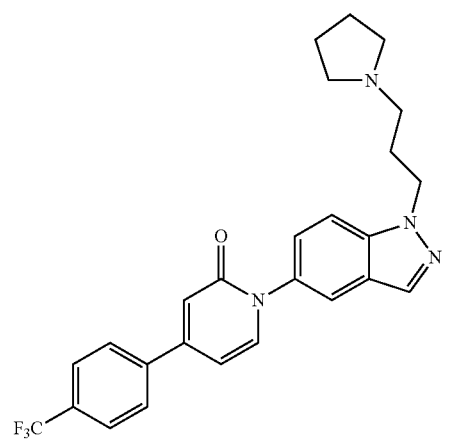
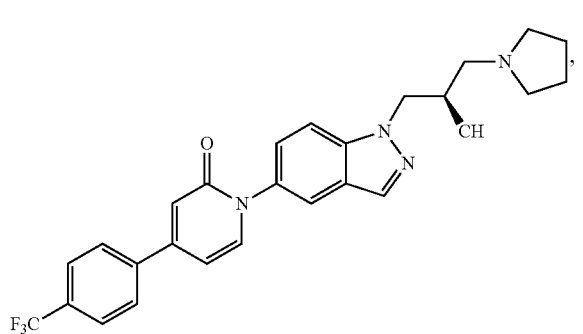
176
-continued
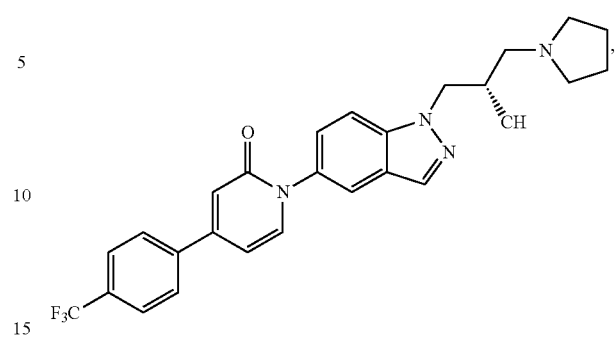
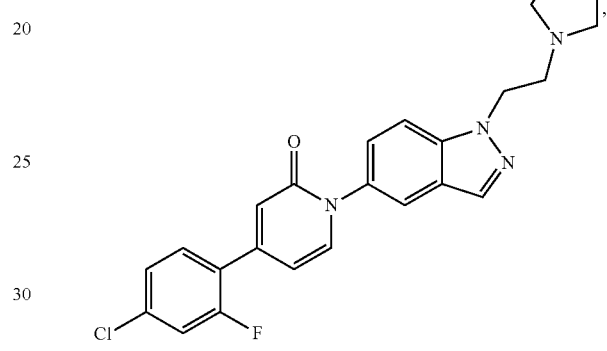
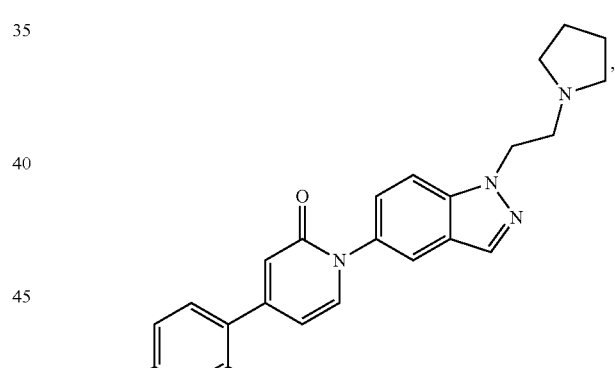
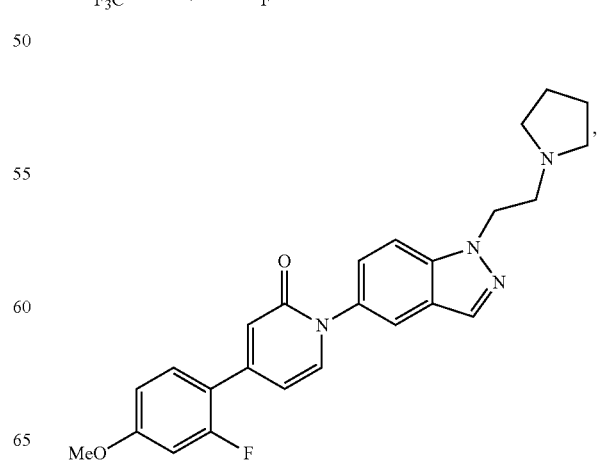

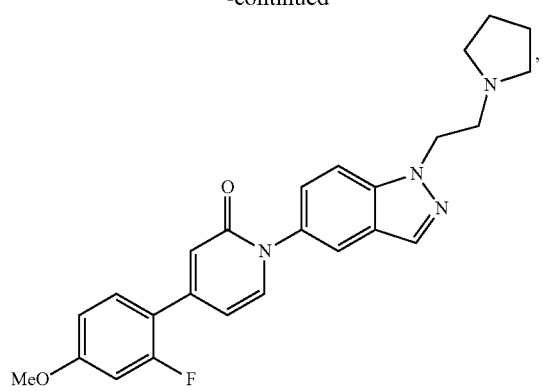
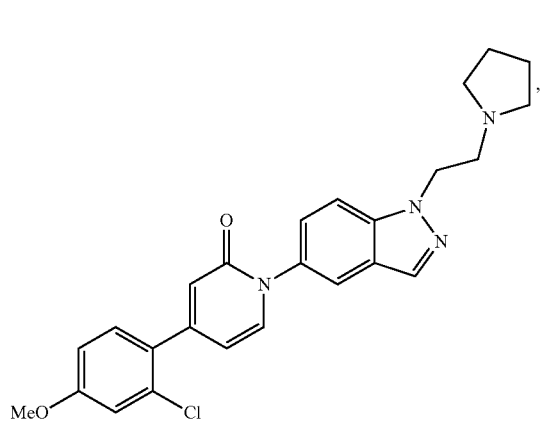
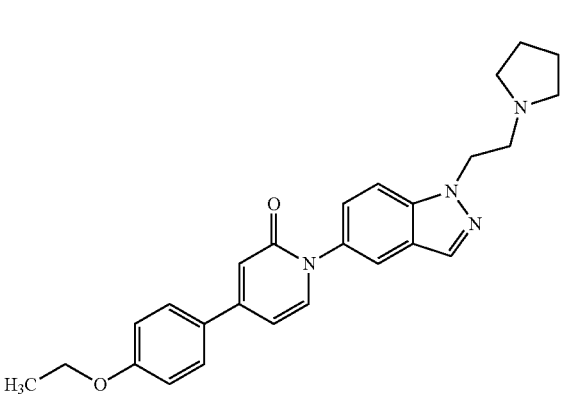
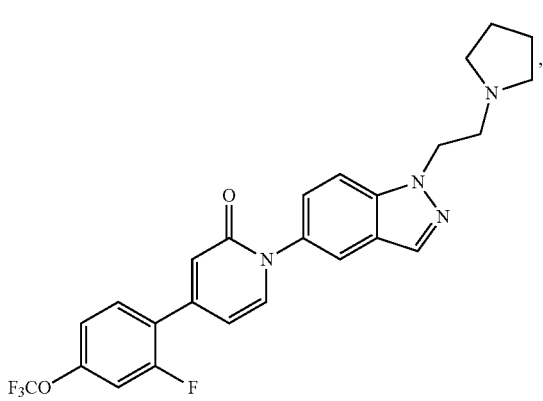
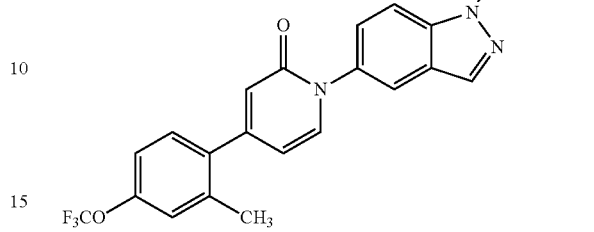
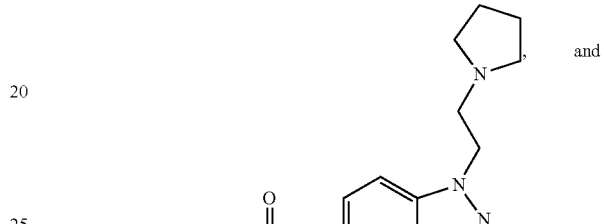
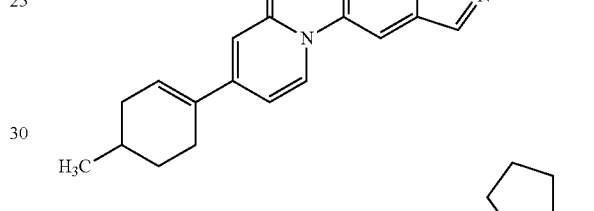
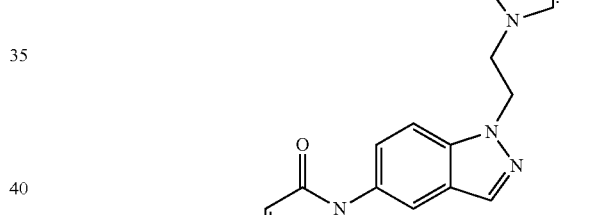
15. A compound according to claim 14, which is a pharmaceutically acceptable salt thereof.
16. A compound according to claim 1, wherein the compound is selected from the group consisting of:
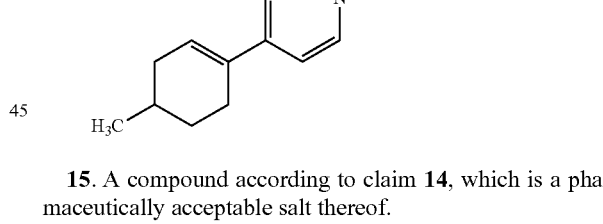
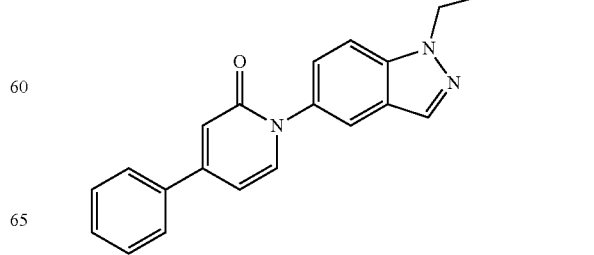

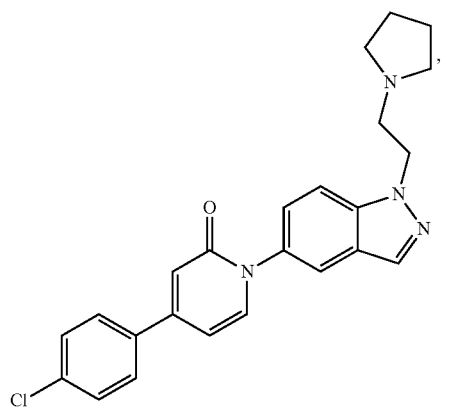
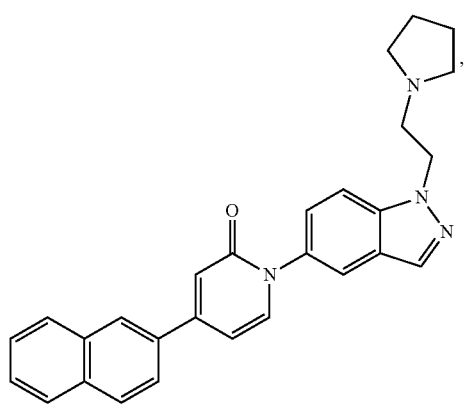
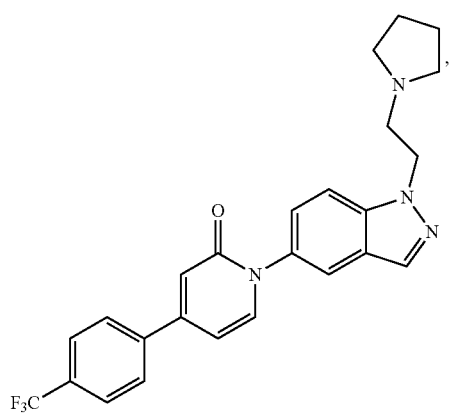
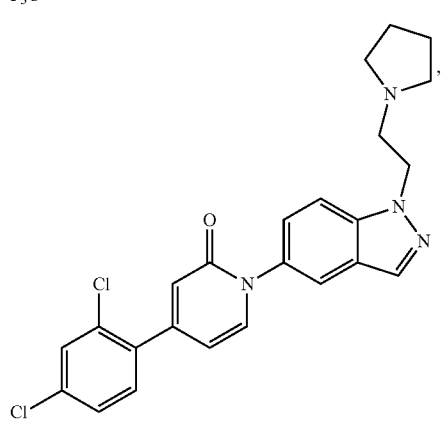
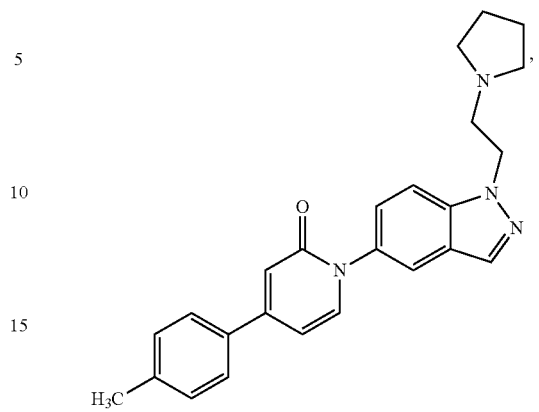
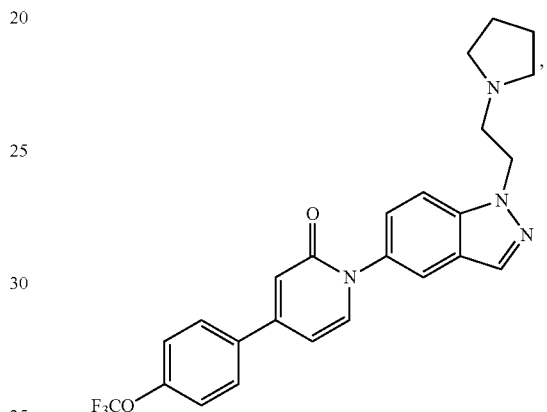
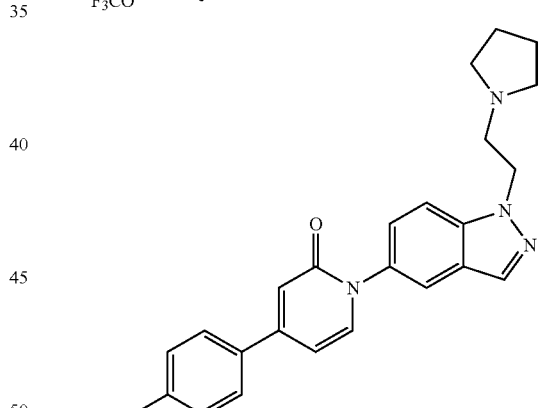
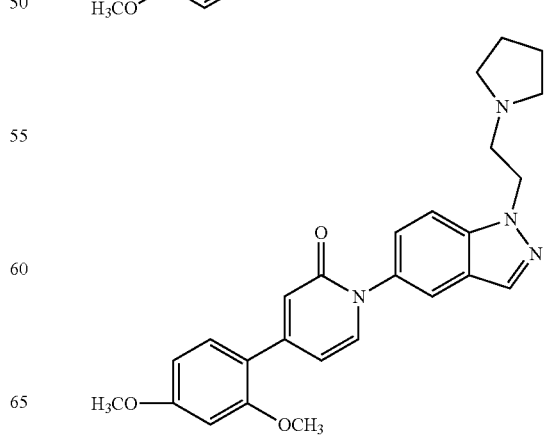

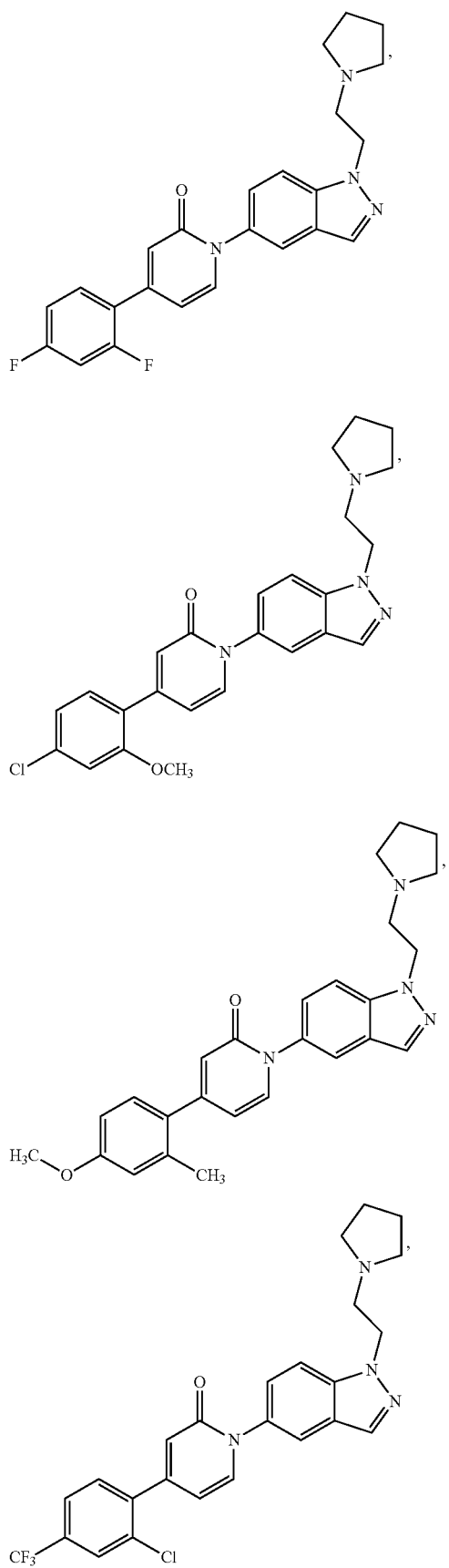
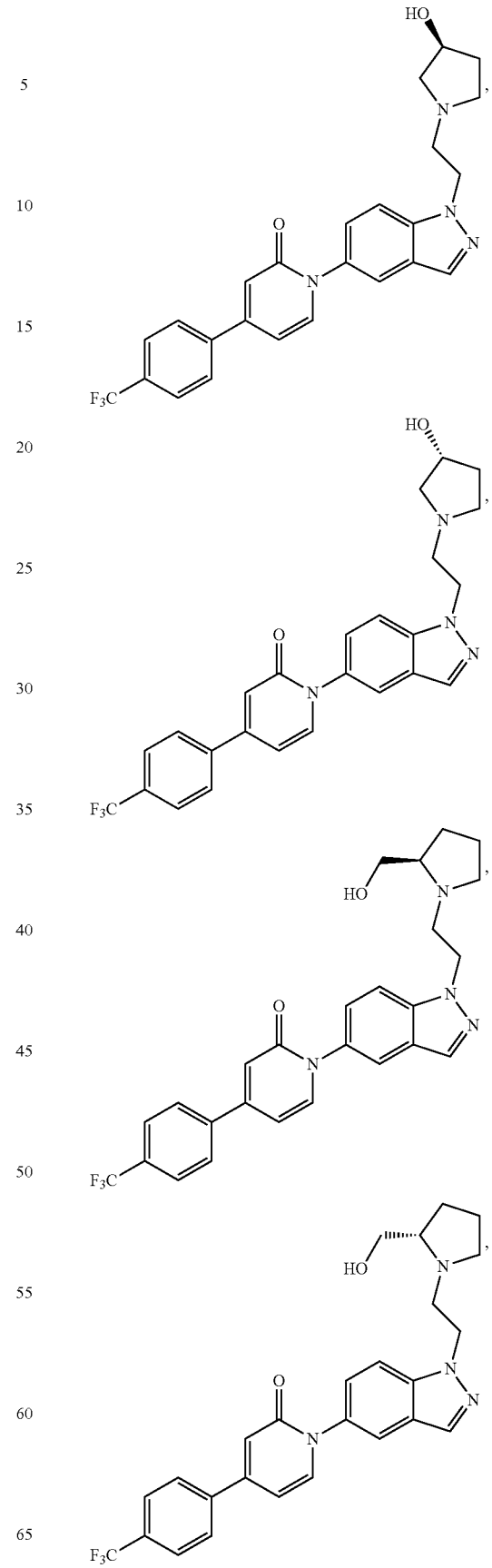

-continued
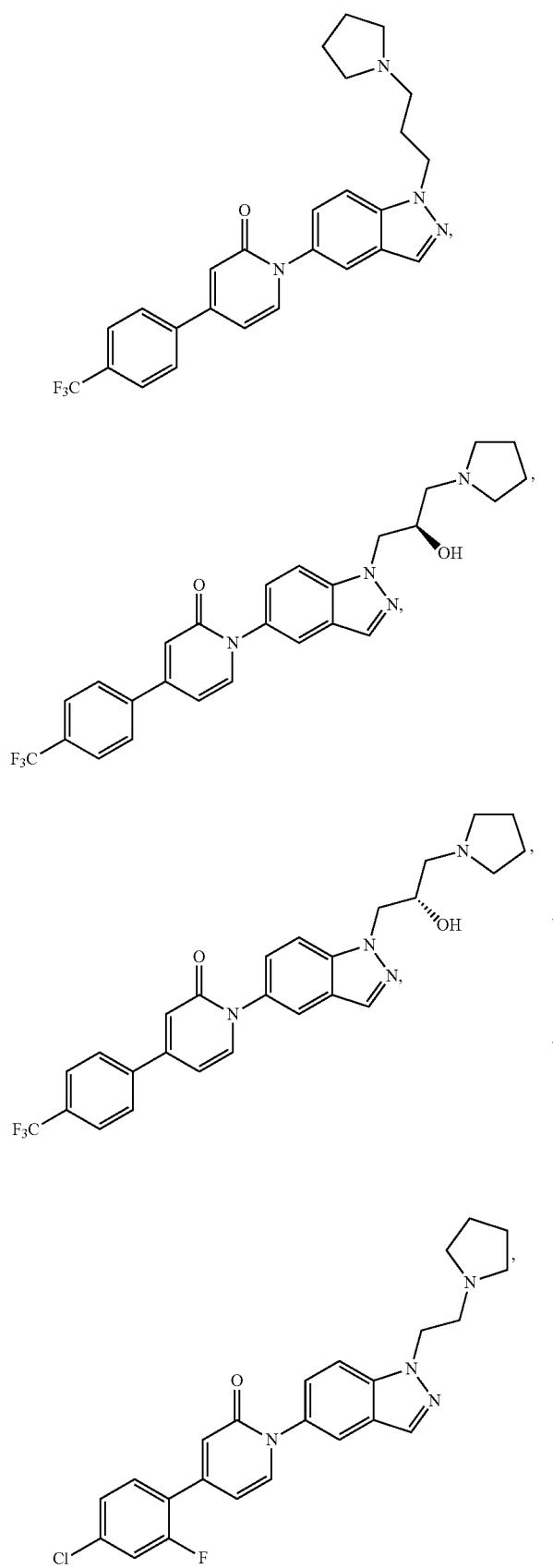
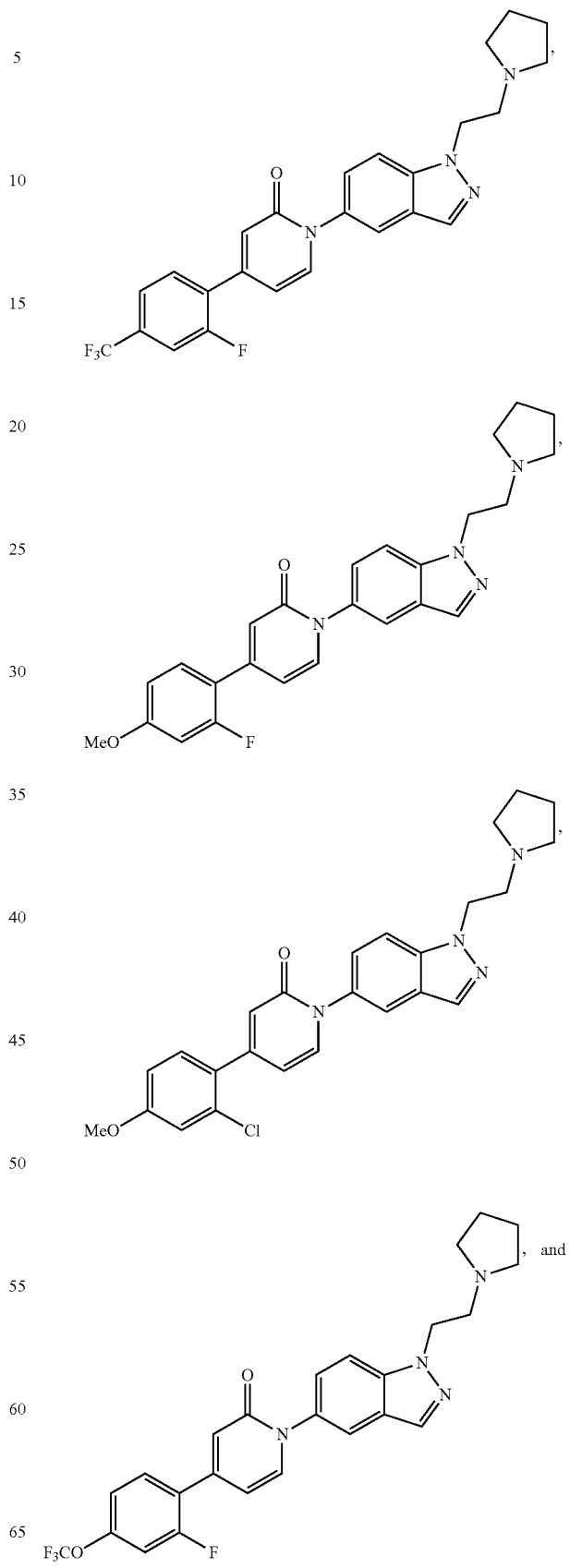

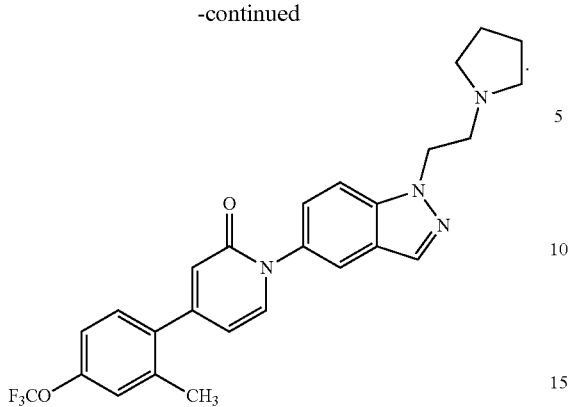
17. A compound according to claim 16, which is a pharmaceutically acceptable salt thereof.
18. A compound according to claim 1, wherein the compound is selected from the group consisting of:
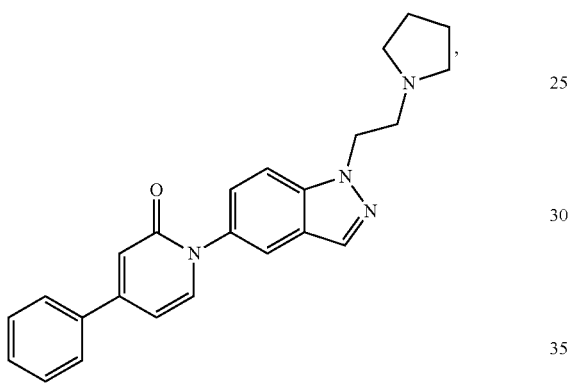
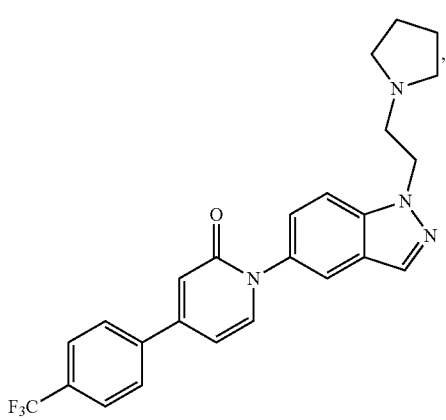
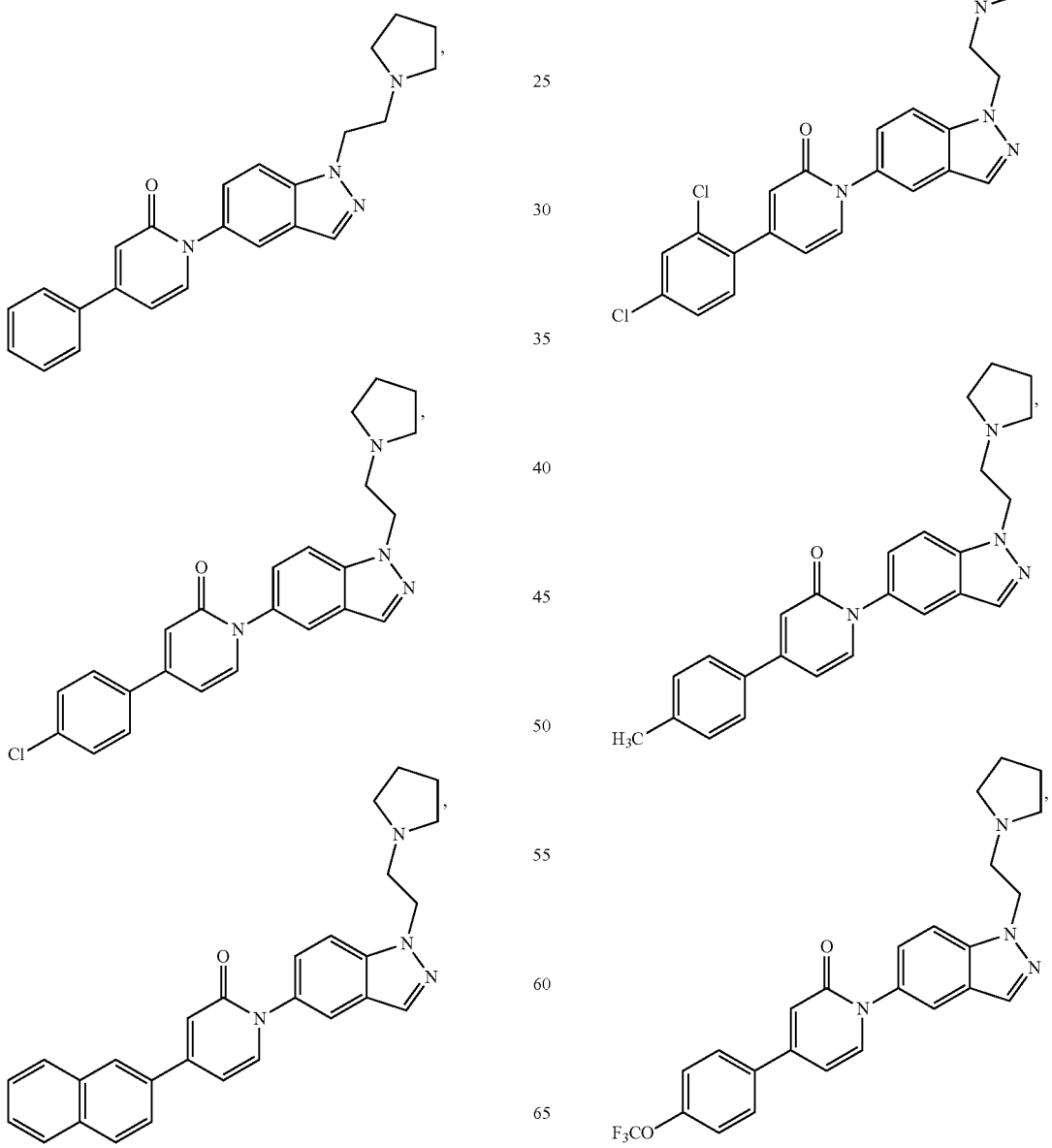

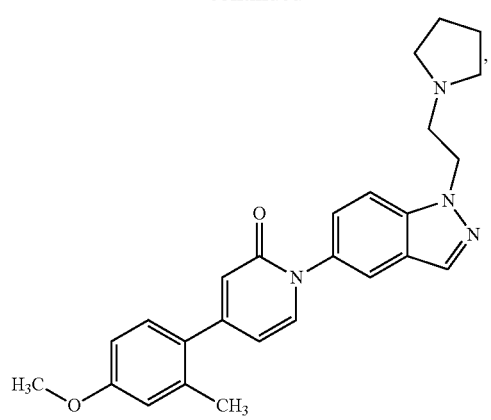
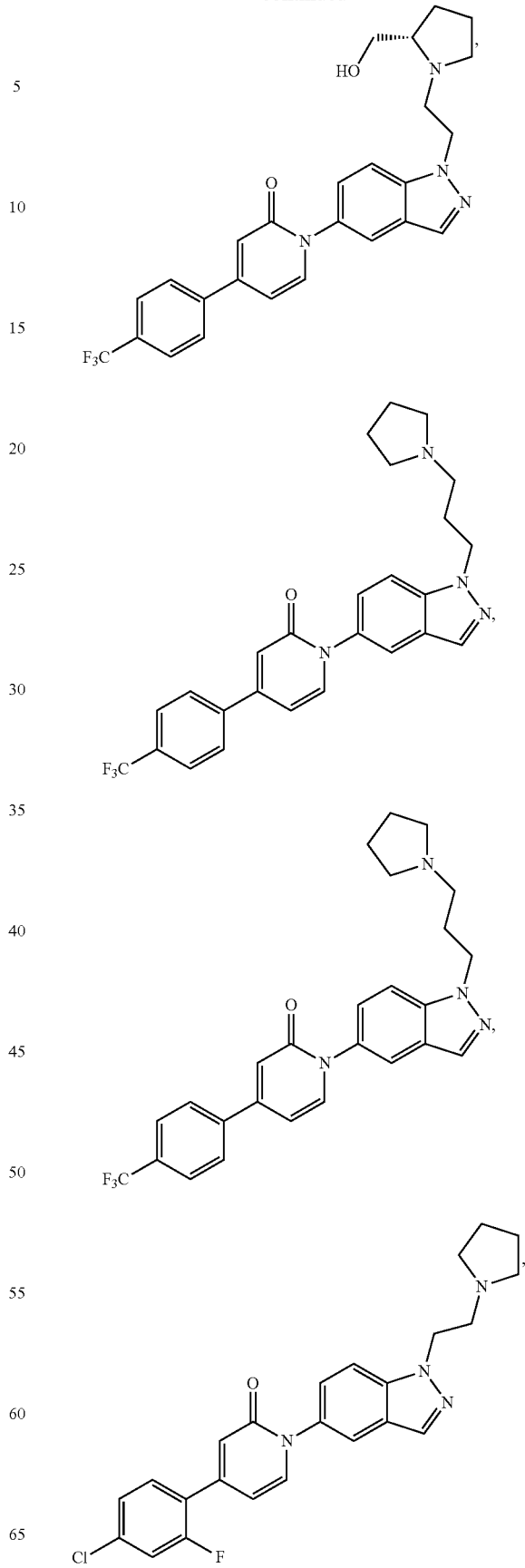

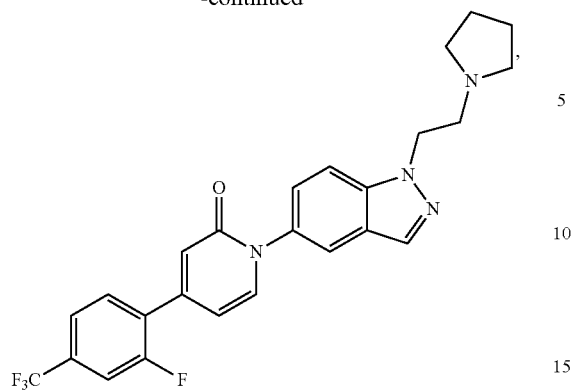
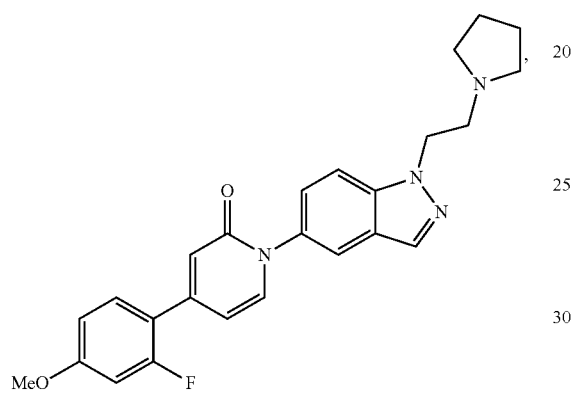
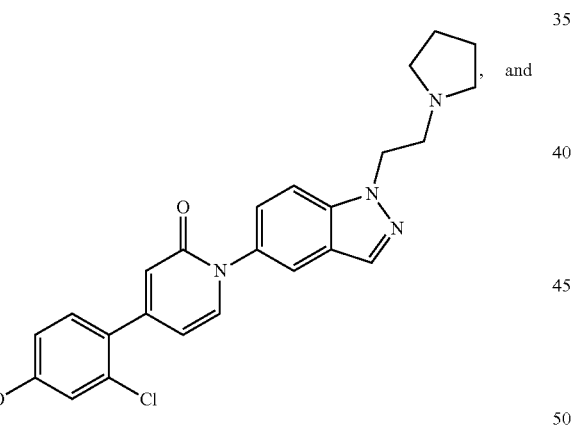
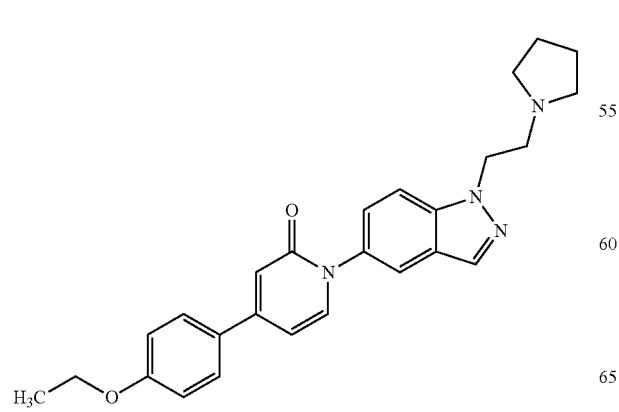
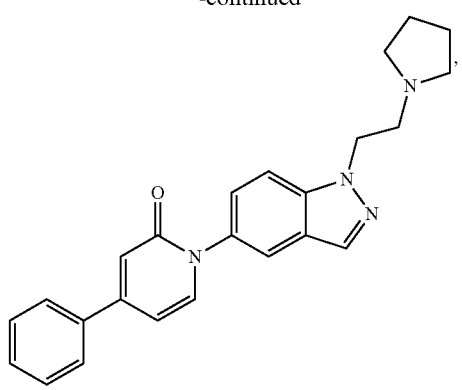
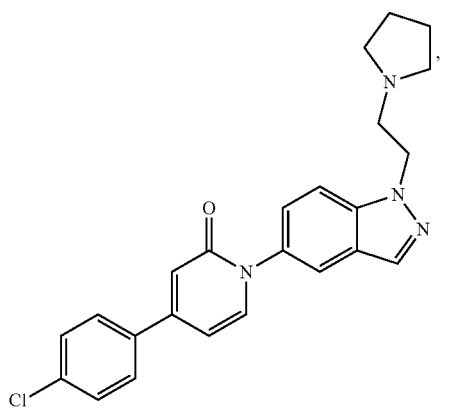
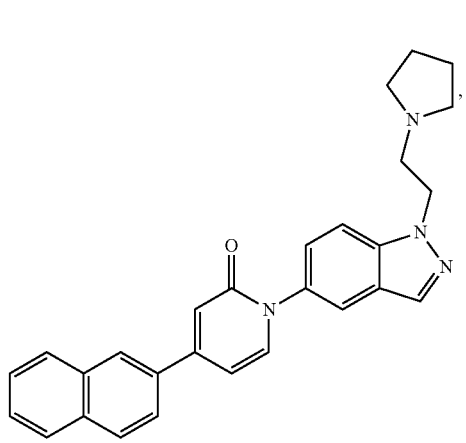
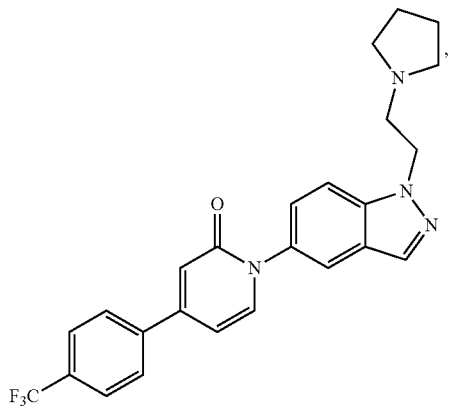

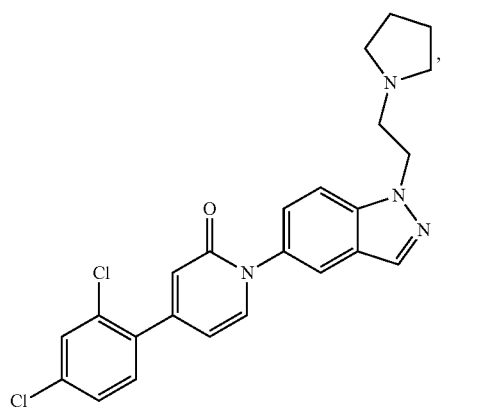
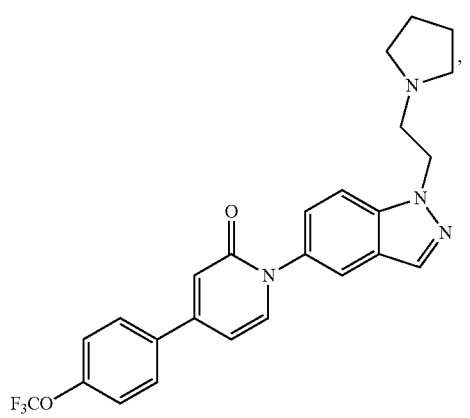
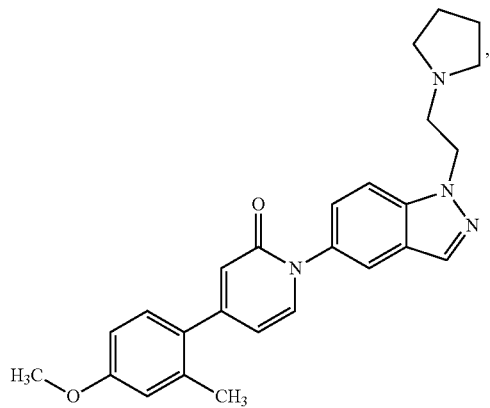
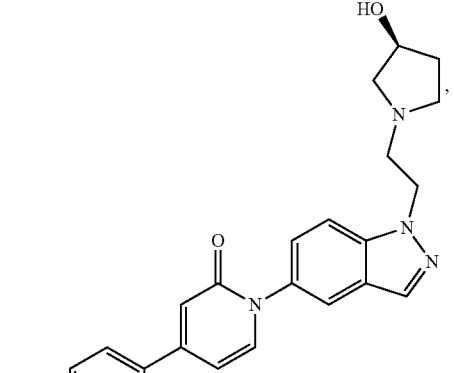
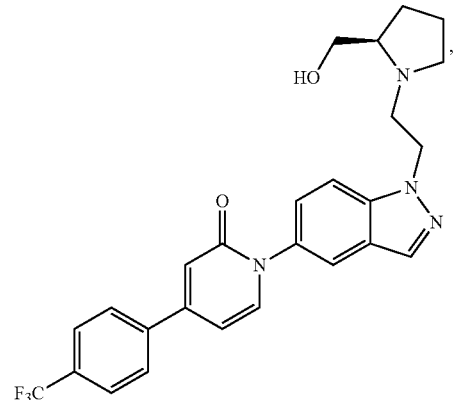
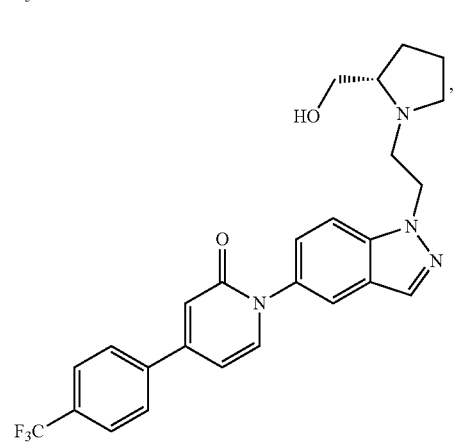
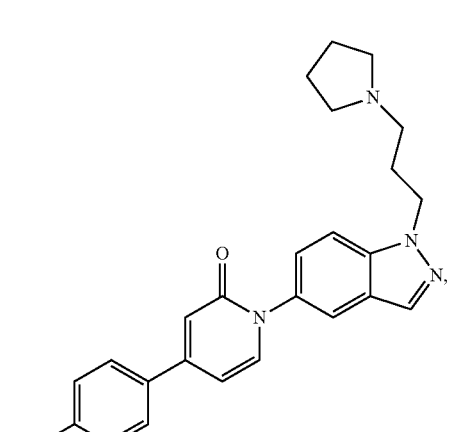
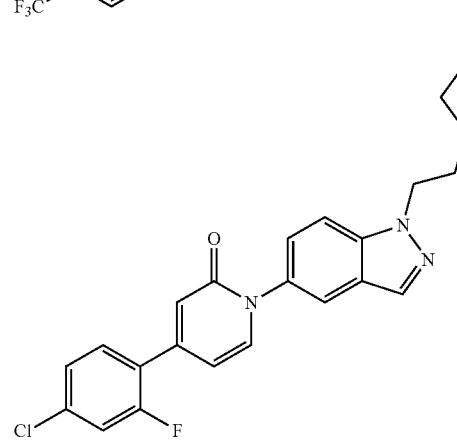

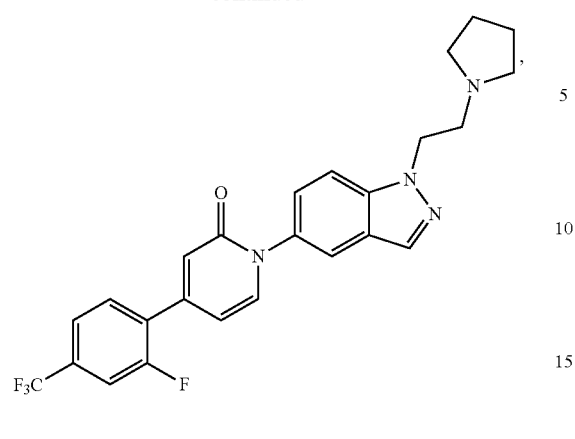
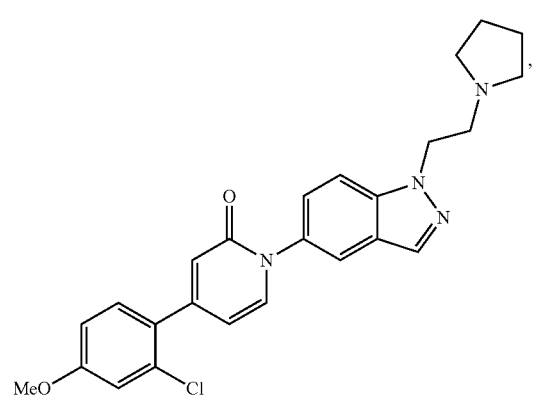
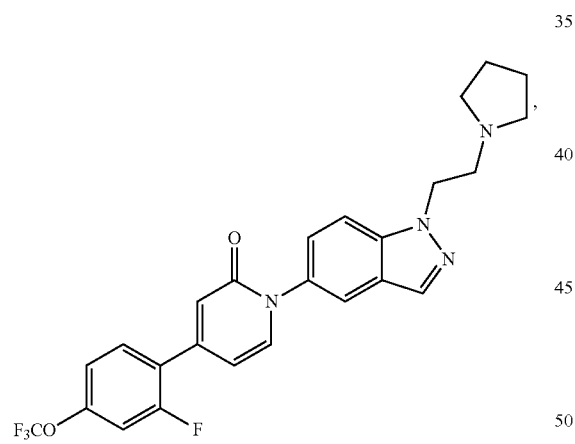
, and
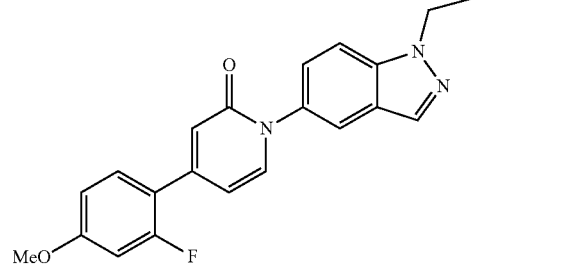
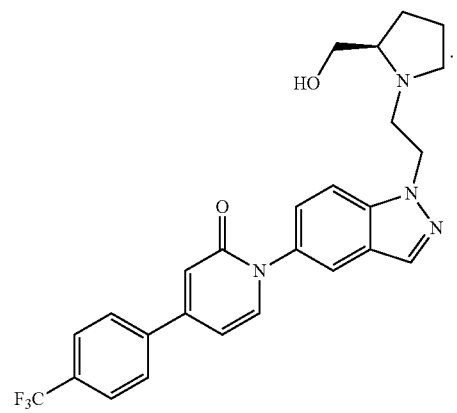
19. A compound according to claim 18, which is a pharmaceutically acceptable salt thereof.
20. A compound according to claim 1, wherein the compound is selected from the group consisting of:
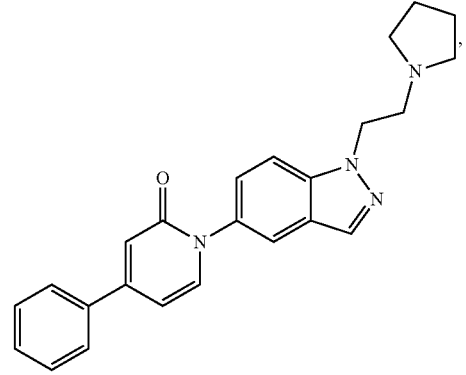
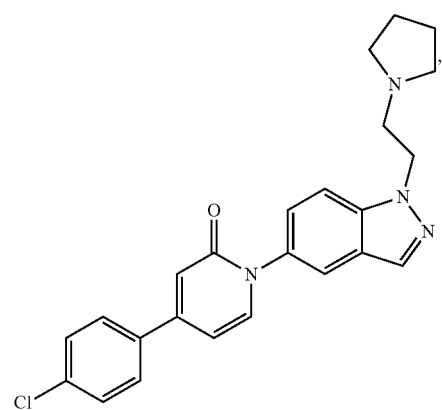

195
-continued
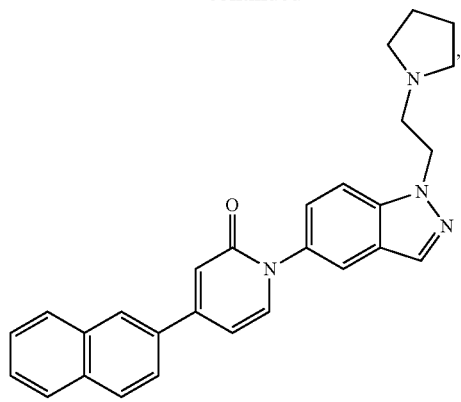
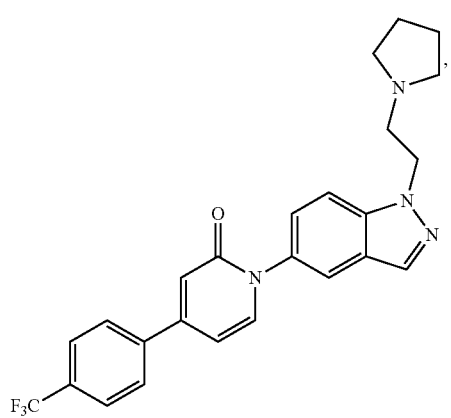
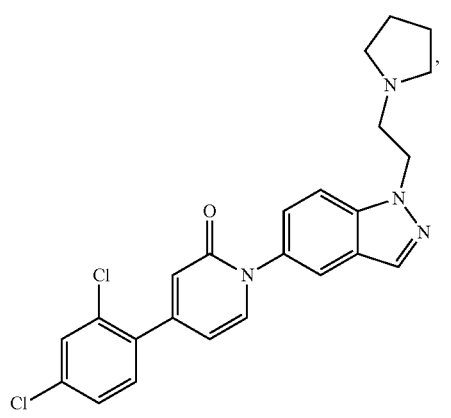
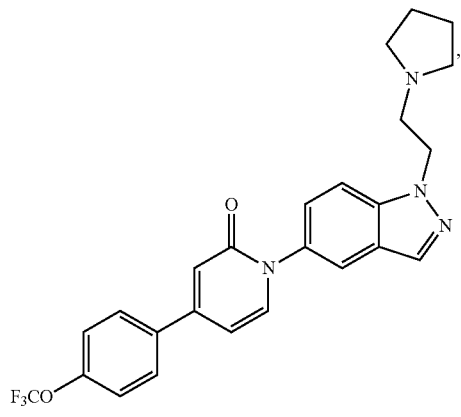
196
-continued
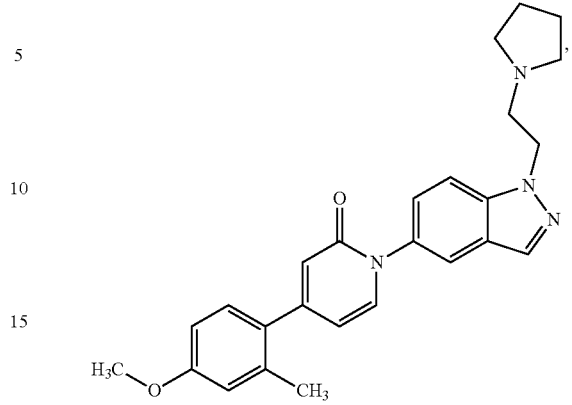
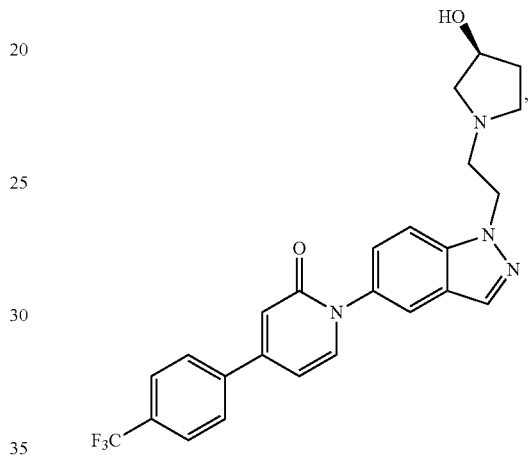
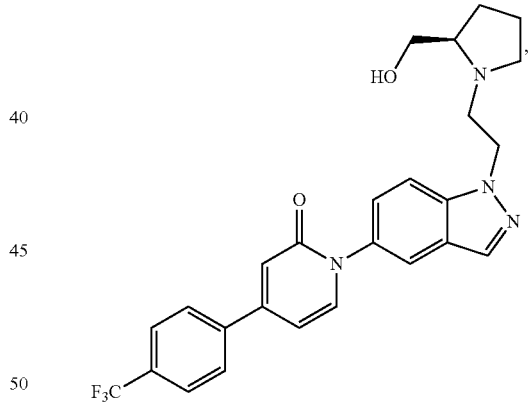
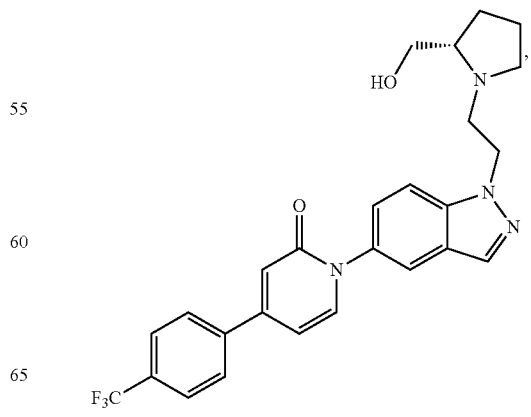

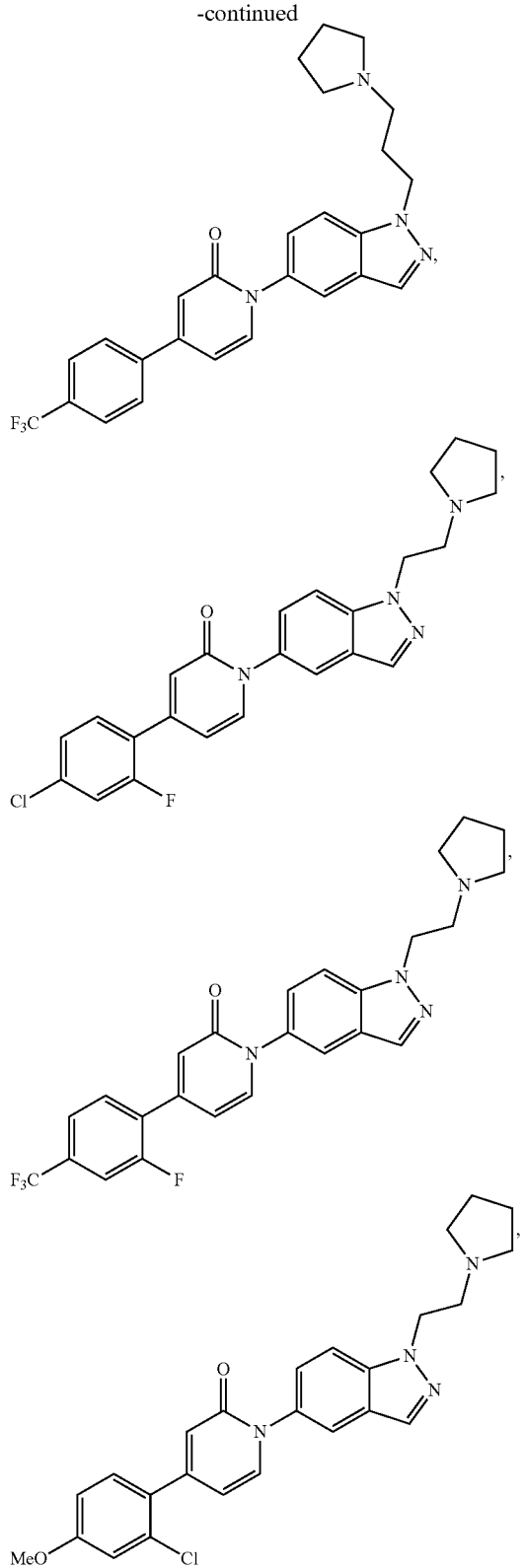
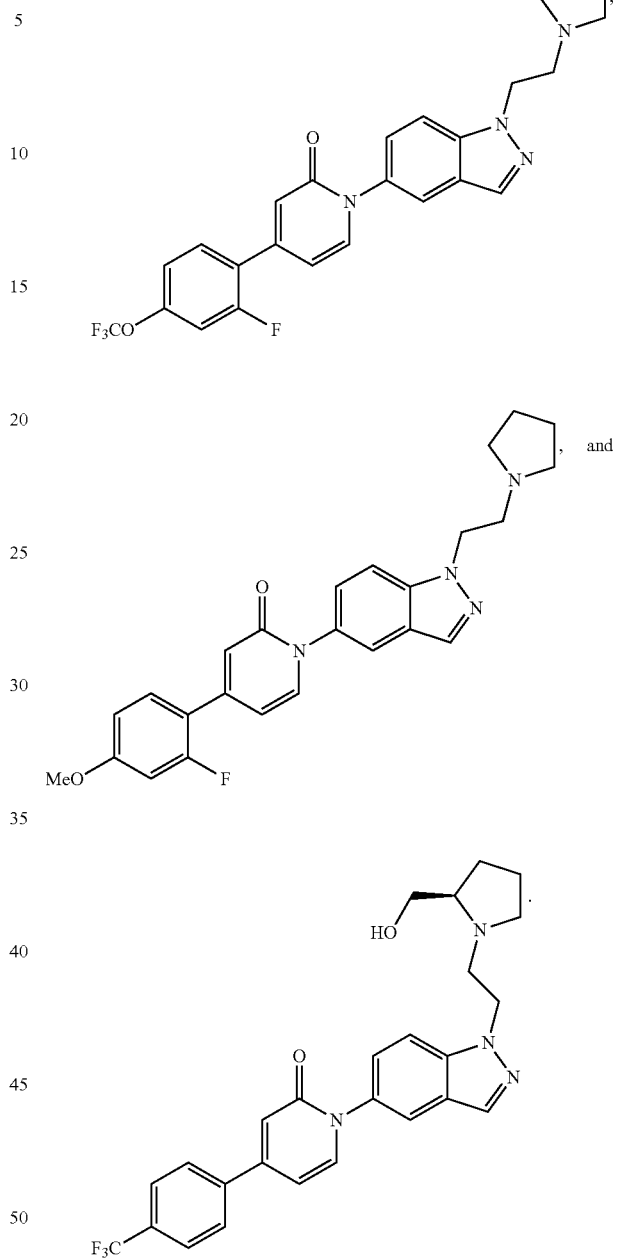
21. A compound according to claim 20, which is a pharmaceutically acceptable salt thereof.
22. A pharmaceutical composition comprising a compound according to claim 1 and a pharmaceutically acceptable carrier, excipient or diluent therefor.
* * * * *